(12) United States Patent
Kudithipudi et al.

(10) Patent No.: US 12,351,809 B2
(45) Date of Patent: Jul. 8, 2025

(54) TISSUE-SPECIFIC PROMOTERS IN PLANTS

(71) Applicants: ALTRIA CLIENT SERVICES LLC, Richmond, VA (US); UNIVERSITY OF VIRGINIA PATENT FOUNDATION, Charlottesville, VA (US)

(72) Inventors: Chengalrayan Kudithipudi, Midlothian, VA (US); Yanxin Shen, Henrico, VA (US); Dongmei Xu, Glen Allen, VA (US); Michael Paul Timko, Charlottesville, VA (US); Roel Rabara, Charlottesville, VA (US)

(73) Assignees: Altria Client Services LLC, Richmond, VA (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 18/449,849

(22) Filed: Aug. 15, 2023

(65) Prior Publication Data
US 2024/0018536 A1 Jan. 18, 2024

Related U.S. Application Data

(63) Continuation of application No. 17/591,188, filed on Feb. 2, 2022, now abandoned.
(Continued)

(51) Int. Cl.
*C12N 15/82* (2006.01)
*C07K 14/415* (2006.01)
*C12P 5/00* (2006.01)

(52) U.S. Cl.
CPC ..... *C12N 15/8262* (2013.01); *C12N 15/8223* (2013.01); *C12N 15/8243* (2013.01);
(Continued)

(58) Field of Classification Search
None
See application file for complete search history.

(56) References Cited

U.S. PATENT DOCUMENTS

| 4,516,590 A | 5/1985 | Teng |
| 4,528,993 A | 7/1985 | Sensabaugh, Jr. et al. |

(Continued)

FOREIGN PATENT DOCUMENTS

| CN | 104 152 463 A | 11/2014 |
| CN | 108070594 A | 5/2018 |

(Continued)

OTHER PUBLICATIONS

Schilmiller et al. "Harnessing plant trichome biochemistry for the production of useful compounds" 2008 Plant J. 54:702-711. (Year: 2008).*

(Continued)

*Primary Examiner* — Matthew R Keogh
*Assistant Examiner* — Rebecca Stephens
(74) *Attorney, Agent, or Firm* — Arnold & Porter Kaye Scholer LLP

(57) ABSTRACT

The present disclosure relates to compositions and methods related to tissue-specific promoters and their uses in plants, including tobacco and cannabis. The provided trichome-specific promoters enable the expression of heterologous polynucleotides in trichome tissues.

19 Claims, 16 Drawing Sheets
Specification includes a Sequence Listing.

Related U.S. Application Data

(60) Provisional application No. 63/145,262, filed on Feb. 3, 2021, provisional application No. 63/145,263, filed on Feb. 3, 2021, provisional application No. 63/145,259, filed on Feb. 3, 2021.

(52) U.S. Cl.
CPC ........ *C07K 14/415* (2013.01); *C12N 2800/22* (2013.01); *C12P 5/007* (2013.01)

(56) References Cited

U.S. PATENT DOCUMENTS

| | | |
|---|---|---|
| 4,660,577 A | 4/1987 | Sensabaugh et al. |
| 4,848,373 A | 7/1989 | Lenkey |
| 4,897,355 A | 1/1990 | Eppstein et al. |
| 4,946,787 A | 8/1990 | Eppstein et al. |
| 4,987,907 A | 1/1991 | Townend |
| 5,049,386 A | 9/1991 | Eppstein et al. |
| 5,159,135 A | 10/1992 | Umbeck |
| 5,188,958 A | 2/1993 | Moloney et al. |
| 5,372,149 A | 12/1994 | Roth et al. |
| 5,463,174 A | 10/1995 | Moloney et al. |
| 5,538,880 A | 7/1996 | Lundquist et al. |
| 5,550,318 A | 8/1996 | Adams et al. |
| 5,591,616 A | 1/1997 | Hiei et al. |
| 5,750,871 A | 5/1998 | Moloney et al. |
| 5,824,877 A | 10/1998 | Hinchee et al. |
| 6,153,812 A | 11/2000 | Fry et al. |
| 6,160,208 A | 12/2000 | Lundquist et al. |
| 6,194,636 B1 | 2/2001 | McElroy et al. |
| 6,232,526 B1 | 5/2001 | McElroy et al. |
| 6,384,301 B1 | 5/2002 | Martinell et al. |
| 6,399,861 B1 | 6/2002 | Anderson et al. |
| 9,115,366 B2 | 8/2015 | Tissier et al. |
| 9,603,335 B2 | 3/2017 | Lewis et al. |
| 2004/0216189 A1 | 10/2004 | Houmard et al. |
| 2005/0178398 A1 | 8/2005 | Breslin et al. |
| 2006/0191548 A1 | 8/2006 | Strickland et al. |
| 2006/0200878 A1 | 9/2006 | Lutfiyya et al. |
| 2006/0260002 A1 | 11/2006 | Ronen et al. |
| 2007/0006341 A1 | 1/2007 | Wagner et al. |
| 2008/0281135 A1 | 11/2008 | Tissier et al. |
| 2021/0010018 A1 | 1/2021 | Tang et al. |
| 2022/0243215 A1 | 8/2022 | Kudithipudi et al. |
| 2022/0243216 A1 | 8/2022 | Kudithipudi et al. |

FOREIGN PATENT DOCUMENTS

| | | |
|---|---|---|
| FR | 2 903 703 A1 | 1/2008 |
| WO | WO 1991/016024 | 10/1991 |
| WO | WO 1991/017424 | 11/1991 |
| WO | WO 2004/041006 A1 | 5/2004 |
| WO | WO 2010/111571 A1 | 9/2010 |
| WO | WO 2017/181018 A1 | 10/2017 |
| WO | WO 2018/057385 A2 | 3/2018 |
| WO | WO 2018/176055 A2 | 9/2018 |
| WO | WO 2019/147873 A2 | 8/2019 |
| WO | WO 2020/185865 A1 | 9/2020 |
| WO | WO 2021/003180 A1 | 1/2021 |

OTHER PUBLICATIONS

Huchelmann et al. "Plant Glandular Trichomes: Natural Cell Factories of High Biotechnological Interest" 2017 Plant Physiology 175:6-22 at page 6. (Year: 2017).*

Aharoni et al., "Volatile science? Metabolic engineering of terpenoids in plants," *Trends in Plant Science*, vol. 10, No. 12, pp. 594-602 (Dec. 2005) (Oxford, UK) Available online: https://doi.org/10.1016/j.tplants.2005.10.005.

Altschul et al. "Basic local alignment search tool." *J. Mol. Biol.* 215, pp. 403-410 (Oct. 1990) (Oxford, United Kingdom). Available online: https://doi.org/10.1016/S0022-2836(05)80360-2.

Altschul et al., "Gapped BLAST and PSI-BLAST: a new general of protein database search programs," Nucleic Acids Res., vol. 25, Issue 17, pp. 3389-3402 (Sep. 1997) (Oxford, United Kingdom). Available online: https://doi.org/10.1093/nar/25.17.3389.

Amaducci et al., "Influence of agronomic factors on yield and quality of hemp (*Cannabis sativa* L.) fibre and implication for an innovative production system," *Field Crops Research*, 107, pp. 161-169 (May 2008) (Oxford, United Kingdom). Available online: DOI:10.1016/j.fcr.2008.02.002.

Brückner et al., "High-level diterpene production by transient expression in Nicotiana benthamiana." *Plant Methods*. 9(1): 46, 10 pages, (Dec. 2013). Available online: doi: https://doi.org/10.1186/1746-4811-9-46.

Canevascini et al., "Tissue-Specific Expression and Promoter Analysis of the Tobacco ltp1 Gene1," *Plant Physiol* 112(2), pp. 513-524 (Oct. 1996). Available online: DOI: 10.1104/pp.112.2.513.

Chalvin et al., "Genetic Control of Glandular Trichome Development," *Trends in Plant Science* 25(5):477-487 (May 2020). Available online: doi: 10.1016/j.tplants.2019.12.025.

Chandra et al., "Comparative transcriptome analysis to identify putative genes related to trichome development in Ocimum Species," *Molecular Biology Reports*, 47:6587-6598 (Aug. 2020). Available online: https://doi.org/10.1007/s11033-020-05710-1.

Chaplin et al. "The Use of Male-Sterile Tobacco in Relation to Topping and Suckering Practices" *Tobacco Science* 7(35), pp. 158-162, (1963). Available online: https://www.coresta.org/sites/default/files/abstracts/Tobacco_Science_1963_7-35_p._158-162_ISSN.0082-4623.pdf.

Chapters 4B and 4C of Tobacco, Production, Chemistry and Technology, Davis & Nielsen, eds., Blackwell Publishing, pp. 70-103, (1999) (Oxford, UK).

Chenna et al., "Multiple sequence alignment with the Clustal series of programs," *Nucleic Acids Research* 31(13), pp. 3497-3500 (Jul. 2003) (Oxford, United Kingdom). Available online: doi: 10.1093/nar/gkg500.

Choi et al., "Tobacco NtLTP1, a glandular-specific lipid transfer protein, is required for lipid secretion from glandular trichomes," *Plant Journal*, 70:480-491 (May 2012). Available online: DOI: 10.1111/j.1365-313X.2011.04886.x.

Database NCBI Accession No. XP_030504371 dated May 18, 2020.
Database UniProtKB Accession No. A0A1S3YF18 dated Apr. 12, 2017.

Feeney et al., Tissue Culture and Agrobacterium-Mediated Transformation of Hemp (*Canniabis sativa* L.), *In Vitro Cell. and Dev. Biol.—Plant*, 39, pp. 578-585 (Nov./Dec. 2003) (Baden-Wuerttemberg, Germany). Available online: DOI:10.1079/IVP2003454.

GenBank Accession MG493458.1, dated Oct. 2, 2018.
Gen Bank Accession No. GQ911584.1, dated Mar. 10, 2010.
GenBank Accession No. KU162868.1, dated May 8, 2017.
Goldman et al., "Female sterile tobacco plants are produced by stigma-specific cell ablation," *EMBO Journal* 13:2976-2984 (Jul. 1994) (Oxford, United Kingdom). Available online: https://doi.org/10.1002/j.1460-2075.1994.tb06596.x.

Griffiths-Jones et al., "Rfam: an RNA family database," *Nucleic Acids Res.*, 31(1), pp. 439-441 (Jan. 2003) (Oxford, United Kingdom). Available online: https://doi.org/10.1093/nar/gkg006.

Horsch et al., "A Simple and General Method for Transferring Genes into Plants," *Science*, vol. 227, Issue 4691, pp. 1229-1231, with cover page and table of contents (Mar. 1985) (Washington, DC). Available online: DOI: 10.1126/science.227.4691.1229.

Huchelmann et al., "Plant Glandular Trichomes: Natural Cell Factories of High Biotechnological Interest," *Plant Physiology* vol. 175, Issue 1., pp. 6-22 (Sep. 2017) (Oxford, UK). https://doi.org/10.1104/pp.17.00727.

International Search Report and Written Opinion issued in International Patent Application No. PCT/US2022/014895 dated Jul. 21, 2022.

International Search Report and Written Opinion issued in International Patent Application No. PCT/US2022/014896 dated Jul. 4, 2022.

International Search Report and Written Opinion issued in International Application No. PCT/US2022/014898 dated Jul. 8, 2022.

(56) References Cited

OTHER PUBLICATIONS

Jiang et al., "Extraction and Analysis of Terpenes/Terpenoids," *Curr Protoc Plant Biol.*, 1(2), pp. 345-358 (Jun. 2016) (Hoboken, New Jersey). Available online: https://doi.org/10.1002/cppb.20024.

Katoh et al., "Specific residues at every third position of siRNA shape its efficient RNAi activity," *Nucleic Acids Res.*, 35(4), pp. e27 (Feb. 2007) (Oxford, UK). Available online: https://doi.org/10.1093/nar/gk11120.

Khvorova et al., "Functional siRNAs and miRNAs Exhibit Strand Bias," *Cell*, vol. 115, Issue 2, pp. 209-216 (Oct. 2003) (Cambridge, MA). Available online: DOI:https://doi.org/10.1016/S0092-8674(03)00801-8.

Kim, "MicroRNA Biogenesis: Coordinated Cropping and Dicing," *Nature Rev. Mol. Cell. Biol.*, 6, pp. 376-385 (May 2005) (Baden-Wuerttemberg, Germany). Available online: https://doi.org/10.1038/nrm1644.

Lange et al., "Metabolic engineering of plant monoterpenes, sesquiterpenes and diterpenes —current status and future opportunities," *Plant Biotechnology Journal* 11(2), 169-196 (Feb. 2013) (Oxford, UK). First published online Nove. 2012: https://doi.org/10.1111/pbi.12022.

Larkin MA et al., "Clustal W and Clustal X version 2.0," *Bioinformatics* 23(21), 2947-2948 (Nov. 2007) (Oxford, United Kingdom). Available online: doi: 10.1093/bioinformatics/btm404.

Laterre et al., "Photosynthetic Trichomes Contain a Specific Rubisco with a Modified pH-Dependent Activity," *Plant Physiology* 173(4), pp. 2110-2120 (April 2017) (Rockville, MD). Available online: DOI: 10.1104/pp.17.00062.

Lee et al., "Increased sesqui- and triterpene production by co-expression of HMG-COA reductase and biotin carboxyl carrier protein in tobacco (*Nicotiana benthamiana*)," *Metabolic Engineering* 52, pp. 20-28 (Mar. 2019) (Oxford, UK). Available online: DOI:10.1016/j.ymben.2018.10.008.

Lim et al., "Petal-specific activity of the promoter of an anthocyanidin synthase gee of tobacco (*Nicotiana tabacum* L.)," *Plant Cell Tissue Organ Cult* 114(3):373-383 (2013).

Liu et al., "NbGIS regulates glandular trichome initiation through GA signaling in tobacco," *Plant Molecular Biology*, 98:153-167 (Aug. 2018). Available online: https://doi.org/10.1007/s11103-018-0772-3.

Livak et al., "Analysis of Relative Gene Expression Data Using Real-Time Quanitative PCR and the $2^{-\Delta\Delta C_T}$ Method," *Methods*, vol. 25, Issue 4, pp. 402-408 (Dec. 2001) (Oxford, United Kingdom). Available online: doi: 10.1006/meth.2001.1262.

Lücker et al., "Metabolic Engineering of monoterpene biosynthesis: two-step production of (+)-trans-isopiperitenol by tobacco," *The Plant Journal* 39(1), pp. 135-145 (Jul. 2004) (online publication). Available online: https://doi.org/10.1111/j.1365-313X.2004.02113.x.

Lücker et al., "Chapter 9: Metabolic Engineering of Terpenoid Biosynthesis in Plants," *Applications of Plant Metabolic Engineering*, R. Verpoorte et al. (eds)., pp. 219-236 (Jan. 2007) Baden-Wuerttemberg, Germany. Available online: https://doi.org/10.1007/978-1-4020-6031-1_9.

Matias-Hernandez et al., "AaMYB1 and its orthologue AtMYB61 affect terpene metabolism and trichome development in *Artemisia annua* and *Arabidopsis thaliana*," *The Plant Journal* 90:520-534 (Jul. 2017). Available online: 10.1111/tpj.13509.

Mayo et al., "Genetic transformation of tobacco NT1 cells with Agrobacterium tumefaciens." *Nature Protocols* vol. 1, No. 3, pp. 1105-1111 (Aug. 2006) (online publication). Available online: https://doi.org/10.1038/nprot.2006.176.

Mizusaki et al., "changes in the activities of ornithine decarboxylase, putrescine N-methyltransferase and N-methylputrescine oxidase in tobacco roots in relation to nicotine biosynthesis," *Plant and Cell Physiology*, 14(1), pp. 103-110 (Feb. 1973) (Oxford, United Kingdom). Available online: https://doi.org/10.1093/oxfordjournals.pcp.a074831.

Nautiyal et al., "Comprehensive transcriptome analysis provides insights into metabolic and gene regulatory networks in trichomes of Nicotiana tabacum," *Plant Molecular Biology* 102(5); pp 625-644 (Jan. 2020) (Baden-Wuerttemberg, Germany). Available online: https://doi.org/10.1007/s11103-020-00968-2.

Ohara et al., "Limonene production in tobacco wih Perilla limonene synthase cDNA," *Journal of Experimental Botany*, 54(393), pp. 2635-2642 (Dec. 2003) (Oxford, UK); Available online: DOI: 10.1093/jxb/erg300.

Pan et al. "Bioinformatics study of 1-deoxy-D-xylulose-5-phosphate synthase (DXS) genes in Solanaceae" *Mol. Bio. Reports* 46:5175-5184) (Jul. 2019). Available online: https://doi.org/10.1007/s11033-019-04975-5.

PlantCare Online Database, Planet: A Network of European Plant Databases, accessed and printed August 4, 2023; Available online: https://bioinformatics.psb.ugent.be/webtools/plantcare/html/.

PlantPan 3.0 Online Database: The Plant Promoter Analysis Navigator accessed and printed Aug. 4, 2023. Available online: http://plantpan.itps.ncku.edu.tw/plantpan3/index.html.

Pottier et al. "Identification of two new trichome-specific promoters of Nicotiana tabacum," *Planta* 251(3), pp. 58, (Feb. 2020) (electronic publication). Available online: https://doi.org/10.1007/s00425-020-03347-9.

Ramsey, "Why Farmers Prefer Feminized Seeds," *Kush.com Online Blog*, accessed and printed online Aug. 4, 2023, https://kush.com/blog/feminized-cannabis-seeds-all-you-need-to-know/.

Reynolds et al., "Rational siRNA design for RNA interference," *Nature Biotechnol.*, 22:326-330 (Feb. 2004) (Baden-Wuerttemberg, Germany). Available online: DOI: 10.1038/nbt936.

Salminen et al., "Lipid transfer proteins: classification, nomenclature, structure, and function," *Planta*, 244(5), pp. 971-997 (Nov. 2016) (Baden-Wuerttemberg, Germany). Available online: 10.1007/s00425-016-2585-4.

Sabzehzari et al., "Photy-miRNAs-based regulation of metabolites biosynthesis in medicinal plants," *Gene* vol. 682, pp. 13-24 (Jan. 2019) (Oxford, UK). Available online: https://doi.org/10.1016/j.gene.2018.09.049.

Seely et al., "Changes in Mouse Kidney Ornithine Decarboxylase Activity Are Brought About by Changes in the Amount of Enzyme Protein as Measured by Radioimmunoassay," *J. Biol. Chem.*, vol. 258, No. 4, pp. 2496-2500 (Feb. 1983) (Oxford, United Kingdom). Available online: https://doi.org/10.1016/S0021-9258(18)32953-3.

Sikora et al., "Influence of Agroclimatic Conditions on Content of Main Cannabinoids in Industrial Hemp (*Cannabis sativa* L.)," *Genetika*, 43(3), pp. 449-456 (Jan. 2011) (electronic publication). Available online: DOI: https://doi.org/10.2298/GENSR1103449S.

Sui et al., "Formation of α- and β-Cembratriene-Diols in Tobacco (*Nicotiana tabacum* L.) Is Regulated by Jasmonate-Signaling Components via Manipulating Multiple Cembranoid Synthetic Genes" *Molecules* 23(2511):1-14 (Sep. 2018). Available online: https://doi.org/10.3390/molecules23102511.

Thompson et al., "Clustal W: Improving the sensitivity of progressive multiple sequence alignment through sequence weighting, position-specific gap penalties and weight matrix choice," *Nucleic Acids Research* 22(22), pp. 4673-4680 (Nov. 1994) (Oxford, United Kingdom). Available online: DOI: 10.1093/nar/22.22.4673.

Tissier et al., "Chapter 18: Tobacco Trichomes as a Platform for Terpenoid Biosynthesis Engineering," *Isoprenoid Synthesis in Plants and Microorganisms: New Concepts and Experimental Approaches*, pp. 271-283 (Aug. 2012) (Baden-Wuerttemberg, Germany). Available online: DOI:10.1007/978-1-4614-4063-5_18.

Tissier, "17: Trichme Specific Expression: Promoters and Their Applications," *Transgenic Plants—Advances and Limitation*, pp. 353-378 with cover page (Mar. 2012) (Electronic Publication). Available online: http://www.intechopen.com/books/transgenic-plants-advances-and-limitations/trichome-specific-expression-promoters-and-their-applications.

Tissier et al., "Plant Volatiles: Going 'In' but not 'Out' of Trichome Cavities," *Trends in Plant Science*, 22(11), pp. 930-938 (Nov. 2017) (Cambridge, MA). Available online: DOI: 10.1016/j.tplants.2017.09.001.

Tso, "Chapter 1 Seed to Smoke" *Tobacco, Production, Chemistry and Technology*, Davis & Nielsen, eds., Blackwell Publishing, Oxford (1999) (Oxford, UK).

(56) References Cited

OTHER PUBLICATIONS

Uni ProtKB Accession No. D3W9H9_ TOBAC (version 40 dated Dec. 2, 2020) (Year: 2020).
Wang et al., "Metabolic engineering of terpene biosynthesis in plants using a trichome-specific transcription factor MsYABBY5 from Spearmint (*Mentha spicata*)," *Plant Biotechnology Journal* vol. 14, Issue 7, pp. 1619-1632 (Feb. 2016) (Oxford, UK). Available online: https://doi.org/10.1111/pbi.12525.
Wernsman et al., "Tobacco: Chapter Seventeen" in *Principles of Cultivar Development, Crop Species*, vol. 2 , W. H. Fehr (ed.), MacMillan Publishing Go., Inc., pp. 669-698, (1987) (New York, NY).
Xu et al., "SIMYC1 Regulates Type VI Glandular Trichome Formation and Terpene Biosynthesis in Tomato Glandular Cells," *The Plant Cell* 30:2988-3005 (Dec. 2018). Available online: https://doi.org/10.1105/tpc.18.00571.
Yan et al. "A Review on Bioactivities of Tobacco Cembranoid Diterpenes," *Biomolecules* 9(30), pp. 1-9 (Jan. 2019). Available online: https://doi.org/10.3390/biom9010030.
Yang et al., "Determination of cannabinoids in biological samples using a new solid phase micro-extraction membrane and liquid chromatography-mass spectrometry," *Forensic Science International*, 162(1-3), pp. 135-139 (Oct. 2006) (Oxford, UK). Available online: https://doi.org/10.1016/j.forsciint.2006.03.036.
Yu et al., "A high-throughput colorimetric assay to measure the activity of glutamate decarboxylase," *Enzyme and Microbial Technology* 49(3), pp. 272-276 (Aug. 2011) (Oxford, United Kingdom). Available online: https://doi.org/10.1016/j.enzmictec.2011.06.007.
Zeng et al., "Both Natural and Designed Micro RNAs Can Inhibit the Expression of Cognate mRNAs When Expressed in Human Cells," *Mol. Cell*, 9(6), pp. 1327-1333 (Jun. 2002) (Cambridge, Massachusetts). Available online: https://www.cell.com/molecular-cell/pdf/S1097-2765(02)00541-5.pdf.
Zhang et al., "Characterization of NtREL1, a novel root-specific gene from tobacco, and upstream promoter activity analysis in homologous and heterologous hosts," *Plant Cell Rep* 35,757-769 (Apr. 2016). Available online: DOI: 10.1007/s00299-015-1918-2.
Guo et al. "Protein tolerance to random amino acid change." *Proceedings of the National Academy of Sciences* 101(25), pp. 9205-9210, (Jun. 2004) (electronic publication), available online: https://doi.org/10.1073/pnas.0403255101.
Matias-Hernandez et al., "AaMYB1 and its orthologue AtMYB61 affect terpene metabolism and trichome development in *Artemisia annua* and *Arabidopsis thaliana*, Supplementary Data," *The Plant Journal* 90:520-534 (Jul. 2017).
NCBI Reference Sequence: XP_016450602.1, "PREDICTED: transcription factor MYB86-like [*Nicotiana tabacum*]," published May 3, 2016, 1 page.
Payne et al. "Heterologous myb genes distinct from GL1 enhance trichome production when overexpressed in Nicotiana tabacum." *Development*, 126(4), pp. 671-682, (Feb. 1999) (electronic publication), available online DOI: https://doi.org/10.1242/dev.126.4.671.
Sierro et al. "The tobacco genome sequence and its comparison with those of tomato and potato," *Nature Communications*, 5, art. 3833, 9 pages, (May 2014) (electronic publication), available online: https://doi.org/10.1038/ncomms4833.
Wang et al. "Analysis and review of trichomes in plants," *BMC Plant Biology* 21, Art. 70, pp. 1-11 (Feb. 2021) (electronic publication), available online: https://doi.org/10.1186/s12870-021-02840-x.
Yang et al. "Genome-wide identification and expression analysis of the R2R3-MYB gene family in tobacco (*Nicotiana tabacum* L.)." *BMC genomics* 23(1), 432, 21 pages, (Jun. 2022) (electronic publication), available online: https://doi.org/10.1186/s12864-022-08658-7.
Sallaud et al., "Characterization of two genes for the biosynthesis of the labdane diterpene Z-abienol in tobacco (*Nicotania tabacum*) gladular trichomes," *The Plant Journal*, 72, pp. 1-17 (Jul. 2012).
Zerbe et al., "Bifunctional cis-Abienol Synthase from *Abies balsamea* Discovered by Transcriptome Sequence and Its Implications for Diterpenoid Fragrance Production," *The Journal of Biological Chemistry* 287(15), pp. 12121-12131 (Apr. 2012).
Zerbe et al., "Plant diterpene synthases: exploring modularity and metabolic diversity for bioengineering," *Trends in Biotechnology* 33(7), pp. 419-429 (Jul. 2015).
GenBank: BAK19150.1, "Lipid transfer protein [*Nicotiana tabacum*], protein Gen Bank: BAK19150.1" dated Apr. 15, 2011, 1 page.
Tian et al., "OvereXpression of BraLTP2, a Lipid Transfer Protein of *Brassica napus*, Results in Increased Trichome Density and Altered Concentration of Secondary Metabolites," *International Journal of Molecular Sciences*, 19(6), 1733, 22 pages, (Jun. 2018), DOI: 10.3390/ijms19061733.
U.S. Appl. No. 17/591,057, filed Feb. 2, 2022, with Final Office Action issued on Jul. 17, 2024.
U.S. Appl. No. 17/591,033, filed Feb. 2, 2022, currently pending.
U.S. Appl. No. 17/591,188, filed Feb. 2, 2022, now abandoned.

\* cited by examiner

GFP  Brightfield

GFP  Brightfield

FIG. 15
FIG. 15A
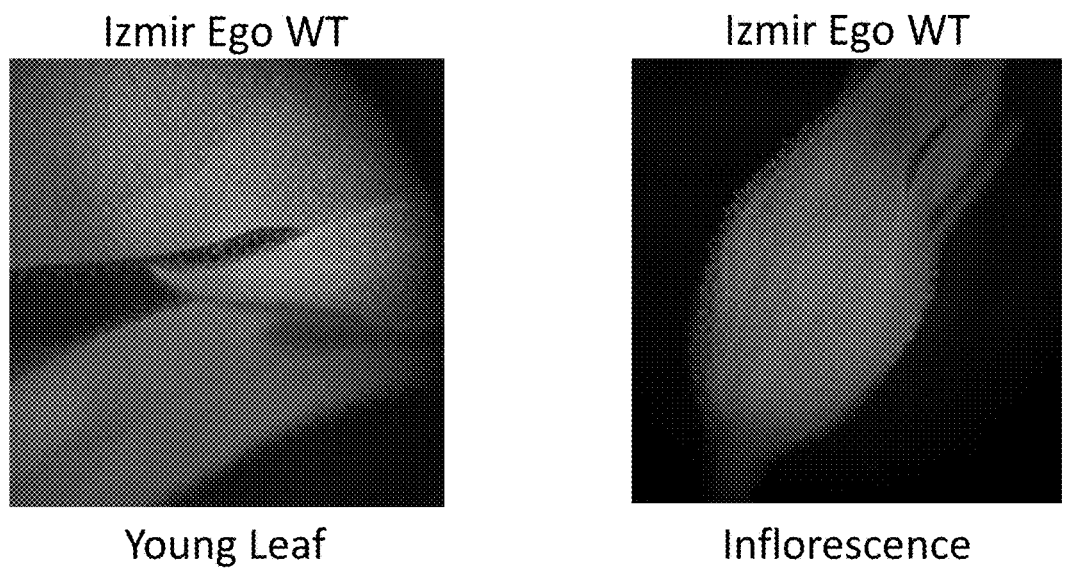
Izmir Ego WT — Young Leaf
Izmir Ego WT — Inflorescence
FIG. 15B
SEQ ID NO: 80::GREEN FLUORESCENT PROTEIN
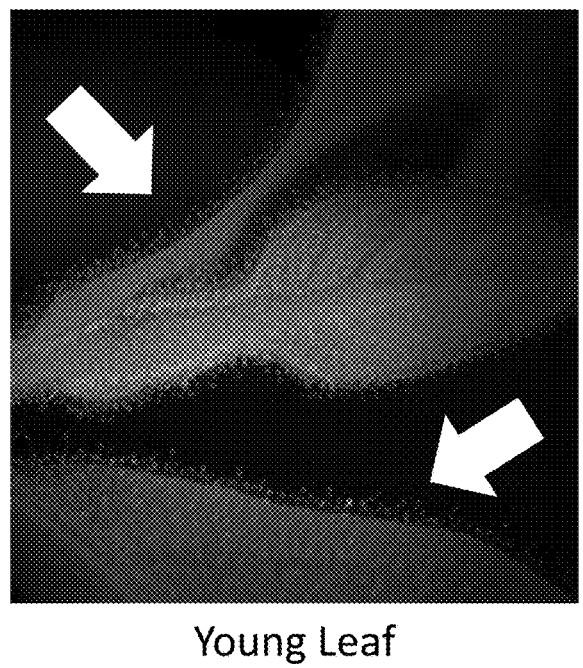
Young Leaf

FIG. 15 (continued)
FIG. 15C
SEQ ID NO: 81::GREEN FLUORESCENT PROTEIN
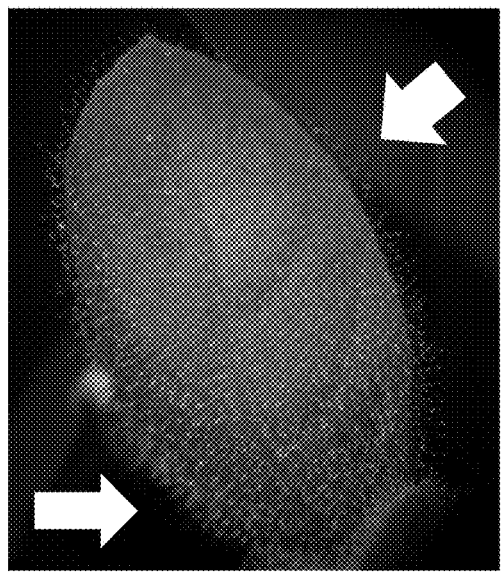
Young Leaf
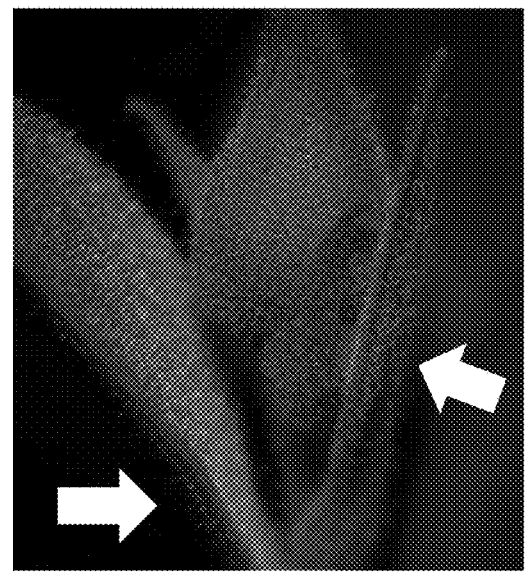
Inflorescence
FIG. 15D
SEQ ID NO: 82::GREEN FLUORESCENT PROTEIN
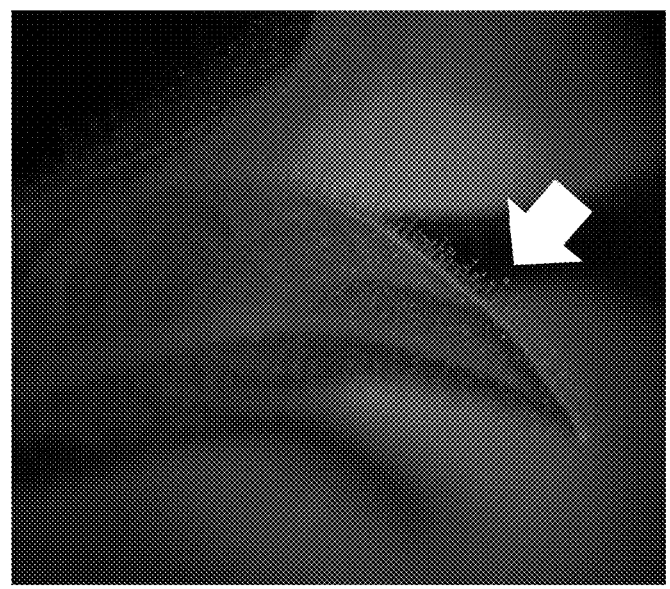
Young Leaf

SEQUENCE LISTING

```
Sequence total quantity: 102
SEQ ID NO: 1              moltype = DNA  length = 53
FEATURE                   Location/Qualifiers
misc_feature              1..53
                          note = Description of Artificial Sequence: Synthetic primer
source                    1..53
                          mol_type = other DNA
                          organism = synthetic construct
SEQUENCE: 1
ggggacaagt ttgtacaaaa aagcaggctt ataaatacct atgaaaatta aat          53

SEQ ID NO: 2              moltype = DNA  length = 54
FEATURE                   Location/Qualifiers
misc_feature              1..54
                          note = Description of Artificial Sequence: Synthetic primer
source                    1..54
                          mol_type = other DNA
                          organism = synthetic construct
SEQUENCE: 2
ggggaccact ttgtacaaga aagctgggta ggcagttatt gttatatgtg atag         54

SEQ ID NO: 3              moltype = DNA  length = 50
FEATURE                   Location/Qualifiers
misc_feature              1..50
                          note = Description of Artificial Sequence: Synthetic primer
source                    1..50
                          mol_type = other DNA
                          organism = synthetic construct
SEQUENCE: 3
ggggacaagt ttgtacaaaa aagcaggctg caataatttt ttatatctat              50

SEQ ID NO: 4              moltype = DNA  length = 48
FEATURE                   Location/Qualifiers
misc_feature              1..48
                          note = Description of Artificial Sequence: Synthetic primer
```

```
source                  1..48
                        mol_type = other DNA
                        organism = synthetic construct
SEQUENCE: 4
ggggaccact ttgtacaaga aagctgggta ctctctctct ttctctcg            48

SEQ ID NO: 5            moltype = DNA  length = 50
FEATURE                 Location/Qualifiers
misc_feature            1..50
                        note = Description of Artificial Sequence: Synthetic primer
source                  1..50
                        mol_type = other DNA
                        organism = synthetic construct
SEQUENCE: 5
ggggacaagt ttgtacaaaa aagcaggcta tttacgagtt tactatactt          50

SEQ ID NO: 6            moltype = DNA  length = 48
FEATURE                 Location/Qualifiers
misc_feature            1..48
                        note = Description of Artificial Sequence: Synthetic primer
source                  1..48
                        mol_type = other DNA
                        organism = synthetic construct
SEQUENCE: 6
ggggaccact ttgtacaaga aagctgggta tttgggaggg aattaaag            48

SEQ ID NO: 7            moltype = DNA  length = 50
FEATURE                 Location/Qualifiers
misc_feature            1..50
                        note = Description of Artificial Sequence: Synthetic primer
source                  1..50
                        mol_type = other DNA
                        organism = synthetic construct
SEQUENCE: 7
ggggacaagt ttgtacaaaa aagcaggcta ttagcatcaa ccgggttagc          50

SEQ ID NO: 8            moltype = DNA  length = 51
FEATURE                 Location/Qualifiers
misc_feature            1..51
                        note = Description of Artificial Sequence: Synthetic primer
source                  1..51
                        mol_type = other DNA
                        organism = synthetic construct
SEQUENCE: 8
ggggacaagt ttgtacaaaa aagcaggctt tcatgaatct caatatggag g        51

SEQ ID NO: 9            moltype = DNA  length = 52
FEATURE                 Location/Qualifiers
misc_feature            1..52
                        note = Description of Artificial Sequence: Synthetic primer
source                  1..52
                        mol_type = other DNA
                        organism = synthetic construct
SEQUENCE: 9
ggggaccact ttgtacaaga aagctgggta gttcaccttc actttaagct ac       52

SEQ ID NO: 10           moltype = DNA  length = 1243
FEATURE                 Location/Qualifiers
misc_feature            1..1243
                        note = Description of Artificial Sequence: Synthetic
                         polynucleotide
source                  1..1243
                        mol_type = other DNA
                        organism = synthetic construct
SEQUENCE: 10
attagcatca accggttag  caattggggc attattgcga tcagcgggag gcaccttgtt    60
gctgagcacc aaattattct ttttgccgtg atggccagac tcaacgtcaa cgttcaagtg  120
agcagaccaa aagtttaact tttttgggat ggcttaagta taagacttta aataataagc  180
ataaaatgag gtgttatgga gattcggatc aaaccaccac tattatccct agccccacgg  240
ttgatgccaa actgttattt tcaaaatcgg ataacaatta catttgtatg cggttttaag  300
aatatgtgat ttaattcaac acgaacaatt aagaatatca ataatcaaa ttagagataa  360
aataatcatc caaacgaatt gcgatattat ggctaaccat gagcttagac tgaccgatga  420
gctcgctctt ggttgacctt cgagcccagc cgtgaatgaa gtacataaca aatgagcaaa  480
aactttaaca atagctaaaa ggcagaaagt aaacttgtat tgctttgatt tacatattac  540
aacatgtgtt acaaaagaaa aacttccacc ctttatatag tggagagttt catcccagt  600
ataaatctaa aaaaggtaaa aatcttcctt tgctggtaat tactaattca tgatcgacat  660
cgagtgagat ttgcaccgta atatccggtt gattgcgata tcacgatcct ctatctgtca  720
tgtgtaaccg tttatcatgc ctcccgagat cttagaattc attcttggac cggggtgcat  780
gcccaataac aggcacattg ttcgcccttc atgaatctca atatggaggg ctttaacct   840
```

```
cgattataat tttgtgtata tgtactcttc ctctattttc tcgtcgaaaa atcggagtaa    900
acattatccc cgattttacc atacacatac gttttgccta aataaaatga caaaagagaa    960
agggtgacga aaactgtcac tatgcctaac taaccctcgt agataccgtc ttccgcgaac   1020
cctacacacc cctaaggccc taaccccttc ttcaccttac tttattaatt acctcactca   1080
cttttgtcct cttatgtaac cgtttccagt ttaattacaa aaaaattcag attactttga   1140
agcatcactt ctctcccttt catataaact cagttttttt gttcgagtct ttatacatat   1200
gtctttatca taactaaagt agtagcttaa agtgaaggtg aac                     1243

SEQ ID NO: 11            moltype = DNA   length = 436
FEATURE                  Location/Qualifiers
misc_feature             1..436
                         note = Description of Artificial Sequence: Synthetic
                          polynucleotide
source                   1..436
                         mol_type = other DNA
                         organism = synthetic construct
SEQUENCE: 11
ttcatgaatc tcaatatgga gggtctttaa cctcgattat aattttgtgt atatgtactc     60
ttcctctatt ttctcgtcga aaatcggag taaacattat cccgattttt accatacaca    120
tacgttttgc ctaaataaaa tgacaaaaga gaaagggtga cgaaaactgt cactatgcct    180
aactaaccct cgtagatacc gtcttccgcg aaccctacac accctaaggg ccctaacccc    240
ttcttcacct tactttatta attacctcac tcacttttgt cctcttatgt aaccgtttcc    300
agttttaatta caaaaaaatt cagattactt tgaagcatca cttctctccc tttcatataa    360
actcagtttt tttgttcgag tctttataca tatgtcttta tcataactaa agtagtagct    420
taaagtgaag gtgaac                                                   436

SEQ ID NO: 12            moltype = DNA   length = 1500
FEATURE                  Location/Qualifiers
misc_feature             1..1500
                         note = Description of Artificial Sequence: Synthetic
                          polynucleotide
source                   1..1500
                         mol_type = other DNA
                         organism = synthetic construct
SEQUENCE: 12
aaaatatttg aaagaaaata ttgtagctaa atgaatattt ttccttcaag ttattaaaag     60
ttgtggcaat ataggttaaa ttagccacat gtttcttgct ttaatagaat tttgtagcta    120
atcattaact tttaccacga gttgaaactt aatataacaa caataacctt ttaaccataa    180
taaaccattt aaatcaaata ttactaaata aataacctttg cttcaagttc tataaaatca    240
tggcaatagt cattacgata aaatgatata accacgaata tattgcaacg ataaattctg    300
taactaatca ttagttttttg cgacgaggta aattttccgt cacagtagca atcttctagg    360
cacattaaaa atttgaaaca aaattttgta gtcaaataaa tatttatctt cttatttaa     420
gaaaataaaa atagttagat aatagttact actatttgtc atgaaaatat caatagatac    480
aaatttaaag tgactataaa tttacgagtt tactatactt tagtcgtaca gtttgcaata    540
atagtatttt aaccacaatt agttatatgt acaaaatttc ataagtgaat aactttttt    600
caatgacaaa aataagagtt gctcaaacaa tatcaagtta caaaaattta atttttaactg    660
taaaagttat atttttccaa aataacataa actatagtaa ttatatatag tttgaagtat    720
taataaaatt taaatatgca aaagttaatt ttaataaacc atttgtatgc ctacttgtag    780
cctctaaact attttatttg ctttatttat caaactcata ttttatttta ttgcaccttg    840
ttagttttgg acgttaatta tatatatttg gtgtaaaatt taaaatatat taacatttgt    900
ggagaattta tgtatgcctg gttcttaact atttttttt tatataactg gttagagtaa    960
tttcttatat ttcagtattt attttttaaat aagtcctcat aaaattgaaga ctttaaaagt   1020
ttttgtgtca ttcctctttt tatttaagaa attgaagaat tccgctaaat ttcatattcc   1080
gctgttattt aactgtttat tcccttgtta atataattgg taagaagttt taaaataaag   1140
gagttaatga tttctaggtt catggccttg cctagcttcta cgagtaagcg ccatcacgac   1200
tcccgaggat aaggaaatcc gggtcgtagc attcactcac aaaaaattac taaaaacaaag   1260
tttacccttc tcccaaaagt aaatttcata tttggctcca cataatgtgt tcaatgagtc   1320
aagtgaagta cttttcattg acaaaaaaaa gttgctgaaa aatgcatatc tcatatttt   1380
tttttttaga gaaatcccat ttcttgccta aacgaaatgc ctataaaaga gcatatattt   1440
gcaacaacag tttgcagaaa ctatcaagtc aaataatccc ccctttaatt ccctcccaaa   1500

SEQ ID NO: 13            moltype = DNA   length = 1000
FEATURE                  Location/Qualifiers
misc_feature             1..1000
                         note = Description of Artificial Sequence: Synthetic
                          polynucleotide
source                   1..1000
                         mol_type = other DNA
                         organism = synthetic construct
SEQUENCE: 13
tttacgagtt tactatactt tagtcgtaca gtttgcaata atagtatttt aaccacaatt     60
agttatatgt acaaaatttc ataagtgaat aactttttt caatgacaaa aataagagtt    120
gctcaaacaa tatcaagtta caaaaattta atttttaactg taaaagttat atttttccaa    180
aataacataa actatagtaa ttatatatag tttgaagtat taataaaatt taaatatgca    240
aaagttaatt ttaataaacc atttgtatgc ctacttgtag cctctaaact attttatttg    300
ctttatttat caaactcata ttttatttta ttgcaccttg ttagttttgg acgttaatta    360
tatatatttg gtgtaaaatt taaaatatat taacatttgt ggagaattta tgtatgcctg    420
gttcttaact atttttttt tatataactg gttagagtaa tttcttatat ttcagtattt    480
attttttaaat aagtcctcat aaaattgaaga ctttaaaagt ttttgtgtca ttcctctttt    540
```

| | | | |
|---|---|---|---|
| tatttaagaa | attgaagaat | tccgctaaat | ttcatattcc gctgttattt aactgtttat | 600 |
| tcccttgtta | atataattgg | taagaagttt | taaaataaag gagttaatga tttctaggtt | 660 |
| catggcttgc | ctagcttcta | cgagtaagcg | ccatcacgac tcccgaggat aaggaaatcc | 720 |
| gggtcgtagc | attcactcac | aaaaattact | aaaaacaaag tttacccttc tcccaaaagt | 780 |
| aaatttcata | tttggctcca | cataatgtgt | tcaatgagtc aagtgaagta cttttcattg | 840 |
| acaaaaaaaa | gttgctgaaa | aatgcatatc | tcatattttt ttttttttaga gaaatcccat | 900 |
| ttcttgccta | aacgaaatgc | ctataaaaga | gcatatattt gcaacaacag tttgcagaaa | 960 |
| ctatcaagtc | aaataatccc | ccctttaatt | ccctcccaaa | 1000 |

```
SEQ ID NO: 14           moltype = DNA  length = 1500
FEATURE                 Location/Qualifiers
misc_feature            1..1500
                        note = Description of Artificial Sequence: Synthetic
                        polynucleotide
source                  1..1500
                        mol_type = other DNA
                        organism = synthetic construct
SEQUENCE: 14
```

| | | | | |
|---|---|---|---|---|
| accagaatca | ccatacaaag | ctatttccag | actcggaatc ccaaatagac atcaatagca | 60 |
| ctgaaatgca | cttcaaccca | atcgtatgaa | attcttccaa aaaggctaac ttccacaata | 120 |
| agtgccaaaa | cgatctcggg | taattccaaa | cccgatctgg acacacaccc aagtccaaaa | 180 |
| taatcataca | aacctgttaa | aacattcaaa | tcccgattcc gaggtcaatt actgaaaaat | 240 |
| cctatcctag | ttaattcttc | caactaaaag | cttccaaaat gagaattcta tttccaaata | 300 |
| aactctgaac | ttcccggaat | tcaattttga | ctatgcgtac aagtcataat acctgaattg | 360 |
| aagctgcaga | tagcctcaaa | tcgctaaaca | acgtgctagg tctcaaaacg ccctgtcggg | 420 |
| tcgttacatt | ataggtgatt | aactacgtat | atacttgcta tcataattca | 480 |
| ggccaactag | taagagtaga | aacaatgaat | ggcacataac aaacgatcac cacgaaatgt | 540 |
| acatgatata | actcacacaa | ggtaggcacg | ctactagaca attaccaata acaacaatgc | 600 |
| ctaggacatc | acaagatatg | acaaatcaat | ccttactatc acggttgagt tgtaacgtgc | 660 |
| aagaatattt | cactcttttt | agggcactaa | gatcactcca ccaacatttc aagagaatcc | 720 |
| ctggcactgc | taaaaagccc | tctacactgt | agtgaatttt tcttagttat ctaaagttaa | 780 |
| ttattcattt | agtattcttt | acattaggtt | cccccttcta ggtcctgcac gtaactagat | 840 |
| tgaatggatt | ggtccactct | attattatag | agtaattatt aaatttttat ttgactaggc | 900 |
| atcactgtt | gcactatcaa | caaagtatta | gttctagcct tctgggtact tcatacctat | 960 |
| gcaaatgata | attttattaa | aacaatagat | gtacatggat ataaatacct atgaaaatta | 1020 |
| aataaattat | aactaagaaa | aaaactttaa | agttcactcc taagatatcg ggttattaca | 1080 |
| tgaccaaaca | caatttgttt | atcaaatact | ttcaaaagaa tttgccaaac gtaaattatt | 1140 |
| tttctccaaa | gtgacttatg | aattactatg | ttgataaaat acttttcaaa gtaactaatg | 1200 |
| tttagaagtc | aaggatgggc | ttcttttgat | tattgaagtt tgtagcaatt gtatgtagtt | 1260 |
| atagtcaggg | tgaccaccag | catctcatat | agcaatacac aagtggatta gcgcatttta | 1320 |
| aatttcaatt | agttcatgca | aatatacacg | taatagcatt ataagccact ttcacaacag | 1380 |
| gcagattagt | ggttttgaaa | tttcaaccaa | tgatatatac tataaattga tcaagcacaa | 1440 |
| accttaattg | agcaacacaa | tttcttacag | caataactat cacatataac aataactgcc | 1500 |

```
SEQ ID NO: 15           moltype = DNA  length = 500
FEATURE                 Location/Qualifiers
misc_feature            1..500
                        note = Description of Artificial Sequence: Synthetic
                        polynucleotide
source                  1..500
                        mol_type = other DNA
                        organism = synthetic construct
SEQUENCE: 15
```

| | | | | |
|---|---|---|---|---|
| ataaatacct | atgaaaatta | aataaattat | aactaagaaa aaaactttaa agttcactcc | 60 |
| taagatatcg | ggttattaca | tgaccaaaca | caatttgttt atcaaatact ttcaaaagaa | 120 |
| tttgccaaac | gtaaattatt | tttctccaaa | gtgacttatg aattactatg ttgataaaat | 180 |
| acttttcaaa | gtaactaatg | tttagaagtc | aaggatgggc ttcttttgat tattgaagtt | 240 |
| tgtagcaatt | gtatgtagtt | atagtcaggg | tgaccaccag catctcatat agcaatacac | 300 |
| aagtggatta | gcgcatttta | aatttcaatt | agttcatgca aatatacacg taatagcatt | 360 |
| ataagccact | ttcacaacag | gcagattagt | ggttttgaaa tttcaaccaa tgatatatac | 420 |
| tataaattga | tcaagcacaa | accttaattg | agcaacacaa tttcttacag caataactat | 480 |
| cacatataac | aataactgcc | | | 500 |

```
SEQ ID NO: 16           moltype = DNA  length = 1500
FEATURE                 Location/Qualifiers
misc_feature            1..1500
                        note = Description of Artificial Sequence: Synthetic
                        polynucleotide
source                  1..1500
                        mol_type = other DNA
                        organism = synthetic construct
SEQUENCE: 16
```

| | | | | |
|---|---|---|---|---|
| taatacttat | tttgtaagaa | ttgcaatatt | gttattttg ttatggactt aaatattaac | 60 |
| catgtttataa | tcttaagttt | atattattag | aaaaacttag tttttgaaag actaatatga | 120 |
| acattagtac | ttatttcaaa | aataagcacc | tagatatatg aaattacttt aagtacttat | 180 |
| ttaaataat | taagtaccac | acatacatac | atatctctac aaactgttaa agttttctat | 240 |
| atgagtactt | attttaaaat | aagagcttaa | atataataaa ttatgttaaa tttcttattt | 300 |
| aaaataataa | aggaccaaac | atgcataaaa | taagtgatga gcttaataag tcaagaagct | 360 |
| aattgataag | cattgatgcc | aaatgcactt | actaactttt ctatattgta ggaaaaatct | 420 |

```
aactttttata tttaaaattt attttttgtaa aacttctcta attttttggac aaaactcttat   480
attgattttt taatcaaagc caaaatattt atttaactat gaaaaaattt taacaactaa      540
tttattatgg taaataatat tgatatggta acttcaagca catgacaaaa attataacta      600
actgcagaag tttattgtct ctctgaatct tgtggctata tcataacaaa tacttgtagc      660
taataagcca acgatgttct cggtttcata taatttgaat tttaaaatag ttttttaaatt    720
taatatttat ttcaaatcat tattgtggct aacatgttat aatcgcagta atatttggag     780
atgcaatact tatatttagc tacaaaattt tattgtatca gaataagttt gtagctatta     840
agttagtttt tgccacaaat ttttataatt gaagcaaaaa tacctattca gctacagtat     900
tttgtatcga gtaatatttt gtgactagaa gattaatatt gctacagtaa tttcagacgt     960
gtggcaaaaa ctcataatta gctacaaaat attgtcgtag caataatttt ttatatctat    1020
taatgcaatt attactacat gcttttataa cttgaggcaa aaatatctaa tagctataac    1080
attttgttag aagtaatttt tgtggctata aaattggtat tgctacagta atttcaaatg    1140
cgtggcaaaa aaatacgatt aactacgaaa ttttattgta gcaataacnt attgtagcaa    1200
taaatttgta gctatttggg taatattgct acgacagtta gcaattatag caaaaatgct    1260
aaattagctt tgttaattta attttgtagc taaactttt tatgaaattt taattttgt     1320
ggctattgtt aggtattagc tacaattttc atatatgtag ctaagaattt gtagctatat    1380
atacataatg ttgtagtggc aaattctaac attgtacgct tggctgccct ttttttttg    1440
gctacaaaac tctaaagtaa aggaactaga aaactcgttt ggcgagagaa agagagagag    1500

SEQ ID NO: 17            moltype = DNA   length = 500
FEATURE                  Location/Qualifiers
misc_feature             1..500
                         note = Description of Artificial Sequence: Synthetic
                          polynucleotide
source                   1..500
                         mol_type = other DNA
                         organism = synthetic construct
SEQUENCE: 17
caataatttt ttatatctat taatgcaatt attactacat gcttttataa cttgaggcaa      60
aaatatctaa tagctataac attttgttag aagtaatttt tgtggctata aaattggtat     120
tgctacagta atttcaaatg cgtggcaaaa aaatacgatt aactacgaaa ttttattgta     180
gcaataacnt attgtagcaa taaatttgta gctatttggg taatattgct acgacagtta     240
gcaattatag caaaaatgct aaattagctt tgttaattta attttgtagc taaactttt     300
tatgaaattt taattttgt ggctattgtt aggtattagc tacaattttc atatatgtag     360
ctaagaattt gtagctatat atacataatg ttgtagtggc aaattctaac attgtacgct    420
tggctgccct ttttttttg gctacaaaac tctaaagtaa aggaactaga aaactcgttt     480
ggcgagagaa agagagagag                                                 500

SEQ ID NO: 18            moltype = AA   length = 365
FEATURE                  Location/Qualifiers
source                   1..365
                         mol_type = protein
                         organism = Nicotiana sp.
SEQUENCE: 18
MAFLATISGH ENMLLSNTLN NNFIFSGKPP QRHSYSFLPK KIQARSVANS SKTFQVKEEE       60
FSSKTEKFIL PKFDFEEYMK MKAIKVNKAL DDAIPMQEPI KIHEAMRYSL LAGGKRVRPI      120
LCMASCEVVG GDESLAIPAA CSVEMIHTMS LIHDDLRRGK PT SHKAFGEDTA              180
VLTGDALLSL AFEHVASKTK DVTPQRVVQA VGELGSAVGS KGLVAGQIVD IASEGKQVSL     240
TELEYIHNHK TGKLLEAAVV CGAIIGGGNE IEVERMRNYA RCLGLLFQVV DDILDVTKSS     300
EELGKTAGKD LVTDKATYPK LMGLEKAREL AGELVAKAMD ELSYFDAAKA APLYHFANYI     360
AHRQN                                                                 365

SEQ ID NO: 19            moltype = AA   length = 802
FEATURE                  Location/Qualifiers
source                   1..802
                         mol_type = protein
                         organism = Nicotiana tabacum
SEQUENCE: 19
MQVIITSSHR FFCHHLHQLK SPTSLSAQKA EFKKHGPRNW LFQTEGSLLY KPVRLNCATS       60
DASYLGNVNE YLESDHSKNS EEKDIQVSRT IQMKGLTEEI KHMLNSMEDG RLNVLAYDTA      120
WVSFIPNTTN NGNDQRPMFP SCLQWIIDNQ LSDGSWGEEI VFCIYDRLLN TLVCVIALTL     180
WNTCLHKRNK GVMFIKENLS KLETGEVENM TSGFELVFPT LLEKAQQLDI DIPYDAPVLK     240
DIYARREVKL TRIPKDVIHT IPTTVLFSLE GLRDDLDWQR LLKLQMPDGS FLISPASTAF     300
AFMETNDEKC LAYLQNVVEK SNGGARQYPF DLVTRLWAID RLQRLGISYY FAEEFKELLN     360
HVFRYWDEEN GIFSGRNSNV SDVDDTCMAI RLLRLHGYDV SPDALNNFKD GDQFVCFRGE     420
VDGSPTHMFN LYRCSQVLFP GEKILEEAKN FTYNFLQQCL ANNRCLDKWV IAKDIPGEIW     480
YALEFPWYAS LPRVEARYYI EQYGGADDIW IGKTLYRMPD VNNNVYLQAA KLDYNRCQSQ     540
HRFEWLIMQE WFEKCNFQQF GISKKYLLVS YFLAAASIPE VEKSRERLAW AKSRIICKMI     600
TSYYNDEATT WTTRNSLLME FKVSHDPTRK NGNETKEILV LKNLRQFLRQ LSEETFEDLG     660
KDIHHQLQNA WETWLVFLRE EKNACQEETE LLVRTINLSG GYMTHDEILF DADYENLSNL     720
TNKVCGKLNE LQNDKVTGGS KNTNIELDMQ ALVKLVFGNT SSNINQDIKQ TFFAVVKTFY     780
YSAHVSEEIM NFHISKVLFQ QV                                              802

SEQ ID NO: 20            moltype = AA   length = 792
FEATURE                  Location/Qualifiers
source                   1..792
                         mol_type = protein
                         organism = Nicotiana sp.
SEQUENCE: 20
```

```
MVLGLRSKII PLPDHKLGNI KLGSVTNAIC HRPCRVRCSH STASSMEEAK ERIRETFGKI   60
ELSPSSYDTA WVAMVPSRYS MNQPCFPQCL DWILENQRED GSWGLNPSHP LLVKDSLSST  120
LASSLLALRKW RIGDNQVQRG LGFIETHGWA VDNKDQISPL GFEIIFPCMI NYAEKLNLDL  180
PLDPNLVNMM LCERELTIER ALKNEFEGNM ANVEYFAEGL GELCHWKEMM LRQRHNGSLF  240
DSPATTAAAL IYHQYDEKCF GYLNSILKLH DNWVPTICPT KIHSNLFLVD ALQNLGVDRY  300
FKTEVKRVLD EIYRLWLEKN EEIFSDVAHC AMAFRLLRMN NYEVSSEELE GFVDQEHFFT  360
TSSGKLMNHV AILELHRASQ VAIHERKDHI LDKISTWTRN FMEQKLLDKH IPDRSKKEME  420
FAMRKFYGTF DRVETRRYIE SYKMDSFKIL KAAYRSSGIN NIDLLKFSEH DFNLCQTRHK  480
EELQQMKRWF TDCKLEQVGL SQQYLYTSYF IIAAILFEPE YADARLAYAK YAIIITAVDD  540
FFDCFICKEE LQNIIELVER WEGYSTVGFR SERVRIFFLA LYKMVEEIAA KAETKQGRCV  600
KDHLINLWID MLKCMLVELD LWKIKSTTPS IEEYLSVACV TIGVPCFVLT SLYLLGPKLS  660
KDVIESSEVS ALCNCTAAVA RLINDIHSYK REQAESSTNM VSILITQSQG TISEEEAIRQ  720
IKEMMESKRR ELLGMVLQNK ESQLPQVCKD LFWTTINAAY SIHTHGDGYR FPEEFKNHIN  780
DVIYKPLNQY SP                                                     792

SEQ ID NO: 21           moltype = AA   length = 687
FEATURE                 Location/Qualifiers
source                  1..687
                        mol_type = protein
                        organism = Nicotiana sp.
SEQUENCE: 21
MILGLRSKII PLPDHKLGNI KLGSVTNAIC HRPCRVRCSH STASSMEEAK ERIRETFGKI   60
ELSPSSYDTA WVAMVPSRYS MNQPCFPQCL DWILENQRED GSWGLNPSHP LLVKDSLSST  120
LASSLLALRKW RIGDNQVQRG LGFIETHGWA VDNKDQISPL GFEIIFPCMI NYAEKLNLDL  180
PLDPNLVNMM LCERELTIER ALKNEFEGNM ANVEYFAEGL GELCHWKEMM LRQRHNGSLF  240
DSPATTAAAL IYHQYDEKCF GYLNSILKLH DNWVPTICPT KIHSNLFLVD ALQNLGVDRY  300
FKTEVKRVLD EIYRLWLEKN EEIFSDVAHC AMAFRLLRMN NYEVSSEELE GFVDQEHFFT  360
TSSGKLMNHV AILELHRASQ VAIHERKDHI LDKISTWTRN FMEQKLLDKH IPDRSKKEME  420
FAMRKFYGTF DRVETRRYIE SYKMDSFKIL KAAYRWEGYS TVGFRSERVR IFFLALYKMV  480
EEIAAKAETK QGRCVKDHLI NLWIDMLKCM LVELDLWKIK STTPSIEEYL SVACVTIGVP  540
CFVLTSLYLL GPKLSKDVIE SSEVSALCNC TAAVARLIND IHSYKREQAE SSTNMVSILI  600
TQSQGTISEE EAIRQIKEMM ESKRRELLGM VLQNKESQLP QVCKDLFWTT INAAYSIHTH  660
GDGYRFPEEF KNHINDVIYK PLNQYSP                                     687

SEQ ID NO: 22           moltype = AA   length = 598
FEATURE                 Location/Qualifiers
source                  1..598
                        mol_type = protein
                        organism = Nicotiana sp.
SEQUENCE: 22
MSQSISPLIC SHFAKFQSNI WRCNTSQLRV IHSSYASFGG RRKERVRRMN RAMDLSSSSR   60
HLADFPSTIW GDHFLSYNSE ITEITTQEKN EHEMLKEIVR KMLVETPDNS TQKLVLIDTI  120
QRLGLAYHFN DEIENSIQNI FNLSQNSEDD DEHNLYVAAL RFRLARQQGY YMSSDVFKQF  180
TNHDGKFKEN HTNDVQGLLS LYEAAHMRVH DEEILEEALI FTTTHLESVI PNLSNSLKVQ  240
VTEALSHPIR KAIPRVGARK YIHIYENIGT HNDLLLKFAK LDFNMLQKLH RKELNELTSW  300
WKDLDRANKF PYAKDRLVEA YFWTVGIYFE PQYSRSRSLV TKVVKMNSII DDTYDAYATF  360
DELVLFTDAI QRWDEGAMDL LPTYLRPIYQ GLLDVFNEME EVLAKEGKAD HIYYAKKEMK  420
KVAEVYFKEA EWLNANYIPK CEEYMKNGLV SSTGPMYGII SLVVMEEIIT KEAFEWLTNE  480
PLILRAASTI CRLMDDMADH EVEQQRGHVA SFVECYMKEY GVSKQEAYVE MRKKITNAWK  540
DINKELLRPT AVPMFILERS LNFSRLADTF LKDDDGYTNP KSKVKDLIAS LFVESVDI    598

SEQ ID NO: 23           moltype = AA   length = 238
FEATURE                 Location/Qualifiers
source                  1..238
                        mol_type = protein
                        organism = Nicotiana sp.
SEQUENCE: 23
MSCQYYLTTT TSSLRIFSFT PRRYAPNSSA SQPHEFFKKQ VLFSSNLQCN AVSRPRAQVI   60
KRDDNVEEVD SAEEQQEEEE TQEVYRSNKI KQHIYAVRLM LQSMDDGEIS ISAYDTAWVA  120
LVKDINGSDT PQFPSSLEWI ANNQLAECSW GDKSIFLAHD RIIINTLACVI ALKSWNLHID  180
KRELGMSFIR ENLSKIGDEN AVHMPIGFEV AFPSLIEIGK KIGIDIPDDS HVLREIYT    238

SEQ ID NO: 24           moltype = AA   length = 606
FEATURE                 Location/Qualifiers
source                  1..606
                        mol_type = protein
                        organism = Nicotiana sp.
SEQUENCE: 24
MASITINHSF SRNPNISFHP QNPLIQTQAL FNFKPSISKC SPIIHCAIRR RPEYTPSHIP   60
DPNYIRIFDT TLRDGEQSPG ATMTTKEKLD VARQLAKLGV DIIEAGFPAS SEADLEAVKL  120
IAKEVGNGVN EEGHVPVICG LARCNKRDID KAWEAVKYAK KPRIHTFIAT SEIHMKFKLK  180
MSRDEVVEKA RSMVAYARSI GCEDVEFSPE DAGRSDPEFL YHILGEVIKA GATTLNIPDT  240
VGYTVPSEFG KLIADIKANT PGIGDVIIST HCQNDLGLST ANTLAGACAG ARQVETVING  300
IGERAGNASL EEVVMALKCR GEQVLGGLYT GINTQHILMS SKMVEEYTGL HVQPHKAIVG  360
ANAFAHESGI HQDGMLKHKD TYEIISPEDI GLNRVNESGI VLGKLSGRHA LQAKMLELGY  420
DIEGKELEDL FWRFKSVAEK KKKITDDDLI ALMSDEVFQP QFVWQLENVQ VTCGSLGLST  480
ATVKLIDADG QEHVSCSVGT GPVDAAYKAV DLIVKVPVAL LEYSLNAVTE GIDAIASTRV  540
LIRGENGHTS THALTGETVH RSFSGTGADM DIVISSVRAY IGALNKMLSF RKLVSKHSKP  600
EGSAVV                                                            606
```

```
SEQ ID NO: 25            moltype = AA   length = 492
FEATURE                  Location/Qualifiers
source                   1..492
                         mol_type = protein
                         organism = Nicotiana sp.
SEQUENCE: 25
MAILISRSRN FNHFLLSTRF RFLSRLNQTS SKTFSHHAKT SSFTTAAGGG FTKPTATFSG   60
ESAAVFRVER FQSNKTGEQL NTLYYEEDNH HQIIDENQVM DFPGGQLPIT PQMKFIAESS  120
EKRLPCYRVL DDDGYPIPGS IFEEVSKELA VKMYSSMVTL QVMDTIFYEA QRQGRLSFYL  180
TTAGEEGINI ASAAALSVDD FVLPQYREVG VILWRGFPLK DIANQLFGNK FDYGKGRQMP  240
CHHGSNELNY LTISSPIATQ IPQAAGVAYS LKMDKKEACA ITYLGDGSTS EGDFHAALNF  300
AAVLDAPVVF ICRNNGWAIS TPVNEQFRSD GVASKGQAYG IRSIRVDGND VLATHSAIRA  360
AREMAIKEQK PILVEAMTYR VAHHSTSDDS TKYRPVEEIE HWKTAKSPIS RFRKWIQRNG  420
WWNDENESEL RGDTRKQVLQ VMQAAEKVEK PPLTDLFTDV YDKVPLNLQE QHKFIRDAVK  480
KSPREYPSDV PI                                                     492

SEQ ID NO: 26            moltype = AA   length = 321
FEATURE                  Location/Qualifiers
source                   1..321
                         mol_type = protein
                         organism = Nicotiana tabacum
SEQUENCE: 26
MAEKITSHEN TRYAVVTGGN KGIGYETCRQ LAKEGIVVVL TARDERRGIE ALEKLKEEYS   60
SNKTDDDQIL FHQLDVMDPA SISSLVDFIK TKFGKLDILV NNAGIGGLMV EGDVVIIKDL  120
IEGDFVTISA ENGEEDGIKK SIEGIERIVT DYELTKQCLE TNFYGAKRMI EAFIPLLQLS  180
NSPRIVNVAS FLGKLKLLCN QWAIGMLSDA KSLREERVDE VLNEFIKDFK EKSIEAKGWP  240
TYFSAYKVSK ASLIAYTRVL ATKYPNFRIN SVCPGFCKTD VNCNTGSLTA EEGAESLVKL  300
ALVPNDGPSG LFFYRKEVTS F                                           321

SEQ ID NO: 27            moltype = DNA   length = 1098
FEATURE                  Location/Qualifiers
source                   1..1098
                         mol_type = unassigned DNA
                         organism = Nicotiana sp.
SEQUENCE: 27
atggcatttt tggctaccat ttctggccat gaaaatatgc ttctttccaa tacccctaaac   60
aataacttta ttttcagtgg aaaacctcca cagagacatt cttatagttt cctccccaag  120
aaaatccagg ccagaagtgt tgcaaactca tccaaaacat ttcaagtcaa agaagaagaa  180
ttctcatcta agacagagaa attcatcttg cctaagtttg actttgaaga atatatgaaa  240
atgaaggcaa ttaaggtaaa caaagcacta gatgatgcaa taccaatgca agagcctata  300
aaaattcatg aagccatgag atactcactt ctagctgggg gaaaacgcgt ccggccgatc  360
ctatgcaggg cttcttgtga agtagtagga ggggatgaat ccttagctat tcctgcagct  420
tgctcggttg agatgatcca caccatgtca ctcatccacg acgatcttcc ttgcatggac  480
aacgatgatc tacgtcgtgg caagcccacg agccacaagg ctttcgggga agacactgca  540
gttctaacag gggatgcact tttgtctttg gcctttgaac atgtagcttc caagactaaa  600
gatgtgacac cccaaagagt ggttcaagcc gttggcaagt tgggttcagc cgttggctcg  660
aaagggcttg tggcggggca gattgtggac atagctagtg agggaaaaca agtgagccta  720
actgaattag agtacattca aaccataaag acagggaaac tattggaggc tgctgtggtt  780
tgtgggcaa taattggggg agggaatgag attgaggtgg agaatgag aactatgct  840
agatgccttg gactgttgtt tcaagtggta gatgatcatc ttgatgttac taagtcatca  900
gaagagttgg gaaagacagc tggtaaagac ctagtgactg ataaggctac atatcctaag  960
ttgatggggc tagaaaaagc tcgggagctc gccggagagc tggtggctaa ggccatggat  1020
gagctgagct actttgatgc tgccaaggcg gcacctcttt atcattttgc taattatatt  1080
gcacatcgcc agaattga                                                1098

SEQ ID NO: 28            moltype = DNA   length = 2409
FEATURE                  Location/Qualifiers
source                   1..2409
                         mol_type = unassigned DNA
                         organism = Nicotiana sp.
SEQUENCE: 28
atgcaagtta taattacgtc cagtcacaga ttttctgcc atcatcttca tcagctcaag   60
agtcctacat cgttgtctgc acagaaagct gagtttaaaa aacatgtacc ccgaaattgg  120
ttgttccaaa ctgaaggctc acttctatat aaaccagttc gtctcaattg tgcaactagt  180
gatgcaagtt atcttggtaa tgtgaatgag tacttagaat ctgatcactc aaaaaactcc  240
gaagaaaagg atattcaggt aagcagaaca atacagatga aggttttgac agaagagatc  300
aaacacatgt tgaattcgat ggaggatgga aggttaaatg tcttagccta tgacacagct  360
tgggtttcct ttattccaaa tactactaat aatggaaatg atcaaagacc tatgtttcca  420
tcttgtcttc aatggattat agacaatcaa ctttctgatg gttcatgggg agaggagatt  480
gtattctgca tatatgatcg actcttgaac cactagtat gtgttattgc attgacatta  540
tggaacacgt gccttcataa gaaacaaa ggtgtgatgt ttatcaaaga aacttaagc  600
aagctagaga caggggaagt tgaaaacatg actagtggat ttgaacttgt gtttcctact  660
ctccttgaaa aagctcaaca actagatatt gacattcctg atgatgctcc agtcttaaag  720
gatatttatg caaggagaga agtaaagtta acaagaattc ctaaagatgt tatccatacg  780
attccgacaa cagtattgtt ttcattagaa ggattaaggg acgacttaga ctggcaaaga  840
cttttaaagc ttcaaatgcc tgatggttca ttcttaatat cccctgcttc cactgccttt  900
gcattcatgg aaacaaatga tgaaagtgt ttggcatatc ttcagaacgt tgttgaaaag  960
agtaatggag gagcgcgaca ataccgttc gacttggtaa cacgactttg ggcaattgat  1020
```

```
cgattacaac gccttggaat ctcttattat tttgcggaag agttcaagga acttttgaat    1080
catgtgttca gatactggga cgaggagaat ggaattttta gtggaaggaa ttcaaacgtt    1140
tctgatgttg atgatacatg catggctata aggttgctaa ggttacatgg gtatgatgtt    1200
agtccagatg cgctaaacaa tttcaaagat ggtgatcaat tcgtttgctt cagaggtgaa    1260
gtggacgggt caccaacaca tatgtttaat ctctatagat gttcccaagt tttattccca    1320
ggagaaaaga ttcttgaaga ggcaaagaat tttacttata acttcttaca gcaatgtctt    1380
gcaaacaacc gatgcttaga caaatgggtc atagctaagg acatcccgg ggagatatgg     1440
tatgcactag aatttccatg gtatgccagc ttacctcggg tggaagctag gtattatata    1500
gaacagtatg gcggagcaga tgatatttgg attggcaaga cgttatacag aatgcccgat    1560
gtcaacaaca atgttatttt acaagctgca aaattggatt acaatagatg ccaaagtcaa    1620
catcgctttg aatggctgat tatgcaagag tggtttgaga agtgcaactt tcaacaattt    1680
ggaataagca aaaagtaccct cctagtttct tatttcctag ctgctgcaag tatatttgaa    1740
gtcgagaagt caagagaacg ccttgcatgg gctaaatctc gtataatatg taagatgatt    1800
acatcttact acaatgatga agccacaact tggacaacta ggaattcatt gctaatgaaa    1860
ttcaaggttt ctcatgatcc gaccagaaaa aatggtaatg aaacaaaaga gatcttagtt    1920
ctcaaaaatc ttcgtcagtt tttgcgccaa ctatcagaag aaacttttga agacctaggc    1980
aaagacatcc atcaccaact acaaaatgct tgggaaacgt ggttggtgtt cttgagggag    2040
gaaaagatg catgtcaaga agaaacagag ttgctggtgc gcacaattaa tctctcgggc     2100
ggctatatga cacatgatga gatattattc gatgcggact acgagaatct gtccaacctt    2160
accaataaag tttgtggcaa gcttaatgag ctccaaaatg acaaggtgac gggcggctca    2220
aagaacacca atattgaact cgacatgcaa gctctcgtaa agtagtgtt tggtaacacc     2280
tcaagcaaca tcaaccaaga cattaagcaa acatttttg cagttgtgaa gacttttctat   2340
tacagtgcgc atgttagtga ggaaataatg aactttcaca tatccaaagt gcttttttcag   2400
caagtctag                                                           2409

SEQ ID NO: 29         moltype = DNA  length = 2379
FEATURE               Location/Qualifiers
source                1..2379
                      mol_type = unassigned DNA
                      organism = Nicotiana tabacum
SEQUENCE: 29
atggtacttg gactgagaag caaaatcata ccacttcctg atcataagtt gggaaatatc    60
aaattaggtt cagtaaccaa tgcaatttgc cacagaccat gtagagtaag atgcagccac    120
agtactgctt catcaatgga agaggcaaag gagagaataa gggaaacatt tggaaaaata    180
gagctatctc cttcttccta tgacacagca tgggtagcta tggtcccttc aagatattc    240
atgaaccaac catgttttcc tcagtgctta gattggattc ttgaaaatca aagagaagat    300
ggatcttggg gcctaaatcc tagccatcca ttgcttgtaa aagactccct tcttccact   360
ctagcatctt tgcttgccct tcgcaaatgg agaattggag ataaccaagt ccaaagaggc    420
cttggcttta ttgaaacgca tggttgggca gtcgataaca aggatcagat ttcaccttta    480
ggatttgaaa ttatatttcc ctgcatgatc aactatgcag agaaacttaa tttggatcta    540
cctttggatc ctaaccttgt aaatatgatg ctctgcgaac gtgaattaac aattgaaaga    600
gccttaaaga atgaattcga ggggaatatg gcaaatgtag aatatttgc tgaagggctc     660
ggtgaattat gtcattgaaa agagatgatg cttcgtcaga gacacaacgg gtcgctcttt    720
gattcaccag ccactactgc agctgccttg atttaccatc agtacgatga gaatgcttt    780
gggtacttga actcaatctt gaactgcac gataattggg tccccactat ttgccctaca    840
aagatacatt caaatctctt cttagttgat gcccttcaaa atcttggagt agatcggtat    900
tttaaaacag aagtcaaaag agtactagat gaaatatcca ggcttttggc tgaaaagaat    960
gaagaaatt tttcagacgt tgctcattgt gccatggcgt ttcgactttt acggatgaat    1020
aactatgaag tttcctcaga agaacttgaa ggatttgtcg accaagaaca tttctttaca    1080
acatcaagtg ggaacttat gaatcacgtt gcaattctcg aacttcaccg agcttcacag    1140
gtggctattc atgaaaggaa agatcacatt ttagataaaa taagtacttg gacaaggaat    1200
tttatggagc aaaaactctt ggacaagcac atccctgata ggtcaaagaa ggagatggaa    1260
tttgctatga ggaattttta tggcacattt gatcgagtgg aaactagacg ttacatcgag    1320
tcatacaaaa tggacagttt taagatctta aaagcggctt acaggtcttc cggtattaac    1380
aacatagact tgctaaagtt ctcagaacac gattttaact tgtgccaaac ccgacacaaa    1440
gaagaacttc aacagatgaa aaggtggttc acagattgca aactcgaaca gtaggatta    1500
tcacaacagt acttatacac tagttacttc ataattgctg ccatactctt tgaacctgaa    1560
tatgctgatg ctcgtctagc atatgcaaag tacgccataa taataacagc ggtggatgat    1620
ttcttcgatt gtttttattg caaagaagaa atgcaaaaca tcatcgaatt agtagagaa    1680
tgggagggat actcaaccgt cggattccgt tcagagaggg ttagaatttt cttttggca    1740
ctttacaaaa tggtagagga aattgcggca aaggcggaaa ctaagcaagg tcgatgtgtc    1800
aaagatcacc ttattaactt gtggattgat atgttgaagt gtatgctggt ggaattggac    1860
cttttggaaaa ttaaatcaac taccccaagc atagaggagt acttgtctgt tgcatgtgta    1920
actattggtg ttccatgttt tgttctcaca tcactatatc ttcttggacc aaaactgtcc    1980
aaggatgtca tagaaagttc tgaggtcagt gccttatgca attgtacagc tgctgtggcc    2040
cgattgatta tgatatacag cagttacaag agagaacaag cagaaagttc aacaaatatg    2100
gtatcaatat taataacaca aagtcaggga actatctctg aagaagaggc tataagacag    2160
ataaaggaaa tgatggaaag taagagaaga gagttgctag ggatggttct acaaaataaa    2220
gaaagccaat tgccacaagt gtgcaaggat ctttttttgga acgcaatcaa cgcagcttat    2280
tctatacata cacatggcga tgggtatcgc ttcccagagg aattcaagaa ccatatcaac    2340
gatgtaattt acaaaccact caatcaatat tcccccataa                          2379

SEQ ID NO: 30         moltype = DNA  length = 2064
FEATURE               Location/Qualifiers
source                1..2064
                      mol_type = unassigned DNA
                      organism = Nicotiana tabacum
SEQUENCE: 30
atgatacttg gactgagaag caaaatcata ccacttcctg atcataagtt gggaaatatc    60
```

-continued

```
aaattaggtt cagtaaccaa tgcaatttgc cacagaccat gtagagtaag atgcagccac    120
agtactgctt catcaatgga agaggcaaag gagagaataa gggaaacatt tggaaaaata    180
gagctatctc cttcttccta tgacacagca tgggtagcta tggtcccttc aagatattct    240
atgaaccaac catgttttcc tcagtgctta gattggattc ttgaaaatca aagagaagat    300
ggatcttggg gcctaaatcc tagccatcca ttgcttgtaa aagactccct ttcttccact    360
ctagcatctt tgcttgccct tcgcaaatgc agaattggag ataaccaagt ccaaagaggc    420
cttggcttta ttgaaacgca tggttgggca gtcgataaca aggatcagat ttcacctta     480
ggatttgaaa ttatatttcc ctgcatgatc aactatgcag agaaacttaa tttggatcta    540
cctttggatc ctaaccttgt aaatatgatg atctgcgaac gtgaattaac aattgaaaga    600
gccttaaaga atgaattcga ggggaatatg gcaaatgtag aatattttgc tgaagggctc    660
ggtgaattat gtcattggaa agagatgatg cttcgtcaga gacacaacgg gtcgctcttt    720
gattcaccag ccactactgc agctgccttg atttaccatc agtacgatga gaaatgcttt    780
gggtacttga actcaatctt gaaactgcac gataattggg tccccactat ttgccctaca    840
aagatacatt caaatctctt cttagttgat gcccttcaaa atcttggagt agatcggtat    900
tttaaaacag aagtcaaaag agtactagat gaaatataca ggctttggct agaaaagaat    960
gaagaaattt tttcagacgt tgctcattgt gccatggcgt ttcgacttt  acggatgaat   1020
aactatgaag tttcctcaga agaacttgaa ggatttgtcg accaagaaca tttctttaca   1080
acatcaagtg ggaaacttat gaatcacgtt gcaattctcg aacttcaccg agcttcacag   1140
gtggctattc atgaaggaa  agatcacatt ttagataaaa taagtacttg gacaaggaat   1200
tttatggagc aaaaactctt ggacaagcac atccctgata ggtcaaagaa ggagatggaa   1260
tttgctatga ggaaatttta tggcacattt gatcgagtgg aaactagacg ttacatcgag   1320
tcatacaaaa tggacagttt taagatctta aaagcggctt acagatggta gggatactca   1380
accgtcggat tccgttcaga gagggttaga attttctttt tggcacttta caaaatggta   1440
gaggaaattg cggcaaaggc ggaaactaag caaggtcgat gtgtcaaaga tcaccttatt   1500
aacttgtgga ttgatatgtt gaagtgtatg ctggtgaaat tggacctttg gaaaattaaa   1560
tcaactaccc caagcataga ggagtacttg tctgttgcat gtgtaactat tggtgttcca   1620
tgtttttgtt ctcacatcac atatcttctt ggaccaaaac tgtccaagga tgtcatagaa   1680
agttctgagg tcagtgcctt atgcaattgt acagctgctg tggcccgatt gattaatgat   1740
atacacagtt acaagagaga acaagcagaa agttcaacaa atatggtatc aatattaata   1800
acacaagtc  agggaactat ctctgaagaa gaggctataa gacagataaa ggaaatgata   1860
gaaagtaaga gaagagagtt gctagggatg gttctacaaa ataaagaag  ccaattgcca   1920
caagtgtgca aggatctttt ttggacgaca atcaacgcag cttattctat acatacacat   1980
ggcgatgggt atcgcttccc agaggaattc aagaaccata tcaacgatgt aatttacaaa   2040
ccactcaatc aatattcccc ataa                                           2064

SEQ ID NO: 31        moltype = DNA   length = 1797
FEATURE              Location/Qualifiers
source               1..1797
                     mol_type = unassigned DNA
                     organism = Nicotiana sp.
SEQUENCE: 31
atgagtcaat caatttctcc attaatctgt tctcactttg cgaaatttca gtcgaatatt     60
tggagatgca atacttctca actcagagtt atacactcat catatgcctc ttttggaggg    120
agaagaaaag agagagtaag aagaatgaat cgagcaatgg atctttcttc aagctctcgt    180
catttggcag attttccctc aacaatttgg ggtgaccatt ttctctccta caattctgaa    240
ataacagaaa ttactaccca agagaaaaat gaacatgaaa tgctaaaaga aatagttcgg    300
aaaatgttgg tagaaactcc agataatagt acacaaaaac tagtcttgat tgacacaatt    360
caaagattgg gattagcata tcatttcaat gatgagattg aaaactccat tcaaaacatc    420
tttaatttgt ctcaaaatag tgaagatgac gatgaacaca acctttatgt tgctgctctt    480
cgttttcgac ttgcgaggca acaaggatat tacatgtctt cagatgtgtt caagcaattc    540
actaaccatg acgaaaatt  caaggaaaat cactactaatg atgttcaagg attattgagt   600
ttgtatgaag cagcacatat gagagtgcac gacgaggaaa ttctagaaga agctcttatc    660
tttaccacga ctcatctcga gtccgtgatc ccgaatttga gcaactcgct taaggtacaa    720
gttactgaag ccttaagcca tcctattcgc aaagctatac caaggtgtgg agcaaggaaa    780
tacatacaca tatatgaaaa cattggaaca cataatgatt tacttttgaa atttgcaaag    840
ttggacttca acatgttaca aaagcttcat cgaaaagagc ttaacgagct aacaagctga    900
tggaaagatt tggatcgtgc aaacaaattt ccatatgcaa aggacagatt agtagaagct    960
tacttttgga cggtgggaat atattttgaa cctcaatata gtcgttcaag aagtttggta   1020
acaaaagtag tcaaaatgaa ctccattatt gatgacactt atgatgctta tgcaacttt    1080
gatgagcttg tgcttttcac ggatgcgatc caaagatggg acgaaggtgc catggatta    1140
ttaccgacat atctgagacc tatttatcaa ggccttctcg acgttttcaa tgaaatggaa   1200
gaagtattgg ccaaagaagg taaagcagat cacatctact atgcgaaaaa agagatgaaa   1260
aaggtggcgg aagtctattt taaggaagct gaatggttga atgctaacta cattccaaaa   1320
tgcgagggt atatgaaaaa tggacttgta agctctaccg gtccgatgta ttggaataatt   1380
tctttggttg ttatggagga aattataaca aaagaggctt tgaatggtt  gacaaatgaa   1440
cctttgattc tcgagctgca atcaacaatt tgtagattaa tggatgatat ggctgatcat   1500
gaagttgaac aacaaagagg acatgttgct tcatttgttg agtgctacat gaagaatat    1560
ggagtttcaa agcaagaagc atatgttgag atgcggaaaa aaatcacaaa tgcgtggaaa   1620
gatataaata aggaactctt gcgccctact ccagtaccaa tgtttatcct cgaacgatct   1680
ttaaatttt  caagattggc cgatacattt ttgaaagatg atgatggata cacaaatccc   1740
aaatccaaag ttaaagactt gattgcttcg ttgtttgtcg aatctgtcga catatga      1797

SEQ ID NO: 32        moltype = DNA   length = 717
FEATURE              Location/Qualifiers
source               1..717
                     mol_type = unassigned DNA
                     organism = Nicotiana sp.
SEQUENCE: 32
atgtcttgtc aatattactt aaccacgacg acctcttctc tcagaatatt ctccttcacc     60
```

```
cccgccgtt  acgcaccgaa  ttcttctgca  agtcaacctc  atgagttctt  taaaaaacaa   120
gtacttttca  gttccaatct  gcaatgcaat  gcggtttcaa  gacctcgcgc  acaagttatc   180
aagcgggacg  acaacgtgga  agaagtagac  agtgcagaag  aacaacaaga  agaagaagaa   240
acacaagagg  tgtacagatc  aaataagata  agcaacata   tttatgccgt  ccggttaatg   300
ttgcaaagta  tggatgatgg  agagataagt  atatcagctt  atgacacagc  ttgggttgct   360
cttgtgaaag  acattaatgg  aagcgatact  cctcaattcc  cttcaagtct  tgaatggatt   420
gccaacaatc  aacttgctga  atgttcgtgg  ggtgacaagt  ccatcttttt  ggctcacgat   480
cgaatcatca  acacattggc  ctgtgttatt  gctttgaaat  cttggaattt  gcacattgac   540
aaaagagaac  taggaatgtc  gtttatcaga  gagaatttaa  gcaagattgg  agatgaaaat   600
gctgtgcata  tgccaatagg  atttgaagtg  gcgtttcctt  cactaattga  gattggaaaa   660
aagataggca  ttgatattcc  ggatgattct  catgtcttga  gagagatata  tacctga      717

SEQ ID NO: 33           moltype = DNA  length = 1821
FEATURE                 Location/Qualifiers
source                  1..1821
                        mol_type = unassigned DNA
                        organism = Nicotiana sp.
SEQUENCE: 33
atggcgtcta  tcaccataaa  ccattcattt  tcccgtaacc  ctaacatctc  attccatccc   60
caaaatcctc  tcattcaaac  ccaagctctc  ttcaatttca  aaccatcaat  ctccaaatgt   120
tcccctatta  tccactgcgc  aatccgccgt  cgacccgaat  atacccccgag  ccacattccc  180
gacccgaact  acattcgcat  cttcgacacc  actctccgcg  acggcgaaca  atccccaggc   240
gccacaatga  ccacaaaaga  aaaactcgac  gttgcgcgtc  agttagctaa  gcttggtgtt   300
gacataattg  aagccggttt  tcctgcttct  tctgaagctg  atctcgaagc  tgtgaaatta   360
atagcgaagg  aagttggaaa  tggtgtgaat  gaagagggac  atgttccggt  aatttgtgga   420
cttgcgaggt  gtaataagag  ggatattgat  aaggcttggg  aggctgtgaa  gtatgcgaaa   480
aaaccgagga  ttcatacgtt  tattgcgact  agtgagatac  atatgaagtt  taagttgaag   540
atgagtagag  atgaagttgt  ggagaaagct  aggagtatgg  ttgcttatgc  taggagtatt   600
ggttgtgagg  atgttgaatt  tagcccagaa  gatgctggaa  gatccgatcc  agagttcctc   660
tatcatatcc  ttggagaggt  catcaaagct  ggggcaacaa  cccttaacat  ccctgatact   720
gttggataca  ctgttcccag  cgaatttgga  aaattgattg  ctgatataaa  ggccaatacc   780
ccaggaattg  gagatgtgat  catctcaaca  cactgccaga  acgatcttgg  gctttctact   840
gccaacacct  tagctggagc  atgcgcaggt  gcaagacaag  tagaagtgac  catcaacgga   900
atcggtgaaa  gagctggaaa  tgcttctttg  gaggaggttg  taatggcctt  aaaatgtcgt   960
ggagagcaag  tactaggtgg  cctgtataca  ggaattaata  cacaacatat  actcatgtca  1020
agcaagatgg  tagaggagta  caccgggctt  catgtcagc   cacacaaggc  cattgttgga  1080
gctaatgcgt  ttgctcatga  aagtggcatc  catcaggatg  gaatgttaaa  acacaaagat  1140
acatatgaga  ttatatctcc  tgaagatatt  gggcttaacc  gagttaatga  atctggcatc  1200
gtccttggga  aactcagtgg  gcgtcatgct  ttgcaagcca  aaatgctcga  gcttggatac  1260
gatattgagg  gaaaagaact  tgaggacctc  ttttggcgat  tcaaatctgt  ggccgagaag  1320
aaaaagaaaa  ttacagatga  tgacctgata  gcattaatgt  cagatgaagt  tttccagcct  1380
caatttgttt  ggcaacttga  aaatgtacag  gttacatgtg  gaagtcttgg  cctttctacg  1440
gcaactgtta  agctcattga  cgctgatggt  caagagcatg  tttcttgttc  tgttggaaca  1500
gggccagttg  atgcggctta  taaggcagtt  gatctcattg  taaaggtacc  tgtagcactc  1560
cttgaatatt  ccttgaatgc  agtcacggaa  ggtatagatg  ccatagcttc  aaccagagtt  1620
ttaattcgtg  gggagaatgg  ccatacatca  acccatgctt  taactggaga  gactgtacac  1680
cgttctttta  gtgaaccgga  agcagatatg  gatattgtta  tctccagtgt  ccgagcctat  1740
attggtgcat  tgaataagat  gttgagtttc  agaaagctgg  tatcgaaaca  cagcaaacct  1800
gaaggcagtg  cagtcgtata  g                                                1821

SEQ ID NO: 34           moltype = DNA  length = 1479
FEATURE                 Location/Qualifiers
source                  1..1479
                        mol_type = unassigned DNA
                        organism = Nicotiana sp.
SEQUENCE: 34
atggcgattt  tgatatcaag  atcaagaaac  tttaaccatt  ttcttctaag  cacaaggttt   60
cgtttcttat  cacgcctaaa  ccaaacaagt  tcaaaaacat  tttcccacca  tgccaaaact  120
tcatcattta  caactgcagc  cggcggtggt  tttacaaagc  cgacggcgca  atttttccggc 180
gagtctgccg  ccgttttccg  ggtagaacgt  ttccagtcca  ataaaactgg  agagcaacta  240
aatacactct  actatgaaga  agataaccat  caccaaatta  ttgatgaaaa  tcaggtcatg  300
gattttcctg  gagggcagct  tccaattact  cctcaaatga  aatttattgc  agagtcatct  360
gaaaagaggt  taccttgtta  tagagtcctt  gatgatgatg  gctatccaat  tccaggcagc  420
atttttgagg  aggtgagcaa  agaattggct  gtaaaaatgt  atagttcaat  ggtgacactt  480
caagttatgg  ataccatatt  ttatgaagca  caaaggcagg  ggaggttatc  tttctatctc  540
actactgctg  agaagaagg   tatcaacata  gcatctgctg  ctgctctctc  cgtcgatgac  600
ttcgtcttgc  ctcagtatag  ggaagtaggg  gttatcttat  ggcggggctt  ccccctgaaa  660
gatattgcca  atcaattgtt  cggaaacaag  tttgattatg  aaaaggaag   gcaaatgcca  720
tgccaccatg  gttctaatga  gctcaattac  ttaactattt  cttcgccaat  agcgacacag  780
attcctcagg  ccgcgggcgt  tgcttactct  ctgaaaatgt  ataaaaagga  ggcttgtgct  840
attacttatc  ttggagatgg  tagcaccagt  gagggtgatt  tcatgctgc   tttaaacttt  900
gcagcggttt  tggacgctcc  tgttgtcttt  atatgccgca  acaatggatg  gccattagc   960
actcctgtaa  acgaacaatt  tcgaagtgat  ggagttgcct  caaagggtca  agcctatgga  1020
attagaagca  ttcgtgtaga  tggcaatgat  gtctcttggca  tctatgtgc   tattcgtgag  1080
gctcgcgaaa  tggcaattaa  ggaacaaaag  ccaatattag  tagaggccat  gacttataga  1140
gtagcccacc  attcaacatc  tgatgattca  accaagtatc  gacccgtcga  agaaatagag  1200
cactggaaaa  cagcaaaaag  tccaatatcc  agattcagaa  atggattca   gagaaatggt  1260
tggtggaatg  atgaaaatga  atctgaactt  cgcggagaca  ccagaaaaca  ggtattgcaa  1320
gtaatgcaag  cagcagagaa  ggtggagaaa  cctccattga  cagatttgtt  tacggatgtt  1380
```

-continued

```
tatgacaaag tgccattaaa tcttcaagag caacacaagt ttattaggga tgctgtaaag    1440
aaatctccaa gagagtatcc ttctgatgtt cctatataa                          1479
```

SEQ ID NO: 35          moltype = DNA   length = 966
FEATURE                Location/Qualifiers
source                 1..966
                       mol_type = unassigned DNA
                       organism = Nicotiana tabacum
SEQUENCE: 35
```
atggcagaaa aaatcaccag ccacgagaac acaaggtatg cagtggtgac aggggaaat    60
aaaggaatag gatatgaaac atgcaggcaa ctagcaaagg aaggaatagt ggtagtgttg   120
acagcaaggg atgaaggag aggaattgaa gctctcgaaa agctcaagga agagtactca   180
agcaataaaa ctgatgatga tcagatttta tttcatcaac ttgatgttat ggatccagct   240
agtatttctt ctcttgtgga cttcatcaaa actaaatttg gaaagctcga tattctagct   300
aacaacgcag ggattggtgg attaatggta gaaggagatg ttgttataat aaaagattta   360
atagaaggag acttcgtaac catttctgct gaaaatgggg aagaggatgg tattaagaaa   420
tcaattgaag gtattgagcg tattgttaca gattatgagt tgacaaaaca atgcctggag   480
acaaacttct atggtgcaaa aagaatgatt gaagcattta ttcccctcct tcagctctct   540
aactccccaa gaattgttaa tgtcgcttct ttcttgggga agttaaagct attgtgcaac   600
caatgggcta taggaatgct aagtgatgct aaaagcctga gagaagaaag ggtgatgaa   660
gtgttgaatg aatttataaa agattttaaa gagaaatcaa tagaagccaa aggatggcca   720
acttatttct cagcttacaa agtctcgaaa gcatccctga ttgcttacac aagggtttta   780
gctacgaaat atccaaattt tcggataaat tctgtgtgtc ctggattttg caaaacagac   840
gtgaactgca atactgggag cttaactgct gaagaaggtg ctgaaagctt ggtgaagctt   900
gctttggtgc caaatgatgg accctctggt ctcttctttt atagaaagga ggtcacctct   960
ttttga                                                              966
```

SEQ ID NO: 36          moltype =       length =
SEQUENCE: 36
000

SEQ ID NO: 37          moltype =       length =
SEQUENCE: 37
000

SEQ ID NO: 38          moltype =       length =
SEQUENCE: 38
000

SEQ ID NO: 39          moltype =       length =
SEQUENCE: 39
000

SEQ ID NO: 40          moltype =       length =
SEQUENCE: 40
000

SEQ ID NO: 41          moltype = DNA   length = 14
FEATURE                Location/Qualifiers
misc_feature           1..14
                       note = Description of Artificial Sequence: Synthetic
                        oligonucleotide
source                 1..14
                       mol_type = other DNA
                       organism = synthetic construct
SEQUENCE: 41
```
atgtacaaaa tttc                                                      14
```

SEQ ID NO: 42          moltype = DNA   length = 14
FEATURE                Location/Qualifiers
misc_feature           1..14
                       note = Description of Artificial Sequence: Synthetic
                        oligonucleotide
source                 1..14
                       mol_type = other DNA
                       organism = synthetic construct
SEQUENCE: 42
```
catgtcaaac gtta                                                      14
```

SEQ ID NO: 43          moltype =       length =
SEQUENCE: 43
000

SEQ ID NO: 44          moltype =       length =
SEQUENCE: 44
000

SEQ ID NO: 45          moltype = DNA   length = 1500
FEATURE                Location/Qualifiers

| source | 1..1500 |
| --- | --- |
| | mol_type = unassigned DNA |
| | organism = Cannabis sp. |

SEQUENCE: 45

```
tcttaaaccc ttatgtgttt atttcattgt tttagaattc atattaggat gttaatgaaa    60
catacttgtt agtaaatcta gatcctcgta aaatatttcc aagaaatata acagctactc   120
agattataca caaaaatccc aatagacaaa aacactgtaa aagtcatact aaaactcaaa   180
aaaaaaaaaa aatacaacca aaccaaatca ataaaaacta aaaaatcatc aatgggcagg   240
caagacttca attgtagttt tgacttgcct gagtgaatca attccggaaa agaattgaaa   300
ttgtggtcgt cgttcaagct cttggctgaa tctcctgatt gttcaagccc tctcatcaga   360
attatctcca ttgttcaagc cctctcatcg gaagctcctg gtttttccat caattttttgg   420
ccatggtcac tatggaggta agtagattga agaagacgaa tgtgagagag aaggcaaagg   480
gtcgaggtgg gcgtggtgca gttttgaggg tgggagttgt ttctcggccg caacaatcca   540
ccatgtttct tagttttttt ttctttttgt tctgggaatc gattgttttt gggtgtggat   600
tgttggttga taggttttgg gggtggtttc tgggcagtga gaaggtgaga agaagaagaa   660
gaagaagaaa gttatggttt gaagaagaag aagaaggaaa atcaggtggg tgggtggggt   720
ttcgtgtgaa gcagaaaaaa gaaaaaaaaa acaagttatt ttatgatttg aaaatattat   780
tttagtttt tttatattat tttaaatttt tttattaaa attataattt ggaccagtaa   840
tacttcaaga cgtggcattt taaaaattaa taaacggaca gttatcttag ggaccaacg   900
actcacagaa aatgtgacct tggggactat taccgccaat tttgaggtt tgggaataat   960
ctccatcaac ccttaatttt tggggacttt taccgcaatt atccctatta tacataatat  1020
tttataacaa gtttttttt attattttt attatttga gaagtaatta aagaggagtt  1080
ttcaatttgt taattttca gattagcttg aaaaaaggat tagcttgaaa atacaattct  1140
ataatcatac aatttcaaag catagaaaaa aaattgttca aaaaataaga aaagaaaatt  1200
aagcataatt ctatattggc tgctacattg caatatacgt acgtacagtc ataaaaatat  1260
gcacatggat gaactattac aattagaaca gaagaaaagt aaatgataaa gcttcttact  1320
cttgactaac tcttattaag tactgttgat taatttgaaa ttttcaaatc aaaatacact  1380
ataaatagct gagtacatga aacgagtttt ccatcaatta aagctaactc catctcgtaa  1440
tttatataat tatatagtga tcgtttatat acatatatat caccaaatcg tgatttcaaa  1500
```

| SEQ ID NO: 46 | moltype = DNA length = 1500 |
| --- | --- |
| FEATURE | Location/Qualifiers |
| source | 1..1500 |
| | mol_type = unassigned DNA |
| | organism = Cannabis sp. |

SEQUENCE: 46

```
aatgtttaca attttaacat gtcgattatt ttcaattact aatttttttga aaaaaaaat    60
gtgtaaagtt aaatatataaa atacataagt caatatttat attttgatat attattaaa   120
taatatattt actaaaattt aatacaaaat tatatatata caaacatatt taaaaatttg   180
tttatatttt aaataaacaa catatatgca tgtttattaa atatttaatt attattaatg   240
tttataatac tagtattgat ctaatatgtt tattatgata atatttttaat agaatcaata   300
taatttgttg attaaaagtt cataaataag tttaaaaata aaacatttat gtttatttttg   360
ttttatgaaa caaagctata aacaaatgtg aaattattta taacattat atttatattt   420
tatattgata atgtttataa attattaatc taatatattt aatatatagt tttataaata   480
aagtatgtat atttatttta ttttacttttt ttttgttgta agaaaaaata tgtatgttta   540
ttgttatttt atataagact taggaaaaat taattacctc atatagattg tacagaaaat   600
taaaattatg tgtctctaat atagaatgta taattaaatg taattttata attttgtatt   660
atatagtata ataaaattat ataatgtata caaaattata aatttctcat atctttttctt   720
ctaattttta tttatttatt tttttaatgt caatatgtat aaagtgttgg actccaaatt   780
aaacacttaa agttaaactt aaattgagtt taattaattc aaattttttg tcaagttgta   840
tttttttaagt agtttgtttg tgcttgtggc ttgttataaaa acatgctatg ccctaatttt   900
gtatacataa cactcaggtg gcatttggtt gaaagaaatg aaaacatata taaaaataaa   960
aatgaaataa aataaaattt aaaagtgtata aaaaatcat tagtttcttt taatgttata  1020
ttaacatgat ttttattct atttttaaat agaatagtca ttccactaaa atagtgtaaa  1080
ggacattcca ttagaatgat attctaaatac tttaaaatgt aaccaaataa ataaataaaa  1140
taaaaataat ttcttttca ttctattcca tttcattact catttttcatt ccattctatt  1200
tcatttaaca aaaatgataa atgaacattt tgttatctt gtagtagtac aaactacaaa  1260
taatagaaaa atgaaacttt aatataagga ggagacaaag tctattattt accttggtga  1320
tcaagtttta tatacaactt tgaaataagt actttctttc tctctcttaa taacataatc  1380
ctacttgagt tcccacttgc atttaccttta atatatact atgtcaacca tgtgtataat  1440
tagatctaac atctacttca aatctaaaga acttattac caactaatca aaatcaaaat  1500
```

| SEQ ID NO: 47 | moltype = DNA length = 1500 |
| --- | --- |
| FEATURE | Location/Qualifiers |
| source | 1..1500 |
| | mol_type = unassigned DNA |
| | organism = Cannabis sp. |

SEQUENCE: 47

```
gtagtacata aatttatagc tgatgataag tctcattctc agtcgaggaa tatctactgt    60
gttttggatc aactgaaaag ggagcttaaa agttcatcca tagctcaatt ttcaaccatg   120
tatttttagt ttataatagt aaagattatt cagtcccgta tagagagaaa acaaatgaca   180
aatcatatga ttcagcagca aaaaatggac ttttttacaac tcaaaataaa acagaaatat   240
cttactataa tataatacat agggataatg tacgttgatc ggtttatgtt aagtacagtt   300
cgtctaatta aaaaaaaaaa aaaacagaaa ccaatccaat aaaattagtc gagttagtca   360
ggttaatccg tccaaatcga tcattaatat atttttttta cattcaattg ctatatttta   420
attagatgta ataacgagac aaatagatat atatttata attcacttaa cagttcaatt   480
caacacataa aagaaacata ttaattttaa ctttatgt ttttaaaatt catataagt   540
atatgatata tataaatatg tatatacata aaaccctttt tgattgtgtt ggttggatta   600
gtaagagttg aatagtgggg ttgatattat tttcaatcca cccaatataa agatcagaca   660
```

```
gattatattt ttatcgaatt tttcgatttg tattttttgt cagcttatct caatttaatt    720
taagcaagtt attcagatta ggcggtttaa aaaaatgaaa taatagcatg aaagttttca    780
gtcataacat taaaaaaaaa aatgtcattt tgttatgatg agtggctatg aactgcagcc    840
agtttttgat ggtattcata tgcaatttta atggctttct tcagcttaat gatttaatta    900
gtagataaga gattcttgaa tctagtactc atgatgtatt tgatatccat agtgaccatt    960
gaagattgaa acagtttaa cttggccttc ctctccatatt gttcaagcat tatttttgga   1020
acatgacgaa agttgttcag gaacccatgt tgtccacatc ctgaatttcc aagcttaaga   1080
gaacaaaaaa tccaaatagg cattcatcac taacttcaca gacatatgtc acatatctct   1140
acatttaatc aaaactgttg tatgctgatg tcttcaattc acaagtggca aaaatgtaag   1200
gtgggacccc aaaaaatttc cactagagcc aaactctaaa tagggaaaac tctacaccac   1260
ctcgtagtac ccaccgaaat cccataccac tcatctttta gaaaagaaaa aaaccacact   1320
tgatctcaca acaaatataa agctgacttc ttttgttgtt tttagaaacc atttccacca   1380
tttttcctaat aaactacttg atactaaaat aatcaaaata agaataaagg aaaggaaagg   1440
aaataatact acaacactgc aattattttc tttctcctgt taaccaagtt tgaggttagg   1500

SEQ ID NO: 48         moltype = DNA   length = 1113
FEATURE               Location/Qualifiers
source                1..1113
                      mol_type = unassigned DNA
                      organism = Cannabis sativa
SEQUENCE: 48
atgagcactg taaatctcac atgggttcaa acctgttcca tgttcaacca aggaggtaga     60
tccagatcct tatcaacttt caatctcaat ctctaccacc ctttgaaaaa aacacccttt    120
tcaatccaaa ccccaaaaca aaaacgaccc acttcaccat tttcatcaat ctcagctgtt    180
ctaaccgagc aagaagccgt taagaaggc gatgaagaaa aatccatctt caatttcaag    240
tcttacatgg tccaaaaagc caactcagtc aaccaagctt tagactcagc cgtttttgctc    300
agagatccca ttatgataca cgagtccatg cgttactcac tcctcgccgg aggaaaacga    360
gtcagaccca tgctctgtct ctcagcctgt gaactcgtag gcggaaaaga atccgtagcc    420
atgccggctg cctgcgccgt cgaaatgatc cacaccatgt ctctaatcca cgacgacctc    480
ccttgtatgg acaacgatga cctccgccgt ggaaagcaca caaaccacaa agtcttcgga    540
gaagacgtgg ccgtttttagc cggcgatgca cttttagcct ttgcttttga gcacatgggc    600
gtctctaccg ttggtgttcc ggcagccaag attgtcaggg cgattggtga gcttgctaag    660
tcaattgggt cagaaggatt agtggctggt caagtggttg atattgattc agagggtttg    720
gctaatgttg ggcttgaaca acttgagttc attcatctcc ataagactgg ggctcttcta    780
gaagcttctg ttgttttggg ggctattctt ggtggtggta cagatgaaga agttgaaaaa    840
cttaggagct ttgctaggtg tattggcttg ctttttcagg ttgttgatga cattcttgat    900
gtgactaaat cttctcaaga attgggtaaa actgctggga agatttggt ggctgataag    960
gttacttatc caaggctaat gggtattgac aaatcaagaa aatttgctga gcaattgaac   1020
acagaagcca aacagcatct ttctggtttt gatcccataa aggctgctcc tttaattgct   1080
ttggctaatt atattgctta taggcaaaat tga                                1113

SEQ ID NO: 49         moltype = DNA   length = 2469
FEATURE               Location/Qualifiers
source                1..2469
                      mol_type = unassigned DNA
                      organism = Cannabis sativa
SEQUENCE: 49
atgccttctc tcttctccca atcactactc ctcccctttct ctcaaaacac taatactctc     60
tcccttttcc atcaaccaaa acttcttcct ccaggtgctt cgctattgga agctaaagac    120
aaacaagtta actttgatcg tgatattcgc tcaaaatgca gcgctatatc aaaaccccgc    180
actcacgacg tgtttcaaag tggtggtctg ccagttataa agtggcacga gattgtgaga    240
gatgacatag atggagaaga agaagatact aagtggacaa gatcgaatga gatcgaggaa    300
cgtgtcgctt caatcaaatc aatgttggag agtatggatg agggagagat aagcatttca    360
gcgtacgaca cagcatgggt agcccttgtg aagatattc atgggagtgg cttacctcaa    420
ttcccatcga gtctccaatg gatcgccaca catcagctct ccgacggttc ttggggcgat    480
gctgacattt tctccgcaca cgatcgcctc atcaacactt tggccttgtg tgttgctttg    540
aaatcttgga acctttatcc cgaaaaatgt caaaaggta tggccttttt caatgcaaat    600
ataagtaagc ttgagaggga gaatccgaa cacatgccta ttggtttcga agtggctttc    660
cttctttac ttgaaatagc tcgaaaatta aaccttgaag tgcctgagga ttctcctgg    720
ttaaagtca tatatgctag gagagattc aagctcacaa ggattccgag ggacataatg    780
cacacagtgc ccacgacgct actccatagc ttggaaggaa tggtaggtct ggactggaa    840
aagcttttga aactgcagtc ccaagatggg tcattcttgt tctccaccatc ctcaactgct    900
tttgcactca tggagaccaa agaccgaaat tgcttgcaat atttaactaa agcggtccaa    960
aggttcaacg ggggtgtccc aaatgtttac ccggttgact tgttcgagca cctttggttc   1020
gcggatcggt tgcagcgctt gggaatatca agattctttg agccacaaat tgaggaatgt   1080
atcgattatg tattcagaaa ttggactgag aaaggaattg gctgggcaag aaattccaag   1140
gttgaagata ttgacgatac cgcaatgggt ttcagactac taagattgca tggtcacaaa   1200
gtttctgccg atgtgttcca acactttaag aaaggtgacg attttttctg ctttcgggcc   1260
cagtcaactc aagcagtgac tgggatgtat aaccttata gagcttctca gttggttttc   1320
cctggagaaa aaattcttga agatgccatg gaattctcat cgaaatttct cagaaaaaaa   1380
caggcgtcca atgaattgct agataaatgg atcataacaa aggacttacc tggtgaggtg   1440
ggtttcgcat tggaggttcc atgaatgca acttacctc gagtagagac cagattctac   1500
attaacagt atggtggaca aaatgatgtt tggattggca agacactcta cagaatgcga   1560
aaagttaaca atgacgaata tctggagtta gcaaaacttg attacaacat ttgccaagct   1620
ttgcattcga ttgagtggca caatttgcta aaatggtacc gagattgtaa gttgaaaat   1680
tatgagtgna gcagaaggaa cctcctcttg gcctattttc ttgctgcggc cagtatttc   1740
gaaccggata gggccgatga gcggcttgca tgggctaaaa cggcagcact gatgcaggcc   1800
atccaatctc atttcgatga ccagaaagct tcttcggagc atcgtatagc ttttgtctct   1860
gcttttaaaa ggagttgtaa catgccatcg tatttgatta caagggtgtc gaacataagt   1920
```

```
                                                     -continued
gatacagatc atggccttct tagaacgttg atgacgactc tcagccacct ctctttggac    1980
acaatgatgc tgtatggtcg ggacatcacc caccatttac gtcaagcttg ggaaaagtgg    2040
ctggtgaagt ggcaagaggg tggtgatgga cattacgaag aagaagcaga attattgatc    2100
caaacaataa accttagctc aggccgtaca cttgtgaagg ccctcttgct gtcaaatcct    2160
cactatgaaa aactcttcag taccacaaac aaagtttgct gcaaaattcg tcactttcaa    2220
agacaaaggc atagggccaa ggcaaatcaa aatggagaat ttaacagaaa catcttaaca    2280
ccagaaatag agtcagatat gcaagaggtt gtgcaattgg tgctacaaaa atcttcagat    2340
gacatgatca acacaaaaat taagcagaca tttctactgg tggccaagtc tttttattat    2400
gctgcctact gtgattctaa gaccatcaat ttccacattg gcaaagtaat atttgagact    2460
gtggactga                                                            2469

SEQ ID NO: 50           moltype = DNA  length = 1251
FEATURE                 Location/Qualifiers
source                  1..1251
                        mol_type = unassigned DNA
                        organism = Cannabis sativa
SEQUENCE: 50
atgctattct caaggggatt tcgtcggatt ccgaccacca ccttcaatgg gttttcccgt     60
tggttcgtct ctcaccgacc cgggtactca cagtcacaga ccactactca ttgttctaga    120
gattcaaccc acaagatttt tggcggtttc gaagaaagtc gtttctgggg ttttgctggc    180
tctagatacc aaattcatca ccagagtagc tccttagttg aggaagaatt agacccttt     240
tctcttgttg cggatgaact ctcacttgtt gctaatagt taagggatat ggtagttgct    300
gaggtgccca agcttgcttc tgctgctgag tacttcttta aaatgggtgt ggaggggaag    360
agatttcgtc caacggtatt attgttaatg caacagcat taaatgttaa ggttcccgag    420
cctgctaaag cgttagcaga tactttaaca cccgagttac gtacaaggca gcaatctgtt    480
gcagaaataa cagagatgat ccatgtggca agcctactac atgatgatgt cttagatgat    540
gcagaaacta gacgcggtgt tggttcgttg aattgcatta tgggaaacaa ggtatccgta    600
ttagcaggag attttctgct ttctcgagct tgtgttgccc tcgcagcttt aaagaatacc    660
gaggtagtta cgctactagc cacggttcta gaacagctcg tgacaggtga aaccatgcaa    720
atgacatgta catctgaaca acgttgtagt atggaatatt atatgcaaaa gacatattac    780
aaaactgcat cgttaatttc gaacagttgc aagtcggttg cagtcattgc tggacaaact    840
acagaagttg caatgctagc attcgagtac ggcaaaaatt tgggttttgc ttatcaattg    900
atagatgata ttcttgattt caccggcacg tcagcttccc tcggaaaggg ttcactatct    960
gacatccgtc atggtattgt tacagctcca ttattacg ccatggaaga gtttcctct     1020
ttgcgcgccg tggttgagca gggatttgaa aacccccaaa atgttgacat tgcactcgac    1080
taccttggaa agagtcgcgg gatccaaaag gcgagggaac ttgcaataaa gcatgcaaac    1140
ctcgctgctg aggcaatcga gtcacttcca gagagcgatg atgaagatgt aaaaaagatcg    1200
agacgagcac tagtagatct cacccaaaga gtcgttacaa gaacaaagtg a             1251

SEQ ID NO: 51           moltype = DNA  length = 1770
FEATURE                 Location/Qualifiers
source                  1..1770
                        mol_type = unassigned DNA
                        organism = Cannabis sativa
SEQUENCE: 51
atgtctacca ataataataa taatattaat aatattattt ctcgaagatc agcaaactat     60
caaccttcac tttggcattt tgattatgta caatcacttt ctaccccttt caaggaagga    120
gcatatgcca aaagagttga aaagtaaag gaagaggtaa gagtaatggt gaagagagca    180
aaagaggagg agaagccttt atctcaactt gagcttattg atgtaatgca aagacttgga    240
atctcttacc actttgagaa tgaaattaat gatacattga agatatata taacaacaat    300
aatgtgtaca acaccaacaa taatgtgtat gccaattctc ttgaatttag actcctaaga    360
caacatggtt atccggtgtc tcaagaaata tttagtacgt gcaaagatga agaggcaat     420
tttatggtgt cttccaatga tatcaaagga atgttatctt tatatgaagc ttcattctat    480
ttggtagaaa atgaagatgg tattttgaaa gagacaagag aaaaaacaaa gaaatatctt    540
gaggaataca taatcatgat catggaaaaa caacaatcat tattagatca aaataataat    600
aatgattatg attatgatta tgaactagtg agccatgcat tggaacttcc acttcattgg    660
agaatgttaa gattggagag taggtggttt attgatgtgt atgagaagag actagacatg    720
aaccctactc tacttacctt agctaaaacta gatttcaaca ttgtccaatc aatataccaa    780
gatgatctta aacatgtctt cagctggtgg gaaagcacta atatgggaaa gaagttggaa    840
tttgcaagag atagaacaat ggtgaattc ttatggacag taggagttgc atttgagcca    900
catttcaaaa gttttagaag aatgattaca aaagtaaatg ctttaataac agtaatagat    960
gacatatat tgtttatgg tgcactagat gaattggagc tcttcactaa cgcagttgag    1020
agatgggata ttagtgctat ggatgggctc cctgagtata tgaagacatg ttttcttgct    1080
ttatacaatt tcataaatga tcttccattt gatgtgttaa aaggggaaga aggcctcgat    1140
gtaataaaat tccttcagaa atcgtgggca gatcttgca aatcttattt aagagaagca    1200
agatggtatt ataatggata cacaccaaga tttgaagagt acattgagaa tgcatggata    1260
tcaatatcag gacctgttat actatcacat ttatactttt ttgtagtgaa tccaaacatg    1320
gaagatgcct tattaagtac ttgctttaat ggataccca ccataatacg acattcatcg    1380
atgattttac gtcttacaga tgatcttgca acttcaacgg atgaattgaa aagaggcgat    1440
gttcccaaat caatccaatg caaaatgtac gaagatggta tatctgaaga ggaagctcgt    1500
caacgtatta agttattaat aagtgaaaca tggaagctta ttaataaga ttacataaat    1560
ttggatgatg atgatgatga tggtgatgac tactctccaa tgttctatga gtctaataat    1620
attaataagg ctttcattga aatgtgttta accttggta gaatggcaca ttgcatttat    1680
caatatggag atggacatgg aattcaagat cgccaaacaa aagatcatgt actatcatta    1740
cttattcacc ctattcctct tacccaatag                                     1770

SEQ ID NO: 52           moltype = DNA  length = 1872
FEATURE                 Location/Qualifiers
source                  1..1872
```

```
                          mol_type = unassigned DNA
                          organism = Cannabis sativa
SEQUENCE: 52
atgcagtgca tagcttttca ccaatttgct tcatcatcat ccctccctat ttggagtagt    60
attgataatc gttttacacc aaaaacttct attacttcta tttcaaaacc aaaaccaaaa   120
ctaaaatcaa aatcaaactt gaaatcgaga tcgagatcaa gtacttgcta ccccatacaa   180
tgtactgtgg tcgataaccc tagttctacg attactaata atagtgatcg aagatcagcc   240
aactatggac ctcccatttg gtcttttgat tttgttcaat ctcttccaat ccaatataag   300
ggtgaatctt atacaagtcg attaaataag ttggagaaag atgtgaaaag gatgctaatt   360
ggagtggaaa actctttagc ccaacttgta ctaattgata caatacaaag acttggaata   420
tcttatcgtt ttgaaaatga aatcatttct atttttgaaag aaaaattcac caataataat   480
aacaaccccta atcctattaa ttatgattta tatgctactg ctctccaatt taggcttcta   540
cgccaatatg gatttgaagt acctcaagaa atttttcaata attttaaaaa tcacaagaca   600
ggagagttca aggcaaatat aagtaatgat attatgggag cattgggctt atatgaagct   660
tcattccatg ggaaaaaggg tgaaagtatt ttggaagaag caagaatttt cacaacaaaa   720
tgtctcaaaa aatacaaatt aatgtcaagt agtaataata ataatatgac attaatatca   780
ttattagtga atcatgcttt ggagatgcca cttcaatgga gaatcacaag atcagaagct   840
aaatggttta ttgaagaaat atatgaaaga aaacaagaca tgaatccaac tttacttgag   900
tttgccaaat tggatttcaa tatgctgcaa tcaacatatc aagaggagct caaagtactc   960
tctaggtggt ggaaggattc taaacttgga gagaaattgc ctttcgttag agatagattg  1020
gtggagtgtt tcttatggca agttggagta agatttgagc cacaattcag ttactttaga  1080
ataatggata caaaactcta tgttctatta acaataattg atgtatatgc tgacatttat  1140
ggaacattgg aggaactaca acttttcact aatgctcttc aaagatggga tttgaaagaa  1200
ttagataagt taccagatta tatgaagaca gctttctact ttacatacaa tttcacaaat  1260
gaattggcat ttgatgtatt acaagaacat ggttttgttc acattgaata cttcaagaaa  1320
ctgatcgtag agttgtgtaa acatcatttg caagaggcaa aatggttttta tagtggatac  1380
aaaccaacat tgcaagaata tgttgagaat ggatggttgt ctgtgggagg acaagttatt  1440
cttatgcatg catatttcgc ttttacaaat cctgttacca agagggcatt ggaatgtcta  1500
aaagacggtc atcctaacat agttcgccat gcatcgataa tattacgact tgcagatgat  1560
ctaggaacat tgtcggatga actgaaaaga ggcgatgttc ctaaatcaat tcaatgttat  1620
atgcacgata ctggtgcttc tgaagatgaa gctcgtgagc acataaaata tttaataagt  1680
gaatcatgga aggagatgaa taatgaagat ggaaatatta actctttttt ctcaaatgaa  1740
tttgttcaag tttgcaaaaa tcttggtaga gcgtcacaat tcatgtatca gtatggcgat  1800
ggacatgctt ctcagaataa tctatcgaaa gagcgcgttt tagggttgat tattactcct  1860
atccccatgt aa                                                      1872

SEQ ID NO: 53            moltype = DNA  length = 1551
FEATURE                  Location/Qualifiers
source                   1..1551
                          mol_type = unassigned DNA
                          organism = Cannabis sativa
SEQUENCE: 53
atggagttcc aacaaataat accctctttc caagtcctcc tcttttcatt ttttatgatt    60
attgtggtga gcatactctt gaagagagct caaacaagca ataggtcagc ttcaaaacta   120
cccccaggtc catggagact acccttcctg ggaaacttgc accaactttt gggccctttg   180
cctcatcaca cattcagaga cttagccaaa aaacatggac catttatgta cctcaaaatt   240
ggacaagtc caaccatagt agtttcatca ccagagtatg ctaaagaggt catgaaagtc   300
catgataatg ctcttgcatc aagacccaat aatcttgtta cgcaaatctt ggcatataat   360
ggtacggaca ttatatttgc tccatatggt cagtattgga agaggtaaa aaagatttgt   420
gtgcaagagc ttctaaccct atctagggtt aaaacttttc aacccattag agaagaagag   480
tcgtttaata ttgtaaaaaa tatagcttca aagttgctt cacctatcaa tcttactcaa   540
atgttgaaaa gtttgtctta tagcatcata gctagggctg cctttggcga gaaagaagt   600
gatcatgatg acttcgtata tattatgaag gaaactgtga aattgctgc agggtttgca   660
tttggagatg tgtttccatc tttgagtttt cttgattggt atactataag taaattcaaa   720
gatttgaaac taaggtcttc aagaatagtg gacagaatta tcaagttaca tatagatgat   780
caagacaagg acaatcttaa gaaaagtgga gaagaggaag acttggttga tgttcttttg   840
aggttttcata aaagtgaaga tcctaataac ttcacattaa caaaggacaa tcttaaagca   900
attattgcta gcatatttgg agctgggagt gatacatcat cagtaactat ggagttggct   960
atggcagaaa tgatgagaaa tccaagagtg atgaaaaaag ctcaagacga ggttagagaa  1020
gtctttggca aaaagggtt tttggatgaa tcttcaatca atgagatgac atacttaaaa  1080
tcagttgtga aagaaacttt aaggttgcat ccccagctg ccatgttatt ccaagagaa   1140
agtagagaaa agtgtgatat taatggttat gaaattccta tgaaaactaa gatacttgta  1200
aatgcatggg caattggaag agatcctaaa tattggattg aacctgagag ttttatgcca  1260
gagaggtttc ttgaaagctc tattgatttt aagggaaata attttgagtt tatcccattc  1320
ggcgctggaa ggagaaatat gtcccggaata tcatttgctc tcaccagtat tgagcttcct  1380
ctagcatttt tgctatatca tttcgattgg aaacttccca tggaatgaa acctgaagag  1440
ttggacatga cagagagatt tggtattaca gtctgtagaa agaaggattt gtacttgatt  1500
ccttctaaat atgaaccacc ttctatggcc aagcaatga atataaagta g            1551

SEQ ID NO: 54            moltype = DNA  length = 1545
FEATURE                  Location/Qualifiers
source                   1..1545
                          mol_type = unassigned DNA
                          organism = Cannabis sativa
SEQUENCE: 54
atggatcttc aactactttc attcccaata atcctcatta ctttattttt tatgtttatg    60
gtagtgaaaa tagttttgaa aatagctcat catcaaacaa agaactcagt ttcaaagcta   120
ccccaggac catggaaatt accattggtg ggaaatatac caaaatctt tggctcttca   180
ccccatgttt cattcagaga cttagccaag aaatatgggc cattcatgta cctcaaaatt   240
```

-continued

```
ggacaaattc caactctaat agtttcatca ccagagtatg ttaaagagat catgagaacc 300
catgatgttg tttttgcatc taggcctcaa actcttgctg ctcagatcat ggcatataat 360
tgtactgaca ttatattttc ttcatatggt gaacattgga gacaactcag aaagatttct 420
atgcaagagc ttctaagccc gggaagagtt caaactttc gaccggttag agaagaagag 480
ttgtgtaatc ttgttgaagg gatcatgaca tcttcaaaag atgggtcacc tatcaatgtt 540
actaaaatgg ttacaaaatg ttcttatggc atcacatcta gggctgcctt tggcaagaaa 600
agcagtgatc acgacgagtt catttcgatt gttgaggaag ctatcgaggc agctggaggc 660
tttgaatttg cagaagtgtt tcctgctttg agatttcttg attggaaaag tcgtcctatt 720
tttgagagca tcaaactaag atcttcaaga ataatgaaa atatcatcaa ggagcatata 780
aaagagaagg aaatttcatt tgagaaaatt ggaaaggatg aagatttggt tgatgttctt 840
ttgaagtttc ataagaatgg agatgatctt ggcggttca ccctaacaaa agacaatatt 900
aaagcagtaa tctttgatat ctttgtagct ggaagtgaaa caacatcttt atctgtagat 960
tgggctatgt agaaatgat gagatatcca aaagtgatga aaaaggctca agaagaggtg 1020
agaaaaatta ttggtacaaa agggtcagtg aatgaatcat caatcaatga gatgaaaatt 1080
ttaaaattag ttgttaaaga aactctaagg ttgcatcctc cagctccttt gttacttcca 1140
agggaaagta cagaaaaatg tgacattgat ggttatgaga tacctaagaa aacaagagta 1200
atagtaaatg cttgggcaat tggaagagat ccaaagtatt ggattgaacc tgagaatttt 1260
atgccagaga ggttatgga aagctctatt gattttaagg gcaacaattt tcagtacatt 1320
ccatttggtg gtggaaggag aatatgtcca ggcatgttat ttggtgttat taatattgag 1380
cttttcactag catatttgtt ataccatttt gattggaaac ttcctaatgg aatgaaccat 1440
gaaaatttgg atatgacaga attatttggt cttacaatga agaaaaaga tgatttgtat 1500
ttgattccta ctatttatga ccattcttct atagcaaaat catga 1545
```

SEQ ID NO: 55       moltype = DNA length = 1512
FEATURE           Location/Qualifiers
source            1..1512
                     mol_type = unassigned DNA
                     organism = Cannabis sativa SEQUENCE: 55
```
atggatctcc aactaccctc tttcccagtc ctccttgtcc ttcttttttc tctccttatg 60
gcagttacca tactcatgaa aagagctcga aactcaaaac tacctccagg gccatggaga 120
cttcccttag tgggaaatct ccaccagctt ttattggggt attcatcatc atcctcatct 180
tacgaggtct tcagtgactt agccaaaaaa catggaccct tcatgtacct cgaaatcgga 240
caagttccaa ccgtaatagt gtcatcacca gagtacgcta aagagatcat gagaacccac 300
gacgtcgttt ttgcgtctag gccacggact cttgccgctc aaatcattgg atacgattgt 360
acggacatcg catttgctcc ctatggtgat tactcgagac agctcagaaa gatttgtatg 420
caagctcttt ttagtcccaa aagagttcaa tctttggaac ccattagaga aagaggtg 480
tttaatacgt tacaacatat cattgctaat tccaataaac tcaattttac tcaaatggtc 540
acaaatttgt cttatagcat cgtatctcga gcagctttg gggaaaaaag cagtgatcat 600
gatgagttca tatcgattgt ggaggaagat ataaaggtag ctggagggtt tgaatttggg 660
gagttgtttc cttctttgag atttcttgat tggaccagta ggcctaaata tgaaagcctc 720
aaacagaggt cttctagaat attggaaaag atcatcaaac aacatatgat taatcagaat 780
aatgagaaaa gtgaagaaga gcaagacttg gttgatgttc ttctcaagta tcataacaag 840
gcaaatcttg ggttaaccct tgacaatatc aaaggagtaa tctgggacat ttttgaagct 900
ggaagtgaaa caacagctgt aacagaggat tgggctatgg tagaattgat gagaaatcca 960
ataatgatga aaaaggctca agatgaggtt agggaagttt tggaagaaa aggattagtt 1020
gataaaacat caatcctga gatgaaatac ttaaaattaa ttattaaaga aactctaagg 1080
ttgcatcctc ctgctccttt tttacttcca agggaaaata gtgaaaaatg tgaaattaat 1140
ggttatgaga tacctaatgg aacaagagta ttggtaaatg tttggggaat tggaagacat 1200
gctaagtatt ggaatgaacc tgaaagtttt ataccagaac ggtttgatga tagctctatt 1260
gacttcaaag gtaataattt tgagtatatt ccatttggtg ctggaaggag aatatgtcct 1320
ggcataacat ttggtgttgt tagtcttgag tattctcttg ctttaatgtt ataccactttt 1380
gattggaaac ttcctaatgg aatgaaacct caagatttag acatgagtga gttatttggc 1440
attgcagtaa ggagaaaaga tgatttgtac ttaattccta caatttatca tcagtcacct 1500
cttgcaaatt aa 1512
```

SEQ ID NO: 56       moltype = DNA length = 804
FEATURE           Location/Qualifiers
source            1..804
                     mol_type = unassigned DNA
                     organism = Cannabis sativa SEQUENCE: 56
```
atgacggaac actcaccact aaccccaaa accaagcttc atggcaaggt ggcagtcgtc 60
accggcggaa ccagcggcat cggagaagcc acggctcgaa agttcgctgc tgatgagcga 120
cgcgccgtcg tgattgcaga tatccaagac gagaaaggcc aaaacgtggc cgcatcaatc 180
ggcctggaac gctccaccta cgtccactgc gacgtgaccg acgaggctca agtcgcagcc 240
ctcatcgact caacggtcca aaagtacggt caagtcgacg tgatgttcag caacgccggg 300
gtgccttgcg agtcggatca gacgattctg gatttggatc tggtggcgta cgataaggtg 360
tttgcggtga acgcgagggg gatgcggcg tgtgtgaagc agcgcgatgg tg 420
gagggtggag tgagggggag cgtgatatgc acgcgagcag atctggcgag tataggaact 480
gagaagtaca cggactacac tatgtcgaag cacgccgttt tggggctggt gaggtcagcg 540
agtcttcagc tggggcgcg tggaattcgc gtgaacgcgg tttcgccggg gccgttgagg 600
acgccttgc tgaaagcgtt tatagatagg agtgaggagg agcaggataa gatgattgag 660
gcttcgttat cgctgaagaa tggaaggact ccgtcggtgg agaacctggc tgatgcggtg 720
tcgtttttgg cttcagatga gtctgagttt atcactggcc ataatcttgc cgtcgacggt 780
ggttatattc atcatccacc ctaa 804
```

SEQ ID NO: 57       moltype = DNA length = 1032
FEATURE           Location/Qualifiers

```
source                  1..1032
                        mol_type = unassigned DNA
                        organism = Cannabis sativa
SEQUENCE: 57
atggaagaag tgagcaataa acaactgctg ctgaagaact atgtttccgg ttatccgaaa    60
gagtcggata tggtcttagc cacttccacc atcaagctta agcttccaga aggctccaat   120
ggtgttctag taaagaacct ttatttgtca tgcgatcctt acatgggacc ccgaatgaag   180
aacctcaaca atggcttttt catagagccc ttcaaacttg gttctcctat cactgggaat   240
ggaatttgta aggtactaaa atctggaaat ccaaacttca aggaaggaga tttggtctct   300
ggagtgacag ggtgggagca atacagtgtt attgagtcca cgaaatatat gtctaaaatt   360
caaaacactg acgtgcctct gtcttactat actggattac taggaatgcc tggtatgact   420
gcttatgctg gcttcttcga ggtttgctct ccgaaaaagg gggaatatgt gttcatttct   480
gcagcatcag gagcagttgg tcagcttgtt gggcagttcg caaagctctt gggttgttat   540
gttgttggaa gtgctggaag gaacgaaaag gttgatttgt tgaagaacaa atttggcttt   600
gatgaggctt tcaactacaa agaagagtct gactttgatg tagctttaaa aaggtatttt   660
ccagaaggta tagatatata ctttgataat gttgggggaa agctgctaga tgctgttcta   720
caaaacatga aagccatgc tcgaatttct gtttgtggaa tgatctccaca gtacaacctt   780
gaacaaactg aaggtgtaca taatctgacg aatcttgtgt ggaaaagtgc tcgaatggtt   840
ggatttctgg ttgctgacta ttaccaccta tacccaaaat ttctcgaata tgttatgcct   900
tacttaaaag aaggaaaaat tgtgtatgtt gaagatatag ctgaagggct aaagagtgcc   960
ccaaaagctt tggtagggct cttcaatgga tgcaatgtgg gaaaacaggt ggttctagtc  1020
tcttcggaat ga                                                      1032

SEQ ID NO: 58          moltype = DNA length = 1884
FEATURE                Location/Qualifiers
source                 1..1884
                       mol_type = unassigned DNA
                       organism = Cannabis sativa
SEQUENCE: 58
atggaacaag agtactcctc ttcatttctc tcaacaaaga gatatgctgt tgttacaggt    60
ggaaacaagg ggatcgggtt tgaaatatgc agacaattag cttcaaatgg catcaaggtc   120
gtgttaactg ccagagatga aaagagggg gttgaagctg ttagaaaact gatcaaagaa   180
tcaaatttca ctagtgaaga caatgtcgtt tttcacaggc ttgatgtcgt tgaccctgac   240
accattgctt cttttggaga ttacatcaaa tcccacttcg ggaagcttga catttttgata   300
aataatgcag gaattgctgg gggtacactt gattcttatg gttatgcaca agccactgag   360
cttgctggtg gtaattggcc agagaacggc aattggaatg agataatgac ccagaactat   420
gaatcggctg aagaatgcct gaaaacaaat tattatggag ccaaagcaac gattgaagca   480
cttgttccac tcctccaatt gtctgattca ccaagaatcg tcaatgtttc atcctctctt   540
ggtctcttac aatacatacc gaatgaatgg gccaaaaca tgctgagcga tgttgataag   600
ctaagagaag agcaaataga tgaggtagtg agtgagtttc tgaatgattt caaacaaggt   660
aagttagaag ccaagaagtg gcctacagag atttcggggt acaagttc gaaagcttcg    720
ctgaacgcgt acacaaggat tttggcgaag aaataccctc aaatgtgcgt taactgtgtg   780
tgccctggct atgtcaaaac tgtatatcact tgcaatactg ggcagttggt tgctgccgaa   840
ggtgctgaaa gtcccgtgat gctagccttg ttgcccctcg ccaagccttc cggcttcttc   900
ttctccagga agcaactctc cccttttctgc cattcattca tcactaaacg aaccaaaaca   960
ttttttattac aaacccaagt tcatcaaca atgtctggag cttcagaaag atatgcaatt  1020
gtaacagggg caaataaggg gattggacta gagatagtga gacaattggc cttgaatgga  1080
gtcaatgtgg tcttaacagc aagagatgag aaaaggggtc ttgaagcttt ggagaaactc  1140
aaagagaaag agaaaaacct ctctcacaaa gtgctgtttc accagctcga cgtggctgat  1200
ccagctgcaa ttgttgctat ggttgatttc attaaaacac atttcggcaa acttgatatt  1260
ttggtgaaca atgctggcgt tggtggaaca gaagaagaca tgcatgcaat tgtagcttct  1320
ttaaatgcta agaccccaaa agaaggtgat attaagaaaa ctactcaaac ttatgagtca  1380
gccaaagaat gcatgcaaat aaactattat ggtgctaaaa aaactgctga agagcttatt  1440
ccccttctcc agttatctga ttcaccacga attgttaatg tttcttctac catgggaaag  1500
ctacagaata tatcaaatga ctgggctaaa ggtgttctta gtgatgctga gagtctcaca  1560
gaggataaaa ttgatgaagt gataagagag tttctgaaag atttcaaaga aggttcattg  1620
gaaaccaaag gctggcctag ttttttgtcc ccatatactg tctcaaagc agcccttact   1680
gccttcacaa gggtactagc aaagaagcac cccaacttta tcatcaactg tgtatgccct  1740
ggatttgtga agacagagat aaacttcaac accggtatttt acagcctgaa gaaggcgct   1800
gcgagtccag taaggttagc attgcttcca aatgatgcac cttcaggcct cttctttgat  1860
cggtcacagg tttcgtcttt ttga                                         1884

SEQ ID NO: 59          moltype = DNA length = 1587
FEATURE                Location/Qualifiers
source                 1..1587
                       mol_type = unassigned DNA
                       organism = Cannabis sativa
SEQUENCE: 59
atgttattat tattccatta caatatgtcc ttcttagact taaccagtaa taatctctct    60
tcctttacca ttttattagc aaccttatta ttctttgtgc tgctatataa atcatggttc   120
tctattaaaa caaattctcc accatcgcct ccaaagcttc caataattgg aaacctccac   180
cagctcgggt gtaccctca ccgaacgctg caggcctgga gcaggcgcta tggccccgtc    240
atgcagctcc ggctaggcag cgtgccggtt ctcgtcatct cctctgccac cgccgctcgt   300
gagattatga agactcacga cattgccttt tccaaccgac ccaagtcctg tgccctgag   360
aagctcctct acaactacag agacattgct tcggcacctt atggcgagta ctggaggcag  420
ataaagagcg tttccgtgct tcatctgttg aataataaaa gggttcagtc ctatagagct  480
gtaagggaag aggagaccaa gctcatggtt gagaagattc gaaagtcttg tgggactggg  540
gtgaatttga gcgagttgtt tgtaaggcta accaacgacg tcgtttgtag ggtggccttg  600
gggagaaagt acggtgaaga aagtggtggg aagaggttta aggagcttct gggggagttt  660
```

```
acggagctac ttgggggttt ctatgtaaga gactattttc ctaagcttgg ttggttgagt   720
cgtgtgagtg gtttggatgg tagaatggat aaagtggcta aggagttcga tgagtttctg   780
gaaggtgttc ttcatgacca tatgaataca aataagaatg ttgatgatga acagaaagat   840
tttgtggata ttttgctttg gattcagagg gaaaactcgc ttggattttc tattgatagg   900
acttccataa aggctctcat attggacaca tttgcagcgg gaacagacac aacctataca   960
gtcctagaat gggcaatgac tgagctcata agacatccaa acgccatgaa aaagcttcaa  1020
aacgagatca gaacaacaat ccttaataag aagataacta acattgccat gccagaagaa  1080
tatattaata gtgttacaga agacgaccta gaaaaaatgc catacttgaa ggcagttttc  1140
aaagaaactc tccgtctgca tccaccaatc cctttaatcg ttcctcgact cacaatacaa  1200
gacatgaaaa taagtggata cgacgtcgct tcaggcaccc aagtattcat caatgcatgg  1260
gcaatcggga gagatccgac cttgtgggaa gaggaaccag acaagtttga acctgagagg  1320
ttttgctga agaacgctgc aattgattac aaaggacatg acttcgagtt gatccctttc  1380
ggggccggga ggcgaggctg ccctgggatt gtatttgcca tggctgttaa cgagcttgct  1440
ttggctagtg tggtctataa gtttgattgg gcgttgttga gtagtgagag agaggatttg  1500
gattattatc atatgactga aaccacaggt ttgactacgc atagaaagtt tcctcttatg  1560
gctgtgccaa ctgaatatta tcaatga                                     1587

SEQ ID NO: 60          moltype = DNA  length = 1701
FEATURE                Location/Qualifiers
source                 1..1701
                       mol_type = unassigned DNA
                       organism = Cannabis sativa
SEQUENCE: 60
atgtctcctt gcgaagctac aattgatgaa aaacgcccta atatgccaaa gtttactcca    60
accatttggg gtgattattt catgtctcat gcttcaagtc atcactcatc tcttatggaa   120
actatggaga ataataacaa agagagttat gagaagatta ttgagatgaa ggaacaagtg   180
aagaataaat tacttcatgg tcttcatcct ttggaaaaac ctttggagac acttgaatat   240
attgatgata ttcaacgatt ggggttgtct tattattttg aaaatgaaat tgaacaaaat   300
ttggagcaat tcataataa ttatcaaaat ctaattgatt ttggtgataa taaccttat   360
gctgatgctc tttgctttcg gttgcttagg caacaagtt ataatattgc atgtgacata   420
ttcgacaagt acaagaatga aaatgaaaaa tttaaagaat caatttcgag tgacattcga   480
ggaatgttga acttgtatga agctgcacaa atgagagttc atggagagaa aatactagac   540
gaagcactta tctttacaac tactcatctt gaatcctcag ttaaaacatg tcaattgagc   600
tctccttatc tagacctagt gaaacctgcc ctaatgcacc cttcgaaa gagcttacaa   660
agaagagagg caagacttta catatcactt tatcatcaac taccttctca tgaggagatt   720
ctttaataac ttgctaaact agatttcaac ctgcttcaaa aactacatca aaaggaacta   780
agttacataa cgaggtggtg gaaggagttt gattacaaaa gtaagcattc atttataaaa   840
gacagaatag tggagtgcta tttctgggtt tatggagtgt ttttgaggc agaaacttcc   900
caaatcagac taataatcac caaattaatt gctattctca caataattga tgatgcttat   960
gatagctttg gtacacttga agaactagag cctttactc aagcaataga aaggtgggat  1020
atatgtgcca tagatactct gcctgagtac atgaaaatat tttacatgaa acttttggag  1080
atctacaatg aaaattgaaca attttctaag gaaagatcat actgccctag ctatgctaag  1140
aaagggggtgc aatctctaat tagagcttat tttaaggaag ccaaatggtt acacacaaaa  1200
tatataccaa cattagaaga atatatgcca gttgggattg atagtgcagg atcttttatg  1260
ctcatttcaa tggtttttat tggaatggga gatattgtta caaacattc tatggattgg  1320
atattttcta atcctcaacc taaaattata caaactatgg caatagttgg aagagttatg  1380
aatgacattg gctaccataa gtcggagcga aagaaatcat caggagaaat tgtggcttca  1440
actgtggagt gttacatgaa acaatatggc gtgactggtg aagaagctat agagaaactt  1500
agccaacaag ttaaagattc atggaaagat ctcaatgaag atcttctcaa tccaatcact  1560
atccctaggc cactcttaat gcaagttcta aagcttgtac gagtgaacca tgagatttat  1620
agagaaggag atggctttac acaacccact ttgctcaaga atttgattca ttctctcatc  1680
atcaatccaa ttgactttg a                                            1701

SEQ ID NO: 61          moltype = DNA  length = 2469
FEATURE                Location/Qualifiers
source                 1..2469
                       mol_type = unassigned DNA
                       organism = Cannabis sativa
SEQUENCE: 61
atgccttctc tcttctccca atcactactt ctcccttct ctcaaaacac taatactctc    60
tcccttttcc atcaaccaaa acttcttcct ccaggtgctt cgctattgga agctaaagac   120
aaacaagtta actttgatcg tgatattcgc tcaaatgca cgctatatc aaaacccgc    180
actcacgacg tgtttcaaag tggtggtctg ccagtttaaa agtggcacga gattgtggag   240
gatgacatag atggagaaga agaagatact aagtggacaa tgatcgaggaa                300
cgtgtcgctt caatcaaatc aatgttggag agtatggatg agggagagat aagcatttca   360
gcgtacgaca cagcatgggt agcccttgtg gaagatattc atgggagtgg cttacctcaa   420
ttcccatcga gtcccaatgg atcgccaca catcagctct ccgacggttc ttggggcgat   480
gctgacattt tctccgcaca cgatcgcctc atcaacactt tggcttgtgt tgttgctttg   540
aaatcttgga accttttattcc cgaaaaatgt caaaaaggta tggccttttt caatgcaaat   600
ataagtaagc ttgagaggga gaatccgaa cacatgccta ttggtttcga agtggctttc   660
ccttctttac ttgaaaatagc tcgaaaatta aaccttgaag tgcctgagga ttctcctgtg   720
ttaaaagtca tatatgctag agagagattc aagctcacaa ggattccgag ggacataatg   780
cacacagtgc ccacgacgct actccatagc ttggaaggaa tggtaggtct ggactgggaa   840
aagctttga aactgcatgc ccaagatggg tcattcttgt tctcaccatc ctcaactgct   900
tttgcactca tggagaccaa agaccgaaat tgcttgcaat atttaactaa agcggttccaa   960
aggttcaacg ggggtgtccc aaatgttac ccggttgact tgttcagca cctttgggtt  1020
gcggatcggt tgcagcgctt gggaatatca agattctttg agccacaaat tgaggaatgt  1080
atcgattatg tattcagaaa ttggactgag aaaggaattg gctgggcaag aaattccaag  1140
gttgaagata ttgacgatac cgcaatgggt ttcagactac taagattgca tggtcacaaa  1200
```

```
gtttctgccg atgtgttcca acactttaag aaaggtgacg attttttctg ctttcggggc    1260
cagtcaactc aagcagtgac tgggatgtat aacctttata gagcttctca gttggttttc    1320
cctggagaaa aaattcttga agatgccatg gaattctcat cgaaattcct cagaaaaaaa    1380
caggcgtcca atgaattgct agataaatgg atcataacaa aggacttacc tggtgaggtg    1440
ggttcgcat tggaggttcc atggaatgca aacttacctc gagtagagac cagattctac     1500
attgaacagt atggtggaca aaatgatgtt tggattggca agacactcta cagaatgcga    1560
aaagttaaca atgacgaata tctggagtta gcaaaacttg attacaacat ttgccaagct    1620
ttgcattcga ttgagtggca caatttgcta aaatggtacc gagattgtaa gttggaaaat    1680
tatggagtga gcagaaggaa cctcctcttg gcctattttc ttgctgcggc cagtattttc    1740
gaaccggata gggccgatga gcggcttgca tgggctaaaa cggcagcact gatgcaggcc    1800
atccaatctc atttcgatga ccagaaagct tcttcggagc atcgtatagc ttttgtctct    1860
gcttttaaaa ggagttgtaa catgccatcg tatttgatta caagggtgtc gaacataagt    1920
gatacagatc atggccttct tagaacgttg atgacgactc tcagccacct ctctttggac    1980
acaatgatgc tgtatggtcg ggacatcacc caccatttac gtcaagcttg ggaaaagtgg    2040
ctggtgaagt ggcaagaggg tggtgatgga cattacgaag aagaagcaga attattgatc    2100
caaacaataa accttagctc aggccgtaca cttgtgaagg ccctcttgct gtcaaatcct    2160
cactatgaaa aactcttcag taccacaaac aaagtttgct gcaaaattcg tcactttcaa    2220
agacaaaggc atagggccaa ggcaaatcaa aatggaagat taacagaaa catcttaaca    2280
ccagaaatag agtcagatat gcaagaggtt gtgcaattgg tgctacaaaa atcttcagat    2340
gacatgatca acacaaaaat taagcagaca tttctactgg tggccaagtc ttttttattat   2400
gctgcctact gtgattctaa gaccatcaat ttccacattg gcaaagtaat atttgagact    2460
gtggactga                                                             2469

SEQ ID NO: 62             moltype = DNA  length = 1902
FEATURE                   Location/Qualifiers
source                    1..1902
                          mol_type = unassigned DNA
                          organism = Cannabis sativa SEQUENCE: 62
atggcgaccg ctattttctc caaccccaag ttctccccca caatcaccac cacctcctcc    60
aaaaaccatt accactacca acgccgtaca catttactac tccacgacaa agtccaagct    120
tttcaagccg cctctcttaa actcaaccca aatcctcatt acaagaaacc ccagatcgtt    180
tcctgccaga gctccggtag cgagtcaccg gacacagaga aggtgcggcg gccggagtac    240
attccgaacc gtatctccga tccaaactat gtacgtatct tcgacactac tctccgagac    300
ggtgagcagt cccctggggc cgccctgacg tcaaaggaga agctggacat tgccagacag    360
cttttccaag ctcggcgttga cataatcgag gctggattcc cgccgcctc gaaagatgac    420
ttcgaggccg tcaagattat tgccaaagag gtcggtaacg ccgttgacgc cgacggctat    480
gttcccgtta tctgtggtct gtcgaggtgt aatgagaacg atattaggag ggcttgggag    540
gcggtcaagt acgccaaaag gcctaggatt catctttca ttgctacaag tccaattcac      600
atggagtaca agttgagaaa gagtaaggag caggtgattg agatcgctag gaacatggtg    660
aagtttgctc ggagtttggg gtgtgatgat gttgagttta gccctgaaga tgctggcagg    720
tctgagaggg aattcttgta tcagattttg ggagaagtta taaggctggg agcaacaact    780
ctaaacatac ctgacactgt tggttacaac gtgccaaaaa aatttggaa attgattgct     840
gacattaaag ccaataccc tggaattgag aatgttgtca tttctacaca ctgtcaaaat     900
gatcttggac tttctactgc aaacacgata tcggggcat gcgcaggtgc tagacaatta     960
gaagtaacaa tcaacggcat tggtgaaaga gccgggaatg catctctgga ggaggttgta    1020
atggccataa aatgccgtgg agatcaacaa ctgggaggac tttatactgg aatcaacaca    1080
agacacatct caatgacaag cataatggtt gaggaataca cagggttgca agtacagcca    1140
cataaggcta ttgttggagc caatgctttt gcacatgaaa gcggtatcca tcaggatgga    1200
atgcttaagc acaaaggtac atatgaaatc atatccccag aagatatagg gcttgaacga    1260
agcaatgaag ctgtatagt ccttggaaaa ctcagtggtc gccatgcatt gaaacaacaa      1320
cttgaggagc ttggttatga gcttgaggat gagcaacttg agagtatatt ctggcgcttc    1380
aaatctgtgg ctgaacttaa gaagaggata actgatgctg acctcagagc actagtttcg    1440
gatgaagttt tcaaccaga agtcatctgg aagttcgttg atttgcaggt tacatgtgga     1500
actcttggtc tttcaactgc aaccgtcaaa cttattggtt cagatgggaa agagcatgtt    1560
gcttgttcag taggaactgg tccagtggac tcggcttaca aagctgttga tctgattgtg    1620
aaggaaccag tagcactcct ggagtattca atgaatgctg ttactgaagg tatagatgca    1680
attgcaacca cccgtgtgct aatccgagag gaaacgagcg acttgtcagg tcatggttca    1740
actgttgaac gagttactcg gacatttagt gggaacgggt caggaatgga tattgtggtt    1800
tcaagtgtaa aggcttacat tggtgcgata aacaagatgt taggtttcaa agataggacc    1860
gttgtgaatt cttctgaaga gagaataccc atatctgcat aa                        1902

SEQ ID NO: 63             moltype = DNA  length = 1566
FEATURE                   Location/Qualifiers
source                    1..1566
                          mol_type = unassigned DNA
                          organism = Cannabis sativa SEQUENCE: 63
atggggaggc actcttgttg ttacaagcag aaactgagaa aagggttgtg gtcaccagaa    60
gaagatgaga aacttcttaa ttatataacc aagcatggac atggctgctg gagctctgtc    120
cctaagctag ctggtcttca gagatgtgga aaaagttgca ggctaaggtg gataaattat    180
ttgaggcctg atttgaaaag aggcccattt tcacaacaag aggagaattt gataattgaa    240
cttcatgcag ttcttggcaa cagatggtca cagattgcag ctcagttacc aggaagaaca    300
gataatgaga ttaaaaactt atggaattct tgcattaaga agaactgag gcaaaaaggg    360
attgacccaa atactcataa gccattatct gaggtagaaa atgacattgg taataaattg    420
gagaacaagg gtaacaaagc tgcaaccaat aacaacaaca atgagaatat taataattct    480
actgttagag cttcttcatt aggaaactta tccaatgatc atcatcatca tcatcatcat    540
catctgaatc tagctgacca gtcacaacca tcaatgcgg ccatcaatcg ttacccacta      600
ttggaagtct catcctcaac tccgccgaca caagaattcc tcatagaaaa atcaacagat    660
```

-continued

```
accagatcat caccatcaat atcatcatca tcaccttgtg attttttctac ctacttctct    720
ttccactcaa acaattacaa tacgacgtcg tccgctgctg cagctgctgc tgtttctcat    780
catcaagatc aaaacaacaa caacaacatg gccagtttct gcttcaacat taatcaaaat    840
tcaactagac ctccacaaca ccatcatcat aatcagatga ttagtaatct catccagcca    900
ctacaacaac aagtatcacc ttcatcaaca acaacagcat catcatcatc accaccctcc    960
aatattccac gtgtaaagcc ctccataagt ctcccttat tatctgatca ccaaaacaac   1020
agtaatagca ctactactac tactacaaca actactggag ccgtacaaaa ttgggaaact   1080
agtactttca gcaacaacgg aagtagtagt agtagctgca atatcgaatt acaaggtaat   1140
aataataaca acaacaacaa cttctttgat cacaacacta attccaccgc cgcggccgcc   1200
gccgccgccg ctcctaataa cttctcgtgg ggattagtca atgaaagtac tgttggtagc   1260
ataaaatctg atgacccaga agacataaaa tggtctgaat atctccatag cccttttctt   1320
cttggtggag gaattagtaa tactaataat caaaattctt cttcttcttc acatcttcaa   1380
cccattttgt acagtaacat tgtgaaacca gaatcacact ttagtaatac tactactgct   1440
acaggatcaa accccacgtg gcatcatcag aacgatcatc atcagctaca agcggcttca   1500
tcagaaataa tgtacactaa taaagatcta cagagacttg ctgtagcttt tggacagacc   1560
ctttag                                                             1566

SEQ ID NO: 64          moltype = AA   length = 370
FEATURE                Location/Qualifiers
source                 1..370
                       mol_type = protein
                       organism = Cannabis sativa
SEQUENCE: 64
MSTVNLTWVQ TCSMFNQGGR SRSLSTFNLN LYHPLKKTPF SIQTPKQKRP TSPFSSISAV    60
LTEQEAVKEG DEEKSIFNFK SYMVQKANSV NQALDSAVLL RDPIMIHESM RYSLLAGGKR   120
VRPMLCLSAC ELVGGKESVA MPAACAVEMI HTMSLIHDDL PCMDNDDLRR GKPTNHKVFG   180
EDVAVLAGDA LLAFAFEHMA VSTVGVPAAK IVRAIGELAK SIGSEGLVAG QVVDIDSEGL   240
ANVGLEQLEF IHLHKTGALL EASVVLGAIL GGGTDEEVEK LRSFARCIGL LFQVVDDILD   300
VTKSSQELGK TAGKDLVADK VTYPRLMGID KSREFAEQLN TEAKQHLSGF DPIKAAPLIA   360
LANYIAYRQN                                                         370

SEQ ID NO: 65          moltype = AA   length = 822
FEATURE                Location/Qualifiers
source                 1..822
                       mol_type = protein
                       organism = Cannabis sativa
SEQUENCE: 65
MPSLFSQSLL LPFSQNTNTL SLFHQPKLLP PGASLLEAKD KQVNFDRDIR SKCSAISKPR    60
THDVFQSGGL PVIKWHEIVE DDIDGEEEDT KWTRSNEIEE RVASIKSMLE SMDEGEISIS   120
AYDTAWVALV EDIHGSGLPQ FPSSLQWIAT HQLSDGSWGD ADIFSAHDRL INTLACVVAL   180
KSWNLYPEKC QKGMAFFNAN ISKLERENPE HMPIGFEVAF PSLLEIARKL NLEVPEDSPV   240
LKVIYARRDF KLTRIPRDIM HTVPTTLLHS LEGMVGLDWE KLLKLQSQDG SFLFSPSSTA   300
FALMETKDRN CLQYLTKAVQ RFNGGVPNVY PVDLFEHLWV ADRLQRLGIS RFFEPQIEEC   360
IDYVFRNWTE KGIGWARNSK VEDIDDDTAMG FRLLRLHGHK VSADVFQHFK KGDDFFCFRG   420
QSTQAVTGMY NLYRASQLVF PGEKILEDAM EFSSKFLRKK QASNELLDKW IITKDLPGEV   480
GFALEVPWNA NLPRVETRFY IEQYGGQNDV WIGKTLYRMR KVNNDEYLEL AKLDYNICQA   540
LHSIEWHNLL KWYRDCKLEN YGVSRRNLLL AYFLAAASIF EPDRADERLA WAKTAALMQA   600
IQSHFDDQKA SSEHRIAFVS AFKRSCNMPS YLITRVSNIS DTDHGLLRTL MTTLSHLSLD   660
TMMLYGRDIT HHLRQAWEKW LVKWQEGGDG HYEEEAELLI QTINLSSGRT LVKALLLSNP   720
HYEKLFSTTN KVCCKIRHFQ RQRHRAKANQ NGEFNRNILT PEIESDMQEV VQLVLQKSSD   780
DMINTKIKQT FLLVAKSFYY AAYCDSKTIN FHIGKVIFET VD                     822

SEQ ID NO: 66          moltype = AA   length = 416
FEATURE                Location/Qualifiers
source                 1..416
                       mol_type = protein
                       organism = Cannabis sativa
SEQUENCE: 66
MLFSRGFRRI PTTTFNGFSR WFVSHRPGYS QSQTTTHCSR DSTHKIFGGF EESRFWGFAG    60
SRYQIHHQSS SLVEEELDPF SLVADELSLV ANRLRDMVVA EVPKLASAAE YFFKMGVEGK   120
RFRPTVLLLM ATALNVKVPE PAKALADTLT PELRTRQQSV AEITEMIHVA SLLHDDVLDD   180
AETRRGVGSL NCIMGNKVSV LAGDFLLSRA CVALAALKNT EVVTLLATVL EQLVTGETMQ   240
MTCTSEQRCS MEYYMQKTYY KTASLISNSC KSVAVIAGQT TEVAMLAFEY GKNLGLAYQL   300
IDDILDFTGT SASLGKGSLS DIRHGIVTAP LLYAMEEFPQ LRAVVEQGFE NPKNVDIALD   360
YLGKSRGIQK ARELAIKHAN LAAEAIESLP ESDDEDVKRS RRALVDLTQR VVTRTK       416

SEQ ID NO: 67          moltype = AA   length = 589
FEATURE                Location/Qualifiers
source                 1..589
                       mol_type = protein
                       organism = Cannabis sativa
SEQUENCE: 67
MSTNNNNNIN NIISRRSANY QPSLWHFDYV QSLSTPFKEG AYAKRVEKVK EEVRVMVKRA    60
KEEEKPLSQL ELIDVMQRLG ISYHFENEIN DTLKDIYNNN NVYNTNNNVY ANSLEFRLLR   120
QHGYPVSQEI FSTCKDERGN FMVSSNDIKG MLSLYEASFY LVENEDGILE ETREKTKKYL   180
EEYIIMIMEK QQSLLDQNNN NDYDYDYELV SHALELPLHW RMLRLESRWF IDVYEKRLDM   240
NPTLLTLAKL DFNIVQSIYQ DDLKHVFSWW ESTNMGKKLE FARDRTMVNF LWTVGVAFEP   300
HFKSFRRMIT KVNALITVID DIYDVYGALD ELELFTNAVE RWDISAMDGL PEYMKTCFLA   360
LYNFINDLPF DVLKGEEGLH VIKFLQKSWA DLCKSYLREA RWYYNGYTPR FEEYIENAWI   420
```

```
SISGPVILSH LYFFVVNPNM EDALLSTCFN GYPTIIRHSS MILRLTDDLA TSTDELKRGD    480
VPKSIQCKMY EDGISEEEAR QRIKLLISET WKLINKDYIN LDDDDDDGDD YSPMFYESNN    540
INKAFIEMCL NLGRMAHCIY QYGDGHGIQD RQTKDHVLSL LIHPIPLTQ                589

SEQ ID NO: 68            moltype = AA  length = 623
FEATURE                  Location/Qualifiers
source                   1..623
                         mol_type = protein
                         organism = Cannabis sativa
SEQUENCE: 68
MQCIAFHQFA SSSSLPIWSS IDNRFTPKTS ITSISKPKPK LKSKSNLKSR SRSSTCYPIQ    60
CTVVDNPSST ITNNSDRRSA NYGPPIWSFD FVQSLPIQYK GESYTSRLNK LEKDVKRMLI    120
GVENSLAQLE LIDTIQRLGI SYRFENEIIS ILKEKFTNNN NNPNPINYDL YATALQFRLL    180
RQYGPFEVPQE IFNNFKNHKT GEFKANISND IMGALGLYEA SFHGKKGESI LEEARIFTTK   240
CLKKYKLMSS SNNNNMTLIS LLVNHALEMP LQWRITRSEA KWFIEEIYER KQDMNPTLLE    300
FAKLDFNMLQ STYQEELKVL SRWWKDSKLG EKLPFVRDRL VECFLWQVGV RFEPQFSYFR    360
IMDTKLYVLL TIIDDMHDIY GTLEELQLFT NALQRWDLKE LDKLPDYMKT AFYFTYNFTN    420
ELAFDVLQEH GFVHIEYFKK LMVELCKHHL QEAKWFYSGY KPTLQEYVEN GWLSVGGQVI    480
LMHAYFAFTN PVTKEALECL KDGHPNIVRH ASIILRLADD LGTLSDELKR GDVPKSIQCY    540
MHDTGASEDE AREHIKYLIS ESWKEMNNED GNINSFFSNE FVQVCKNLGR ASQFMYQYGD    600
GHASQNNLSK ERVLGLIITP IPM                                           623

SEQ ID NO: 69            moltype = AA  length = 516
FEATURE                  Location/Qualifiers
source                   1..516
                         mol_type = protein
                         organism = Cannabis sativa
SEQUENCE: 69
MEFQQIIPSF QVLLFSFFMI IVVSILLKRA QTSNRSASKL PPGPWRLPFL GNLHQLLGPL    60
PHHTFRDLAK KHGPFMYLKI GQVPTIVVSS PEYAKEVMKV HDNALASRPN NLVTQILAYN    120
GTDIIFAPYG QYWKEVKKIC VQELLTLSRV KTFQPIREEE SFNIVKNIAS KVGSPINLTQ    180
MLKSLSYSII ARAAFGEKRS DHDDFVYIMK ETVKLSAGFA FGDVFPSLSF LDWYTISKFK    240
DLKLRSSRIV DRIIKLHIDD QDKDNLKKSG EEEDLVDVLL RFHKSEDPNN FTLTKDNLKA    300
IIASIFGAGS DTSSVTMELA MAEMMRNPRV MKKAQDEVRE VFGKKGFLDE SSINEMTYLK    360
SVVKETLRLH PPAAMLFPRE SREKCDINGY EIPMKTKILV NAWAIGRDPK YWIEPESFMP    420
ERFLESSIDF KGNNFEFIPF GAGRRICPGI SFALTSIELP LAFLLYHFDW KLPNGMKPEE    480
LDMTERFGIT VCRKKDLYLI PSKYEPPSMA KAMNIK                             516

SEQ ID NO: 70            moltype = AA  length = 514
FEATURE                  Location/Qualifiers
source                   1..514
                         mol_type = protein
                         organism = Cannabis sativa
SEQUENCE: 70
MDLQLLSFPI ILITLFFMFM VVKIVLKIAH HQTKNSVSKL PPGPWKLPLV GNIHQIFGSS    60
PHVSFRDLAK KYGPFMYLKI GQIPTLIVSS PEYVKEIMRT HDVVFASRPQ TLAAQIMAYN    120
CTDIIFSSYG EHWRQLRKIS MQELLSPGRV QTFRPVREEE LCNLVEGIMT SSKDGSPINV    180
TKMVTKCSYG ITSRAAFGKK SSDHDEFISI VEEAIEAAGG FEFAEVFPAL RFLDWKSRPI    240
FESIKLRSSR IMENIIKEHI KEKEISFEKI GKDEDLVDVL LKFHKNGDDL GRFTLTKDNI    300
KAVIFDIFVA GSETTSLSVD WAMVEMMRYP KVMKKAQEEV RKIIGTKGSV NESSINEMKY    360
LKLVVKETLR LHPPAPLLLP RESTEKCDID GYEIPKKTRV IVNAWAIGRD PKYWIEPENF    420
MPERFMESSI DFKGNNFEYI PFGGGRRICP GMLFGVINIE LSLAYLLYHF DWKLPNGMNH    480
ENLDMTELFG LTMRRKDDLY LIPTIYDHSS IAKS                               514

SEQ ID NO: 71            moltype = AA  length = 503
FEATURE                  Location/Qualifiers
source                   1..503
                         mol_type = protein
                         organism = Cannabis sativa
SEQUENCE: 71
MDLQLPSFPV LLSLLFSLLM AVTILMKRAR NSKLPPGPWR LPLVGNLHQL LLGYSSSSSS    60
YEVFSDLAKK HGPFMYLEIG QVPTVIVSSP EYAKEIMRTH DVVFASRPRT LAAQIIGYDC    120
TDIAFAPYGD YWRQLRKICM QALFSPKRVQ SLEPIREKEV FNTLQHIIAN SNKLNFTQMV    180
TNLSYSIVSR AAFGEKSSDH DEFISIVEED IKVAGGFEFG ELFPSLRFLD WTSRPKYESL    240
KQRSSRILEK IIKQHMINQN NEKSEEEQDL VDVLLKYHNK ANLGLTLDNI KGVIWDIFEA    300
GSETTAVTED WAMVELMRNP IMMKKAQDEV REVFGRKGLV DKTSIHEMKY LKLIIKETLR    360
LHPPAPFLLP RENSEKCEIN GYEIPNGTRV LVNVWGIGRH AKYWNEPESF IPERFDDSSI    420
DFKGNNFEYI PFGAGRRICP GITFGVVSLE YSLALMLYHF DWKLPNGMKP QDLDMSELFG    480
IAVRRKDDLY LIPTIYHQSP LAN                                           503

SEQ ID NO: 72            moltype = AA  length = 267
FEATURE                  Location/Qualifiers
source                   1..267
                         mol_type = protein
                         organism = Cannabis sativa
SEQUENCE: 72
MTEHSPLTPK TKLHGKVAVV TGGASGIGEA TARKFAADGA RAVVIADIQD EKGQNVAASI    60
GLERSTYVHC DVTDEAQVAA LIDSTVQKYG QVDVMFSNAG VPCESDQTIL DLDLVAYDKV    120
FAVNARGMAA CVKHAARAMV EGGVRGSVIC TASNLASIGT EKYTDYTMSK HAVLGLVRSA    180
```

```
SLQLGARGIR VNAVSPGPLR TPLLKAFIDR SEEEQDKMIE ASLSLKNGRT PSVENVADAV   240
SFLASDESEF ITGHNLAVDG GYIHHPP                                      267

SEQ ID NO: 73           moltype = AA  length = 343
FEATURE                 Location/Qualifiers
source                  1..343
                        mol_type = protein
                        organism = Cannabis sativa
SEQUENCE: 73
MEEVSNKQLL LKNYVSGYPK ESDMVLATST IKLKLPEGSN GVLVKNLYLS CDPYMGPRMK   60
NLNNGFFIEP FKLGSPITGN GICKVLKSGN PNFKEGDLVS GVTGWEQYSV IESTKYMSKI   120
QNTDVPLSYY TGLLGMPGMT AYAGFFEVCS PKKGEYVFIS AASGAVGQLV GQFAKLLGCY   180
VVGSAGRNEK VDLLKNKFGF DEAFNYKEES DFDVALKRYF PEGIDIYFDN VGGKLLDAVL   240
QNMRSHARIS VCGMISQYNL EQTEGVHNLT NLVWKSARMV GFLVADYYHL YPKFLEYVMP   300
YLKEGKIVYV EDIAEGLKSA PKALVGLFNG CNVGKQVVLV SSE                    343

SEQ ID NO: 74           moltype = AA  length = 627
FEATURE                 Location/Qualifiers
source                  1..627
                        mol_type = protein
                        organism = Cannabis sativa
SEQUENCE: 74
MEQEYSSSFL STKRYAVVTG GNKGIGFEIC RQLASNGIKV VLTARDEKRG VEAVEKLIKE   60
SNFTSEDNVV FHRLDVVDPD TIASLADYIK SHFGKLDILI NNAGIAGGTL DSYGYAQATE   120
LAGGNWPENG NWNEIMTQNY ESAEECLKTN YYGAKATIEA LVPLLQLSDS PRIVNVSSSL   180
GLLQYIPNEW AKNMLSDVDK LREEQIDEVV SEFLNDFKQG KLEAKKWPTE ISGYKVSKAS   240
LNAYTRILAK KYPQMCVNCV CPGYVKTDIT CNTGQLVAAE GAESPVMLAL LPLAKPSGFF   300
FSRKQLSPFC HSFITKRTKT FLLQTQVSST MSGASERYAI VTGANKGIGL EIVRQLALNG   360
VNVVLTARDE KRGLEALEKL KEKEKNLSHK VLFHQLDVAD PASIVAMVDF IKTHFGKLDI   420
LVNNAGVGGT EEDMHAIVAS LNAKTPKEGD IKKTTQTYES AKECMQINYY GAKKTAEELI   480
PLLQLSDSPR IVNVSSTMGK LQNISNDWAK GVLSDAESLT EDKIDEVIRE FLKDFKEGSL   540
ETKGWPSFLS PYTVSKAALT AFTRVLAKKH PNFIINCVCP GFVKTEINFN TGILQPEEGA   600
ASPVRLALLP NDAPSGLFFD RSQVSSF                                      627

SEQ ID NO: 75           moltype = AA  length = 528
FEATURE                 Location/Qualifiers
source                  1..528
                        mol_type = protein
                        organism = Cannabis sativa
SEQUENCE: 75
MLLLFHYNMS FLDLTSNNLS SFTILLATLL FFVLLYKSWF SIKTNSPPSP PKLPIIGNLH   60
QLGLYPHRTL QAWSRRYGPV MQLRLGSVPV LVISSATAAR EIMKTHDIAF SNRPKSCALE   120
KLLYNYRDIA SAPYGEYWRQ IKSVSVLHLL NNKRVQSYRA VREEETKLMV EKIRKSCGTG   180
VNLSELFVRL TNDVVCRVAL GRKYGEESGG KRFKELLGEF TELLGGFYVR DYFPKLGWLS   240
RVSGLDGRMD KVAKEFDEFL EGVLHDHMNT NKNVDDEQKD FVDILLWIQR ENSLGFSIDR   300
TSIKALILDT FAAGTDTTYT VLEWAMTELI RHPNAMKKLQ NEIRTTILNK KITNIAMPEE   360
YINSVTEDDL EKMPYLKAVF KETLRLHPPI PLIVPRLTIQ DMKISGYDVA SGTQVFINAW   420
AIGRDPTLWE EEPDKFEPER FLLKNAAIDY KGHDFELIPF GAGRRGCPGI VFAMAVNELA   480
LASVVYKFDW ALLSSGEEDL DYYHMTETTG LTTHRKFPLM AVPTEYYQ               528

SEQ ID NO: 76           moltype = AA  length = 566
FEATURE                 Location/Qualifiers
source                  1..566
                        mol_type = protein
                        organism = Cannabis sativa
SEQUENCE: 76
MSPCEATIDE KRPNMPKFTP TIWGDYFMSH ASSHHSSLME TMENNNKESY EKIIEMKEQV   60
KNKLLHGLHP LENPLETEY IDDIQRLGLS YYFENEIEQN LEQFHNNYQN LIDFGDNNLY    120
ADALCFRLLR QQGYNIACDI FDKYKNENEK FKESISSDIR GMLNLYEAAQ MRVHGEKILD   180
EALIFTTTHL ESSVKTCQLS SPYLDLVKHA LMHPIRKSLQ RREARLYISL YHQLPSHEEI   240
LLILAKLDFN LLQKLHQKEL SYITRWWKEF DYKSKHSFIK DRIVECYFWV YGVFFEAETS   300
QIRLIITKLI AILTIIDDAY DSFGTLEELE PFTQAIERWD ICAIDTLPEY MKIFYMKLLE   360
IYNEIEQFSK ERSYCPSYAK KGVQSLIRAY FKEAKWLHTK YIPTLEEYMP VGDISAGSFM   420
LISMVFIGMG DIVTKHSMDW IFSNPQPKII QTMAIVGRVM NDIGYHKSER KKSSGEIVAS   480
TVECYMKQYG VTGEEAIEKL SQQVKDSWKD LNEDLLNPIT IPRPLLMQVL KLVRVNHEIY   540
REGDGFTQPT LLKNLIHSLI INPIDF                                       566

SEQ ID NO: 77           moltype = AA  length = 822
FEATURE                 Location/Qualifiers
source                  1..822
                        mol_type = protein
                        organism = Cannabis sativa
SEQUENCE: 77
MPSLFSQSLL LPFSQNTNTL SLFHQPKLLP PGASLLEAKD KQVNFDRDIR SKCSAISKPR   60
THDVFQSGGL PVIKWHEIVE DDIDGEEEDT KWTRSNEIEE RVASIKSMLE SMDEGEISIS   120
AYDTAWVALV EDIHGSGLPQ FPSSLQWIAT HQLSDGSWGD ADIFSAHDRL INTLACVVAL   180
KSWNLYPEKC QKGMAFFNAN ISKLERENPE HMPIGFEVAF PSLLEIARKL NLEVPEDSPV   240
LKVIYARRDF KLTRIPRDIM HTVPTTLLHS LEGMVGLDWE KLLKLQSQDG SFLFSPSSTA   300
FALMETKDRN CLQYLTKAVQ RFNGGVPNVY PVDLFEHLWV ADRLQRLGIS RFFEPQIEEC   360
```

```
IDYVFRNWTE KGIGWARNSK VEDIDDTAMG FRLLRLHGHK VSADVFQHFK KGDDFFCFRG  420
QSTQAVTGMY NLYRASQLVF PGEKILEDAM EFSSKFLRKK QASNELLDKW IITKDLPGEV  480
GFALEVPWNA NLPRVETRFY IEQYGGQNDV WIGKTLYRMR KVNNDEYLEL AKLDYNICQA  540
LHSIEWHNLL KWYRDCKLEN YGVSRRNLLL AYFLAAASIF EPDRADERLA WAKTAALMQA  600
IQSHFDDQKA SSEHRIAFVS AFKRSCNMPS YLITRVSNIS DTDHGLLRTL MTTLSHLSLD  660
TMMLYGRDIT HHLRQAWEKW LVKWQEGGDG HYEEEAELLI QTINLSSGRT LVKALLLSNP  720
HYEKLFSTTN KVCCKIRHFQ RQRHRAKANQ NGEFNRNILT PEIESDMQEV VQLVLQKSSD  780
DMINTKIKQT FLLVAKSFYY AAYCDSKTIN FHIGKVIFET VD                    822

SEQ ID NO: 78           moltype = AA  length = 633
FEATURE                 Location/Qualifiers
source                  1..633
                        mol_type = protein
                        organism = Cannabis sativa
SEQUENCE: 78
MATAIFSNPK FSPTITTTSS KNHYHYQRRT HLLLHDKVQA FQAASLKLNP NPHYKKPQIV   60
SCQSSGSESP DTEKVRRPEY IPNRISDPNY VRIFDTTLRD GEQSPGAALT SKEKLDIARQ  120
LSKLGVDIIE AGFPAASKDD FEAVKIIAKE VGNAVDADGY VPVICGLSRC NENDIRRAWE  180
AVKYAKRPRI HTFIATSPIH MEYKLRKSKE QVIEIARNMV KFARSLGCDD VEFSPEDAGR  240
SEREFLYQIL GEVIKAGATT LNIPDTVGYN VPKEFGELIA DIKANTPGIE NVVISTHCQN  300
DLGLSTANTI SGACAGARQL EVTINGIGER AGNASLEEVV MAIKCRGDQQ LGGLYTGINT  360
RHISMTSIMV EEYTGLQVQP HKAIVGANAF AHESGIHQDG MLKHKGTYEI ISPEDIGLER  420
SNEAGIVLGK LSGRHALKQQ LEELGYELED EQLESIFWRF KSVAELKKRI TDADLRALVS  480
DEVFQPEVIW KFVDLQVTCG TLGLSTATVK LIGSDGKEHV ACSVGTGPVD SAYKAVDLIV  540
KEPVALLEYS MNAVTEGIDA IATTRVLIRE ETSDLSGHGS TVERVTRTFS GNGSGMDIVV  600
SSVKAYIGAI NKMLGFKDRT VVNSSEERIP ISA                              633

SEQ ID NO: 79           moltype = AA  length = 521
FEATURE                 Location/Qualifiers
source                  1..521
                        mol_type = protein
                        organism = Cannabis sativa
SEQUENCE: 79
MGRHSCCYKQ KLRKGLWSPE EDEKLLNYIT KHGHGCWSSV PKLAGLQRCG KSCRLRWINY   60
LRPDLKRGPF SQQEENLIIE LHAVLGNRWS QIAAQLPGRT DNEIKNLWNS CIKKKLRQKG  120
IDPNTHKPLS EVENDIGNKL ENKGNKAATN NNNNENINNS TVRASSLGNL SNDHHHHHHH  180
HLNLADQSQP SMAAINRYPL LEVSSSTPPT QEFFIEKSTD TRSSPSISSS SPCDFSTYFS  240
FHSNNYNTTS SAAAAAAVSH HQDQNNNNNM ASFCFNINQN STRPPQHHHH NQMISNLIQP  300
LQQQVSPSST TTASSSSPPS NIPRVKPSIS LPLLSDHQNN SNSTTTTTTT TTGAVQNWET  360
STFSNNGSSS SSCNIELQGN NNNNNNNFFD HNTNSTAAAA AAAAPNNFSW GLVNESTVGS  420
IKSDDPEDIK WSEYLHSPFL LGGGISNTNN QNSSSSSHLQ PILYSNIVKP ESHFSNTTTA  480
TGSNPTWHHQ NDHHQLQAAS SEIMYTNKDL QRLAVAFGQT L                     521

SEQ ID NO: 80           moltype = DNA  length = 1974
FEATURE                 Location/Qualifiers
misc_feature            1..1974
                        note = Description of Artificial Sequence: Synthetic
                         polynucleotide
source                  1..1974
                        mol_type = other DNA
                        organism = synthetic construct
SEQUENCE: 80
actaaatttt gattacttta aaactgtggc tattctttaa ttatcagttg taaatctggc    60
tattttaaaa attaactagt tttacgcttg ccaatttacc acaactcctc ctttgttagc   120
atgtaataat atgagggagc tcacacagac cgagtaaatt ccctatgagc agtggtggat   180
ctagagggca atgtgcgagt tcctggattg cacagtcctt gtatatatat attaaaaaat   240
ttattaaata tctataaata tttaattgtc aacccaatta ctaacttgag cccgatcatt   300
atagaaattc ataaatttca aagtctggaa tcgcctaagt tggtcaacta aaatctcctc   360
ttgagctact aatcacttct agaagagagt acacagcagt ctcattttaat gcaacatcaa   420
cctactgaaa agggaaatga tcaggaccaa agtttacttt aaagagtcaa aacttcataa   480
accgtataga tagataatat agcttgacaa aatagacccc gtggtaaaat catcatttca   540
atagaaatta ggaaaagcaa tttgtttttt ccttatcaga tgtcgagagt ctatcggaaa   600
caatctttat atcttttcaa ggtaaagtaa agctgcgtac accgtaccct ctccaaaccc   660
cacttatgag attacgttga attattattg ttgttgttgt tgttgttgat gtcaagatta   720
acttgcttgt tatctttact atttgttaga tacctactat ttttcatcga cacaagtaat   780
aaataatttt gtcgtagatt atccacaaga tagctacctc ctataaatat tatatgtacc   840
gaataattct ccccatcata tttaagcata tgaaaaaatc acctatcttt ttaaatgttt   900
cataattttc atcttacttt attaaccgtt agaccacgct ttaatccgta acttcacttg   960
tatttaagag atttcaactc aataaaaaag atgacaggtg gaaaaggaaa atgtcggcat  1020
gtttagttga aaaaaaactt gtactgttat tttctgtggc acattcaaga tcgtattcat  1080
agtaataaaa agtttggtcc tggctagctg aaaaatttgg ttagtaggga atgcatgcat  1140
gtaaacgccg cccttcatta aaagattgta tgctactata ttttttggga tctttacgta  1200
aaatagctga tcatatttac tgtttacttt ttctagccat atacatagat catacattga  1260
ttatatatga tatgcacat atattatata aatcatgtat atattataac tcaaccggat  1320
atttttagtt ttgagtggtt aagtgagcgg ctatttggat taattattca tatttttttt  1380
ggtttcccac tttgtgtccg gtatcctctt tggagtttga ttaatttgga ttcgtggtgg  1440
aaaattcaat tttggagtgt aaagctctcc ctaccaaaca agggcggatt taggccgtat  1500
ggtgcacatg tacccatggt ttttccgcca aataggtatt tatgtatat atttcataaa  1560
attgatctaa tattatctgt tgagccccat gctccaaaaa agttgaatag tgcacctggt  1620
```

```
tgaattctaa gttattcatc caaaggaaca tggatagatt ctagcttagc acttcttttt   1680
tctggctttt tcaatggtgc acctatgatc tagaaatcct agattcgcct ctgctaccat   1740
aggcgactcc atacccaagg ctcgaaactg aaatctctga ttaaagatag aggagagtac   1800
ttaccgctcc aatacaacct tggtgcctcg tggtaggttg tatagtacac tttaataaac   1860
aagaaagctt aagcgttaaa attaacttca tttctcaagc tataaatacc atcatgaaac   1920
aacacaattt atactacaat acactccaag ttttttttaga ggaaaaaaaa aatg         1974

SEQ ID NO: 81            moltype = DNA   length = 1055
FEATURE                  Location/Qualifiers
misc_feature             1..1055
                         note = Description of Artificial Sequence: Synthetic
                         polynucleotide
source                   1..1055
                         mol_type = other DNA
                         organism = synthetic construct
SEQUENCE: 81
tattaaccgt tagaccacgc tttaatccgt aacttcactt gtatttaaga gatttcaact    60
caataaaaaa gatgacaggt ggaaaaggaa aatgtcggca tgtttagttg aaaaaaaact   120
tgtactgtta ttttctgtgg cacattcaag atcgtattca tagtaataaa aagtttggtc   180
ctggctagct gaaaaatttg gttagtaggg aatgcatgca tgtaaacgcc gcccttcatt   240
aaaagattgt atgctactat attttttggg atctttacgt aaaatagctg atcatattta   300
ctgtttactt tttctagcca tatacataga tcatacattg attatatatg attatgcaca   360
tatattatat aaatcatgta tatattatac ctcaaccgga tatttttagt tttgagtggt   420
taagtgagcg gctatttgga ttaattattc atatttttt tggtttccca ctttgtgtcc    480
ggtatcctct ttggagtttg attaatttgg attcgtggtg gaaaattcaa ttttggagtg   540
taaagctctc cctaccaaac aagggcggat ttaggccgta tggtgcacat gtacccatgg   600
tttttccgcc aaataggtat tttatgtata tatttcataa aattgatcta atattatctg   660
ttgagcccca tgctccaaaa aagttgaata gtgcacctgg ttgaattcta agttattcat   720
ccaaaggaac atggatagat tctagcttag cacttctttt ttctggcttt tcaatggttg   780
cacctatgat ctagaaatcc ttgattcgcc tctgctacca taggcgactc catacccaag   840
gctcgaaact gaaatctctg attaaagata gaggagagta cttaccgctc caatacaacc   900
ttggtgcctc gtggtaggtt gtatagtaca ctttaataaa caagaaagct taagcgttaa   960
aattaacttc atttctcaag ctataaatac catcatgaaa caacacaatt tatactacaa  1020
tacactccaa gttttttttag aggaaaaaaa aaatg                             1055

SEQ ID NO: 82            moltype = DNA   length = 476
FEATURE                  Location/Qualifiers
misc_feature             1..476
                         note = Description of Artificial Sequence: Synthetic
                         polynucleotide
source                   1..476
                         mol_type = other DNA
                         organism = synthetic construct
SEQUENCE: 82
atggtgcaca tgtacccatg gttttttccgc caaataggta ttttatgtat atatttcata    60
aaattgatct aatattatct gttgagcccc atgctccaaa aaagttgaat agtgcacctg   120
gttgaattct aagttattca tccaaaggaa catggatagt ttctagctta gcacttcttt   180
tttctggctt tttcaatggt gcacctatga tctagaaatc cttgattcgc ctctgctacc   240
ataggcgact ccatacccaa ggctcgaaac tgaaatctct gattaaagat agaggagagt   300
acttaccgct ccaatacaac cttggtgcct cgtggtaggt tgtatagtac actttaataa   360
acaagaaagc ttaagcgtta aaattaactt catttctcaa gctataaata ccatcatgaa   420
acaacacaat ttatactaca atacactcca agtttttttta gaggaaaaaa aaaatg      476

SEQ ID NO: 83            moltype = DNA   length = 10
FEATURE                  Location/Qualifiers
misc_feature             1..10
                         note = Description of Artificial Sequence: Synthetic
                         oligonucleotide
source                   1..10
                         mol_type = other DNA
                         organism = synthetic construct
SEQUENCE: 83
atgtcggcat                                                           10

SEQ ID NO: 84            moltype = DNA   length = 10
FEATURE                  Location/Qualifiers
misc_feature             1..10
                         note = Description of Artificial Sequence: Synthetic
                         oligonucleotide
source                   1..10
                         mol_type = other DNA
                         organism = synthetic construct
SEQUENCE: 84
gaattattat                                                           10

SEQ ID NO: 85            moltype = DNA   length = 14
FEATURE                  Location/Qualifiers
misc_feature             1..14
                         note = Description of Artificial Sequence: Synthetic
```

```
                         oligonucleotide
source                   1..14
                         mol_type = other DNA
                         organism = synthetic construct
SEQUENCE: 85
gttgaattat tatt                                                            14

SEQ ID NO: 86            moltype = DNA   length = 10
FEATURE                  Location/Qualifiers
misc_feature             1..10
                         note = Description of Artificial Sequence: Synthetic
                         oligonucleotide
source                   1..10
                         mol_type = other DNA
                         organism = synthetic construct
SEQUENCE: 86
tttaattatc                                                                 10

SEQ ID NO: 87            moltype = DNA   length = 10
FEATURE                  Location/Qualifiers
misc_feature             1..10
                         note = Description of Artificial Sequence: Synthetic
                         oligonucleotide
source                   1..10
                         mol_type = other DNA
                         organism = synthetic construct
SEQUENCE: 87
catttaatgc                                                                 10

SEQ ID NO: 88            moltype = DNA   length = 10
FEATURE                  Location/Qualifiers
misc_feature             1..10
                         note = Description of Artificial Sequence: Synthetic
                         oligonucleotide
source                   1..10
                         mol_type = other DNA
                         organism = synthetic construct
SEQUENCE: 88
gatgacaggt                                                                 10

SEQ ID NO: 89            moltype = DNA   length = 10
FEATURE                  Location/Qualifiers
misc_feature             1..10
                         note = Description of Artificial Sequence: Synthetic
                         oligonucleotide
source                   1..10
                         mol_type = other DNA
                         organism = synthetic construct
SEQUENCE: 89
taaatatcta                                                                 10

SEQ ID NO: 90            moltype = DNA   length = 10
FEATURE                  Location/Qualifiers
misc_feature             1..10
                         note = Description of Artificial Sequence: Synthetic
                         oligonucleotide
source                   1..10
                         mol_type = other DNA
                         organism = synthetic construct
SEQUENCE: 90
ctttaattat                                                                 10

SEQ ID NO: 91            moltype = DNA   length = 14
FEATURE                  Location/Qualifiers
misc_feature             1..14
                         note = Description of Artificial Sequence: Synthetic
                         oligonucleotide
source                   1..14
                         mol_type = other DNA
                         organism = synthetic construct
SEQUENCE: 91
cacatgtacc catg                                                            14

SEQ ID NO: 92            moltype = DNA   length = 10
FEATURE                  Location/Qualifiers
misc_feature             1..10
                         note = Description of Artificial Sequence: Synthetic
                         oligonucleotide
source                   1..10
```

```
                        mol_type = other DNA
                        organism = synthetic construct
SEQUENCE: 92
tagattctag                                                          10

SEQ ID NO: 93           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 93
atagattcta                                                          10

SEQ ID NO: 94           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 94
caaagatatc                                                          10

SEQ ID NO: 95           moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 95
ggattttaca gt                                                       12

SEQ ID NO: 96           moltype = DNA  length = 11
FEATURE                 Location/Qualifiers
misc_feature            1..11
                        note = Description of Artificial Sequence: Synthetic
                         oligonucleotide
source                  1..11
                        mol_type = other DNA
                        organism = synthetic construct
SEQUENCE: 96
tataaatatc t                                                        11

SEQ ID NO: 97           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 97
cctataaaaa                                                          10

SEQ ID NO: 98           moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 98
caaagatatc                                                          10

SEQ ID NO: 99           moltype = DNA  length = 11
FEATURE                 Location/Qualifiers
misc_feature            1..11
                        note = Description of Artificial Sequence: Synthetic
                         oligonucleotide
source                  1..11
                        mol_type = other DNA
                        organism = synthetic construct
```

```
SEQUENCE: 99
atagaaatca a                                                                11

SEQ ID NO: 100         moltype = DNA  length = 10
FEATURE                Location/Qualifiers
misc_feature           1..10
                       note = Description of Artificial Sequence: Synthetic
                       oligonucleotide
source                 1..10
                       mol_type = other DNA
                       organism = synthetic construct
SEQUENCE: 100
attctctaac                                                                  10

SEQ ID NO: 101         moltype = DNA  length = 10
FEATURE                Location/Qualifiers
misc_feature           1..10
                       note = Description of Artificial Sequence: Synthetic
                       oligonucleotide
source                 1..10
                       mol_type = other DNA
                       organism = synthetic construct
SEQUENCE: 101
aaggataagg                                                                  10

SEQ ID NO: 102         moltype = DNA  length = 10
FEATURE                Location/Qualifiers
misc_feature           1..10
                       note = Description of Artificial Sequence: Synthetic
                       oligonucleotide
source                 1..10
                       mol_type = other DNA
                       organism = synthetic construct
SEQUENCE: 102
tatataaatc                                                                  10
```

TISSUE-SPECIFIC PROMOTERS IN PLANTS

CROSS-REFERENCE TO RELATED APPLICATIONS

This application is a continuation of U.S. patent application Ser. No. 17/591,188, filed on Feb. 2, 2022, which claims the benefit of: U.S. Provisional Patent Application No. 63/145,259, filed Feb. 3, 2021; U.S. Provisional Patent Application No. 63/145,262, filed Feb. 3, 2021; and U.S. Provisional Patent Application No. 63/145,263, filed Feb. 3, 2021, all of which are incorporated by reference herein in their entireties.

INCORPORATION OF SEQUENCE LISTING

This application contains a Sequence Listing conforming to the rules of WIPO Standard ST.26 is hereby incorporated by reference in its entirety. The Sequence Listing is named "P34834US02_SL," and is 173,064 bytes in size (measured in MS-Windows®) and created on Aug. 14, 2023.

FIELD

The present disclosure relates to trichome-preferred and trichome-specific promoters and their uses in plants, including tobacco and cannabis.

SEQUENCES

Table 1 provides nucleic acid sequences and amino acid sequences used in this disclosure.

TABLE 1

Sequences for this disclosure

| SEQ ID NO | Sequence Description | Sequence Type | Sequence |
|---|---|---|---|
| 1 | NtPhy0.5kb-Fwd | Nucleic acid | GGGGACAAGTTTGTACAAAAAAGCAGGCTTATAAATACCT ATGAAAATTAAAT |
| 2 | NtPhy-Rev | Nucleic acid | GGGGACCACTTTGTACAAGAAAGCTGGGTAGGCAGTTATT GTTATATGTGATAG |
| 3 | NtCyc-0.5-Fwd | Nucleic acid | GGGGACAAGTTTGTACAAAAAAGCAGGCTGCAATAATTTT TTATATCTAT |
| 4 | NyCyc-Rev | Nucleic acid | GGGGACCACTTTGTACAAGAAAGCTGGGTACTCTCTCTCT TTCTCTCG |
| 5 | NtPSO-1.0-Fwd | Nucleic acid | GGGGACAAGTTTGTACAAAAAAGCAGGCTATTTACGAGTT TACTATACTT |
| 6 | NtPSO-Rev | Nucleic acid | GGGGACCACTTTGTACAAGAAAGCTGGGTATTTGGGAGGG AATTAAAG |
| 7 | NtRbcST11243bp-Fwd | Nucleic acid | GGGGACAAGTTTGTACAAAAAAGCAGGCTATTAGCATCAA CCGGGTTAGC |
| 8 | NtRbcST_436bp-Fwd | Nucleic acid | GGGGACAAGTTTGTACAAAAAAGCAGGCTTTCATGAATCT CAATATGGAGG |
| 9 | NtRbcST-Rev | Nucleic acid | GGGGACCACTTTGTACAAGAAAGCTGGGTAGTTCACCTTC ACTTTAAGCTAC |
| 10 | RbcsT promoter (1243 nt) | Nucleic acid | ATTAGCATCAACCGGGTTAGCAATTGGGGCATTATTGCGA TCAGCGGGAGGCACCTTGTTGCTGAGCACCAAATTATTCT TTTTGCCGTGATGGCCAGACTCAACGTCAACGTTCAAGTG AGCAGACCAAAAGTTTAACTTTTTTGGGATGGCTTGAAAT TAAGACTTTAAATAATAAGCATAAAATGAGGTGTTATGGA GATTCGGATCAAACCACCACTATTATCCCTAGCCCCACGG TTGATGCCAAACTGTTTATTTCAAAATCGGATAACAATTA CATTTGTATGCGGTTTTAAGAATATGTGATTTAATTCAAC ACGAACAATTAAGAATATCAAATAATCAAATTAGAGATAA AATAATCATCCAAACGAATTGCGATATTATGGCTAACCAT GAGCTTAGACTGACCGATGAGCTCGCTCTTGGTTGACCTT CGAGCCCAGCCGTGAATGAAGTACATAACAAATGAGCAAA AACTTTAACAATAGCTAAAAGGCAGAAAGTAAACTTGTAT TGCTTTGATTTACATATTACAACATGTGTTACAAAAGAAA AACTTCCACCCTTTATATAGTGGAGAGTTTCATCCCCAGT ATAAATCTAAAAAAGGTAAAAATCTTCCTTTGCTGGTAAT TACTAATTCATGATCGACATCGAGTGAGATTTGCACCGTA ATATCCGGTTGATTGCGATATCACGATCCTCTATCTGTCA TGTGTAACCGTTTATCATGCCTCCCGAGATCTTAGAATTC ATTCTTGGACCGGGGTGCATGCCCAATAACAGGCACATTG TTCGCCCTTCATGAATCTCAATATGGAGGGTCTTTAACCT CGATTATAATTTTGTGTATATGTACTCTTCCTCTATTTTC TCGTCGAAAAATCGGAGTAAACATTATCCCCGATTTTACC ATACACATACGTTTTGCCTAAATAAAATGACAAAAGAGAA AGGGTGACGAAAACTGTCACTATGCCTAACTAACCCTCGT AGATACCGTCTTCCGCGAACCCTACACACCCCTAAGGCCC |

TABLE 1-continued

Sequences for this disclosure

| SEQ ID NO | Sequence Description | Sequence Type | Sequence |
|---|---|---|---|
| | | | TAACCCCTTCTTCACCTTACTTTATTAATTACCTCACTCA<br>CTTTTGTCCTCTTATGTAACCGTTTCCAGTTTAATTACAA<br>AAAAATTCAGATTACTTTGAAGCATCACTTCTCTCCCTTT<br>CATATAAACTCAGTTTTTTTGTTCGAGTCTTTATACATAT<br>GTCTTTATCATAACTAAAGTAGTAGCTTAAAGTGAAGGTG<br>AAC |
| 11 | RbcsT promoter (436 nt) | Nucleic acid | TTCATGAATCTCAATATGGAGGGTCTTTAACCTCGATTAT<br>AATTTTGTGTATATGTACTCTTCCTCTATTTTCTCGTCGA<br>AAAATCGGAGTAAACATTATCCCCGATTTTACCATACACA<br>TACGTTTTGCCTAAATAAAATGACAAAAGAGAAAGGGTGA<br>CGAAAACTGTCACTATGCCTAACTAACCCTCGTAGATACC<br>GTCTTCCGCGAACCCTACACACCCCTAAGGCCCTAACCCC<br>TTCTTCACCTTACTTTATTAATTACCTCACTCACTTTTGT<br>CCTCTTATGTAACCGTTTCCAGTTTAATTACAAAAAAATT<br>CAGATTACTTTGAAGCATCACTTCTCTCCCTTTCATATAA<br>ACTCAGTTTTTTTGTTCGAGTCTTTATACATATGTCTTTA<br>TCATAACTAAAGTAGTAGCTTAAAGTGAAGGTGAAC |
| 12 | NtPSO 1.5 kb promoter | Nucleic acid | AAAATATTTGAAAGAAAATATTGTAGCTAAATGAATATTT<br>TTCCTTCAAGTTATTAAAAGTTGTGGCAATATAGGTTAAA<br>TTAGCCACATGTTTCTTGCTTTAATAGAATTTTGTAGCTA<br>ATCATTAACTTTTACCACGAGTTGAAACTTAATATAACAA<br>CAATAACCTTTTAACCATAATAAACCATTTAAATCAAATA<br>TTACTAAATAAATAACTTTGCTTCAAGTTCTATAAAATCA<br>TGGCAATAGTCATTACGATAAAATGATATAACCACGAATA<br>TATTGCAACGATAAATTCTGTAACTAATCATTAGTTTTTG<br>CGACGAGGTAAATTTTCCGTCACAGTAGCAATCTTCTAGG<br>CACATTAAAAATTTGAAACAAAATTTTGTAGTCAAATAAA<br>TATTTATCTTCTTATTTTAAGAAAATAAAAATAGTTAGAT<br>AATAGTTACTACTATTTGTCATGAAAATATCAATAGATAC<br>AAATTTAAAGTGACTATAAATTTACGAGTTTACTATACTT<br>TAGTCGTACAGTTTGCAATAATAGTATTTTAACCACAATT<br>AGTTATATGTACAAAATTTCATAAGTGAATAACTTTTTTT<br>CAATGACAAAAATAAGAGTTGCTCAAACAATATCAAGTTA<br>CAAAAATTTAATTTTAACTGTAAAAGTTATATTTTTCCAA<br>AATAACATAAACTATAGTAATTATATATAGTTTGAAGTAT<br>TAATAAATTTAAATATGCAAAAGTTAATTTTAATAAACC<br>ATTTGTATGCCTACTTGTAGCCTCTAAACTATTTTATTTG<br>CTTTATTTATCAAACTCATATTTTATTTTATTGCACCTTG<br>TTAGTTTTGGACGTTAATTATATATATTTGGTGTAAAATT<br>TAAAATATATTAACATTTGTGGAGAATTTATGTATGCCTG<br>GTTCTTAACTATTTTTTTTTATATAACTGGTTAGAGTAA<br>TTTCTTATATTTCAGTATTTATTTTTAAATAAGTCCTCAT<br>AAATTGAAGACTTTAAAAGTTTTTGTGTCATTCCTCTTTT<br>TATTTAAGAAATTGAAGAATTCCGCTAAATTTCATATTCC<br>GCTGTTATTTAACTGTTTATTCCCTTGTTAATATAATTGG<br>TAAGAAGTTTTAAAATAAAGGAGTTAATGATTTCTAGGTT<br>CATGGCTTGCCTAGCTTCTACGAGTAAGCGCCATCACGAC<br>TCCCGAGGATAAGGAAATCCGGGTCGTAGCATTCACTCAC<br>AAAAATTACTAAAACAAAGTTTACCCTTCTCCCAAAAGT<br>AAATTTCATATTTGGCTCCACATAATGTGTTCAATGAGTC<br>AAGTGAAGTACTTTTCATTGACAAAAAAAAGTTGCTGAAA<br>AATGCATATCTCATATTTTTTTTTTAGAGAAATCCCAT<br>TTCTTGCCTAAACGAAATGCCTATAAAAGAGCATATATTT<br>GCAACAACAGTTTGCAGAAACTATCAAGTCAAATAATCCC<br>CCCTTTAATTCCCTCCCAAA |
| 13 | NtPSO 1.0 kb promoter | Nucleic acid | TTTACGAGTTTACTATACTTTAGTCGTACAGTTTGCAATA<br>ATAGTATTTTAACCACAATTAGTTATATGTACAAAATTTC<br>ATAAGTGAATAACTTTTTTTCAATGACAAAAATAAGAGTT<br>GCTCAAACAATATCAAGTTACAAAAATTTAATTTTAACTG<br>TAAAAGTTATATTTTTCCAAAATAACATAAACTATAGTAA<br>TTATATATAGTTTGAAGTATTAATAAAATTTAAATATGCA<br>AAAGTTAATTTTAATAAACCATTTGTATGCCTACTTGTAG<br>CCTCTAAACTATTTTATTTGCTTTATTTATCAAACTCATA<br>TTTTATTTTATTGCACCTTGTTAGTTTTGGACGTTAATTA<br>TATATATTTGGTGTAAAATTTAAAATATATTAACATTTGT<br>GGAGAATTTATGTATGCCTGGTTCTTAACTATTTTTTTT<br>TATATAACTGGTTAGAGTAATTTCTTATATTTCAGTATTT<br>ATTTTTAAATAAGTCCTCATAAATTGAAGACTTTAAAAGT<br>TTTTGTGTCATTCCTCTTTTTATTTAAGAAATTGAAGAAT<br>TCCGCTAAATTTCATATTCCGCTGTTATTTAACTGTTTAT<br>TCCCTTGTTAATATAATTGGTAAGAAGTTTTAAAATAAAG<br>GAGTTAATGATTTCTAGGTTCATGGCTTGCCTAGCTTCTA |

TABLE 1-continued

Sequences for this disclosure

| SEQ ID NO | Sequence Description | Sequence Type | Sequence |
|---|---|---|---|
| | | | CGAGTAAGCGCCATCACGACTCCCGAGGATAAGGAAATCC<br>GGGTCGTAGCATTCACTCACAAAAATTACTAAAAACAAAG<br>TTTACCCTTCTCCCAAAAGTAAATTTCATATTTGGCTCCA<br>CATAATGTGTTCAATGAGTCAAGTGAAGTACTTTTCATTG<br>ACAAAAAAAGTTGCTGAAAAATGCATATCTCATATTTTT<br>TTTTTTTAGAGAAATCCCATTTCTTGCCTAAACGAAATGC<br>CTATAAAAGAGCATATATTTGCAACAACAGTTTGCAGAAA<br>CTATCAAGTCAAATAATCCCCCCTTTAATTCCCTCCCAAA<br>ACCAGAATCACCATACAAAGCTATTTCCAGACTCGGAATC<br>CCAAATAGACATCAATAGCACTGAAATGCACTTCAACCCA<br>ATCGTATGAAATTCTTCCAAAAAGGCTAACTTCCACAATA<br>AGTGCCAAAACGATCTCGGGTAATTCCAAACCCGATCTGG<br>ACACACACCCAAGTCCAAAATAATCATACAAACCTGTTAA<br>AACATTCAAATCCCGATTCCGAGGTCAATTACTGAAAAT<br>CCTATCCTAGTTAATTCTTCCAACTAAAAGCTTCCAAAAT<br>GAGAATTCTATTTCCAAATAAACTCTGAACTTCCCGGAAT<br>TCAATTTTGACTATGCGTACAAGTCATAATACCTGAATTG<br>AAGCTGCAGATAGCCTCAAATCGCTAAACAACGTGCTAGG<br>TCTCAAAACGCCCTGTCGGGTCGTTACATTATAGGTGATT<br>AACTACGTATATACTTGTGCAAGTGTTCTATCATAATTCA<br>GGCCAACTAGTAAGAGTAGAAACAATGAATGGCACATAAC<br>AAACGATCACCACGAAATGTACATGATATAACTCACACAA<br>GGTAGGCACGCTACTAGACAATTACCAATAACAACAATGC |
| 14 | NtPHY 1.5 kb promoter | Nucleic acid | CTAGGACATCACAAGATATGACAAATCAATCCTTACTATC<br>ACGGTTGAGTTGTAACGTGCAAGAATATTTCACTCTTTTT<br>AGGGCACTAAGATCACTCCACCAACATTTCAAGAGAATCC<br>CTGGCACTGCTAAAAAGCCCTCTACACTGTAGTGAATTTT<br>TCTTAGTTATCTAAAGTTAATTATTCATTTAGTATTCTTT<br>ACATTAGGTTCCCCCTTCTAGGTCCTGCACGTAACTAGAT<br>TGAATGGATTGGTCCACTCTATTATTATAGAGTAATTATT<br>AAATTTTTATTTGACTAGGCATCACTAGTTGCACTATCAA<br>CAAAGTATTAGTTCTAGCCTTCTGGGTACTTCATACCTAT<br>GCAAATGATAATTTTATTAAAACAATAGATGTACATGGAT<br>ATAAATACCTATGAAAATTAAATAAATTATAACTAAGAAA<br>AAAACTTTAAAGTTCACTCCTAAGATATCGGGTTATTACA<br>TGACCAAACACAATTTGTTTATCAAATACTTTCAAAAGAA<br>TTTGCCAAACGTAAATTATTTTTCTCCAAAGTGACTTATG<br>AATTACTATGTTGATAAAATACTTTTCAAAGTAACTAATG<br>TTTAGAAGTCAAGGATGGGCTTCTTTTGATTATTGAAGTT<br>TGTAGCAATTGTATGTAGTTATAGTCAGGGTGACCACCAG<br>CATCTCATATAGCAATACACAAGTGGATTAGCGCATTTTA<br>AATTTCAATTAGTTCATGCAAATATACACGTAATAGCATT<br>ATAAGCCACTTTCACAACAGGCAGATTAGTGGTTTTGAAA<br>TTTCAACCAATGATATATACTATAAATTGATCAAGCACAA<br>ACCTTAATTGAGCAACACAATTTCTTACAGCAATAACTAT<br>CACATATAACAATAACTGCC |
| 15 | NtPHY 0.5 kb promoter | Nucleic acid | ATAAATACCTATGAAAATTAAATAAATTATAACTAAGAAA<br>AAAACTTTAAAGTTCACTCCTAAGATATCGGGTTATTACA<br>TGACCAAACACAATTTGTTTATCAAATACTTTCAAAAGAA<br>TTTGCCAAACGTAAATTATTTTTCTCCAAAGTGACTTATG<br>AATTACTATGTTGATAAAATACTTTTCAAAGTAACTAATG<br>TTTAGAAGTCAAGGATGGGCTTCTTTTGATTATTGAAGTT<br>TGTAGCAATTGTATGTAGTTATAGTCAGGGTGACCACCAG<br>CATCTCATATAGCAATACACAAGTGGATTAGCGCATTTTA<br>AATTTCAATTAGTTCATGCAAATATACACGTAATAGCATT<br>ATAAGCCACTTTCACAACAGGCAGATTAGTGGTTTTGAAA<br>TTTCAACCAATGATATATACTATAAATTGATCAAGCACAA<br>ACCTTAATTGAGCAACACAATTTCTTACAGCAATAACTAT<br>CACATATAACAATAACTGCC |
| 16 | NtCYC 1.5 kb promoter | Nucleic acid | TAATACTTATTTTGTAAGAATTGCAATATTGTTATTTTTG<br>TTATGGACTTAAATATTAACCATGTTATAATCTTAAGTTT<br>ATATTATTAGAAAAACTTAGTTTTTGAAAGACTAATATGA<br>ACATTAGTACTTATTTCAAAAATAAGCACCTAGATATATG<br>AAATTACTTTAAGTACTTATTTAAAATAATTAAGTACCAC<br>ACATACATACATATCTCTACAAACTGTTAAAGTTTTCTAT<br>ATGAGTACTTATTTTAAAATAAGAGCTTAAATATAATAAA<br>TTATGTTAAATTTCTTATTTAAAATAATAAAGGACCAAAC<br>ATGCATAAAATAAAGTATGAGCTTAATAAGTCAAGAAGCT<br>AATTGATAAGCATTGATGCCAAATGCACTTACTAACTTTT<br>CTATATTGTAGGAAAAATCTAACTTTTATATTTAAAATTT<br>ATTTTTGTAAAACTTCTCTAATTTTTGGACAAACTCTTAT<br>ATTGATTTTTAATCAAAGCCAAAATATTTTATTTAACTAT |

TABLE 1-continued

Sequences for this disclosure

| SEQ ID NO | Sequence Description | Sequence Type | Sequence |
|---|---|---|---|
| | | | GAAAAAATTTTAACAACTAATTTATTATGGTAAATAATAT
TGATATGGTAACTTCAAGCACATGACAAAAATTATAACTA
ACTGCAGAAGTTTATTGTCTCTCTGAATCTTGTGGCTATA
TCATAACAAATACTTGTAGCTAATAAGCCAACGATGTTCT
CGGTTTCATATAATTTGAATTTTAAAATAGTTTTTAAATT
TAATATTTATTTCAAATCATTATTGTGGCTAACATGTTAT
AATCGCAGTAATATTTGGAGATGCAATACTTATATTTAGC
TACAAAATTTTATTGTATCAGAATAAGTTTGTAGCTATTA
AGTTAGTTTTTGCCACAAATTTTTATAATTGAAGCAAAAA
TACCTATTCAGCTACAGTATTTTGTATCGAGTAATATTTT
GTGACTAGAAGATTAATATTGCTACAGTAATTTCAGACGT
GTGGCAAAAACTCATAATTAGCTACAAAATATTGTCGTAG
CAATAATTTTTTATATCTATTAATGCAATTATTACTACAT
GCTTTTATAACTTGAGGCAAAAATATCTAATAGCTATAAC
ATTTTGTTAGAAGTAATTTTTGTGGCTATAAAATTGGTAT
TGCTACAGTAATTTCAAATGCGTGGCAAAAAAATACGATT
AACTACGAAATTTATTGTAGCAATAACNTATTGTAGCAA
TAAATTTGTAGCTATTTGGGTAATATTGCTACGACAGTTA
GCAATTATAGCAAAAATGCTAAATTAGCTTTGTTAATTTA
ATTTTGTAGCTAAACTTTTTTATGAAATTTTAATTTTTGT
GGCTATTGTTAGGTATTAGCTACAATTTTCATATATGTAG
CTAAGAATTTGTAGCTATATATACATAATGTTGTAGTGGC
AAATTCTAACATTGTACGCTTGGCTGCCCTTTTTTTTTG
GCTACAAAACTCTAAAGTAAAGGAACTAGAAAACTCGTTT
GGCGAGAGAAAGAGAGAGAG |
| 17 | NtCYC 0.5 kb promoter | Nucleic acid | CAATAATTTTTTATATCTATTAATGCAATTATTACTACAT
GCTTTTATAACTTGAGGCAAAAATATCTAATAGCTATAAC
ATTTTGTTAGAAGTAATTTTTGTGGCTATAAAATTGGTAT
TGCTACAGTAATTTCAAATGCGTGGCAAAAAAATACGATT
AACTACGAAATTTATTGTAGCAATAACNTATTGTAGCAA
TAAATTTGTAGCTATTTGGGTAATATTGCTACGACAGTTA
GCAATTATAGCAAAAATGCTAAATTAGCTTTGTTAATTTA
ATTTTGTAGCTAAACTTTTTTATGAAATTTTAATTTTTGT
GGCTATTGTTAGGTATTAGCTACAATTTTCATATATGTAG
CTAAGAATTTGTAGCTATATATACATAATGTTGTAGTGGC
AAATTCTAACATTGTACGCTTGGCTGCCCTTTTTTTTTG
GCTACAAAACTCTAAAGTAAAGGAACTAGAAAACTCGTTT
GGCGAGAGAAAGAGAGAGAG |
| 18 | Geranylgeranyl diphosphate synthase (g49326) | Amino acid | MAFLATISGHENMLLSNTLNNNFIFSGKPPQRHSYSFLPK
KIQARSVANSSKTFQVKEEEFSSKTEKFILPKFDFEEYMK
MKAIKVNKALDDAIPMQEPIKIHEAMRYSLLAGGKRVRPI
LCMASCEVVGGDESLAIPAACSVEMIHTMSLIHDDLPCMD
NDDLRRGKPTSHKAFGEDTAVLTGDALLSLAFEHVASKTK
DVTPQRVVQAVGELGSAVGSKGLVAGQIVDIASEGKQVSL
TELEYIHNHKTGKLLEAAVVCGAIIGGGNEIEVERMRNYA
RCLGLLFQVVDDILDVTKSSEELGKTAGKDLVTDKATYPK
LMGLEKARELAGELVAKAMDELSYFDAAKAAPLYHFANYI
AHRQN |
| 19 | 8-hydroxy-copalyl diphosphate synthase (HE588139) | Amino acid | MQVIITSSHRFFCHHLHQLKSPTSLSAQKAEFKKHGPRNW
LFQTEGSLLYKPVRLNCATSDASYLGNVNEYLESDHSKNS
EEKDIQVSRTIQMKGLTEEIKHMLNSMEDGRLNVLAYDTA
WVSFIPNTTNNGNDQRPMFPSCLQWIIDNQLSDGSWGEEI
VFCIYDRLLNTLVCVIALTLWNTCLHKRNKGVMFIKENLS
KLETGEVENMTSGFELVFPTLLEKAQQLDIDIPYDAPVLK
DIYARREVKLTRIPKDVIHTIPTTVLFSLEGLRDDLDWQR
LLKLQMPDGSFLISPASTAFAFMETNDEKCLAYLQNVVEK
SNGGARQYPFDLVTRLWAIDRLQRLGISYYFAEEFKELLN
HVFRYWDEENGIFSGRNSNVSDVDDTCMAIRLLRLHGYDV
SPDALNNFKDGDQFVCFRGEVDGSPTHMENLYRCSQVLFP
GEKILEEAKNFTYNFLQQCLANNRCLDKWVIAKDIPGEIW
YALEFPWYASLPRVEARYYIEQYGGADDIWIGKTLYRMPD
VNNNVYLQAAKLDYNRCQSQHRFEWLIMQEWFEKCNFQQF
GISKKYLLVSYFLAAASIFEVEKSRERLAWAKSRIICKMI
TSYYNDEATTWTTRNSLLMEFKVSHDPTRKNGNETKEILV
LKNLRQFLRQLSEETFEDLGKDIHHQLQNAWETWLVFLRE
EKNACQEETELLVRTINLSGGYMTHDEILFDADYENLSNL
TNKVCGKLNELQNDKVTGGSKNTNIELDMQALVKLVFGNT
SSNINQDIKQTFFAVVKTFYYSAHVSEEIMNFHISKVLFQ
QV |

TABLE 1-continued

Sequences for this disclosure

| SEQ ID NO | Sequence Description | Sequence Type | Sequence |
|---|---|---|---|
| 20 | Cis-abienol synthase ISOFORM 1 | Amino acid | MVLGLRSKIIPLPDHKLGNIKLGSVTNAICHRPCRVRCSH STASSMEEAKERIRETFGKIELSPSSYDTAWVAMVPSRYS MNQPCFPQCLDWILENQREDGSWGLNPSHPLLVKDSLSST LASLLALRKWRIGDNQVQRGLGFIETHGWAVDNKDQISPL GFEIIFPCMINYAEKLNLDLPLDPNLVNMMLCERELTIER ALKNEFEGNMANVEYFAEGLGELCHWKEMMLRQRHNGSLF DSPATTAAALIYHQYDEKCFGYLNSILKLHDNWVPTICPT KIHSNLFLVDALQNLGVDRYFKTEVKRVLDEIYRLWLEKN EEIFSDVAHCAMAFRLLRMNNYEVSSEELEGFVDQEHFFT TSSGKLMNHVAILELHRASQVAIHERKDHILDKISTWTRN FMEQKLLDKHIPDRSKKEMEFAMRKFYGTFDRVETRRYIE SYKMDSFKILKAAYRSSGINNIDLLKFSEHDENLCQTRHK EELQQMKRWFTDCKLEQVGLSQQYLYTSYFIIAAILFEPE YADARLAYAKYAIIITAVDDFFDCFICKEELQNIIELVER WEGYSTVGFRSERVRIFFLALYKMVEEIAAKAETKQGRCV KDHLINLWIDMLKCMLVELDLWKIKSTTPSIEEYLSVACV TIGVPCFVLTSLYLLGPKLSKDVIESSEVSALCNCTAAVA RLINDIHSYKREQAESSTNMVSILITQSQGTISEEEAIRQ IKEMMESKRRELLGMVLQNKESQLPQVCKDLFWTTINAAY SIHTHGDGYRFPEEFKNHINDVIYKPLNQYSP |
| 21 | Cis-abienol synthase ISOFORM 2 | Amino acid | MILGLRSKIIPLPDHKLGNIKLGSVTNAICHRPCRVRCSH STASSMEEAKERIRETFGKIELSPSSYDTAWVAMVPSRYS MNQPCFPQCLDWILENQREDGSWGLNPSHPLLVKDSLSST LASLLALRKWRIGDNQVQRGLGFIETHGWAVDNKDQISPL GFEIIFPCMINYAEKLNLDLPLDPNLVNMMLCERELTIER ALKNEFEGNMANVEYFAEGLGELCHWKEMMLRQRHNGSLF DSPATTAAALIYHQYDEKCFGYLNSILKLHDNWVPTICPT KIHSNLFLVDALQNLGVDRYFKTEVKRVLDEIYRLWLEKN EEIFSDVAHCAMAFRLLRMNNYEVSSEELEGFVDQEHFFT TSSGKLMNHVAILELHRASQVAIHERKDHILDKISTWTRN FMEQKLLDKHIPDRSKKEMEFAMRKFYGTEDRVETRRYIE SYKMDSFKILKAAYRWEGYSTVGFRSERVRIFFLALYKMV EEIAAKAETKQGRCVKDHLINLWIDMLKCMLVELDLWKIK STTPSIEEYLSVACVTIGVPCFVLTSLYLLGPKLSKDVIE SSEVSALCNCTAAVARLINDIHSYKREQAESSTNMVSILI TQSQGTISEEEAIRQIKEMMESKRRELLGMVLQNKESQLP QVCKDLFWTTINAAYSIHTHGDGYRFPEEFKNHINDVIYK PLNQYSP |
| 22 | Cembratrienol synthase 2a (g58533) | Amino acid | MSQSISPLICSHFAKFQSNIWRCNTSQLRVIHSSYASFGG RRKERVRRMNRAMDLSSSSRHLADFPSTIWGDHFLSYNSE ITEITTQEKNEHEMLKEIVRKMLVETPDNSTQKLVLIDTI QRLGLAYHENDEIENSIQNIFNLSQNSEDDDEHNLYVAAL RFRLARQQGYYMSSDVFKQFTNHDGKFKENHTNDVQGLLS LYEAAHMRVHDEEILEEALIFTTTHLESVIPNLSNSLKVQ VTEALSHPIRKAIPRVGARKYIHIYENIGTHNDLLLKFAK LDENMLQKLHRKELNELTSWWKDLDDRANKFPYAKDRIVEA YFWTVGIYFEPQYSRSRSLVTKVVKMNSIIDDTYDAYATF DELVLFTDAIQRWDEGAMDLLPTYLRPIYQGLLDVENEME EVLAKEGKADHIYYAKKEMKKVAEVYFKEAEWLNANYIPK CEEYMKNGLVSSTGPMYGIISLVVMEEIITKEAFEWLTNE PLILRAASTICRLMDDMADHEVEQQRGHVASFVECYMKEY GVSKQEAYVEMRKKITNAWKDINKELLRPTAVPMFILERS LNFSRLADTFLKDDDGYTNPKSKVKDLIASLFVESVDI |
| 23 | Levopimaradiene synthetase (g33184) | Amino acid | MSCQYYLTTTTSSLRIFSFTPRRYAPNSSASQPHEFFKKQ VLFSSNLQCNAVSRPRAQVIKRDDNVEEVDSAEEQQEEEE TQEVYRSNKIKQHIYAVRLMLQSMDDGEISISAYDTAWVA LVKDINGSDTPQFPSSLEWIANNQLAECSWGDKSIFLAHD RIINTLACVIALKSWNLHIDKRELGMSFIRENLSKIGDEN AVHMPIGFEVAFPSLIEIGKKIGIDIPDDSHVLREIYT |
| 24 | 2-isopropylmalate synthetase (g36718) | Amino acid | MASITINHSFSRNPNISFHPQNPLIQTQALENFKPSISKC SPIIHCAIRRRPEYTPSHIPDPNYIRIFDTTLRDGEQSPG ATMTTKEKLDVARQLAKLGVDIIEAGFPASSEADLEAVKL IAKEVGNGVNEEGHVPVICGLARCNKRDIDKAWEAVKYAK KPRIHTFIATSEIHMKFKLKMSRDEVVEKARSMVAYARSI GCEDVEFSPEDAGRSDPEFLYHILGEVIKAGATTINIPDT VGYTVPSEFGKLIADIKANTPGIGDVIISTHCQNDLGLST ANTLAGACAGARQVEVTINGIGERAGNASLEEVVMALKCR GEQVLGGLYTGINTQHILMSSKMVEEYTGLHVQPHKAIVG ANAFAHESGIHQDGMLKHDTYEIISPEDIGLNRVNESGI VLGKLSGRHALQAKMLELGYDIEGKELEDLFWRFKSVAEK |

TABLE 1-continued

Sequences for this disclosure

| SEQ ID NO | Sequence Description | Sequence Type | Sequence |
|---|---|---|---|
| | | | KKKITDDDLIALMSDEVFQPQFVWQLENVQVTCGSLGLST ATVKLIDADGQEHVSCSVGTGPVDAAYKAVDLIVKVPVAL LEYSLNAVTEGIDAIASTRVLIRGENGHTSTHALTGETVH RSFSGTGADMDIVISSVRAYIGALNKMLSFRKLVSKHSKP EGSAVV |
| 25 | 2-oxoisovalerate dehydrogenase subunit alpha (g63865) | Amino acid | MAILISRSRNFNHFLLSTRFRFLSRLNQTSSKTFSHHAKT SSFTTAAGGGFTKPTATFSGESAAVERVERFQSNKTGEQL NTLYYEEDNHHQIIDENQVMDFPGGQLPITPQMKFIAESS EKRLPCYRVLDDDGYPIPGSIFEEVSKELAVKMYSSMVTL QVMDTIFYEAQRQGRLSFYLTTAGEEGINIASAAALSVDD FVLPQYREVGVILWRGFPLKDIANQLFGNKFDYGKGRQMP CHHGSNELNYLTISSPIATQIPQAAGVAYSLKMDKKEACA ITYLGDGSTSEGDFHAALNFAAVLDAPVVFICRNNGWAIS TPVNEQFRSDGVASKGQAYGIRSIRVDGNDVLATHSAIRA AREMAIKEQKPILVEAMTYRVAHHSTSDDSTKYRPVEEIE HWKTAKSPISRFRKWIQRNGWWNDENESELRGDTRKQVLQ VMQAAEKVEKPPLTDLFTDVYDKVPLNLQEQHKFIRDAVK KSPREYPSDVPI |
| 26 | Neomenthol Dehydrogenase (NtNMD; g29387) | Amino acid | MAEKITSHENTRYAVVTGGNKGIGYETCRQLAKEGIVVVL TARDERRGIEALEKLKEEYSSNKTDDDQILFHQLDVMDPA SISSLVDFIKTKFGKLDILVNNAGIGGLMVEGDVVIIKDL IEGDFVTISAENGEEDGIKKSIEGIERIVTDYELTKQCLE TNFYGAKRMIEAFIPLLQLSNSPRIVNVASFLGKLKLLCN QWAIGMLSDAKSLREERVDEVLNEFIKDFKEKSIEAKGWP TYFSAYKVSKASLIAYTRVLATKYPNFRINSVCPGFCKTD VNCNTGSLTAEEGAESLVKLALVPNDGPSGLFFYRKEVTS F |
| 27 | Geranylgeranyl diphosphate synthase (g49326) | Nucleic acid | ATGGCATTTTTGGCTACCATTTCTGGCCATGAAAATATGC TTCTTTCCAATACCCTAAACAATAACTTTATTTTCAGTGG AAAACCTCCACAGAGACATTCTTATAGTTTCCTCCCCAAG AAAATCCAGGCCAGAAGTGTTGCAAACTCATCCAAAACAT TTCAAGTCAAAGAAGAAGAATTCTCATCTAAGACAGAGAA ATTCATCTTGCCTAAGTTTGACTTTGAAGAATATATGAAA ATGAAGGCAATTAAGGTAAACAAAGCACTAGATGATGCAA TACCAATGCAAGAGCCTATAAAAATTCATGAAGCCATGAG ATACTCACTTCTAGCTGGGGGAAAACGCGTCCGGCCGATC CTATGCATGGCTTCTTGTGAAGTAGTAGGAGGGGATGAAT CCTTAGCTATTCCTGCAGCTTGCTCGGTTGAGATGATCCA CACCATGTCACTCATCCACGACGATCTTCCTTGCATGGAC AACGATGATCTACGTCGTGGCAAGCCCACGAGCCACAAGG CTTTTCGGGGAAGACACTGCAGTTCTAACAGGGGATGCACT TTTGTCTTTGGCCTTTGAACATGTAGCTTCCAAGACTAAA GATGTGACACCCCAAAGAGTGGTTCAAGCCGTTGGCGAAT TGGGTTCAGCCGTTGGCTCGAAAGGGCTTGTGGCGGGGCA GATTGTGGACATAGCTAGTGAGGGAAAACAAGTGAGCCTA ACTGAATTAGAGTACATTCACAACCATAAGACAGGGAAAC TATTGGAGGCTGCTGTGGTTTGTGGGGCAATAATTGGGGG AGGGAATGAGATTGAGGTGGAGAGAATGAGGAACTATGCT AGATGCCTTGGACTGTTGTTTCAAGTGGTAGATGATATTC TTGATGTTACTAAGTCATCAGAAGAGTTGGGAAAGACAGC TGGTAAAGACCTAGTGACTGATAAGGCTACATATCCTAAG TTGATGGGGCTAGAAAAAGCTCGGGAGCTCGCCGGAGAGC TGGTGGCTAAGGCCATGGATGAGCTGAGCTACTTTGATGC TGCCAAGGCGGCACCTCTTTATCATTTTGCTAATTATATT GCACATCGCCAGAATTGA |
| 28 | 8-hydroxy-copalyl diphosphate synthase (HE588139) | Nucleic acid | ATGCAAGTTATAATTACGTCCAGTCACAGATTTTTCTGCC ATCATCTTCATCAGCTCAAGAGTCCTACATCGTTGTCTGC ACAGAAAGCTGAGTTTAAAAAACATGGACCCCGAAATTGG TTGTTCCAAACTGAAGGCTCACTTCTATATAAACCAGTTC GTCTCAATTGTGCAACTAGTGATGCAAGTTATCTTGGTAA TGTGAATGAGTACTTAGAATCTGATCACTCAAAAAACTCC GAAGAAAAGGATATTCAGGTAAGCAGAACAATACAGATGA AAGGTTTGACAGAAGAGATCAAACACATGTTGAATTCGAT GGAGGATGGAAGGTTAAATGTCTTAGCCTATGACACAGCT TGGGTTTCCTTTATTCCAAATACTACTAATAATGGAAATG ATCAAAGACCTATGTTTCCATCTTGTCTTCAATGGATTAT AGACAATCAACTTTCTGATGGTTCATGGGGAGAGGAGATT GTATTCTGCATATATGATCGACTCTTGAACACACTAGTAT GTGTTATTGCATTGACATTATGGAACACGTGCCTTCATAA GAGAAACAAGGTGTGATGTTTATCAAAGAAAACTTAAGC AAGCTAGAGACAGGGGAAGTTGAAAACATGACTAGTGGAT |

TABLE 1-continued

Sequences for this disclosure

| SEQ ID NO | Sequence Description | Sequence Type | Sequence |
|---|---|---|---|
| | | | TTGAACTTGTGTTTCCTACTCTCCTTGAAAAAGCTCAACA<br>ACTAGATATTGACATTCCGTATGATGCTCCAGTCTTAAAG<br>GATATTTATGCAAGGAGAGAAGTAAAGTTAACAAGAATTC<br>CTAAAGATGTTATCCATACGATTCCGACAACAGTATTGTT<br>TTCATTAGAAGGATTAAGGGACGACTTAGACTGGCAAAGA<br>CTTTTAAAGCTTCAAATGCCTGATGGTTCATTCTTAATAT<br>CCCCTGCTTCCACTGCCTTTGCATTCATGGAAACAAATGA<br>TGAAAAGTGTTTGGCATATCTTCAGAACGTTGTTGAAAAG<br>AGTAATGGAGGAGCGCGACAATACCCGTTCGACTTGGTAA<br>CACGACTTTGGGCAATTGATCGATTACAACGCCTTGGAAT<br>CTCTTATTATTTTGCGGAAGAGTTCAAGGAACTTTTGAAT<br>CATGTGTTCAGATACTGGGACGAGGAGAATGGAATTTTTA<br>GTGGAAGGAATTCAAACGTTTCTGATGTTGATGATACATG<br>CATGGCTATAAGGTTGCTAAGGTTACATGGGTATGATGTT<br>AGTCCAGATGCGCTAAACAATTTCAAAGATGGTGATCAAT<br>TCGTTTGCTTCAGAGGTGAAGTGGACGGGTCACCAACACA<br>TATGTTTAATCTCTATAGATGTTCCCAAGTTTTATTCCCA<br>GGAGAAAAGATTCTTGAAGAGGCAAAGAATTTTACTTATA<br>ACTTCTTACAGCAATGTCTTGCAAACAACCGATGCTTAGA<br>CAAATGGGTCATAGCTAAGGACATCCCCGGGGAGATATGG<br>TATGCACTAGAATTTCCATGGTATGCCAGCTTACCTCGGG<br>TGGAAGCTAGGTATTATATAGAACAGTATGGCGGAGCAGA<br>TGATATTTGGATTGGCAAGACGTTATACAGAATGCCCGAT<br>GTCAACAACAATGTTTATTTACAAGCTGCAAAATTGGATT<br>ACAATAGATGCCAAAGTCAACATCGCTTTGAATGGCTGAT<br>TATGCAAGAGTGGTTTGAGAAGTGCAACTTTCAACAATTT<br>GGAATAAGCAAAAGTACCTCCTAGTTTCTTATTTCCTAG<br>CTGCTGCAAGTATATTTGAAGTCGAGAAGTCAAGAGAACG<br>CCTTGCATGGGCTAAATCTCGTATAATATGTAAGATGATT<br>ACATCTTACTACAATGATGAAGCCACAACTTGGACAACTA<br>GGAATTCATTGCTAATGGAATTCAAGGTTTCTCATGATCC<br>GACCAGAAAAAATGGTAATGAAACAAAAGAGATCTTAGTT<br>CTCAAAAATCTTCGTCAGTTTTTGCGCCAACTATCAGAAG<br>AAACTTTTGAAGACCTAGGCAAAGACATCCATCACCAACT<br>ACAAAATGCTTGGGAAACGTGGTTGGTGTTCTTGAGGGAG<br>GAAAAGAATGCATGTCAAGAAGAAACAGAGTTGCTGGTGC<br>GCACAATTAATCTCTCGGGCGGCTATATGACACATGATGA<br>GATATTATTCGATGCGGACTACGAGAATCTGTCCAACCTT<br>ACCAATAAAGTTTGTGGCAAGCTTAATGAGCTCCAAAATG<br>ACAAGGTGACGGGCGGCTCAAAGAACACCAATATTGAACT<br>CGACATGCAAGCTCTCGTAAAGTTAGTGTTTGGTAACACC<br>TCAAGCAACATCAACCAAGACATTAAGCAAACATTTTTTG<br>CAGTTGTGAAGACTTTCTATTACAGTGCGCATGTTAGTGA<br>GGAAATAATGAACTTTCACATATCCAAAGTGCTTTTTCAG<br>CAAGTCTAG |
| 29 | Cis-abienol Synthase Isoform 1 (NtaABS) | Nucleic acid | ATGGTACTTGGACTGAGAAGCAAAATCATACCACTTCCTG<br>ATCATAAGTTGGGAAATATCAAATTAGGTTCAGTAACCAA<br>TGCAATTTGCCACAGACCATGTAGAGTAAGATGCAGCCAC<br>AGTACTGCTTCATCAATGGAAGAGGCAAAGGAGAGAATAA<br>GGGAAACATTTGGAAAATAGAGCTATCTCCTTCTTCCTA<br>TGACACAGCATGGGTAGCTATGGTCCCTTCAAGATATTCT<br>ATGAACCAACCATGTTTTCCTCAGTGCTTAGATTGGATTC<br>TTGAAAATCAAAGAGAAGATGGATCTTGGGGCCTAAATCC<br>TAGCCATCCATTGCTTGTAAAAGACTCCCTTTCTTCCACT<br>CTAGCATCTTTGCTTGCCCTTCGCAAATGGAGAATTGGAG<br>ATAACCAAGTCCAAAGAGGCCTTGGCTTTATTGAAACGCA<br>TGGTTGGGCAGTCGATAACAAGGATCAGATTTCACCTTTA<br>GGATTTGAAATTATATTTCCCTGCATGATCAACTATGCAG<br>AGAAACTTAATTTGGATCTACCTTTGGATCCTAACCTTGT<br>AAATATGATGCTCTGCGAACGTGAATTAACAATTGAAAGA<br>GCCTTAAAGAATGAATTCGAGGGGAATATGGCAAATGTAG<br>AATATTTTGCTGAAGGGCTCGGTGAATTATGTCATTGGAA<br>AGAGATGATGCTTCGTCAGAGACACAACGGGTCGCTCTTT<br>GATTCACCAGCCACTACTGCAGCTGCCTTGATTTACCATC<br>AGTACGATGAGAAATGCTTTGGGTACTTGAACTCAATCTT<br>GAAACTGCACGATAATTGGGTCCCCACTATTTGCCCTACA<br>AAGATACATTCAAATCTCTTCTTAGTTGATGCCCTTCAAA<br>ATCTTGGAGTAGATCGGTATTTTAAAACAGAAGTCAAAAG<br>AGTACTAGATGAAATATACAGGCTTTGGCTAGAAAAGAAT<br>GAAGAAATTTTTTCAGACGTTGCTCATTGTGCCATGGCGT<br>TTCGACTTTTACGGATGAATAACTATGAAGTTTCCTCAGA<br>AGAACTTGAAGGATTTGTCGACCAAGAACATTTCTTTACA<br>ACATCAAGTGGGAAACTTATGAATCACGTTGCAATTCTCG<br>AACTTCACCGAGCTTCACAGGTGGCTATTCATGAAAGGAA |

TABLE 1-continued

Sequences for this disclosure

| SEQ ID NO | Sequence Description | Sequence Type | Sequence |
|---|---|---|---|
| | | | AGATCACATTTTAGATAAAATAAGTACTTGGACAAGGAAT<br>TTTATGGAGCAAAAACTCTTGGACAAGCACATCCCTGATA<br>GGTCAAAGAAGGAGATGGAATTTGCTATGAGGAAATTTTA<br>TGGCACATTTGATCGAGTGGAAACTAGACGTTACATCGAG<br>TCATACAAAATGGACAGTTTTAAGATCTTAAAAGCGGCTT<br>ACAGGTCTTCCGGTATTAACAACATAGACTTGCTAAAGTT<br>CTCAGAACACGATTTTAACTTGTGCCAAACCCGACACAAA<br>GAAGAACTTCAACAGATGAAAAGGTGGTTCACAGATTGCA<br>AACTCGAACAAGTAGGATTATCACAACAGTACTTATACAC<br>TAGTTACTTCATAATTGCTGCCATACTCTTTGAACCTGAA<br>TATGCTGATGCTCGTCTAGCATATGCAAAGTACGCCATAA<br>TAATAACAGCGGTGGATGATTTCTTCGATTGTTTTATTTG<br>CAAAGAAGAACTGCAAAACATCATCGAATTAGTAGAGAGA<br>TGGGAGGGATACTCAACCGTCGGATTCCGTTCAGAGAGGG<br>TTAGAATTTTCTTTTTGGCACTTTACAAAATGGTAGAGGA<br>AATTGCGGCAAAGGCGGAAACTAAGCAAGGTCGATGTGTC<br>AAAGATCACCTTATTAACTTGTGGATTGATATGTTGAAGT<br>GTATGCTGGTGGAATTGGACCTTTGGAAAATTAAATCAAC<br>TACCCCAAGCATAGAGGAGTACTTGTCTGTTGCATGTGTA<br>ACTATTGGTGTTCCATGTTTTGTTCTCACATCACTATATC<br>TTCTTGGACCAAAACTGTCCAAGGATGTCATAGAAAGTTC<br>TGAGGTCAGTGCCTTATGCAATTGTACAGCTGCTGTGGCC<br>CGATTGATTAATGATATACACAGTTACAAGAGAGAACAAG<br>CAGAAAGTTCAACAAATATGGTATCAATATTAATAACACA<br>AAGTCAGGGAACTATCTCTGAAGAAGAGGCTATAAGACAG<br>ATAAAGGAAATGATGGAAAGTAAGAGAAGAGAGTTGCTAG<br>GGATGGTTCTACAAAATAAAGAAAGCCAATTGCCACAAGT<br>GTGCAAGGATCTTTTTTGGACGACAATCAACGCAGCTTAT<br>TCTATACATACACATGGCGATGGGTATCGCTTCCCAGAGG<br>AATTCAAGAACCATATCAACGATGTAATTTACAAACCACT<br>CAATCAATATTCCCCATAA |
| 30 | Cis-abienol Synthase Isoform 2 (NtABS) | Nucleic acid | ATGATACTTGGACTGAGAAGCAAAATCATACCACTTCCTG<br>ATCATAAGTTGGGAAATATCAAATTAGGTTCAGTAACCAA<br>TGCAATTTGCCACAGACCATGTAGAGTAAGATGCAGCCAC<br>AGTACTGCTTCATCAATGGAAGAGGCAAAGGAGAGAATAA<br>GGGAAACATTTGGAAAAATAGAGCTATCTCCTTCTTCCTA<br>TGACACAGCATGGGTAGCTATGGTCCCTTCAAGATATTCT<br>ATGAACCAACCATGTTTTCCTCAGTGCTTAGATTGGATTC<br>TTGAAAATCAAAGAGAAGATGGATCTTGGGGCCTAAATCC<br>TAGCCATCCATTGCTTGTAAAAGACTCCCTTTCTTCCACT<br>CTAGCATCTTTGCTTGCCCCTTCGCAAATGGAGAATTGGAG<br>ATAACCAAGTCCAAAGAGGCCTTGGCTTTATTGAAACGCA<br>TGGTTGGGCAGTCGATAACAAGGATCAGATTTCACCTTTA<br>GGATTTGAAATTATATTTCCCTGCATGATCAACTATGCAG<br>AGAAACTTAATTTGGATCTACCTTTGGATCCTAACCTTGT<br>AAATATGATGCTCTGCGAACGTGAATTAACAATTGAAAGA<br>GCCTTAAAGAATGAATTCGAGGGGAATATGGCAAATGTAG<br>AATATTTTGCTGAAGGGCTCGGTGAATTATGTCATTGGAA<br>AGAGATGATGCTTCGTCAGAGACACAACGGGTCGCTCTTT<br>GATTCACCAGCCACTACTGCAGCTGCCTTGATTTACCATC<br>AGTACGATGAGAAATGCTTTGGGTACTTGAACTCAATCTT<br>GAAACTGCACGATAATTGGGTCCCCACTATTTGCCCTACA<br>AAGATACATTCAAATCTCTTCTTAGTTGATGCCCTTCAAA<br>ATCTTGGAGTAGATCGGTATTTTAAAACAGAAGTCAAAAG<br>AGTACTAGATGAAATATACAGGCTTTGGCTAGAAAAGAAT<br>GAAGAAATTTTTTCAGACGTTGCTCATTGTGCCATGGCGT<br>TTCGACTTTTACGGATGAATAACTATGAAGTTTCCTCAGA<br>AGAACTTGAAGGATTGTCGACCAAGAACATTTCTTTACA<br>ACATCAAGTGGGAAACTTATGAATCACGTTGCAATTCTCG<br>AACTTCACCGAGCTTCACAGGTGGCTATTCATGAAAGGAA<br>AGATCACATTTTAGATAAAATAAGTACTTGGACAAGGAAT<br>TTTATGGAGCAAAAACTCTTGGACAAGCACATCCCTGATA<br>GGTCAAAGAAGGAGATGGAATTTGCTATGAGGAAATTTTA<br>TGGCACATTTGATCGAGTGGAAACTAGACGTTACATCGAG<br>TCATACAAAATGGACAGTTTTAAGATCTTAAAAGCGGCTT<br>ACAGATGGAGGGATACTCAACCGTCGGATTCCGTTCAGA<br>GAGGGTTAGAATTTTCTTTTTGGCACTTTACAAAATGGTA<br>GAGGAAATTGCGGCAAAGGCGGAAACTAAGCAAGGTCGAT<br>GTGTCAAAGATCACCTTATTAACTTGTGGATTGATATGTT<br>GAAGTGTATGCTGGTGGAATTGGACCTTTGGAAAATTAAA<br>TCAACTACCCCAAGCATAGAGGAGTACTTGTCTGTTGCAT<br>GTGTAACTATTGGTGTTCCATGTTTTGTTCTCACATCACT<br>ATATCTTCTTGGACCAAAACTGTCCAAGGATGTCATAGAA<br>AGTTCTGAGGTCAGTGCCTTATGCAATTGTACAGCTGCTG |

TABLE 1-continued

Sequences for this disclosure

| SEQ ID NO | Sequence Description | Sequence Type | Sequence |
|---|---|---|---|
| | | | TGGCCCGATTGATTAATGATATACACAGTTACAAGAGAGA
ACAAGCAGAAAGTTCAACAAATATGGTATCAATATTAATA
ACACAAAGTCAGGGAACTATCTCTGAAGAAGAGGCTATAA
GACAGATAAAGGAAATGATGGAAAGTAAGAGAAGAGAGTT
GCTAGGGATGGTTCTACAAAATAAAGAAAGCCAATTGCCA
CAAGTGTGCAAGGATCTTTTTTGGACGACAATCAACGCAG
CTTATTCTATACATACACATGGCGATGGGTATCGCTTCCC
AGAGGAATTCAAGAACCATATCAACGATGTAATTTACAAA
CCACTCAATCAATATTCCCCATAA |
| 31 | Cembratrienol synthase 2a (g58533) | Nucleic acid | ATGAGTCAATCAATTTCTCCATTAATCTGTTCTCACTTTG
CGAAATTTCAGTCGAATATTTGGAGATGCAATACTTCTCA
ACTCAGAGTTATACACTCATCATATGCCTCTTTTGGAGGG
AGAAGAAAAGAGAGAGTAAGAAGAATGAATCGAGCAATGG
ATCTTTCTTCAAGCTCTCGTCATTTGGCAGATTTTCCCTC
AACAATTTGGGGTGACCATTTTCTCTTCCTACAATTCTGAA
ATAACAGAAATTACTACCCAAGAGAAAAATGAACATGAAA
TGCTAAAAGAAATAGTTCGGAAAATGTTGGTAGAAACTCC
AGATAATAGTACACAAAAACTAGTCTTGATTGACACAATT
CAAAGATTGGGATTAGCATATCATTTCAATGATGAGATTG
AAAACTCCATTCAAAACATCTTTAATTTGTCTCAAAATAG
TGAAGATGACGATGAACAACCTTTATGTTGCTGCTCTT
CGTTTTCGACTTGCGAGGCAACAAGGATATTACATGTCTT
CAGATGTGTTCAAGCAATTCACTAACCATGACGGAAAATT
CAAGGAAAATCATACTAATGATGTTCAAGGATTATTGAGT
TTGTATGAAGCAGCACATATGAGAGTGCACGACGAGGAAA
TTCTAGAAGAAGCTCTTATCTTTACCACGACTCATCTCGA
GTCCGTGATCCCGAATTTGAGCAACTCGCTTAAGGTACAA
GTTACTGAAGCCTTAAGCCATCCTATTCGCAAAGCTATAC
CAAGGGTGGGAGCAAGGAAATACATACACATATATGAAAA
CATTGGAACACATAATGATTTACTTTTGAAATTTGCAAAG
TTGGACTTCAACATGTTACAAAAGCTTCATCGAAAAGAGC
TTAACGAGCTAACAAGCTGGTGGAAAGATTTGGATCGTGC
AAACAAATTTCCATATGCAAAGGACAGATTAGTAGAAGCT
TACTTTTGGACGGTGGGAATATATTTTGAACCTCAATATA
GTCGTTCAAGAAGTTTGGTAACAAAAGTAGTCAAATGAA
CTCCATTATTGATGACACTTATGATGCTTATGCAACTTTT
GATGAGCTTGTGCTTTTCACGGATGCGATCCAAAGATGGG
ACGAAGGTGCCATGGATTTATTACCGACATATCTGAGACC
TATTTATCAAGGCCTTCTCGACGTTTTCAATGAAATGGAA
GAAGTATTGGCCAAAGAAGGTAAAGCAGATCACATCTACT
ATGCGAAAAAGAGATGAAAAAGGTGGCGGAAGTCTATTT
TAAGGAAGCTGAATGGTTGAATGCTAACTACATTCCAAAA
TGCGAGGAGTATATGAAAAATGGACTTGTAAGCTCTACCG
GTCCGATGTATGGAATAATTTCTTTGGTTGTTATGGAGGA
AATTATAACAAAAGAGGCTTTTGAATGGTTGACAAATGAA
CCTTTGATTCTTCGAGCTGCATCAACAATTTGTAGATTAA
TGGATGATATGGCTGATCATGAAGTTGAACAACAAAGAGG
ACATGTTGCTTCATTTGTTGAGTGCTACATGAAAGAATAT
GGAGTTTCAAAGCAAGAAGCATATGTTGAGATGCGGAAAA
AAATCACAAATGCGTGGAAAGATATAAATAAGGAACTCTT
GCGCCCTACTGCAGTACCAATGTTTATCCTCGAACGATCT
TTAAATTTTTCAAGATTGGCCGATACATTTTTGAAAGATG
ATGATGGATACACAAATCCCAAATCCAAAGTTAAAGACTT
GATTGCTTCGTTGTTTGTCGAATCTGTCGACATATGA |
| 32 | Levopimaradiene synthetase (g33184) | Nucleic acid | ATGTCTTGTCAATATTACTTAACCACGACGACCTCTTCTC
TCAGAATATTCTCCTTCACCCCCCGCCGTTACGCACCGAA
TTCTTCTGCAAGTCAACCTCATGAGTTCTTTAAAAAACAA
GTACTTTTCAGTTCCAATCTGCAATGCAATGCGGTTTCAA
GACCTCGCGCACAAGTTATCAAGCGGGACGACAACGTGGA
AGAAGTAGACAGTGCAGAAGAACAACAAGAAGAAGAAGAA
ACACAAGAGGTGTACAGATCAAATAAGATAAAGCAACATA
TTTATGCCGTCCGGTTAATGTTGCAAAGTATGGATGATGG
AGAGATAAGTATATCAGCTTATGACACAGCTTGGGTTGCT
CTTGTGAAAGACATTAATGGAAGCGATACTCCTCAATTCC
CTTCAAGTCTTGAATGGATTGCCAACAATCAACTTGCTGA
ATGTTCGTGGGTGACAAGTCCATCTTTTTGGCTCACGAT
CGAATCATCAACACATTGGCCTGTGTTATTGCTTTGAAAT
CTTGGAATTTGCACATTGACAAAAGAGAACTAGGAATGTC
GTTTATCAGAGAGAATTTAAGCAAGATTGGAGATGAAAAT
GCTGTGCATATGCCAATAGGATTTGAAGTGGCGTTTCCTT
CACTAATTGAGATTGGAAAAAAGATAGGCATTGATATTCC
GGATGATTCTCATGTCTTGAGAGAGATATATACCTGA |

TABLE 1-continued

Sequences for this disclosure

| SEQ ID NO | Sequence Description | Sequence Type | Sequence |
|---|---|---|---|
| 33 | 2-isopropylmalate synthetase (g36718) | Nucleic acid | ATGGCGTCTATCACCATAAACCATTCATTTTCCCGTAACC CTAACATCTCATTCCATCCCCAAAATCCTCTCATTCAAAC CCAAGCTCTCTTCAATTTCAAACCATCAATCTCCAAATGT TCCCCTATTATCCACTGCGCAATCCGCCGTCGACCCGAAT ATACCCCGAGCCACATTCCCGACCCGAACTACATTCGCAT CTTCGACACCACTCTCCGCGACGGCGAACAATCCCCAGGC GCCACAATGACCACAAAAGAAAAACTCGACGTTGCGCGTC AGTTAGCTAAGCTTGGTGTTGACATAATTGAAGCCGGTTT TCCTGCTTCTTCTGAAGCTGATCTCGAAGCTGTGAAATTA ATAGCGAAGGAAGTTGGAAATGGTGTGAATGAAGAGGGAC ATGTTCCGGTAATTTGTGGACTTGCGAGGTGTAATAAGAG GGATATTGATAAGGCTTGGGAGGCTGTGAAGTATGCGAAA AAACCGAGGATTCATACGTTTATTGCGACTAGTGAGATAC ATATGAAGTTTAAGTTGAAGATGAGTAGAGATGAAGTTGT GGAGAAAGCTAGGAGTATGGTTGCTTATGCTAGGAGTATT GGTTGTGAGGATGTTGAATTTAGCCCAGAAGATGCTGGAA GATCCGATCCAGAGTTCCTCTATCATATCCTTGGAGAGGT CATCAAAGCTGGGGCAACAACCCTTAACATCCCTGATACT GTTGGATACACTGTTCCCAGCGAATTTGGAAAATTGATTG CTGATATAAAGGCCAATACCCCAGGAATTGGAGATGTGAT CATCTCAACACACTGCCAGAACGATCTTGGGCTTTCTACT GCCAACACCTTAGCTGGAGCATGCGCAGGTGCAAGACAAG TAGAAGTGACCATCAACGGAATCGGTGAAAGAGCTGGAAA TGCTTCTTTTGGAGGAGGTTGTAATGGCCTTAAAATGTCGT GGGAGAGCAAGTACTAGGTGGCCTGTATACAGGAATTAATA CACAACATATACTCATGTCAAGCAAGATGGTAGAGGAGTA CACCGGGCTTCATGTGCAGCCACACAAGGCCATTGTTGGA GCTAATGCGTTTGCTCATGAAAGTGGCATCCATCAGGATG GAATGTTAAAACACAAAGATACATATGAGATTATATCTCC TGAAGATATTGGGCTTAACCGAGTTAATGAATCTGGCATC GTCCTTGGGAAACTCAGTGGGCGTCATGCTTTGCAAGCCA AAATGCTCGAGCTTGGATACGATATTGAGGGAAAAGAACT TGAGGACCTCTTTTGGCGATTCAAATCTGTGGCCAGAGAG AAAAAGAAAATTACAGATGATGACCTGATAGCATTAATGT CAGATGAAGTTTTCCAGCCTCAATTTGTTTGGCAACTTGA AAATGTACAGGTTACATGTGGAAGTCTTGGCCTTTCTACG GCAACTGTTAAGCTCATTGACGCTGATGGTCAAGAGCATG TTTCTTGTTCTGTTGGAACGGGGCCAGTTGATGCGGCTTA TAAGGCAGTTGATCTCATTGTAAAGGTACCTGTAGCACTC CTTGAATATTCCTTGAATGCAGTCACGGAAGGTATAGATG CCATAGCTTCAACCAGAGTTTTAATTCGTGGGGAGAATGG CCATACATCAACCCATGCTTTAACTGGAGAGACTGTACAC CGTTCTTTTAGTGGAACCGGAGCAGATATGGATATTGTTA TCTCCAGTGTCCGAGCCTATATTGGTGCATTGAATAAGAT GTTGAGTTTCAGAAAGCTGGTATCGAAACACAGCAAACCT GAAGGCAGTGCAGTCGTATAG |
| 34 | 2-oxoisovalerate dehydrogenase (g63865) | Nucleic acid | ATGGCGATTTTGATATCAAGATCAAGAAACTTTAACCATT TTCTTCTAAGCACAAGGTTTCGTTTCTTATCACGCCTAAA CCAAACAAGTTCAAAAACATTTTCCCACCATGCCAAAACT TCATCATTTACAACTGCAGCCGGCGGTGGTTTTACAAAGC CGACGGCGACATTTTCCGGCGAGTCTGCCGCCGTTTTCCG GGTAGAACGTTTCCAGTCCAATAAAACTGGAGAGCAACTA AATACACTCTACTATGAAGAAGATAACCATCACCAAATTA TTGATGAAAATCAGGTCATGGATTTTCCTGGAGGGCAGCT TCCAATTACTCCTCAAATGAAATTTATTGCAGAGTCATCT GAAAAGAGGTTACCTTGTTATAGAGTCCTTGATGATGATG GCTATCCAATTCCAGGCAGCATTTTTGAGGAGGTGAGCAA AGAATTGGCTGTAAAAATGTATAGTTCAATGGTGACACTT CAAGTTATGGATACCATATTTATGAAGCACAAAGGCAGG GGAGGTTATCTTTCTATCTCACTACTGCTGGAGAAGAAGG TATCAACATAGCATCTGCTGCTGCTCTCTCCGTCGATGAC TTCGTCTTGCCTCAGTATAGGGAAGTAGGGGTTATCTTAT GGCGGGGCTTCCCCCTGAAAGATATTGCCAATCAATTGTT CGGAAACAAGTTTGATTATGGAAAAGGAAGGCAAATGCCA TGCCACCATGGTTCTAATGAGCTCAATTACTTAACTATTT CTTCGCCAATAGCGACACAGATTCCTCAGGCCGCGGGCGT TGCTTACTCTCTGAAAATGGATAAAAAGGAGGCTTGTGCT ATTACTTATCTTGGAGATGGTAGCACCAGTGAGGGTGATT TTCATGCTGCTTTAAACTTTTGCAGCGGTTTTGGACGCTCC TGTTGTCTTTATATGCCGCAACAATGGATGGGCCATTAGC ACTCCTGTAAACGAACAATTTCGAAGTGATGGAGTTGCCT CAAAGGGTCAAGCCTATGGAATTAGAAGCATTCGTGTAGA TGGCAATGATGTCTTGGCAACTCATAGTGCTATTCGTGCA GCTCGCGAAATGGCAATTAAGGAACAAAAGCCAATATTAG |

TABLE 1-continued

Sequences for this disclosure

| SEQ ID NO | Sequence Description | Sequence Type | Sequence |
|---|---|---|---|
| | | | TAGAGGCCATGACTTATAGAGTAGCCCACCATTCAACATC<br>TGATGATTCAACCAAGTATCGACCCGTCGAAGAAATAGAG<br>CACTGGAAAACAGCAAAAGTCCAATATCCAGATTCAGAA<br>AATGGATTCAGAGAAATGGTTGGTGGAATGATGAAAATGA<br>ATCTGAACTTCGCGGAGACACCAGAAAACAGGTATTGCAA<br>GTAATGCAAGCAGCAGAGAAGGTGGAGAAACCTCCATTGA<br>CAGATTTGTTTACGGATGTTTATGACAAAGTGCCATTAAA<br>TCTTCAAGAGCAACACAAGTTTATTAGGGATGCTGTAAAG<br>AAATCTCCAAGAGAGTATCCTTCTGATGTTCCTATATAA |
| 35 | Neomenthol Dehydrogenase (NtNMD; g29387) | Nucleic acid | ATGGCAGAAAAAATCACCAGCCACGAGAACACAAGGTATG<br>CAGTGGTGACAGGGGGAAATAAAGGAATAGGATATGAAAC<br>ATGCAGGCAACTAGCAAAGGAAGGAATAGTGGTAGTGTTG<br>ACAGCAAGGGATGAAAGGAGAGGAATTGAAGCTCTCGAAA<br>AGCTCAAGGAAGAGTACTCAAGCAATAAAACTGATGATGA<br>TCAGATTTTATTTCATCAACTTGATGTTATGGATCCAGCT<br>AGTATTTCTTCTCTTGTGGACTTCATCAAAACTAAATTTG<br>GAAAGCTCGATATTCTGGTTAACAACGCAGGGATTGGTGG<br>ATTAATGGTAGAAGGAGATGTTGTTATAATAAAAGATTTA<br>ATAGAAGGAGACTTCGTAACCATTTCTGCTGAAAATGGGG<br>AAGAGGATGGTATTAAGAAATCAATTGAAGGTATTGAGCG<br>TATTGTTACAGATTATGAGTTGACAAAACAATGCCTGGAG<br>ACAAACTTCTATGGTGCAAAAAGAATGATTGAAGCATTTA<br>TTCCCCTCCTTCAGCTCTCTAACTCCCCAAGAATTGTTAA<br>TGTCGCTTCTTTCTTGGGGAAGTTAAAGCTATTGTGCAAC<br>CAATGGGCTATAGGAATGCTAAGTGATGCTAAAAGCCTGA<br>GAGAAGAAAGGGTGGATGAAGTGTTAATGAATTTATAAA<br>AGATTTTAAAGAGAAATCAATAGAAGCCAAAGGATGGCCA<br>ACTTATTTCTCAGCTTACAAAGTCTCGAAAGCATCCCTGA<br>TTGCTTACACAAGGGTTTTAGCTACGAAATATCCAAATTT<br>TCGGATAAATTCTGTGTGTCCTGGATTTTGCAAAACAGAC<br>GTGAACTGCAATACTGGGAGCTTAACTGCTGAAGAAGGTG<br>CTGAAAGCTTGGTGAAGCTTGCTTTGGTGCCAAATGATGG<br>ACCCTCTGGTCTCTTCTTTTATAGAAAGGAGGTCACCTCT<br>TTTTGA |
| | Regulatory element (TATA-box) | Nucleic acid | TATA |
| | Regulatory element (Unnamed_1) | Nucleic acid | CGTGG |
| | Regulatory element (AT-TATA-box) | Nucleic acid | TATATAAA |
| | Regulatory element (MYC) | Nucleic acid | CATTTG |
| | Regulatory element (CAAT-box) | Nucleic acid | CAAAT/CAAT |
| 41 | Regulatory element (Unnamed) | Nucleic acid | ATGTACAAATTTC |
| 42 | Regulatory element (Unnamed) | Nucleic acid | CATGTCAAACGTTA |
| | Regulatory element (Unnamed_4) | Nucleic acid | CTCC |
| | Regulatory element (MYB) | Nucleic acid | TAACCA/CAACAG |
| 45 | *Cannabis* Cyclase promoter | Nucleic acid | TCTTAAACCCTTATGTGTTTATTTCATTGTTTTAGAA<br>TTCATATTAGGATGTTAATGAAACATACTTGTTAGTA<br>AATCTAGATCCTCGTAAAATATTTCCAAGAAATATAA<br>CAGCTACTCAGATTATACACAAAAATCCCAATAGACA<br>AAAACACTGTAAAAGTCATACTAAAACTCAAAAAAAA |

TABLE 1-continued

Sequences for this disclosure

| SEQ ID NO | Sequence Description | Sequence Type | Sequence |
|---|---|---|---|
| | | | AAAAAAATACAACCAAACCAAATCAATAAAAACTAAA<br>AAATCATCAATGGGCAGGCAAGACTTCAATTGTAGTT<br>TTGACTTGCCTGAGTGAATCGATTCCGGAAAAGAATT<br>GAAATTGTGGTCGTCGTTCAAGCTCTTGGCTGAATCT<br>CCTGATTGTTCAAGCCCTCTCATCAGAATTATCTCCA<br>TTGTTCAAGCCCTCTCATCGGAAGCTCCTGGTTTTTC<br>CATCAATTTTTGGCCATGGTCACTATGGAGGTAAGTA<br>GATTGAAGAAGACGAATGTGAGAGAGAAGGCAAAGGG<br>TCGAGGTGGGCGTGGTGCAGTTTTTGAGGTGGGAGTT<br>GTTTCTCGGCCGCAACAATCCACCATGTTTCTTAGTT<br>TTTTTTTCTTTTTGTTCTGGGAATCGATTGTTTTTGG<br>GTGTGGATTGTTGGTTGATAGGTTTTGGGGGTGGTTT<br>CTGGGCAGTGAGAAGGTGAGAAGAAGAAGAAGAAGAA<br>GAAAGTTATGGTTTGAAGAAGAAGAAGAAGGAAAATC<br>AGGTGGGTGGGTGGGGTTTCGTGTGAAGCAGAAAAAA<br>GAAAAAAAAAACAAGTTATTTTATGATTTGAAAATAT<br>TATTTTTAGTTTTTTTATATTATTTTAAATTTTTTTT<br>ATTAAAATTATAATTTGGACCAGTAATACTTCAAGAC<br>GTGGCATTTTAAAAATTAATAAACGGACAGTTATCTT<br>AGGGACCAACGGACTCACAGAAAATGTGACCTTGGGG<br>ACTATTACCGCCAATTTTTGAGGTTTGGGAATAATCT<br>CCATCAACCCTTAATTTTTGGGGACTTTTACCGCAAT<br>TATCCCTATTATACATAATATTTTATAACAAGTTTTT<br>TTTTATTATTTTTATTATTTGATGAAGTAATTAAAG<br>AGGAGTTTTCAATTTGTTAATTTTTCAGATTAGCTTG<br>AAAAAAGGATTAGCTTGAAAATACAATTCTATAATCA<br>TACAATTTCAAAGCATAGAAAAAAAATTGTTCAAAAA<br>ATAAGAAAAGAAAATTAAGCATAATTCTATATTGGCT<br>GCTACATTGCAATATACGTACGTACAGTCATAAAAAT<br>ATGCACATGGATGAACTATTACAATTAGAACAGAAGA<br>AAAGTAAATGATAAAGCTTCTTACTCTTGACTAACTC<br>TTATTAAGTACTGTTGATTAATTTGAAATTTTCAAAT<br>CAAAATACACTATAAATAGCTGAGTACATGAAACGAG<br>TTTTCCATCAATTAAAGCTAACTCCATCTCGTAATTT<br>ATATAATTATATAGTGATCGTTTATATACATATATAT<br>CACCAAATCGTGATTTCAAA |
| 46 | Cannabis PSO promoter | Nucleic acid | AATGTTTACAATTTTAACATGTCGATTATTTTCAATT<br>ACTAATTTTTTGAAAAAAAAATGTGTAAAGTTAAAT<br>ATAAAAATACATAAGTCAATATTTATATTTTGATATA<br>TTATTAAAATAATATATTTACTAAAATTTAATACAAA<br>ATTATATATATACAAACATATTTAAAAATTTGTTTAT<br>ATTTTAAATAAACAACATATATGCATGTTTATTAAAT<br>ATTTAATTATTATTAATGTTTATAATACTAGTATTGA<br>TCTAATATGTTTATTATGATAATATTTTAATAGAATC<br>AATATAATTTGTTGATTAAAAGTTCATAAATAAGTTT<br>AAAAATAAAACATTTATGTTTATTTTGTTTTATGAAA<br>CAAAGCTATAAACAAATGTGAAATTATGTATAAACAT<br>TATATTTATATTTTATATTGATAATGTTTATAAATTA<br>TTAATCTAATATATTTAATATATAGTTTTATAAATAA<br>AGTATGTATATTTATTTTATTTTACTTTTTTTTGTTG<br>TAAGAAAAAATATGTATGTTTATTGTTTATTTATATA<br>AGACTTAGGAAAAATTAATTACCTCATATAGATTGTA<br>CAGAAAATTAAAATTATGTGTCTCTAATATAGAATGT<br>ATAATTAAATGTAAATAAATTATTTTGTATTATATAG<br>TATAATAAAATTATATAATGTATACAAAATTATAAAT<br>TTCTCATATCTTTTCTTCTAATTTTTATTTATTTATT<br>TTTTTAATGTCAATATGTATAAAGTGTTGGACTCCAA<br>TATAAACACTTAAAGTTAAACTTAAATTGAGTTTAAT<br>TAATTCAAATTTTTTGTCAAGTTGTATTTTTAAGTA<br>GTTTGTTTGTGCTTGTGGCTTGTTATAAAACATGCTA<br>TGCCCTAATTTTGTATACATAACACTAAGGTGGCATT<br>TGGTTGAAAGAAATGAAAACATATATAAAAATAAAAA<br>TGAAATAAAATAAAATTTAAAATGTATAAAAAAATCA<br>TTAGTTTCTTTTAATGTTATATTAACATGATTTTTTA<br>TTCTATTTTAAAATAGAATAGTCATTCCACTAAAATA<br>GTGTAAAGGACATTCCATTAGAATGATATTCTAATAC<br>TTTAAAATGTAACCAAATAAATAAATAAAATAAAAT<br>AATTTCTTTTTCATTCTATTCCATTTCATTACTCATT<br>TTCATTCCATTCTATTTCATTTAACAAAAATGATAAA<br>TGAACATTTTTGTTATCTTGTAGTAGTACAAACTACA<br>AATAATAGAAAAATGAAACTTTAATATAAGGAGGAGA<br>CAAAGTCTATTATTTACCTTGGTGATCAAGTTTTATA<br>TACAACTTTGAAATAAGTACTTTCTTTCTCTCTCTTA<br>TTAACATAATCCTACTTGAGTTCCCACTTGCATTTAC |

TABLE 1-continued

Sequences for this disclosure

| SEQ ID NO | Sequence Description | Sequence Type | Sequence |
|---|---|---|---|
| | | | CTTAATATAATACTATGTCAACCATGTGTATAATTAG ATCTAACATCTACTTCAAATCTAAAGAACTTATTTAC CAACTAATCAAAATCAAAT |
| 47 | Cannabis Ribulose bisphosphate carboxylase small chain promoter | Nucleic acid | GTAGTACATAAATTTATAGCTGATGATAAGTCTCATT CTCAGTCGAGGAATATCTACTGTGTTTTGGATCAACT GAAAAGGGAGCTTAAAAGTTCATCCATAGCTCAATTT TCAACCATGTATTTTTAGTTTATAATAGTAAAGATTA TTCAGTCCCGTATAGAGAGAAAACAAATGACAAATCA TATGATTCAGCAGCAAAAAATGGACTTTTTACAACTC AAAATAAAACAGAAATATCTTACTATAATATAATACA TAGGGATAATGTACGTTGATCGGTTTATGTTAAGTAC AGTTCGTCTAATTAAAAAAAAAAAAAAACAGAAACCA ATCCAATAAAATTAGTCGAGTTAGTCAGGTTAATCCG TCCAAATCGATCATTAATATATTTTTTTTACATTCAA TTGCTATATTTTAATTAGATGTAATAACGAGACAAAT AGATATATATTTATAAATTACACTTACAGTTCAATTC AACACATAAAAGAAACATATTAATTTTAACTTTATAT GTTTTAAAAATTCATATAAAGTATATGATATATATAA ATATGTATATACATAAAAACCCTTTTGATTGTGTTGG TTGGATTAGTAAGAGTTGAATAGTGGGGTTGATATTA TTTTCAATCCACCCAATATAAAGATCAGACAGATTAT ATTTTTATCGAATTTTTCGATTTGTATTTTTGTCAG CTTATCTCAATTTAATTTAAGCAAGTTATTCAGATTA GGCGGTTTAAAAAAATGAAATAATAGCATGAAAGTTT TCAGTCATAACATTAAAAAAAAAAAATGTCATTTTGTT ATGATGAGTGGCTATGAACTGCAGCCAGTTTTTGATG GTATTCATATGCAATTTTAATGGCTTTCTTCAGCTTA ATGATTTAATTAGTAGATAAGAGATTCTTGAATCTAG TACTCATGATGTATTTGATATCCATAGTGACCATTGA AGATTGAAACAGTTTTAACTTGGCTTCTCTCTCATAT TGTTCAAGCATTATTTTTGGAACATGACGAAAGTTGT TCAGGAACCCATGTTGTCCACATCCTGAATTTCCAAG CTTAAGAGAACAAAAAATCCAAATAGGCATTCATCAC TAACTTCACAGACATATGTCACATATCTCTACATTTA ATCAAAACTGTTGTATGCTGATGTCTTCAATTCACAA GTGGCAAAAATGTAAGGTGGGACCCCAAAAAATTTCC ACTAGAGCCAAACTCTAAATAGGGAAAACTCTACACC ACCTCGTAGTACCCACCGAAATCCCATACCACTCATC TTTTAGAAAAGAAAAAAACCACACTTGATCTCACAAC AAATATAAAGCTGACTTCTTTTGTTGTTTTTAGAAAC CATTTCCACCATTTTCCTAATAAACTACTTGATACTA AAATAATCAAAATAAGAATAAAGGAAAGGAAAGGAAA TAATACTACAACACTGCAATTATTTTCTTTCTCCTGT TAACCAAGTTTGAGGTTAGG |
| 48 | geranylgeranyl pyrophosphate synthase. chloroplastic [Cannabis sativa] | Nucleic acid | ATGAGCACTGTAAATCTCACATGGGTTCAAACCTGTT CCATGTTCAACCAAGGAGGTAGATCCAGATCCTTATC AACTTTCAATCTCAATCTCTACCACCCTTTGAAAAAA ACACCCTTTTCAATCCAAACCCCAAAACAAAAACGAC CCACTTCACCATTTTCATCAATCTCAGCTGTTCTAAC CGAGCAAGAAGCCGTTAAAGAAGGCGATGAAGAAAAA TCCATCTTCAATTTCAAGTCTTACATGGTCCAAAAAG CCAACTCAGTCAACCAAGCTTTAGACTCAGCCGTTTT GCTCAGAGATCCCATTATGATACACGAGTCCATGCGT TACTCACTCCTCGCCGGAGGAAAACGAGTCAGACCCA TGCTCTGTCTCTCAGCCTGTGAACTCGTAGGCGGAAA AGAATCCGTAGCCATGCCGGCTGCCTGCGCCGTCGAA ATGATCCACACCATGTCTCTAATCCACGACGACCTCC CTTGTATGGACAACGATGACCTCCGCCGTGGAAAGCC CACAAACCACAAAGTCTTCGGAGAAGACGTGGCCGTT TTAGCCGGCGATGCACTTTTAGCCTTTGCTTTTGAGC ACATGGCGGTCTCTACCGTTGGTGTTCCGGCAGCCAA GATTGTCAGGGCGATTGGTGAGCTTGCTAAGTCAATT GGGTCAGAAGGATTAGTGGCTGGTCAAGTGGTTGATA TTGATTCAGAGGGTTTGGCTAATGTTGGGCTTGAACA ACTTGAGTTCATTCATCTCCATAAGACTGGGGCTCTT CTAGAAGCTTCTGTTGTTTTGGGGGCTATTCTTGGTG GTGGTACAGATGAAGAAGTTGAAAAACTTAGGAGCTT TGCTAGGTGTATTGGCTGCTTTTTCAGGTTGTTGAT GACATTCTTGATGTGACTAAATCTTCTCAAGAATTGG GTAAAACTGCTGGGAAAGATTTGGTGGCTGATAAGGT TACTTATCCAAGGCTAATGGGTATTGACAAATCAAGA GAATTTGCTGAGCAATTGAACACAGAAGCCAAACAGC ATCTTTCTGGTTTTGATCCCATAAAGGCTGCTCCTTT |

TABLE 1-continued

Sequences for this disclosure

| SEQ ID NO | Sequence Description | Sequence Type | Sequence |
|---|---|---|---|
| | | | AATTGCTTTGGCTAATTATATTGCTTATAGGCAAAAT TGA |
| 49 | (-)-kolavenyl diphosphate synthase TPS28. chloroplastic [Cannabis sativa] | Nucleic acid | ATGCCTTCTCTCTTCTCCCAATCACTACTTCTCCCTT TCTCTCAAAACACTAATACTCTCTCCCTTTTCCATCA ACCAAAACTTCTTCCTCCAGGTGCTTCGCTATTGGAA GCTAAAGACAAACAAGTTAACTTTGATCGTGATATTC GCTCAAAATGCAGCGCTATATCAAAACCCCGCACTCA CGACGTGTTTCAAAGTGGTGGTCTGCCAGTTATAAAG TGGCACGAGATTGTGGAGGATGACATAGATGGAGAAG AAGAAGATACTAAGTGGACAAGATCGAATGAGATCGA GGAACGTGTCGCTTCAATCAAATCAATGTTGGAGAGT ATGGATGAGGGAGAGATAAGCATTTCAGCGTACGACA CAGCATGGGTAGCCCTTGTGGAAGATATTCATGGGAG TGGCTTACCTCAATTCCCATCGAGTCTCCAATGGATC GCCACACATCAGCTCTCCGACGGTTCTTGGGGCGATG CTGACATTTTCTCCGCACACGATCGCCTCATCAACAC TTTGGCTTGTGTTGTTGCTTTGAAATCTTGGAACCTT TATCCCGAAAAATGTCAAAAAGGTATGGCCTTTTTCA ATGCAAATATAAGTAAGCTTGAGAGGGAGAATCCGGA ACACATGCCTATTGGTTTCGAAGTGGCTTTCCCTTCT TTACTTGAAATAGCTCGAAAATTAAACCTTGAAGTGC CTGAGGATTCTCCTGTGTTAAAAGTCATATATGCTAG GAGAGATTTCAAGCTCACAAGGATTCCGAGGGACATA ATGCACACAGTGCCCACGACGCTACTCCATAGCTTGG AAGGAATGGTAGGTCTGGACTGGGAAAAGCTTTTGAA ACTGCAGTCCCAAGATGGGTCATTCTTGTTCTCACCA TCCTCAACTGCTTTTGCACTCATGGAGACCAAAGACC GAAATTGCTTGCAATATTTAACTAAAGCGGTCCAAAG GTTCAACGGGGGTGTCCCAAATGTTTACCCGGTTGAC TTGTTCGAGCACCTTTGGGTTGCGGATCGGTTGCAGC GCTTGGGAATATCAAGATTCTTTGAGCCACACAAATTGA GGAATGTATCGATTATGTATTCAGAAATTGGACTGAG AAAGGAATTGGCTGGGCAAGAAATTCCAAGGTTGAAG ATATTGACGATACCGCAATGGGTTTCAGACTACTAAG ATTGCATGGTCACAAAGTTTCTGCCGATGTGTTCCAA CACTTTAAGAAAGGTGACGATTTTTTCTGCTTTCGGG GCCAGTCAACTCAAGCAGTGACTGGGATGTATAACCT TTATAGAGCTTCTCAGTTGGTTTTCCCTGGAGAAAAA ATTCTTGAAGATGCCATGGAATTCTCATCGAAATTTC TCAGAAAAAAACAGGCGTCCAATGAATTGCTAGATAA ATGGATCATAACAAAGGACTTACCTGGTGAGGTGGGT TTCGCATTGGAGGTTCCATGGAATGCAAACTTACCTC GAGTAGAGACCAGATTCTACATTGAACAGTATGGTGG ACAAAATGATGTTTGGATTGGCAAGACACTCTACAGA ATGCGAAAAGTTAACAATGACGAATATCTGGAGTTAG CAAAACTTGATTACAACATTTGCCAAGCTTTGCATTC GATTGAGTGGCACAATTTGCTAAAATGGTACCGAGAT TGTAAGTTGGAAAATTATGGAGTGAGCAGAAGGAACC TCCTCTTGGCCTATTTTCTTGCTGCGGCCAGTATTTT CGAACCGGATAGGGCCGATGAGCGGCTTGCATGGGCT AAAACGGCAGCACTGATGCAGGCCATCCAATCTCATT TCGATGACCAGAAAGCTTCTTCGGAGCATCGTATAGC TTTTGTCTCTGCTTTTAAAAGGAGTTGTAACATGCCA TCGTATTTGATTACAAGGGTGTCGAACATAAGTGATA CAGATCATGGCCTTCTTAGAACGTTGATGACGACTCT CAGCCACCTCTCTTTGGACACAATGATGCTGTATGGT CGGGACATCACCCACCATTTACGTCAAGCTTGGGAAA AGTGGCTGGTGAAGTGGCAAGAGGGTGGTGATGGACA TTACGAAGAAGAAGCAGAATTATTGATCCAAACAATA AACCTTAGCTCAGGCCGTACACTTGTGAAGGCCCTCT TGCTGTCAAATCCTCACTATGAAAAACTCTTCAGTAC CACAAACAAAGTTTGCTGCAAAATTCGTCACTTTCAA AGACAAAGGCATAGGGCCAAGGCAAATCAAAATGGAG AATTTAACAGAAACATCTTAACACCAGAAATAGAGTC AGATATGCAAGAGGTTGTGCAATTGGTGCTACAAAAA TCTTCAGATGACATGATCAACACAAAAATTAAGCAGA CATTTCTACTGGTGGCCAAGTCTTTTTATTATGCTGC CTACTGTGATTCTAAGACCATCAATTTCCACATTGGC AAAGTAATATTTGAGACTGTGGACTGA |
| 50 | solanesyl diphosphate synthase 3. chloroplastic/ | Nucleic acid | ATGCTATTCTCAAGGGGATTTCGTCGGATTCCGACCA CCACCTTCAATGGGTTTTCCCGTTGGTTCGTCTCTCA CCGACCCGGGTACTCACAGTCACAGACCACTACTCAT TGTTCTAGAGATTCAACCCACAAGATTTTTGGCGGTT |

TABLE 1-continued

Sequences for this disclosure

| SEQ ID NO | Sequence Description | Sequence Type | Sequence |
|---|---|---|---|
|  | mitochondrial [*Cannabis sativa*] |  | TCGAAGAAAGTCGTTTCTGGGGTTTTGCTGGCTCTAG ATACCAAATTCATCACCAGAGTAGCTCCTTAGTTGAG GAAGAATTAGACCCTTTTTCTCTTGTTGCGGATGAAC TCTCACTTGTTGCTAATAGGTTAAGGGATATGGTAGT TGCTGAGGTGCCCAAGCTTGCTTCTGCTGCTGAGTAC TTCTTTAAAATGGGTGTGGAGGGGAAGAGATTTCGTC CAACGGTATTATTGTTAATGGCAACAGCATTAAATGT TAAGGTTCCCGAGCCTGCTAAAGCGTTAGCAGATACT TTAACACCCGAGTTACGTACAAGGCAGCAATCTGTTG CAGAAATAACAGAGATGATCCATGTGGCAAGCCTACT ACATGATGATGTCTTAGATGATGCAGAAACTAGACGC GGTGTTGGTTCGTTGAATTGCATTATGGGAAACAAGG TATCGGTATTAGCAGGAGATTTTCTGCTTTCTCGAGC TTGTGTTGCCCTCGCAGCTTTAAAGAATACCGAGGTA GTTACGCTACTAGCCACGGTTCTAGAACAGCTCGTGA CAGGTGAAACCATGCAAATGACATGTACATCTGAACA ACGTTGTAGTATGGAATATTATATGCAAAAGACATAT TACAAAACTGCATCGTTAATTTCGAACAGTTGCAAGT CGGTTGCAGTCATTGCTGGACAAACTACAGAAGTTGC AATGCTAGCATTCGAGTACGGCAAAAATTTGGGTTTG GCTTATCAATTGATAGATGATATTCTTGATTTCACCG GCACGTCAGCTTCCCTCGGAAAGGGGTTCACTATCTGA CATCCGTCATGGTATTGTTACAGCTCCATTATTGTAC GCCATGGAAGAGTTTCCTCAGTTGCGCGCCGTGGTTG AGCAGGGATTTGAAAACCCCAAAAATGTTGACATTGC ACTCGACTACCTTGGAAAGAGTCGCGGGATCCAAAAG GCGAGGGAACTTGCAATAAAGCATGCAAACCTCGCTG CTGAGGCAATCGAGTCACTTCCAGAGAGCGATGATGA AGATGTAAAAAGATCGAGACGAGCACTAGTAGATCTC ACCCAAAGAGTCGTTACAAGAACAAAGTGA |
| 51 | terpene synthase 10-like isoform X1 [*Cannabis sativa*] | Nucleic acid | ATGTCTACCAATAATAATAATAATATTAATAATATTA TTTCTCGAAGATCAGCAAACTATCAACCTTCACTTTG GCATTTTGATTATGTACAATCACTTTCTACCCCTTTC AAGGAAGGAGCATATGCCAAAAGAGTTGAGAAAGTAA AGGAAGAGGTAAGAGTAATGGTGAAGAGAGCAAAAGA GGAGGAGAAGCCTTTATCTCAACTTGAGCTTATTGAT GTAATGCAAAGACTTGGAATCTCTTACCACTTTGAGA ATGAAATTAATGATACATTGAAAGATATATATAACAA CAATAATGTGTACAACACCAACAATAATGTGTATGCC AATTCTCTTGAATTTAGACTCCTAAGACAACATGGTT ATCCGGTGTCTCAAGAAATATTTAGTACGTGCAAAGA TGAAAGAGGCAATTTTATGGTGTCTTCCAATGATATC AAAGGAATGTTATCTTTATATGAAGCTTCATTCTATT TGGTAGAAAATGAAGATGGTATTTTGGAAGAGACAAG AGAAAAAACAAAGAAATATCTTGAGGAATACATAATC ATGATCATGGAAAAACAACAATCATTATTAGATCAAA ATAATAATAATGATTATGATTATGATTATGAACTAGT GAGCCATGCATTGGAACTTCCACTTCATTGGAGAATG TTAAGATTGGAGAGTAGGTGGTTTATTGATGTGTATG AGAAGAGACTAGACATGAACCCTACTCTACTTACCTT AGCTAAACTAGATTTCAACATTGTCCAATCAATATAC CAAGATGATCTTAAACATGTCTTCAGCTGGTGGGAAA GCACTAATATGGGAAAGAAGTTGGAATTTGCAAGAGA TAGAACAATGGTGAATTTCTTATGGACAGTAGGAGTT GCATTTGAGCCACATTTCAAAAGTTTTAGAAGAATGA TTACAAAAGTAAATGCTTTAATAACAGTAATAGATGA CATATATGATGTTTATGGTGCACTAGATGAATTGGAG CTCTTCACTAACGCAGTTGAGAGATGGGATATTAGTG CTATGGATGGGCTCCCTGAGTATATGAAGACATGTTT TCTTGCTTTATACAATTTCATAAATGATCTTCCATTT GATGTGTTAAAAGGGGAAGAAGGCCTCCATGTAATAA AATTCCTTCAGAAATCGTGGGCAGATCTTTGCAAATC TTATTTAAGAGAAGCAAGATGGTATTATAATGGATAC ACACCAAGATTTGAAGAGTACATTGAGAATGCATGGA TATCAATATCAGGACCTGTTATACTATCACATTTATA CTTTTTTGTAGTGAATCCAAACATGGAAGATGCCTTA TTAAGTACTTGCTTTAATGGATACCCTACCATAATAC GACATTCATCGATGATTTACGTCTTACAGATGATCT TGCAACTTCAACGGATGAATTGAAAAGAGGCGATGTT CCCAAATCAATCCAATGCAAAATGTACGAAGATGGTA TATCTGAAGAGGAAGCTCGTCAACGTATTAAGTTATT AATAAGTGAAACATGGAAGCTTATTAATAAAGATTAC ATAAATTTGGATGATGATGATGATGATGATGGTGATGACT ACTCTCCAATGTTCTATGAGTCTAATAATATTAATAA |

TABLE 1-continued

Sequences for this disclosure

| SEQ ID NO | Sequence Description | Sequence Type | Sequence |
|---|---|---|---|
| | | | GGCTTTCATTGAAATGTGTTTAAACCTTGGTAGAATG GCACATTGCATTTATCAATATGGAGATGGACATGGAA TTCAAGATCGCCAAACAAAAGATCATGTACTATCATT ACTTATTCACCCTATTCCTCTTACCCAATAG |
| 52 | (−)-limonene synthase. chloroplastic isoform X1 [Cannabis sativa] | Nucleic acid | ATGCAGTGCATAGCTTTTCACCAATTTGCTTCATCAT CATCCCTCCCTATTTGGAGTAGTATTGATAATCGTTT TACACCAAAAACTTCTATTACTTCTATTTCAAAACCA AAACCAAAACTAAAATCAAAATCAAACTTGAAATCGA GATCGAGATCAAGTACTTGCTACCCCATACAATGTAC TGTGGTCGATAACCCTAGTTCTACGATTACTAATAAT AGTGATCGAAGATCAGCCAACTATGGACCTCCCATTT GGTCTTTTGATTTTGTTCAATCTCTTCCAATCCAATA TAAGGGTGAATCTTATACAAGTCGATTAAATAAGTTG GAGAAAGATGTGAAAGGATGCTAATTGGAGTGGAAA ACTCTTTAGCCCAACTTGAACTAATTGATACAATACA AAGACTTGGAATATCTTATCGTTTTGAAAATGAAATC ATTTCTATTTTGAAAGAAAAATTCACCAATAATAATA ACAACCCTAATCCTATTAATTATGATTTATATGCTAC TGCTCTCCAATTTAGGCTTCTACGCCAATATGGATTT GAAGTACCTCAAGAAATTTTCAATAATTTTAAAAATC ACAAGACAGGAGAGTTCAAGGCAAATATAAGTAATGA TATTATGGGAGCATTGGGCTTATATGAAGCTTCATTC CATGGGAAAAAGGGTGAAAGTATTTTGGAAGAAGCAA GAATTTTCACAACAAAATGTCTCAAAAAATACAAATT AATGTCAAGTAGTAATAATAATAATATGACATTAATA TCATTATTAGTGAATCATGCTTTGGAGATGCCACTTC AATGGAGAATCACAAGATCAGAAGCTAAATGGTTTAT TGAAGAAATATATGAAAGAAAACAAGACATGAATCCA ACTTTACTTGAGTTTGCCAAATTGGATTTCAATATGC TGCAATCAACATATCAAGAGGAGCTCAAAGTACTCTC TAGGTGGTGGAAGGATTCTAAACTTGGAGAGAAATTG CCTTTCGTTAGAGATAGATTGGTGGAGTGTTTCTTAT GGCAAGTTGGAGTAAGATTTGAGCCACAATTCAGTTA CTTTAGAATAATGGATACAAAACTCTATGTTCTATTA ACAATAATTGATGATATGCATGACATTTATGGAACAT TGGAGGAACTACAACTTTTCACTAATGCTCTTCAAAG ATGGGATTTGAAAGAATTAGATAAGTTACCAGATTAT ATGAAGACAGCTTTCTACTTTACATACAATTTCACAA ATGAATTGGCATTTGATGTATTACAAGAACATGGTTT TGTTCACATTGAATACTTCAAGAAACTGATGGTAGAG TTGTGTAAACATCATTTGCAAGAGGCAAAATGGTTTT ATAGTGGATACAAACCAACATTGCAAGAATATGTTGA GAATGGATGGTTGTCTGTGGGAGGACAAGTTATTCTT ATGCATGCATATTTCGCTTTTACAAATCCTGTTACCA AAGAGGCATTGGAATGTCTAAAAGACGGTCATCCTAA CATAGTTCGCCATGCATCGATAATATTACGACTTGCA GATGATCTAGGAACATTGTCGGATGAACTGAAAAGAG GCGATGTTCCTAAATCAATTCAATGTTATATGCACGA TACTGGTGCTTCTGAAGATGAAGCTCGTGAGCACATA AAATATTTAATAAGTGAATCATGGAAGGAGATGAATA ATGAAGATGGAAATATTAACTCTTTTTTCTCAAATGA ATTTGTTCAAGTTTGCAAAAATCTTGGTAGAGCGTCA CAATTCATGTATCAGTATGGCGATGGACATGCTTCTC AGAATAATCTATCGAAAGAGCGCGTTTTAGGGTTGAT TATTACTCCTATCCCCATGTAA |
| 53 | cytochrome P450 71D11 [Cannabis sativa] | Nucleic acid | ATGGAGTTCCAACAAATAATACCCTCTTTCCAAGTCC TTCTCTTTTCATTTTTTATGATTATTGTGGTGAGCAT ACTCTTGAAGAGAGCTCAAACAAGCAATAGGTCAGCT TCAAAACTACCCCCAGGTCCATGGAGACTACCCTTCC TGGGAAACTTGCACCAACTTTTGGGCCCTTTGCCTCA TCACACATTCAGAGACTTAGCCAAAAAACATGGACCA TTTATGTACCTCAAAATTGGACAAGTTCCAACCATAG TAGTTTCATCACCAGAGTATGCTAAAGAGGTCATGAA AGTCCATGATAATGCTCTTGCATCAAGACCCAATAAT CTTGTTACGCAAATCTTGGCATATAATGGTACGGACA TTATATTTGCTCCATATGGTCAGTATTGGAAGAGGGT AAAAAAGATTTGTGTGCAAGAGCTTCTAACCCTATCT AGGGTTAAAACTTTTCAACCCATTAGAGAAGAAGAGT CGTTTAATATTGTAAAAAATATAGCTTCAAAAGTTGG CTCACCTATCAATCTTACTCAAATGTTGAAAAGTTTG TCTTATAGCATCATAGCTAGGGCTGCCTTTGGCGAGA AAAGAAGTGATCATGATGACTTCGTATATATTATGAA GGAAACTGTGAAATTGTCTGCAGGGTTTGCATTTGGA |

TABLE 1-continued

Sequences for this disclosure

| SEQ ID NO | Sequence Description | Sequence Type | Sequence |
|---|---|---|---|
| | | | GATGTGTTTCCATCTTTGAGTTTTCTTGATTGGTATA
CTATAAGTAAATTCAAAGATTTGAAACTAAGGTCTTC
AAGAATAGTGGACAGAATTATCAAGTTACATATAGAT
GATCAAGACAAGGACAATCTTAAGAAAAGTGGAGAAG
AGGAAGACTTGGTTGATGTTCTTTTGAGGTTTCATAA
AAGTGAAGATCCTAATAACTTCACATTAACAAAGGAC
AATCTTAAAGCAATTATTGCTAGCATATTTGGAGCTG
GGAGTGATACATCATCAGTAACTATGGAGTTGGCTAT
GGCAGAAATGATGAGAAATCCAAGAGTGATGAAAAAA
GCTCAAGACGAGGTTAGAGAAGTCTTTGGCAAAAAAG
GGTTTTTGGATGAATCTTCAATCAATGAGATGACATA
CTTAAAATCAGTTGTGAAAGAAACTTTAAGGTTGCAT
CCCCCAGCTGCCATGTTATTTCCAAGAGAAAGTAGAG
AAAAGTGTGATATTAATGGTTATGAAATTCCTATGAA
AACTAAGATACTTGTAAATGCATGGGCAATTGGAAGA
GATCCTAAATATTGGATTGAACCTGAGAGTTTTATGC
CAGAGAGGTTTCTTGAAAGCTCTATTGATTTTAAGGG
AAATAATTTTGAGTTTATCCCATTCGGCGCTGGAAGG
AGAATATGTCCCGGAATATCATTTGCTCTCACCAGTA
TTGAGCTTCCTCTAGCATTTTTGCTATATCATTTCGA
TTGGAAACTTCCCAATGGAATGAAACCTGAAGAGTTG
GACATGACAGAGAGATTTGGTATTACAGTCTGTAGAA
AGAAGGATTGTACTTGATTCCTTCTAAATATGAACC
ACCTTCTATGGCCAAAGCAATGAATATAAAGTAG |
| 54 | cytochrome P450 71D9 [Cannabis sativa] | Nucleic acid | ATGGATCTTCAACTACTTTCATTCCCAATAATCCTCA
TTACTTTATTTTTTATGTTTATGGTAGTGAAAATAGT
TTTGAAAATAGCTCATCATCAAACAAAGAACTCAGTT
TCAAAGCTACCCCCAGGACCATGGAAATTACCATTGG
TGGGAAATATACACCAAATCTTTGGCTCTTCACCCCA
TGTTTCATTCAGAGACTTAGCCAAGAAATATGGGCCA
TTCATGTACCTCAAAATTGGACAAATTCCAACTCTAA
TAGTTTCATCACCAGAGTATGTTAAAGAGATCATGAG
AACCCATGATGTTGTTTTTGCATCTAGGCCTCAAACT
CTTGCTGCTCAGATCATGGCATATAATTGTACTGACA
TTATATTTTCTTCATATGGTGAACATTGGAGACAACT
CAGAAAGATTTCTATGCAAGAGCTTCTAAGCCCGGGA
AGAGTTCAAACTTTTCGACCGGTTAGAGAAGAAGAGT
TGTGTAATCTTGTTGAAGGGATCATGACATCTTCAAA
AGATGGGTCACCTATCAATGTTACTAAAATGGTTACA
AAATGTTCTTATGGCATCACATCTAGGGCTGCCTTTG
GCAAGAAAAGCAGTGATCACGACGAGTTCATTTCGAT
TGTTGAGGAAGCTATCGAGGCAGCTGGAGGCTTTGAA
TTTGCAGAAGTGTTTCCTGCTTTGAGATTTCTTGATT
GGAAAAGTCGTCCTATTTTTGAGAGCATCAAACTAAG
ATCTTCAAGAATAATGGAAAATATCATCAAGGAGCAT
ATAAAAGAGAAGGAAATTTCATTTGAGAAAATTGGAA
AGGATGAAGATTTGGTTGATGTTCTTTTGAAGTTTCA
TAAGAATGGAGATGATCTTGGGCGGTTCACCCTAACA
AAAGACAATATTAAAGCAGTAATCTTTGATATCTTTG
TAGCTGGAAGTGAAACAACATCTTTATCTGTAGATTG
GGCTATGGTAGAAATGATGAGATATCCAAAAGTGATG
AAAAAGGCTCAAGAAGAGGTGAGAAAAATTATTGGTA
CAAAAGGGTCAGTGAATGAATCATCAATCAATGAGAT
GAAATACTTAAAATTAGTTGTTAAAGAAACTCTAAGG
TTGCATCCTCCAGCTCCTTTGTTACTTCCAAGGGAAA
GTACAGAAAATGTGACATTGATGGTTATGAGATACC
TAAGAAAACAAGAGTAATAGTAAATGCTTGGGCAATT
GGAAGAGATCCAAAGTATTGGATTGAACCTGAGAATT
TTATGCCAGAGAGGTTTATGGAAAGCTCTATTGATTT
TAAGGGCAACAATTTTGAGTACATTCCATTTGGTGGT
GGAAGGAGAATATGTCCAGGCATGTTATTTGGTGTTA
TTAATATTGAGCTTTCACTAGCATATTTGTTATACCA
TTTTGATTGGAAACTTCCTAATGGAATGAACCATGAA
AATTTGGATATGACAGAATTATTTGGTCTTACAATGA
GAAGAAAAGATGATTTGTATTTGATTCCTACTATTTA
TGACCATTCTTCTATAGCAAAATCATGA |
| 55 | cytochrome P450 71D11 [Cannabis sativa] | Nucleic acid | ATGGATCTCCAACTACCCTCTTTCCCAGTCCTCTTGT
CCCTTCTTTTTTCTCTCCTTATGGCAGTTACCATACT
CATGAAAAGAGCTCGAAACTCAAAACTACCTCCAGGG
CCATGGAGACTTCCCTTAGTGGGAAATCTCCACCAGC
TTTTATTGGGGTATTCATCATCATCCTCATCTTACGA
GGTCTTCAGTGACTTAGCCAAAAAACATGGACCCTTC
ATGTACCTCGAAATCGGACAAGTTCCAACCGTAATAG |

TABLE 1-continued

Sequences for this disclosure

| SEQ ID NO | Sequence Description | Sequence Type | Sequence |
|---|---|---|---|
| | | | TGTCATCACCAGAGTACGCTAAAGAGATCATGAGAAC<br>CCACGACGTCGTTTTTGCGTCTAGGCCACGGACTCTT<br>GCCGCTCAAATCATTGGATACGATTGTACGGACATCG<br>CATTTGCTCCCTATGGTGATTACTGGAGACAGCTCAG<br>AAAGATTTGTATGCAAGCTCTTTTTAGTCCCAAAGA<br>GTTCAATCTTTGGAACCCATTAGAGAGAAAGAGGTGT<br>TTAATACGTTACAACATATCATTGCTAATTCCAATAA<br>ACTCAATTTTACTCAAATGGTCACAAATTTGTCTTAT<br>AGCATCGTATCTCGAGCAGCTTTTGGGGAAAAAAGCA<br>GTGATCATGATGAGTTCATATCGATTGTGGAGGAAGA<br>TATAAAGGTAGCTGGAGGGTTTGAATTTGGGGAGTTG<br>TTTCCTTCTTTGAGATTTCTTGATTGGACCAGTAGGC<br>CTAAATATGAAAGCCTCAAACAGAGGTCTTCTAGAAT<br>ATTGGAAAAGATCATCAAACAACATATGATTAATCAG<br>AATAATGAGAAAAGTGAAGAAGAGCAAGACTTGGTTG<br>ATGTTCTTCTCAAGTATCATAACAAGGCAAATCTTGG<br>GTTAACCCTTGACAATATCAAAGGAGTAATCTGGGAC<br>ATTTTTGAAGCTGGAAGTGAAACAACAGCTGTAACAG<br>AGGATTGGGCTATGGTAGAATTGATGAGAAATCCAAT<br>AATGATGAAAAAGGCTCAAGATGAGGTTAGGGAAGTT<br>TTTGGAAGAAAAGGATTAGTTGATAAAACATCAATCC<br>ATGAGATGAAATACTTAAAATTAATTATTAAAGAAAC<br>TCTAAGGTTGCATCCTCCTGCTCCTTTTTTACTTCCA<br>AGGGAAAATAGTGAAAAATGTGAAATTAATGGTTATG<br>AGATACCTAATGGAACAAGAGTATTGGTAAATGTTTG<br>GGGAATTGGAAGACATGCTAAGTATTGGAATGAACCT<br>GAAAGTTTTATACCAGAACGGTTTGATGATAGCTCTA<br>TTGACTTCAAAGGTAATAATTTTGAGTATATTCCATT<br>TGGTGCTGGAAGGAGAATATGTCCTGGCATAACATTT<br>GGTGTTGTTAGTCTTGAGTATTCTCTTGCTTTAATGT<br>TATACCACTTTGATTGGAAACTTCCTAATGGAATGAA<br>ACCTCAAGATTTAGACATGAGTGAGTTATTTGGCATT<br>GCAGTAAGGAGAAAAGATGATTTGTACTTAATTCCTA<br>CAATTTATCATCAGTCACCTCTTGCAAATTAA |
| 56 | (−)-<br>isopiperitenol/<br>(−)-carveol<br>dehydrogenase.<br>mitochondrial-<br>like [Cannabis<br>sativa] | Nucleic acid | ATGACGGAACACTCACCACTAACCCCCAAAACCAAGC<br>TTCATGGCAAGGTGGCAGTCGTCACCGGCGGAGCCAG<br>CGGCATCGGAGAAGCCACGGCTCGAAAGTTCGCTGCT<br>GATGGAGCACGCGCCGTCGTGATTGCAGATATCCAAG<br>ACGAGAAAGGCCAAAACGTGGCCGCATCAATCGGCCT<br>GGAACGCTCCACCTACGTCCACTGCGACGTGACCGAC<br>GAGGCTCAAGTCGCAGCCCTCATCGACTCAACGGTCC<br>AAAAGTACGGTCAAGTCGACGTGATGTTCAGCAACGC<br>CGGGGTGCCTTGCGAGTCGGATCAGACGATTCTGGAT<br>TTGGATCTGGTGGCGTACGATAAGGTGTTTGCGGTGA<br>ACGCGAGGGGGATGGCGGCGTGTGTGAAGCACGCGGC<br>GAGGGCGATGGTGGAGGGTGGAGTGAGGGGGAGCGTG<br>ATATGCACGGCGAGCAATCTGGCGAGTATAGGAACTG<br>AGAAGTACACGGACTACACTATGTCGAAGCACGCCGT<br>TTTGGGGCTGGTGAGGTCAGCGAGTCTTCAGCTGGGG<br>GCGCGTGGAATTCGCGTGAACGCGGTTTCGCCGGGGC<br>CGTTGAGGACGCCTTTGCTGAAAGCGTTTATAGATAG<br>GAGTGAGGAGGAGCAGGATAAGATGATTGAGGCTTCG<br>TTATCGCTGAAGAATGGAAGGACTCCGTCGGTGGAGA<br>ACGTGGCTGATGCGGTGTCGTTTTTGGCTTCAGATGA<br>GTCTGAGTTTATCACTGGCCATAATCTTGCCGTCGAC<br>GGTGGTTATATTCATCATCCACCCTAA |
| 57 | 2-alkenal<br>reductase<br>(NADP(+)-<br>dependent)<br>[Cannabis<br>sativa] | Nucleic acid | ATGGAAGAAGTGAGCAATAAACAACTGCTGCTGAAGA<br>ACTATGTTTCCGGTTATCCGAAAGAGTCGGATATGGT<br>CTTAGCCACTTCCACCATCAAGCTTAAGCTTCCAGAA<br>GGCTCCAATGGTGTTCTAGTAAAGAACCTTTATTTGT<br>CATGCGATCCTTACATGGGACCCCGAATGAAGAACCT<br>CAACAATGGCTTTTTCATAGAGCCCTTCAAACTTGGT<br>TCTCCTATCACTGGGAATGGAATTTGTAAGGTACTAA<br>AATCTGGAAATCCAAACTTCAAGGAAGGAGATTTGGT<br>CTCTGGAGTGACAGGGTGGGAGCAATACAGTGTTATT<br>GAGTCCACGAAATATATGCTAAAATTCAAAACACTG<br>ACGTGCCTCTGTCTTACTATACTGGATTACTAGGAAT<br>GCCTGGTATGACTGCTTATGCTGGCTTCTTCGAGGTT<br>TGCTCTCCGAAAAGGGGGAATATGTGTTCATTTCTG<br>CAGCATCAGGAGCAGTTGGTCAGCTTGTTGGGCAGTT<br>CGCAAAGCTCTTGGGTTGTTATGTTGTTGGAAGTGCT<br>GGAAGGAACGAAAAGGTTGATTTGTTGAAGAACAAAT<br>TTGGCTTTGATGAGGCTTTCAACTACAAAGAAGAGTC</br> |

TABLE 1-continued

Sequences for this disclosure

| SEQ ID NO | Sequence Description | Sequence Type | Sequence |
|---|---|---|---|
| | | | TGACTTTGATGTAGCTTTAAAAAGGTATTTTCCAGAA
GGTATAGATATATACTTTGATAATGTTGGGGGAAAGC
TGCTAGATGCTGTTCTACAAAACATGAGAAGCCATGC
TCGAATTTCTGTTTGTGGAATGATCTCACAGTACAAC
CTTGAACAAACTGAAGGTGTACATAATCTGACGAATC
TTGTGTGGAAAAGTGCTCGAATGGTTGGATTTCTGGT
TGCTGACTATTACCACCTATACCCAAAATTTCTCGAA
TATGTTATGCCTTACTTAAAAGAAGGAAAAATTGTGT
ATGTTGAAGATATAGCTGAAGGGCTAAAGAGTGCCCC
AAAAGCTTTGGTAGGGCTCTTCAATGGATGCAATGTG
GGAAAACAGGTGGTTCTAGTCTCTTCGGAATGA |
| 58 | uncharacterized protein LOC115704491 [Cannabis sativa] | Nucleic acid | ATGGAACAAGAGTACTCCTCTTCATTTCTCTCAACAA
AGAGATATGCTGTTGTTACAGGTGGAAACAAGGGGAT
CGGGTTTGAAATATGCAGACAATTAGCTTCAAATGGC
ATCAAGGTCGTGTTAACTGCCAGAGATGAAAAGAGGG
GTGTTGAAGCTGTTGAGAAACTGATCAAAGAATCAAA
TTTCACTAGTGAAGACAATGTCGTTTTTCACAGGCTT
GATGTCGTTGACCCTGACACCATTGCTTCTTTGGCAG
ATTACATCAAATCCCACTTCGGGAAGCTTGACATTTT
GATAAATAATGCAGGAATTGCTGGGGGTACACTTGAT
TCTTATGGTTATGCACAAGCCACTGAGCTTGCTGGTG
GTAATTGGCCAGAGAACGGCAATTGGAATGAGATAAT
GACCCAGAACTATGAATCGGCTGAAGAATGCCTGAAA
ACAAATTATTATGGAGCCAAAGCAACGATTGAAGCAC
TTGTTCCACTCCTCCAATTGTCTGATTCACCAAGAAT
CGTCAATGTTTCATCCTCTCTTGGTCTCTTACAATAC
ATACCGAATGAATGGGCCAAAAACATGCTGAGCGATG
TTGATAAGCTAAGAGAAGAGCAAATAGATGAGGTAGT
GAGTGAGTTTCTGAATGATTTCAAACAAGGTAAGTTA
GAAGCCAAGAAGTGGCCTACAGAGATTTCGGGGTACA
AAGTTTCGAAAGCTTCGCTGAACGCGTACACAAGGAT
TTTGGCGAAGAAATACCCTCAAATGTGCGTTAACTGT
GTGTGCCCTGGCTATGTCAAAACTGATATCACTTGCA
ATACTGGGCAGTTGGTTGCTGCCGAAGGTGCTGAAAG
TCCCGTGATGCTAGCCTTGTTGCCCCTCGCCAAGCCT
TCCGGCTTCTTCTTCTCCAGGAAGCAACTCTCCCCTT
TCTGCCATTCATTCATCACTAAACGAACCAAAACATT
TTTATTACAAACCCAAGTTTCATCAACAATGTCTGGA
GCTTCAGAAAGATATGCAATTGTAACAGGGGCAAATA
AGGGGATTGGACTAGAGATAGTGAGACAATTGGCCTT
GAATGGAGTCAATGTGGTCTTAACAGCAAGAGATGAG
AAAAGGGGTCTTGAAGCTTTGGAGAAACTCAAAGAGA
AAGAGAAAACCTCTCTCACAAAGTGCTGTTTCACCA
GCTCGACGTGGCTGATCCAGCTAGCATTGTTGCTATG
GTTGATTTCATTAAAACACATTTCGGCAAACTTGATA
TTTTGGTGAACAATGCTGGCGTTGGTGGAACAGAAGA
AGACATGCATGCAATTGTAGCTTCTTTAAATGCTAAG
ACCCCAAAAGAAGGTGATATTAAGAAAACTACTCAA
CTTATGAGTCAGCCAAAGAATGCATGCAAATAAACTA
TTATGGTGCTAAAAAAACTGCTGAAGAGCTTATTCCC
CTTCTCCAGTTATCTGATTCACCACGAATTGTTAATG
TTTCTTCTACCATGGGAAAGCTACAGAATATATCAAA
TGACTGGGCTAAAGGTGTTCTTAGTGATGCTGAGAGT
CTCACAGAGGATAAAATTGATGAAGTGATAAGAGAGT
TTCTGAAAGATTTCAAAGAAGGTTCATTGGAAACCAA
AGGCTGGCCTAGTTTTTTTGTCCCCATATACTGTCTCA
AAAGCAGCCCTTACTGCCTTCACAAGGGTACTAGCAA
AGAAGCACCCCAACTTTATCATCAACTGTGTATGCCC
TGGATTTGTGAAGACAGAGATAAACTTCAACACCGGT
ATTTTACAGCCTGAAGAAGGCGCTGCGAGTCCAGTAA
GGTTAGCATTGCTTCCAAATGATGCACCTTCAGGCCT
CTTCTTTGATCGGTCACAGGTTTCGTCTTTTTGA |
| 59 | cytochrome P450 71A22-like [Cannabis sativa] | Nucleic acid | ATGTTATTATTATTCCATTACAATATGTCCTTCTTAG
ACTTAACCAGTAATAATCTCTCTTCCTTTACCATTTT
ATTAGCAACCTTATTATTCTTTGTGCTGCTATATAAA
TCATGGTTCTCTATTAAAACAAATTCTCCACCATCGC
CTCCAAAGCTTCCAATAATTGGAAACCTCCACCAGCT
CGGGTTGTACCCTCACCGAACGCTGCAGGCCTGGAGC
AGGCGCTATGGCCCCGTCATGCAGCTCCGGCTAGGCA
GCGTGCCGGTTCTCGTCATCTCCTCTGCCACCGCCGC
TCGTGAGATTATGAAGACTCACGACATTGCCTTTTCC
AACCGACCCAAGTCCTGTGCCCTCGAGAAGCTCCTCT
ACAACTACAGAGACATTGCTTCGGCACCTTATGGCGA |

TABLE 1-continued

Sequences for this disclosure

| SEQ ID NO | Sequence Description | Sequence Type | Sequence |
|---|---|---|---|
| | | | GTACTGGAGGCAGATAAAGAGCGTTTCCGTGCTTCAT
CTGTTGAATAATAAAAGGGTTCAGTCCTATAGAGCTG
TAAGGGAAGAGGAGACCAAGCTCATGGTTGAGAAGAT
TCGAAAGTCTTGTGGGACTGGGGTGAATTTGAGCGAG
TTGTTTGTAAGGCTAACCAACGACGTCGTTTGTAGGG
TGGCCTTGGGGAGAAAGTACGGTGAAGAAAGTGGTGG
GAAGAGGTTTAAGGAGCTTCTGGGGGAGTTTACGGAG
CTACTTGGGGGTTTCTATGTAAGAGACTATTTTCCTA
AGCTTGGTTGGTTGAGTCGTGTGAGTGGTTTGGATGG
TAGAATGGATAAAGTGGCTAAGGAGTTCGATGAGTTT
CTGGAAGGTGTTCTTCATGACCATATGAATACAAATA
AGAATGTTGATGATGAACAGAAAGATTTTGTGGATAT
TTTGCTTTGGATTCAGAGGGAAAACTCGCTTGGATTT
TCTATTGATAGGACTTCCATAAAGGCTCTCATATTGG
ACACATTTGCAGCGGGAACAGACACAACCTATACAGT
CCTAGAATGGGCAATGACTGAGCTCATAAGACATCCA
AACGCCATGAAAAAGCTTCAAAACGAGATCAGAACAA
CAATCCTTAATAAGAAGATAACTAACATTGCCATGCC
AGAAGAATATATTAATAGTGTTACAGAAGACGACCTA
GAAAAAATGCCATACTTGAAGGCAGTTTTCAAAGAAA
CTCTCCGTCTGCATCCACCAATCCCTTTAATCGTTCC
TCGACTCACAATACAAGACATGAAAATAAGTGGATAC
GACGTCGCTTCAGGCACCCAAGTATTCATCAATGCAT
GGGCAATCGGGAGAGATCCGACCTTGTGGGAAGAGGA
ACCAGACAAGTTTGAACCTGAGAGGTTTTTGCTGAAG
AACGCTGCAATTGATTACAAAGGACATGACTTCGAGT
TGATCCCTTTCGGGGCCGGGAGGCGAGGCTGCCCTGG
GATTGTATTTGCCATGGCTGTTAACGAGCTTGCTTTG
GCTAGTGTGGTCTATAAGTTTGATTGGGCGTTGTTGA
GTAGTGGAGAAGAGGATTTGGATTATTATCATATGAC
TGAAACCACAGGTTTGACTACGCATAGAAAGTTTCCT
CTTATGGCTGTGCCAACTGAATATTATCAATGA |
| 60 | (−)-germacrene D synthase-like [Cannabis sativa] | Nucleic acid | ATGTCTCCTTGCGAAGCTACAATTGATGAAAAACGCC
CTAATATGCCAAAGTTTACTCCAACCATTTGGGGTGA
TTATTTCATGTCTCATGCTTCAAGTCATCACTCATCT
CTTATGGAAACTATGGAGAATAATAACAAAGAGAGTT
ATGAGAAGATTATTGAGATGAAGGAACAAGTGAAGAA
TAAATTACTTCATGGTCTTCATCCTTTGGAAAACCCT
TTGGAGACACTTGAATATATTGATGATATTCAACGAT
TGGGGTTGTCTTATTATTTTGAAAATGAAATTGAACA
AAATTTGGAGCAATTTCATAATAATTATCAAAATCTA
ATTGATTTTGGTGATAATAACCTTTATGCTGATGCTC
TTTGCTTTCGGTTGCTTAGGCAACAAGGTTATAATAT
TGCATGTGACATATTCGACAAGTACAAGAATGAAAAT
GAAAAATTTAAAGAATCAATTTCGAGTGACATTCGAG
GAATGTTGAACTTGTATGAAGCTGCACAAATGAGAGT
TCATGGAGAGAAAATACTAGACGAAGCACTTATCTTT
ACAACTACTCATCTTGAATCCTCAGTTAAAACATGTC
AATTGAGCTCTCCTTATCTAGACCTAGTGAAACATGC
CCTAATGCACCCTATTCGAAAGAGCTTACAAAGAAGA
GAGGCAAGACTTTACATATCACTTTATCATCAACTAC
CTTCTCATGAGGAGATTCTTTTAATACTTGCTAAACT
AGATTTCAACCTGCTTCAAAAACTACATCAAAAGGAA
CTAAGTTACATAACGAGGTGGTGGAAGGAGTTTGATT
ACAAAAGTAAGCATTCATTTATAAAAGACAGAATAGT
GGAGTGCTATTTCTGGGTTTATGGAGTGTTTTTTGAG
GCAGAAACTTCCCAAATCAGACTAATAATCACCAAAT
TAATTGCTATTCTCACAATAATTGATGATGCTTATGA
TAGCTTTGGTACACTTGAAGAACTAGAGCCTTTTACT
CAAGCAATAGAAAGGTGGGATATATGTGCCATAGATA
CTCTGCCTGAGTACATGAAAATATTTTACATGAAACT
TTTGGAGATCTACAATGAAATTGAACAATTTTCTAAG
GAAAGATCATACTGCCCTAGCTATGCTAAGAAAGGGG
TGCAATCTCTAATTAGAGCTTATTTTAAGGAAGCCAA
ATGGTTACACACAAAATATATACCAACATTAGAAGAA
TATATGCCAGTTGGGATTGATAGTGCAGGATCTTTTA
TGCTCATTTCAATGGTTTTATTGGAATGGGAGATAT
TGTTACAAAACATTCTATGGATTGGATATTTTCTAAT
CCTCAACCTAAAATTATACAAACTATGGCAATAGTTG
GAAGAGTTATGAATGACATTGGCTACCATAAGTCGGA
GCGAAAGAAATCATCAGGAGAAATTGTGGCTTCAACT
GTGGAGTGTTACATGAAACAATATGGCGTGACTGGTG
AAGAAGCTATAGAGAAACTTAGCCAACAAGTTAAAGA
TTCATGGAAAGATCTCAATGAAGATCTTCTCAATCCA |

TABLE 1-continued

Sequences for this disclosure

| SEQ ID NO | Sequence Description | Sequence Type | Sequence |
|---|---|---|---|
| | | | ATCACTATCCCTAGGCCACTCTTAATGCAAGTTCTAA<br>AGCTTGTACGAGTGAACCATGAGATTTATAGAGAAGG<br>AGATGGCTTTACACAACCCACTTTGCTCAAGAATTTG<br>ATTCATTCTCTCATCATCAATCCAATTGACTTTTGA |
| 61 | (-)-kolavenyl diphosphate synthase TPS28, chloroplastic [*Cannabis sativa*] | Nucleic acid | ATGCCTTCTCTCTTCTCCCAATCACTACTTCTCCCTT<br>TCTCTCAAAACACTAATACTCTCTCCCTTTTCCATCA<br>ACCAAAACTTCTTCCTCCAGGTGCTTCGCTATTGGAA<br>GCTAAAGACAAACAAGTTAACTTTGATCGTGATATTC<br>GCTCAAAATGCAGCGCTATATCAAAACCCCGCACTCA<br>CGACGTGTTTCAAAGTGGTGGTCTGCCAGTTATAAAG<br>TGGCACGAGATTGTGGAGGATGACATAGATGGAGAG<br>AAGAAGATACTAAGTGGACAAGATCGAATGAGATCGA<br>GGAACGTGTCGCTTCAATCAAATCAATGTTGGAGAGT<br>ATGGATGAGGGAGAGATAAGCATTTCAGCGTACGACA<br>CAGCATGGGTAGCCCTTGTGGAAGATATTCATGGGAG<br>TGGCTTACCTCAATTCCCATCGAGTCTCCAATGGATC<br>GCCACACATCAGCTCTCCGACGGTTCTTGGGGCGATG<br>CTGACATTTTCTCCGCACACGATCGCCTCATCAACAC<br>TTTGGCTTGTGTTGTTGCTTTGAAATCTTGGAACCTT<br>TATCCCGAAAAATGTCAAAAAGGTATGGCCTTTTTCA<br>ATGCAAATATAAGTAAGCTTGAGAGGGAGAATCCGGA<br>ACACATGCCTATTGGTTTCGAAGTGGCTTTCCCTTCT<br>TTACTTGAAATAGCTCGAAAATTAAACCTTGAAGTGC<br>CTGAGGATTCTCCTGTGTTAAAAGTCATATATGCTAG<br>GAGAGATTTCAAGCTCACAAGGATTCCGAGGGACATA<br>ATGCACACAGTGCCCACGACGCTACTCCATAGCTTGG<br>AAGGAATGGTAGGTCTGGACTGGGAAAAGCTTTTGAA<br>ACTGCAGTCCCAAGATGGGTCATTCTTGTTCTCACCA<br>TCCTCAACTGCTTTTGCACTCATGGAGACCAAAGACC<br>GAAATTGCTTGCAATATTTAACTAAAGCGGTCCAAAG<br>GTTCAACGGGGTGTCCCAAATGTTTACCCGGTTGAC<br>TTGTTCGAGCACCTTTGGGTTGCGGATCGGTTGCAGC<br>GCTTGGGAATATCAAGATTCTTTGAGCCACAAATTGA<br>GGAATGTATCGATTATGTATTCAGAAATTGGACTGAG<br>AAAGGAATTGGCTGGGCAAGAAATTCCAAGGTTGAAG<br>ATATTGACGATACCGCAATGGGTTTCAGACTACTAAG<br>ATTGCATGGTCACAAAGTTTCTGCCGATGTGTTCCAA<br>CACTTTAAGAAAGGTGACGATTTTTTCTGCTTTCGGG<br>GCCAGTCAACTCAAGCAGTGACTGGGATGTATAACCT<br>TTATAGAGCTTCTCAGTTGGTTTTCCCTGGAGAAAAA<br>ATTCTTGAAGATGCCATGGAATTCTCATCGAAATTTC<br>TCAGAAAAAAACAGGCGTCCAATGAATTGCTAGATAA<br>ATGGATCATAACAAAGGACTTACCTGGTGAGGTGGGT<br>TTCGCATTGGAGGTTCCATGGAATGCAAACTTACCTC<br>GAGTAGAGACCAGATTCTACATTGAACAGTATGGTGG<br>ACAAAATGATGTTTGGATTGGCAAGACACTCTACAGA<br>ATGCGAAAAGTTAACAATGACGAATATCTGGAGTTAG<br>CAAAACTTGATTACAACATTTGCCAAGCTTTGCATTC<br>GATTGAGTGGCACAATTTGCTAAAATGGTACCGAGAT<br>TGTAAGTTGGAAAATTATGGAGTGAGCAGAAGGAACC<br>TCCTCTTGGCCTATTTTCTTGCTGCGGCCAGTATTTT<br>CGAACCGGATAGGGCCGATGAGCGGCTTGCATGGGCT<br>AAAACGGCAGCACTGATGCAGGCCATCCAATCTCATT<br>TCGATGACCAGAAAGCTTCTTCGGAGCATCGTATAGC<br>TTTTGTCTCTGCTTTTAAAAGGAGTTGTAACATGCCA<br>TCGTATTTGATTACAAGGGTGTCGAACATAAGTGATA<br>CAGATCATGGCCTTCTTAGAACGTTGATGACGACTCT<br>CAGCCACCTCTCTTTGGACACAATGATGCTGTATGGT<br>CGGGACATCACCCACCATTTACGTCAAGCTTGGGAAA<br>AGTGGCTGGTGAAGTGGCAAGAGGGTGGTGATGGACA<br>TTACGAAGAAGAAGCAGAATTATTGATCAAACAATA<br>AACCTTAGCTCAGGCCGTACACTTGTGAAGGCCCTCT<br>TGCTGTCAAATCCTCACTATGAAAAACTCTTCAGTAC<br>CACAAACAAAGTTTGCTGCAAAATTCGTCACTTTCAA<br>AGACAAAGGCATAGGGCCAAGGCAAATCAAAATGGAG<br>AATTTAACAGAAACATCTTAACACCAGAAATAGAGTC<br>AGATATGCAAGAGGTTGTGCAATTGGTGCTACAAAAA<br>TCTTCAGATGACATGATCAACACAAAAATTAAGCAGA<br>CATTTCTACTGGTGGCCAAGTCTTTTTATTATGCTGC<br>CTACTGTGATTCTAAGACCATCAATTTCCACATTGGC<br>AAAGTAATATTTGAGACTGTGGACTGA |
| 62 | 2-isopropylmalate | Nucleic acid | ATGGCGACCGCTATTTTCTCCAACCCCAAGTTCTCCC<br>CCACAATCACCACCACCTCCTCCAAAAACCATTACCA |

TABLE 1-continued

Sequences for this disclosure

| SEQ ID NO | Sequence Description | Sequence Type | Sequence |
|---|---|---|---|
| | synthase 2, chloroplastic [*Cannabis sativa*] | | CTACCAACGCCGTACACATTTACTACTCCACGACAAA GTCCAAGCTTTTCAAGCCGCCTCTCTTAAACTCAACC CAAATCCTCATTACAAGAAACCCCAGATCGTTTCCTG CCAGAGCTCCGGTAGCGAGTCACCGGACACAGAGAAG GTGCGGCGGCCGGAGTACATTCCGAACCGTATCTCCG ATCCAAACTATGTACGTATCTTCGACACTACTCTCCG AGACGGTGAGCAGTCCCCTGGGGCCGCCCTGACGTCA AAGGAGAAGCTGGACATTGCCAGACAGCTTTCCAAGC TCGGCGTTGACATAATCGAGGCTGGATTCCCCGCCGC CTCGAAAGATGACTTCGAGGCCGTCAAGATTATTGCC AAAGAGGTCGGTAACGCCGTTGACGCCGACGGCTATG TTCCCGTTATCTGTGGTCTGTCGAGGTGTAATGAGAA CGATATTAGGAGGGCTTGGGAGGCGGTCAAGTACGCC AAAAGGCCTAGGATTCATACTTTCATTGCTACAAGTC CAATTCACATGGAGTACAAGTTGAGAAAGAGTAAGGA GCAGGTGATTGAGATCGCTAGGAACATGGTGAAGTTT GCTCGGAGTTTGGGGTGTGATGATGTTGAGTTTAGCC CTGAAGATGCTGGCAGGTCTGAGAGGGAATTCTTGTA TCAGATTTTGGGAGAAGTTATAAAGGCTGGAGCAACA ACTCTAAACATACCTGACACTGTTGGTTACAACGTGC CAAAAGAATTTGGAGAATTGATTGCTGACATTAAAGC CAATACCCCTGGAATTGAGAATGTTGTCATTTCTACA CACTGTCAAAATGATCTTGGACTTTCTACTGCAAACA CGATATCGGGGGCATGCGCAGGTGCTAGACAATTAGA AGTAACAATCAACGGCATTGGTGAAAGAGCCGGGAAT GCATCTCTGGAGGAGGTTGTAATGGCCATAAAATGCC GTGGAGATCAACAACTGGGAGGACTTTATACTGGAAT CAACACAAGACACATCTCAATGACAAGCATAATGGTT GAGGAATACACAGGGTTGCAAGTACAGCCACATAAGG CTATTGTTGGAGCCAATGCTTTTGCACATGAAAGCGG TATCCATCAGGATGGAATGCTTAAGCACAAAGGTACA TATGAAATCATATCCCCAGAAGATATAGGGCTTGAAC GAAGCAATGAAGCTGGTATAGTCCTTGGAAAACTCAG TGGTCGCCATGCATTGAAACAACAACTTGAGGAGCTT GGTTATGAGCTTGAGGATGAGCAACTTGAGAGTATAT TCTGGCGCTTCAAATCTGTGGCTGAACTTAAGAAGAG GATAACTGATGCTGACCTCAGAGCACTAGTTTCGGAT GAAGTTTTTCAACCAGAAGTCATCTGGAAGTTCGTTG ATTTGCAGGTTACATGTGAACTCTTGGTCTTTCAAC TGCAACCGTCAAACTTATTGGTTCAGATGGGAAAGAG CATGTTGCTTGTTCAGTAGGAACTGGTCCAGTGGACT CGGCTTACAAAGCTGTTGATCTGATTGTGAAGGAACC AGTAGCACTCCTGGAGTATTCAATGAATGCTGTTACT GAAGGTATAGATGCAATTGCAACCACCCGTGTGCTAA TCCGAGAGGAAACGAGCGACTTGTCAGGTCATGGTTC AACTGTTGAACGAGTTACTCGGACATTTAGTGGGAAC GGGTCAGGAATGGATATTGTGGTTTCAAGTGTAAAGG CTTACATTGGTGCGATAAACAAGATGTTAGGTTTCAA AGATAGGACCGTTGTGAATTCTTCTGAAGAGAGAATA CCCATATCTGCATAA |
| 63 | transcription factor MYB61 isoform X1 [*Cannabis sativa*] | Nucleic acid | ATGGGGAGGCACTCTTGTTGTTACAAGCAGAAACTGA GAAAAGGGTTGTGGTCACCAGAAGAAGATGAGAAACT TCTTAATTATATAACCAAGCATGGACATGGCTGCTGG AGCTCTGTCCCTAAGCTAGCTGGTCTTCAGAGATGTG GAAAAAGTTGCAGGCTAAGGTGGATAAATTATTTGAG GCCTGATTTGAAAAGAGGCCCATTTTCACAACAAGAG GAGAATTTGATAATTGAACTTCATGCAGTTCTTGGCA ACAGATGGTCACAGATTGCAGCTCAGTTACCAGGAAG AACAGATAATGAGATTAAAAACTTATGGAATTCTTGC ATTAAGAAGAAACTGAGGCAAAAAGGGATTGACCCAA ATACTCATAAGCCATTATCTGAGGTAGAAAATGACAT TGGTAATAAATTGGAGAACAAGGGTAACAAAGCTGCA ACCAATAACAACAACAATGAGAATATTAATAATTCTA CTGTTAGAGCTTCTTCATTAGGAAACTTATCCAATGA TCATCATCATCATCATCATCATCTGAATCTAGCT GACCAGTCACAACCATCAATGGCGGCCATCAATCGTT ACCCACTATTGGAAGTCTCATCCTCAACTCCGCCGAC ACAAGAATTCTTCATAGAAAAATCAACAGATACCAGA TCATCACCATCAATATCATCATCATCACCTTGTGATT TTTCTACCTACTTCTCTTTCCACTCAAACAATTACAA TACGACGTCGTCCGCTGCTGCAGCTGCTGCTGTTTCT CATCATCAAGATCAAAACAACAACAACAACATGGCCA GTTTCTGCTTCAACATTAATCAAAATTCAACTAGACC TCCACAACACCATCATCATAATCAGATGATTAGTAAT |

TABLE 1-continued

Sequences for this disclosure

| SEQ ID NO | Sequence Description | Sequence Type | Sequence |
|---|---|---|---|
| | | | CTCATCCAGCCACTACAACAACAAGTATCACCTTCAT CAACAACAACAGCATCATCATCATCACCACCCTCCAA TATTCCACGTGTAAAGCCCTCCATAAGTCTCCCCTTA TTATCTGATCACCAAAACAACAGTAATAGCACTACTA CTACTACTACAACAACTACTGGAGCCGTACAAAATTG GGAAACTAGTACTTTCAGCAACAACGGAAGTAGTAGT AGTAGCTGCAATATCGAATTACAAGGTAATAATAATA ACAACAACAACAACTTCTTTGATCACAACACTAATTC CACCGCCGCGGCCGCCGCCGCCGCCGCTCCTAATAAC TTCTCGTGGGGATTAGTCAATGAAAGTACTGTTGGTA GCATAAAATCTGATGACCCAGAAGACATAAAATGGTC TGAATATCTCCATAGCCCTTTTCTTCTTGGTGGAGGA ATTAGTAATACTAATAATCAAAATTCTTCTTCTTCTT CACATCTTCAACCCATTTTGTACAGTAACATTGTGAA ACCAGAATCACACTTTAGTAATACTACTACTGCTACA GGATCAAACCCCACGTGGCATCATCAGAACGATCATC ATCAGCTACAAGCGGCTTCATCAGAAATAATGTACAC TAATAAAGATCTACAGAGACTTGCTGTAGCTTTTGGA CAGACCCTTTAG |
| 64 | geranylgeranyl pyrophosphate synthase. chloroplastic [Cannabis sativa] | Amino acid | MSTVNLTWVQTCSMFNQGGRSRSLSTENLNLYHPLKK TPFSIQTPKQKRPTSPESSISAVLTEQEAVKEGDEEK SIFNFKSYMVQKANSVNQALDSAVLLRDPIMIHESMR YSLLAGGKRVRPMLCLSACELVGGKESVAMPAACAVE MIHTMSLIHDDLPCMDNDDLRRGKPTNHKVFGEDVAV LAGDALLAFAFEHMAVSTVGVPAAKIVRAIGELAKSI GSEGLVAGQVVDIDSEGLANVGLEQLEFIHLHKTGAL LEASVVLGAILGGGTDEEVEKLRSFARCIGLLFQVVD DILDVTKSSQELGKTAGKDLVADKVTYPRLMGIDKSR EFAEQLNTEAKQHLSGEDPIKAAPLIALANYIAYRQN |
| 65 | (-)-kolavenyl diphosphate synthase TPS28. chloroplastic [Cannabis sativa] | Amino acid | MPSLFSQSLLLPFSQNTNTLSLFHQPKLLPPGASLLE AKDKQVNFDRDIRSKCSAISKPRTHDVFQSGGLPVIK WHEIVEDDIDGEEEDTKWTRSNEIEERVASIKSMLES MDEGEISISAYDTAWVALVEDIHGSGLPQFPSSLQWI ATHQLSDGSWGDADIFSAHDRLINTLACVVALKSWNL YPEKCQKGMAFFNANISKLERENPEHMPIGFEVAFPS LLEIARKLNLEVPEDSPVLKVIYARRDEKLTRIPRDI MHTVPTTLLHSLEGMVGLDWEKLLKLQSQDGSFLESP SSTAFALMETKDRNCLQYLTKAVQRENGGVPNVYPVD LFEHLWVADRLQRLGISRFFEPQIEECIDYVERNWTE KGIGWARNSKVEDIDDTAMGFRLLRLHGHKVSADVFQ HFKKGDDFFCFRGQSTQAVTGMYNLYRASQLVFPGEK ILEDAMEFSSKELRKKQASNELLDKWIITKDLPGEVG FALEVPWNANLPRVETRFYIEQYGGQNDVWIGKTLYR MRKVNNDEYLELAKLDYNICQALHSIEWHNLLKWYRD CKLENYGVSRRNLLLAYFLAAASIFEPDRADERLAWA KTAALMQAIQSHEDDQKASSEHRIAFVSAFKRSCNMP SYLITRVSNISDTDHGLLRTLMTTLSHLSLDTMMLYG RDITHHLRQAWEKWLVKWQEGGDGHYEEEAELLIQTI NLSSGRTLVKALLLSNPHYEKLESTTNKVCCKIRHFQ RQRHRAKANQNGEENRNILTPEIESDMQEVVQLVLQK SSDDMINTKIKQTFLLVAKSFYYAAYCDSKTINFHIG KVIFETVD |
| 66 | solanesyl diphosphate synthase 3. chloroplastic/ mitochondrial [Cannabis sativa] | Amino acid | MLFSRGERRIPTTTENGFSRWFVSHRPGYSQSQTTTH CSRDSTHKIFGGFEESREWGFAGSRYQIHHQSSSLVE EELDPFSLVADELSLVANRLRDMVVAEVPKLASAAEY FFKMGVEGKRFRPTVLLLMATALNVKVPEPAKALADT LTPELRTRQQSVAEITEMIHVASLLHDDVLDDAETRR GVGSLNCIMGNKVSVLAGDELLSRACVALAALKNTEV VTLLATVLEQLVTGETMQMTCTSEQRCSMEYYMQKTY YKTASLISNSCKSVAVIAGQTTEVAMLAFEYGKNLGL AYQLIDDILDFTGTSASLGKGSLSDIRHGIVTAPLLY AMEEFPQLRAVVEQGFENPKNVDIALDYLGKSRGIQK ARELAIKHANLAAEAIESLPESDDEDVKRSRRALVDL TQRVVTRTK |
| 67 | terpene synthase 10-like isoform X1 [Cannabis sativa] | Amino acid | MSTNNNNNINNIISRRSANYQPSLWHFDYVQSLSTPF KEGAYAKRVEKVKEEVRVMVKRAKEEEKPLSQLELID VMQRLGISYHFENEINDTLKDIYNNNNVYNTNNNVYA NSLEFRLLRQHGYPVSQEIFSTCKDERGNFMVSSNDI KGMLSLYEASFYLVENEDGILEETREKTKKYLEEYII MIMEKQQSLLDQNNNDYDYDYELVSHALELPLHWRM LRLESRWFIDVYEKRLDMNPTLLTLAKLDENIVQSIY |

TABLE 1-continued

Sequences for this disclosure

| SEQ ID NO | Sequence Description | Sequence Type | Sequence |
|---|---|---|---|
| | | | QDDLKHVESWWESTNMGKKLEFARDRTMVNFLWTVGV AFEPHFKSFRRMITKVNALITVIDDIYDVYGALDELE LFTNAVERWDISAMDGLPEYMKTCFLALYNFINDLPF DVLKGEEGLHVIKFLQKSWADLCKSYLREARWYYNGY TPRFEEYIENAWISISGPVILSHLYFFVVNPNMEDAL LSTCENGYPTIIRHSSMILRLTDDLATSTDELKRGDV PKSIQCKMYEDGISEEEARQRIKLLISETWKLINKDY INLDDDDDGDDYSPMFYESNNINKAFIEMCLNLGRM AHCIYQYGDGHGIQDRQTKDHVLSLLIHPIPLTQ |
| 68 | (−)-limonene synthase. chloroplastic isoform X1 [Cannabis sativa] | Amino acid | MQCIAFHQFASSSSLPIWSSIDNRFTPKTSITSISKP KPKLKSKSNLKSRSRSSTCYPIQCTVVDNPSSTITNN SDRRSANYGPPIWSFDFVQSLPIQYKGESYTSRLNKL EKDVKRMLIGVENSLAQLELIDTIQRLGISYRFENEI ISILKEKFTNNNNNPNINYDLYATALQFRLLRQYGE EVPQEIFNNFKNHKTGEFKANISNDIMGALGLYEASE HGKKGESILEEARIFTTKCLKKYKLMSSSNNNNMTLI SLLVNHALEMPLQWRITRSEAKWFIEEIYERKQDMNP TLLEFAKLDENMLQSTYQEELKVLSRWWKDSKLGEKL PFVRDRLVECFLWQVGVRFEPQFSYFRIMDTKLYVLL TIIDDMHDIYGTLEELQLFTNALQRWDLKELDKLPDY MKTAFYFTYNFTNELAFDVLQEHGFVHIEYFKKLMVE LCKHHLQEAKWFYSGYKPTLQEYVENGWLSVGGQVIL MHAYFAFTNPVTKEALECLKDGHPNIVRHASIILRLA DDLGTLSDELKRGDVPKSIQCYMHDTGASEDEAREHI KYLISESWKEMNNEDGNINSFFSNEFVQCKNLGRAS QFMYQYGDGHASQNNLSKERVLGLIITPIPM |
| 69 | cytochrome P450 71D11 [Cannabis sativa] | Amino acid | MEFQQIIPSFQVLLFSFFMIIVVSILLKRAQTSNRSA SKLPPGPWRLPFLGNLHQLLGPLPHHTERDLAKKHGP FMYLKIGQVPTIVVSSPEYAKEVMKVHDNALASRPNN LVTQILAYNGTDIIFAPYGQYWKEVKKICVQELLTLS RVKTFQPIREEESFNIVKNIASKVGSPINLTQMLKSL SYSIIARAAFGEKRSDHDDFVYIMKETVKLSAGFAFG DVFPSLSFLDWYTISKFKDLKLRSSRIVDRIIKLHID DQDKDNLKKSGEEEDLVDVLLRFHKSEDPNNFTLTKD NLKAIIASIFGAGSDTSSVTMELAMAEMMRNPRVMKK AQDEVREVFGKKGELDESSINEMTYLKSVVKETLRLH PPAAMLFPRESREKCDINGYEIPMKTKILVNAWAIGR DPKYWIEPESEMPERFLESSIDFKGNNFEFIPFGAGR RICPGISFALTSIELPLAFLLYHEDWKLPNGMKPEEL DMTERFGITVCRKKDLYLIPSKYEPPSMAKAMNIK |
| 70 | cytochrome P450 71D9 [Cannabis sativa] | Amino acid | MDLQLLSFPIILITLFFMEMVVKIVLKIAHHQTKNSV SKLPPGPWKLPLVGNIHQIFGSSPHVSERDLAKKYGP FMYLKIGQIPTLIVSSPEYVKEIMRTHDVVFASRPQT LAAQIMAYNCTDIIFSSYGEHWRQLRKISMQELLSPG RVQTFRPVREEELCNLVEGIMTSSKDGSPINVTKMVT KCSYGITSRAAFGKKSSDHDEFISIVEEAIEAAGGFE FAEVFPALRELDWKSRPIFESIKLRSSRIMENIIKEH IKEKEISFEKIGKDEDLVDVLLKFHKNGDDLGRETLT KDNIKAVIFDIFVAGSETTSLSVDWAMVEMMRYPKVM KKAQEEVRKIIGTKGSVNESSINEMKYLKLVVKETLR LHPPAPLLLPRESTEKCDIDGYEIPKKTRVIVNAWAI GRDPKYWIEPENEMPERFMESSIDFKGNNFEYIPFGG GRRICPGMLFGVINIELSLAYLLYHEDWKLPNGMNHE NLDMTELFGLTMRRKDDLYLIPTIYDHSSIAKS |
| 71 | cytochrome P450 71D11 [Cannabis sativa] | Amino acid | MDLQLPSFPVLLSLLESLLMAVTILMKRARNSKLPPG PWRLPLVGNLHQLLLGYSSSSSSYEVESDLAKKHGPF MYLEIGQVPTVIVSSPEYAKEIMRTHDVVFASRPRTL AAQIIGYDCTDIAFAPYGDYWRQLRKICMQALFSPKR VQSLEPIREKEVENTLQHIIANSNKLNFTQMVTNLSY SIVSRAAFGEKSSDHDEFISIVEEDIKVAGGFEFGEL FPSLRFLDWTSRPKYESLKQRSSRILEKIIKQHMINQ NNEKSEEQDLVDVLLKYHNKANLGLTLDNIKGVIWD IFEAGSETTAVTEDWAMVELMRNPIMMKKAQDEVREV FGRKGLVDKTSIHEMKYLKLIIKETLRLHPPAPELLP RENSEKCEINGYEIPNGTRVLVNVWGIGRHAKYWNEP ESFIPERFDDSSIDEKGNNFEYIPFGAGRRICPGITE GVVSLEYSLALMLYHFDWKLPNGMKPQDLDMSELFGI AVRRKDDLYLIPTIYHQSPLAN |
| 72 | (−)-isopiperitenol/ | Amino acid | MTEHSPLTPKTKLHGKVAVVTGGASGIGEATARKFAA DGARAVVIADIQDEKGQNVAASIGLERSTYVHCDVTD |

TABLE 1-continued

Sequences for this disclosure

| SEQ ID NO | Sequence Description | Sequence Type | Sequence |
|---|---|---|---|
| | (−)-carveol dehydrogenase, mitochondrial-like [Cannabis sativa] | | EAQVAALIDSTVQKYGQVDVMFSNAGVPCESDQTILD LDLVAYDKVFAVNARGMAACVKHAARAMVEGGVRGSV ICTASNLASIGTEKYTDYTMSKHAVLGLVRSASLQLG ARGIRVNAVSPGPLRTPLLKAFIDRSEEEQDKMIEAS LSLKNGRTPSVENVADAVSFLASDESEFITGHNLAVD GGYIHHPP |
| 73 | 2-alkenal reductase (NADP(+)-dependent) [Cannabis sativa] | Amino acid | MEEVSNKQLLLKNYVSGYPKESDMVLATSTIKLKLPE GSNGVLVKNLYLSCDPYMGPRMKNLNNGFFIEPFKLG SPITGNGICKVLKSGNPNFKEGDLVSGVTGWEQYSVI ESTKYMSKIQNTDVPLSYYTGLLGMPGMTAYAGFFEV CSPKKGEYVFISAASGAVGQLVGQFAKLLGCYVVGSA GRNEKVDLLKNKFGFDEAFNYKEESDEDVALKRYFPE GIDIYFDNVGGKLLDAVLQNMRSHARISVCGMISQYN LEQTEGVHNLTNLVWKSARMVGELVADYYHLYPKFLE YVMPYLKEGKIVYVEDIAEGLKSAPKALVGLENGCNV GKQVVLVSSE |
| 74 | uncharacterized protein LOC115704491 [Cannabis sativa] | Amino acid | MEQEYSSSFLSTKRYAVVTGGNKGIGFEICRQLASNG IKVVLTARDEKRGVEAVEKLIKESNFTSEDNVVEHRL DVVDPDTIASLADYIKSHFGKLDILINNAGIAGGTLD SYGYAQATELAGGNWPENGNWNEIMTQNYESAEECLK TNYYGAKATIEALVPLLQLSDSPRIVNVSSSLGLLQY IPNEWAKNMLSDVDKLREEQIDEVVSEFLNDEKQGKL EAKKWPTEISGYKVSKASLNAYTRILAKKYPQMCVNC VCPGYVKTDITCNTGQLVAAEGAESPVMLALLPLAKP SGFFFSRKQLSPFCHSFITKRTKTFLLQTQVSSTMSG ASERYAIVTGANKGIGLEIVRQLALNGVNVVLTARDE KRGLEALEKLKEKEKNLSHKVLFHQLDVADPASIVAM VDFIKTHEGKLDILVNNAGVGGTEEDMHAIVASLNAK TPKEGDIKKTTQTYESAKECMQINYYGAKKTAEELIP LLQLSDSPRIVNVSSTMGKLQNISNDWAKGVLSDAES LTEDKIDEVIREFLKDFKEGSLETKGWPSFLSPYTVS KAALTAFTRVLAKKHPNFIINCVCPGFVKTEINENTG ILQPEEGAASPVRLALLPNDAPSGLFFDRSQVSSF |
| 75 | cytochrome P450 71A22-like [Cannabis sativa] | Amino acid | MLLLFHYNMSFLDLTSNNLSSFTILLATLLFFVLLYK SWFSIKTNSPPSPPKLPIIGNLHQLGLYPHRTLQAWS RRYGPVMQLRLGSVPVLVISSATAAREIMKTHDIAFS NRPKSCALEKLLYNYRDIASAPYGEYWRQIKSVSVLH LLNNKRVQSYRAVREEETKLMVEKIRKSCGTGVNLSE LFVRLTNDVVCRVALGRKYGEESGGKRFKELLGEFTE LLGGFYVRDYFPKLGWLSRVSGLDGRMDKVAKEFDEF LEGVLHDHMNTNKNVDDEQKDFVDILLWIQRENSLGE SIDRTSIKALILDTFAAGTDTTYTVLEWAMTELIRHP NAMKKLQNEIRTTILNKKITNIAMPEEYINSVTEDDL EKMPYLKAVEKETLRLHPPIPLIVPRLTIQDMKISGY DVASGTQVFINAWAIGRDPTLWEEEPDKFEPERFLLK NAAIDYKGHDFELIPFGAGRRGCPGIVFAMAVNELAL ASVVYKFDWALLSSGEEDLDYYHMTETTGLTTHRKEP LMAVPTEYYQ |
| 76 | (−)-germacrene D synthase-like [Cannabis sativa] | Amino acid | MSPCEATIDEKRPNMPKFTPTIWGDYFMSHASSHHSS LMETMENNNKESYEKIIEMKEQVKNKLLHGLHPLENP LETLEYIDDIQRLGLSYYFENEIEQNLEQFHNNYQNL IDFGDNNLYADALCFRLLRQQGYNIACDIEDKYKNEN EKFKESISSDIRGMLNLYEAAQMRVHGEKILDEALIF TTTHLESSVKTCQLSSPYLDLVKHALMHPIRKSLQRR EARLYISLYHQLPSHEEILLILAKLDENLLQKLHQKE LSYITRWWKEFDYKSKHSFIKDRIVECYFWVYGVFFE AETSQIRLIITKLIAILTIIDDAYDSFGTLEELEPPFT QAIERWDICAIDTLPEYMKIFYMKLLEIYNEIEQFSK ERSYCPSYAKKGVQSLIRAYFKEAKWLHTKYIPTLEE YMPVGIDSAGSFMLISMVFIGMGDIVTKHSMDWIESN PQPKIIQTMAIVGRVMNDIGYHKSERKKSSGEIVAST VECYMKQYGVTGEEAIEKLSQQVKDSWKDLNEDLLNP ITIPRPLLMQVLKLVRVNHEIYREGDGFTQPTLLKNL IHSLIINPIDE |
| 77 | (−)-kolavenyl diphosphate synthase TPS28, chloroplastic | Amino acid | MPSLFSQSLLLPFSQNTNTLSLFHQPKLLPPGASLLE AKDKQVNFDRDIRSKCSAISKPRTHDVFQSGGLPVIK WHEIVEDDIDGEEEDTKWTRSNEIEERVASIKSMLES MDEGEISISAYDTAWVALVEDIHGSGLPQFPSSLQWI ATHQLSDGSWGDADIFSAHDRLINTLACVVALKSWNL |

TABLE 1-continued

Sequences for this disclosure

| SEQ ID NO | Sequence Description | Sequence Type | Sequence |
|---|---|---|---|
| | [Cannabis sativa] | | YPEKCQKGMAFFNANISKLERENPEHMPIGFEVAFPS LLEIARKLNLEVPEDSPVLKVIYARRDEKLTRIPRDI MHTVPTTLLHSLEGMVGLDWEKLLKLQSQDGSFLESP SSTAFALMETKDRNCLQYLTKAVQRENGGVPNVYPVD LFEHLWVADRLQRLGISRFFEPQIEECIDYVERNWTE KGIGWARNSKVEDIDDTAMGERLLRLHGHKVSADVFQ HFKKGDDFFCFRGQSTQAVTGMYNLYRASQLVFPGEK ILEDAMEFSSKFLRKKQASNELLDKWIITKDLPGEVG FALEVPWNANLPRVETRFYIEQYGGQNDVWIGKTLYR MRKVNNDEYLELAKLDYNICQALHSIEWHNLLKWYRD CKLENYGVSRRNLLLAYFLAAASIFEPDRADERLAWA KTAALMQAIQSHEDDQKASSEHRIAFVSAFKRSCNMP SYLITRVSNISDTDHGLLRTLMTTLSHLSLDTMMLYG RDITHHLRQAWEKWLVKWQEGGDGHYEEEAELLIQTI NLSSGRTLVKALLLSNPHYEKLFSTINKVCCKIRHFQ RQRHRAKANQNGEFNRNILTPEIESDMQEVVQLVLQK SSDDMINTKIKQTFLLVAKSFYYAAYCDSKTINFHIG KVIFETVD |
| 78 | 2-isopropylmalate synthase 2. chloroplastic [Cannabis sativa] | Amino acid | MATAIFSNPKESPTITTTSSKNHYHYQRRTHLLLHDK VQAFQAASLKLNPNPHYKKPQIVSCQSSGSESPDTEK VRRPEYIPNRISDPNYVRIFDTTLRDGEQSPGAALTS KEKLDIARQLSKLGVDIIEAGFPAASKDDFEAVKIIA KEVGNAVDADGYVPVICGLSRCNENDIRRAWEAVKYA KRPRIHTFIATSPIHMEYKLRKSKEQVIEIARNMVKF ARSLGCDDVEFSPEDAGRSEREFLYQILGEVIKAGAT TLNIPDTVGYNVPKEFGELIADIKANTPGIENVVIST HCQNDLGLSTANTISGACAGARQLEVTINGIGERAGN ASLEEVVMAIKCRGDQQLGGLYTGINTRHISMTSIMV EEYTGLQVQPHKAIVGANAFAHESGIHQDGMLKHKGT YEIISPEDIGLERSNEAGIVLGKLSGRHALKQQLEEL GYELEDEQLESIFWRFKSVAELKKRITDADLRALVSD EVFQPEVIWKFVDLQVTCGTLGLSTATVKLIGSDGKE HVACSVGTGPVDSAYKAVDLIVKEPVALLEYSMNAVT EGIDAIATTRVLIREETSDLSGHGSTVERVTRTESGN GSGMDIVVSSVKAYIGAINKMLGFKDRTVVNSSEERI PISA |
| 79 | transcription factor MYB61 isoform X1 [Cannabis sativa] | Amino acid | MGRHSCCYKQKLRKGLWSPEEDEKLLNYITKHGHGCW SSVPKLAGLQRCGKSCRLRWINYLRPDLKRGPFSQQE ENLIIELHAVLGNRWSQIAAQLPGRTDNEIKNLWNSC IKKKLRQKGIDPNTHKPLSEVENDIGNKLENKGNKAA TNNNNNENINNSTVRASSIGNLSNDHHHHHHHHLNLA DQSQPSMAAINRYPLLEVSSSTPPTQEFFIEKSTDTR SSPSISSSSPCDESTYFSFHSNNYNTTSSAAAAAAVS HHQDQNNNNNMASFCFNINQNSTRPPQHHHHNQMISN LIQPLQQQVSPSSTTTASSSSPPSNIPRVKPSISLPL LSDHQNNSNSTTTTTTTTGAVQNWETSTESNNGSSS SSCNIELQGNNNNNNNNFFDHNTNSTAAAAAAAAPNN FSWGLVNESTVGSIKSDDPEDIKWSEYLHSPELLGGG ISNTNNQNSSSSSHLQPILYSNIVKPESHFSNTTTAT GSNPTWHHQNDHHQLQAASSEIMYTNKDLQRLAVAFG QTL |
| 80 | MALD1 promoter | Nucleic acid | ACTAAATTTTGATTACTTTAAAACTGTGGCTATTCTT TAATTATCAGTTGTAAATCTGGCTATTTTTAAAATTA ACTAGTTTTACGCTTGCCAATTTACCACAACTCCTCC TTTGTTAGCATGTAATAATATGAGGGAGCTCACACAG ACCGAGTAAATTCCCTATGAGCAGTGGTGGATCTAGA GGGCAATGTGCGAGTTCCTGGATTGCACAGTCCTTGT ATATATATATTAAAAAATTTATTAAATATCTATAAAT ATTTAATTGTCAACCCAATTACTAACTTGAGCCCGAT CATTATAGAAATTCATAAATTTCAAAGTCTGGAATCG CCTAAGTTGGTCAACTAAAATCTCCTCTTGAGCTACT AATCACTTCTAGAAGAGAGTACACAGCAGTCTCATTT AATGCAACATCAACCTACTGAAAAGGGAAATGATCAG GACCAAAGTTTACTTTAAAGAGTCAAAACTTCATAAA CCGTATAGATAGATAATATAGCTTGACAAAATAGACC CCGTGGTAAAATCATCATTTCAATAGAAATTAGGAAA AGCAATTTGTTTTTTCCTTATCAGATGTCGAGAGTCT ATCGGAAACAATCTTTATATCTTTTCAAGGTAAAGTA AAGCTGCGTACACCGTACCCTCTCCAAACCCCACTTA TGAGATTACGTTGAATTATTATTGTTGTTGTTGTTGT TGTTGATGTCAAGATTAACTTGCTTGTTATCTTTACT ATTTGTTAGATACCTACTATTTTTCATCGACACAAGT |

TABLE 1-continued

Sequences for this disclosure

| SEQ ID NO | Sequence Description | Sequence Type | Sequence |
|---|---|---|---|
| | | | AATAAATAATTTTGTCGTAGATTATCCACAAGATAGC<br>TACCTCCTATAAATATTATATGTACCGAATAATTCTC<br>CCCATCATATTTAAGCATATGAAAAAATCACCTATCT<br>TTTTAAATGTTTCATAATTTTCATCTTACTTTATTAA<br>CCGTTAGACCACGCTTTAATCCGTAACTTCACTTGTA<br>TTTAAGAGATTTCAACTCAATAAAAAAGATGACAGGT<br>GGAAAAGGAAATGTCGGCATGTTTAGTTGAAAAAAA<br>ACTTGTACTGTTATTTTCTGTGGCACATTCAAGATCG<br>TATTCATAGTAATAAAAAGTTTGGTCCTGGCTAGCTG<br>AAAAATTTGGTTAGTAGGGAATGCATGCATGTAAACG<br>CCGCCCTTCATTAAAAGATTGTATGCTACTATATTTT<br>TTGGGATCTTTACGTAAAATAGCTGATCATATTTACT<br>GTTTACTTTTTCTAGCCATATACATAGATCATACATT<br>GATTATATATGATTATGCACATATATTATATAAATCA<br>TGTATATATTATACCTCAACCGGATATTTTTAGTTTT<br>GAGTGGTTAAGTGAGCGGCTATTTGGATTAATTATTC<br>ATATTTTTTTGGTTTCCCACTTTGTGTCCGGTATCC<br>TCTTTGGAGTTTGATTAATTTGGATTCGTGGTGGAAA<br>ATTCAATTTTGGAGTGTAAAGCTCTCCCTACCAAACA<br>AGGGCGGATTTAGGCCGTATGGTGCACATGTACCCAT<br>GGTTTTTCCGCCAAATAGGTATTTTATGTATATATTT<br>CATAAAATTGATCTAATATTATCTGTTGAGCCCCATG<br>CTCCAAAAAAGTTGAATAGTGCACCTGGTTGAATTCT<br>AAGTTATTCATCCAAAGGAACATGGATAGATTCTAGC<br>TTAGCACTTCTTTTTTCTGGCTTTTTCAATGGTGCAC<br>CTATGATCTAGAAATCCTAGATTCGCCTCTGCTACCA<br>TAGGCGACTCCATACCCAAGGCTCGAAACTGAAATCT<br>CTGATTAAAGATAGAGGAGAGTACTTACCGCTCCAAT<br>ACAACCTTGGTGCCTCGTGGTAGGTTGTATAGTACAC<br>TTTAATAAACAAGAAAGCTTAAGCGTTAAAATTAACT<br>TCATTTCTCAAGCTATAAATACCATCATGAAACAACA<br>CAATTTATACTACAATACACTCCAAGTTTTTTTAGAG<br>GAAAAAAAAAATG |
| 81 | MALD1 promoter (truncated) | Nucleic acid | TATTAACCGTTAGACCACGCTTTAATCCGTAACTTCA<br>CTTGTATTTAAGAGATTTCAACTCAATAAAAAAGATG<br>ACAGGTGGAAAAGGAAATGTCGGCATGTTTAGTTGA<br>AAAAAAACTTGTACTGTTATTTTCTGTGGCACATTCA<br>AGATCGTATTCATAGTAATAAAAAGTTTGGTCCTGGC<br>TAGCTGAAAAATTTGGTTAGTAGGGAATGCATGCATG<br>TAAACGCCGCCCTTCATTAAAAGATTGTATGCTACTA<br>TATTTTTTGGGATCTTTACGTAAAATAGCTGATCATA<br>TTTACTGTTTACTTTTTCTAGCCATATACATAGATCA<br>TACATTGATTATATATGATTATGCACATATATTATAT<br>AAATCATGTATATATTATACCTCAACCGGATATTTTT<br>AGTTTTGAGTGGTTAAGTGAGCGGCTATTTGGATTAA<br>TTATTCATATTTTTTTGGTTTCCCACTTTGTGTCCG<br>GTATCCTCTTTGGAGTTTGATTAATTTGGATTCGTGG<br>TGGAAAATTCAATTTTGGAGTGTAAAGCTCTCCCTAC<br>CAAACAAGGGCGGATTTAGGCCGTATGGTGCACATGT<br>ACCCATGGTTTTTCCGCCAAATAGGTATTTTATGTAT<br>ATATTTCATAAAATTGATCTAATATTATCTGTTGAGC<br>CCCATGCTCCAAAAAAGTTGAATAGTGCACCTGGTTG<br>AATTCTAAGTTATTCATCCAAAGGAACATGGATAGAT<br>TCTAGCTTAGCACTTCTTTTTTCTGGCTTTTTCAATG<br>GTGCACCTATGATCTAGAAATCCTTGATTCGCCTCTG<br>CTACCATAGGCGACTCCATACCCAAGGCTCGAAACTG<br>AAATCTCTGATTAAAGATAGAGGAGTACTTACCGC<br>TCCAATACAACCTTGGTGCCTCGTGGTAGGTTGTATA<br>GTACACTTTAATAAACAAGAAAGCTTAAGCGTTAAAA<br>TTAACTTCATTTCTCAAGCTATAAATACCATCATGAA<br>ACAACACAATTTATACTACAATACACTCCAAGTTTTT<br>TTAGAGGAAAAAAAAATG |
| 82 | MALD1 promoter (truncated) | Nucleic acid | ATGGTGCACATGTACCCATGGTTTTTCCGCCAAATAG<br>GTATTTTATGTATATATTTCATAAAATTGATCTAATA<br>TTATCTGTTGAGCCCCATGCTCCAAAAAAGTTGAATA<br>GTGCACCTGGTTGAATTCTAAGTTATTCATCCAAAGG<br>AACATGGATAGATTCTAGCTTAGCACTTCTTTTTTCT<br>GGCTTTTTCAATGGTGCACCTATGATCTAGAAATCCT<br>TGATTCGCCTCTGCTACCATAGGCGACTCCATACCCA<br>AGGCTCGAAACTGAAATCTCTGATTAAAGATAGAGGA<br>GAGTACTTACCGCTCCAATACAACCTTGGTGCCTCGT<br>GGTAGGTTGTATAGTACACTTTAATAAACAAGAAAGC<br>TTAAGCGTTAAAATTAACTTCATTTCTCAAGCTATAA |

TABLE 1-continued

Sequences for this disclosure

| SEQ ID NO | Sequence Description | Sequence Type | Sequence |
|---|---|---|---|
|  |  |  | ATACCATCATGAAACAACACAATTTATACTACAATAC ACTCCAAGTTTTTTTAGAGGAAAAAAAAAATG |
| 83 | B3; ARF transcription factor binding site | Nucleic acid | ATGTCGGCAT |
| 84 | bZIP; Homeodomain; HD-ZIP transcription factor binding site | Nucleic acid | GAATTATTAT |
| 85 | Homeodomain; bZIP; HD-ZIP transcription factor binding site | Nucleic acid | GTTGAATTATTATT |
| 86 | Homeodomain; bZIP; HD-ZIP; WOX transcription factor binding site | Nucleic acid | TTTAATTATC |
| 87 | Homeodomain; bZIP; HD-ZIP transcription factor binding site | Nucleic acid | CATTTAATGC |
| 88 | Homeodomain; TALE transcription factor binding site | Nucleic acid | GATGACAGGT |
| 89 | MYB-related transcription factor binding site | Nucleic acid | TAAATATCTA |
| 90 | Sox; YABBY transcription factor binding site | Nucleic acid | CTTTAATTAT |
| 91 | AP2 transcription factor binding site | Nucleic acid | CACATGTACCCATG |
| 92 | Myb/SANT; G2-like transcription factor binding site | Nucleic acid | TAGATTCTAG |
| 93 | MYB; G2-like transcription factor binding site | Nucleic acid | ATAGATTCTA |
| 94 | Circadian motif | Nucleic acid | CAAAGATATC |
| 95 | Unnamed_1 motif | Nucleic acid | GGATTTTACAGT |
| 96 | Unnamed_6 motif | Nucleic acid | TATAAATATCT |

TABLE 1-continued

Sequences for this disclosure

| SEQ ID NO | Sequence Description | Sequence Type | Sequence |
|---|---|---|---|
| 97 | TATA-box motif | Nucleic acid | CCTATAAAAA |
| 98 | Circadian motif | Nucleic acid | CAAAGATATC |
| 99 | AT-rich element motif | Nucleic acid | ATAGAAATCAA |
| 100 | TC-rich repeats motif | Nucleic acid | ATTCTCTAAC |
| 101 | GATA-motif | Nucleic acid | AAGGATAAGG |
| 102 | TATA-box motif | Nucleic acid | TATATAAATC |

BACKGROUND

Glandular trichomes are epidermal outgrowths in plants that are the site of metabolic compound synthesis and storage. Their presence on stem and leaf tissues provides protection for plants against various biotic and abiotic stresses. Glandular trichomes also play a role in the biosynthesis and storage of specialized metabolites.

Metabolites produced and secreted by glandular trichomes are often hydrophobic (e.g., fatty acid derivatives, flavonoids, terpenoids). Terpenoids constitute the largest and most diverse class of plant metabolites. The olefinic backbone of terpenoids is made of multiples of the five-carbon (C) isoprene unit, with the major groups being monoterpenes (10C), sesquiterpenes (15C), and diterpenes (20C). These terpenoids are produced through the condensation of five-carbon isoprene units (dimethylallyl diphosphate [DMAPP] and isopentenyl diphosphate [IPP]) most often by the sequential head-to-tail addition of DMAPP to IPP.

Due to the important role of glandular trichomes in the biosynthesis and secretion of terpenoids, there is a need for the identification of trichome-preferred, or trichome-specific, promoters and associated cis-regulatory elements.

SUMMARY

In one aspect, this disclosure provides a modified plant, seed, or plant part, comprising a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof.

In one aspect, this disclosure provides a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof.

In one aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 80% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b).

In one aspect, this disclosure provides a method comprising preparing a tobacco product using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof.

In one aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof.

In one aspect, this disclosure provides a method comprising transforming a plant cell with a recombinant nucleic acid molecule, where the recombinant nucleic acid molecule comprises a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof.

In one aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof; and (b) selecting for at least one progeny seed produced in step (a), or a plant germinated therefrom, where the at least one progeny seed or plant germinated therefrom comprises the recombinant nucleic acid molecule.

BRIEF DESCRIPTION OF THE DRAWINGS

FIG. 15 comprises FIG. 15A, FIG. 15B, FIG. 15C, and FIG. 15D. FIG. 15A depicts trichomes in young leaf and inflorescence tissue of the wildtype tobacco line Izmir Ego. FIG. 15B depicts the expression of GREEN FLUORESCENT PROTEIN (G3GFP) driven by the 1971 nucleotide long MALDI promoter (SEQ ID NO: 80) in young leaf tissue. White arrows point to G3GFP accumulation. FIG. 15C depicts the expression of GREEN FLUORESCENT PROTEIN (G3GFP) driven by the 1055 nucleotide long MALDI promoter (SEQ ID NO: 81) in young leaf and inflorescence tissue. White arrows point to G3GFP accumulation. FIG. 15D depicts the expression of GREEN FLUORESCENT PROTEIN (G3GFP) driven by the 476 nucleotide long MALDI promoter (SEQ ID NO: 82). White arrow points to G3GFP accumulation.

DETAILED DESCRIPTION

Figure 1:
FIG. 1 depicts a tobacco glandular trichome.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

When the term "about" is used in reference to a number, it is understood to mean plus or minus 10%. For example, "about 100" would include from 90 to 110.

As used herein, the singular form "a," "an," and "the" include plural references unless the context clearly dictates otherwise. For example, the term "a compound" or "at least one compound" may include a plurality of compounds, including mixtures thereof.

Any tobacco plant, or part thereof, provided herein is specifically envisioned for use with any method provided herein. Similarly, any modified tobacco plant, or part thereof, is specifically envisioned for use with any method provided herein. Any nucleic acid sequence, amino acid sequence, or other composition provided herein is specifically envisioned for use with any method provided herein.

Any cannabis plant, or part thereof, provided herein is specifically envisioned for use with any method provided herein. Similarly, any modified cannabis plant, or part thereof, is specifically envisioned for use with any method provided herein. Any nucleic acid sequence, amino acid sequence, or other composition provided herein is specifically envisioned for use with any method provided herein.

Trichomes, in general, are hair-like epidermal outgrowths covering most aerial plant tissues. Trichomes tend to be multicellular, but unicellular trichomes are known as well. Multiple types of trichomes can be found on an individual plant, and trichomes vary in shape, size, and cellular organization. An individual trichome can be classified as a glandular trichome or a non-glandular trichome.

Glandular trichomes (see FIG. 1) are characterized by the presence of a head made of cells that can secrete or store large quantities of specialized metabolites (e.g., terpenes). Within the group of glandular trichomes, a trichome can be further characterized as being peltate or capitate. A capitate glandular trichome typically possesses a stalk with a length that is more than twice the height of the head, and the number of cells in the trichome is highly variable. A peltate trichome is a short-stalked trichome with a large head made of between four and eighteen cells arranged in one or two concentric circles.

In an aspect, a trichome is a glandular trichome. In an aspect, a glandular trichome is a capitate glandular trichome. In an aspect, a glandular trichome is a peltate glandular trichome. In an aspect, a glandular trichome is selected from the group consisting of a capitate glandular trichome and a peltate glandular trichome.

In an aspect, this disclosure provides a modified plant, seed, or plant part comprising a recombinant nucleic acid molecule comprising a trichome-specific promoter operably linked to a heterologous polynucleotide. In another aspect, this disclosure provides a modified plant, seed, or plant part comprising a recombinant nucleic acid molecule comprising a glandular trichome-specific promoter operably linked to a heterologous polynucleotide. In an aspect, this disclosure provides a modified plant, seed, or plant part comprising a recombinant nucleic acid molecule comprising a capitate glandular trichome-specific promoter operably linked to a heterologous polynucleotide. In an aspect, this disclosure provides a modified plant, seed, or plant part comprising a recombinant nucleic acid molecule comprising a peltate glandular trichome-specific promoter operably linked to a heterologous polynucleotide.

In an aspect, this disclosure provides a modified plant, seed, or plant part comprising a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 85% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 90% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 92.5% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 95% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 96% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 97% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 98% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 99% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence at least 99.5% identical to a sequence selected from the group consisting of SEQ ID NOs: 10-17, 45-47, and 80-82, or a functional fragment thereof. In an aspect, this disclosure provides a modified plant, seed, or plant part comprising a recombinant nucleic acid molecule comprising a promoter operably linked to a heterologous polynucleotide, where the promoter comprises a nucleic acid sequence 100% identical to a sequence selected from the group consisting of SEQ ID NOs: 10-17, 45-47, and 80-82, or a functional fragment thereof.

As commonly understood in the art, the term "promoter" refers to a DNA sequence that contains an RNA polymerase binding site, a transcription start site, and/or a TATA box and assists or promotes the transcription and expression of an associated transcribable polynucleotide sequence and/or gene (or transgene). A promoter can be synthetically produced, varied, or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein.

Promoters

Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. As a non-limiting example, a trichome tissue-preferred promoter exhibits higher activity in trichomes, but may also exhibit activity, albeit at lower levels, in additional tissues such as stem, leaves, and floral tissues. A "tissue-specific" promoter causes expression only in a specific tissue. As a non-limiting example, a trichome tissue-specific promoter drives expression only in trichomes. In an aspect, a tissue-specific promoter is a trichome tissue-specific promoter. In another aspect, a tissue-preferred promoter is a trichome tissue-preferred promoter. In an aspect, a trichome tissue-specific promoter is selected from the group consisting of SEQ ID NOs: 10-17, 45-47, and 80-82, or a functional fragment thereof. In an aspect, a trichome tissue-preferred promoter is selected from the group consisting of SEQ ID NOs: 10-17, 45-47, and 80-82, or a functional fragment thereof.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. In an aspect, a promoter provided herein is operably linked to a heterologous nucleic acid molecule.

In an aspect, a promoter comprises a sequence at least 70% identical to a sequence selected from the group consisting of SEQ ID NOs: 10-17, 45-47, and 80-82. In an aspect, a promoter comprises a sequence at least 75% identical to a sequence selected from the group consisting of SEQ ID NOs: 10-17, 45-47, and 80-82. In an aspect, a promoter comprises a sequence at least 80% identical to a sequence selected from the group consisting of SEQ ID NOs: 10-17, 45-47, and 80-82. In an aspect, a promoter comprises a sequence at least 85% identical to a sequence selected from the group consisting of SEQ ID NOs: 10-17, 45-47, and 80-82. In an aspect, a promoter comprises a sequence at least 90% identical to a sequence selected from the group consisting of SEQ ID NOs: 10-17, 45-47, and 80-82. In an aspect, a promoter comprises a sequence at least 92.5% identical to a sequence selected from the group consisting of SEQ ID NOs: 10-17, 45-47, and 80-82. In an aspect, a promoter comprises a sequence at least 95% identical to a sequence selected from the group consisting of SEQ ID NOs: 10-17, 45-47, and 80-82. In an aspect, a promoter comprises a sequence at least 96% identical to a sequence selected from the group consisting of SEQ ID NOs: 10-17, 45-47, and 80-82. In an aspect, a promoter comprises a sequence at least 97% identical to a sequence selected from the group consisting of SEQ ID NOs: 10-17, 45-47, and 80-82. In an aspect, a promoter comprises a sequence at least 98% identical to a sequence selected from the group consisting of SEQ ID NOs: 10-17, 45-47, and 80-82. In an aspect, a promoter comprises a sequence at least 99% identical to a sequence selected from the group consisting of SEQ ID NOs: 10-17, 45-47, and 80-82. In an aspect, a promoter comprises a sequence 100% identical to a sequence selected from the group consisting of SEQ ID NOs: 10-17, 45-47, and 80-82.

It is appreciated in the art that a fragment of a promoter sequence can function to drive transcription of an operably linked nucleic acid molecule. For example, without being limiting, if a 1000 bp promoter is truncated to 500 bp, and the 500 bp fragment is capable of driving transcription, the 500 bp fragment is referred to as a "functional fragment." As non-limiting examples, SEQ ID NO: 11 can be considered a functional fragment of SEQ ID NO: 10; SEQ ID NO: 13 can be considered a functional fragment of SEQ ID NO: 12; SEQ ID NO: 15 can be considered a functional fragment of SEQ ID NO: 14; and SEQ ID NO: 17 can be considered a functional fragment of SEQ ID NO: 16.

In an aspect, a trichome-preferred promoter comprises at least one regulatory element motif selected from the group consisting of TATA, CGTGG, TATATAAA, CATTTG, CAAAT, CAAT, CTCC, TAACCA, CAACAG, and SEQ ID NOs: 41 and 42. In an aspect, a trichome-preferred promoter comprises at least two different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-preferred promoter comprises at least three different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-preferred promoter comprises at least four different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-preferred promoter comprises at least five different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-preferred promoter comprises at least six different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-preferred promoter comprises at least seven different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-preferred promoter comprises at least eight different regulatory element motifs selected from the group consisting of TATA, CGTGG, TATATAAA, CATTTG, CAAAT, CAAT, CTCC, TAACCA, CAACAG, and SEQ ID NOs: 41 and 42.

In an aspect, a trichome-specific promoter comprises at least one regulatory element motif selected from the group consisting of TATA, CGTGG, TATATAAA, CATTTG, CAAAT, CAAT, CTCC, TAACCA, CAACAG, and SEQ ID NOs: 41 and 42. In an aspect, a trichome-specific promoter comprises at least two different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-specific promoter comprises at least three different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-specific promoter comprises at least four different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-specific promoter comprises at least five different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-specific promoter comprises at least six different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-specific promoter comprises at least seven different regulatory element motifs selected from the group consisting of TATA, CGTGG, TATATAAA, CATTTG, CAAAT, CAAT, CTCC, TAACCA, CAACAG, and SEQ ID NOs: 41 and 42. In an aspect, a trichome-specific promoter comprises at least eight different regulatory element motifs selected from the group consisting of TATA, CGTGG, TATATAAA, CATTTG, CAAAT, CAAT, CTCC, TAACCA, CAACAG, and SEQ ID NOs: 41 and 42.

Plants

In an aspect, a plant provided herein is a modified plant. In an aspect, a seed provided herein is a modified seed. In an aspect, a plant part provided herein is a modified plant part. As used herein, "modified," in the context of a plant, seed, or plant part, refers to a plant, seed, or plant part, comprising a genetic alteration introduced for certain purposes and beyond natural polymorphisms. Without being limiting, a modified plant, seed, or plant part comprises a recombinant nucleic acid molecule. In another aspect, a modified plant, seed, or plant part comprises a genetic modification. In an aspect, a modified plant, seed, or plant part is a transgenic plant, seed, or plant part.

In an aspect, a plant is a tobacco plant. In an aspect, a plant is a *Nicotiana* plant. In an aspect, a tobacco plant is a *Nicotiana tabacum* plant.

In an aspect, a *Nicotiana* plant, seed, or plant part is selected from the group consisting of *Nicotiana tabacum, Nicotiana amplexicaulis* PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572.

In an aspect, a seed is a tobacco seed. In an aspect, a seed is a *Nicotiana* seed. In an aspect, a tobacco seed is a *Nicotiana tabacum* seed.

In an aspect, a plant part is a tobacco plant part. In an aspect, a plant part is a *Nicotiana* plant part. In an aspect, a tobacco plant part is a *Nicotiana tabacum* plant part.

In an aspect, a plant is a cannabis plant. In an aspect, a plant is a *Cannabis* plant. In an aspect, a cannabis plant is a *Cannabis sativa* plant. In an aspect, a cannabis plant is a *Cannabis indica* plant. In an aspect, a cannabis plant is a *Cannabis ruderalis* plant. In an aspect, a cannabis plant is selected from the group consisting of *Cannabis sativa, Cannabis indica*, and *Cannabis ruderalis*.

In an aspect, a seed is a cannabis seed. In an aspect, a seed is a *Cannabis* seed. In an aspect, a cannabis seed is a *Cannabis sativa* seed. In an aspect, a cannabis seed is a *Cannabis indica* seed. In an aspect, a cannabis seed is a *Cannabis ruderalis* seed. In an aspect, a cannabis seed is selected from the group consisting of *Cannabis sativa, Cannabis indica*, and *Cannabis ruderalis*.

In an aspect, a plant part is a cannabis plant part. In an aspect, a plant part is a *Cannabis* plant part. In an aspect, a cannabis plant part is a *Cannabis sativa* plant part. In an aspect, a cannabis plant part is a *Cannabis* indica plant part. In an aspect, a cannabis plant part is a *Cannabis ruderalis* plant part. In an aspect, a cannabis plant part is selected from the group consisting of *Cannabis sativa, Cannabis indica*, and *Cannabis ruderalis*.

In an aspect, a plant part provided includes, but is not limited to, a leaf, a stem, a root, a trichome, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, a plant part does not include a seed. In an aspect, this disclosure provides plant cells, tissues, and organs that are not reproductive material and do not mediate the natural reproduction of the plant. In another aspect, this disclosure also provides plant cells, tissues, and organs that are reproductive material and mediate the natural reproduction of the plant. In another aspect, this disclosure provides plant cells, tissues, and organs that cannot maintain themselves via photosynthesis. In another aspect, this disclosure provides somatic plant cells. Somatic cells, contrary to germline cells, do not mediate plant reproduction.

Cells, tissues and organs can be from seed, fruit, leaf, cotyledon, hypocotyl, meristem, embryos, endosperm, root, shoot, stem, trichome, pod, flower, inflorescence, stalk, pedicel, style, stigma, receptacle, petal, sepal, pollen, anther, filament, ovary, ovule, pericarp, phloem, vascular tissue. In another aspect, this disclosure provides a plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco and cannabis plants naturally reproduce via seeds, not via asexual reproduction or vegetative propagation. In an aspect, this disclosure provides plant endosperm.

This disclosure provides cells from plants provided herein.

As used herein, a "progeny plant" or "progeny seed" can be from any filial generation, e.g., $F_1, F_2, F_3, F_4, F_5, F_6, F_7$, etc.

In an aspect, a tobacco plant, seed, or plant part, is of a tobacco variety selected from the group consisting of a flue-cured variety, a bright variety, a Burley variety, a Virginia variety, a Maryland variety, a dark variety, a Galpão variety, an Oriental variety, and a Turkish variety.

In an aspect, a tobacco cell is of a tobacco variety selected from the group consisting of a flue cured variety, a bright variety, a Burley variety, a Virginia variety, a Maryland variety, a dark variety, a Galpão variety, an Oriental variety, and a Turkish variety.

In an aspect, a tobacco leaf is of a tobacco variety selected from the group consisting of a flue cured variety, a bright variety, a Burley variety, a Virginia variety, a Maryland variety, a dark variety, a Galpão variety, an Oriental variety, and a Turkish variety.

In an aspect, a cured tobacco leaf or plant part is of a tobacco variety selected from the group consisting of a flue cured variety, a bright variety, a Burley variety, a Virginia variety, a Maryland variety, a dark variety, a Galpão variety, an Oriental variety, and a Turkish variety. Skilled artisans further understand that cured tobacco does not constitute a living organism and is not capable of growth or reproduction Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, tobacco plants, seeds, or plant parts provided herein are of a flue-cured tobacco variety selected from the group consisting of the varieties listed in Table 2, and any variety essentially derived from any one of the foregoing varieties. See WO 2004/041006 A1. In a further aspect, tobacco plants, seeds, or plant parts provided herein are in a flue-cured variety selected from the group consisting of K326, K346, and NC196.

TABLE 2

Flue-cured Tobacco Varieties 400 (TC 225)
401 (TC 226)
401 Cherry Red (TC 227)
401 Cherry Red Free (TC 228)
Cash (TC 250)
Cash (TI 278)
CC 101
CC 1063
CC 13
CC 143
CC 200
CC 27
CC 301
CC 33
CC 35
CC 37
CC 400
CC 500
CC 600
CC 65
CC 67
CC 700
CC 800
CC 900
Coker 139 (TC 259)
Coker 139 yb1, yb2
Coker 140 (TC 260)
Coker 176 (TC 262)
Coker 187 (TC 263)
Coker 187-Hicks (TC 265)
Coker 209 (TC 267)
Coker 258 (TC 270)
Coker 298 (TC 272)
Coker 316 (TC 273)
Coker 319 (TC 274)
Coker 347 (TC 275)
Coker 371-Gold (TC 276)
Coker 411 (TC 277)
Coker 48 (TC 253)
Coker 51 (TC 254)
Coker 86 (TC 256)
CU 263 (TC 619)
CU 561
DH95-1562-1
Dixie Bright 101 (TC 290)
Dixie Bright 102 (TC 291)
Dixie Bright 244 (TC 292)
Dixie Bright 27 (TC 288)
Dixie Bright 28 (TC 289)
GF 157
GF 318
GL 26H
GL 338
GL 350
GL 368
GL 395
GL 600
GL 737
GL 939
GL 939 (TC 628)
Hicks (TC 310)
Hicks Broadleaf (TC 311)
K 149 (TC 568)
K 317
K 326
K 326 (TC 319)
K 340 (TC 320)
K 346
K 346 (TC 569)
K 358
K 394 (TC 321)
K 399
K 399 (TC 322)

TABLE 2-continued

Flue-cured Tobacco Varieties

K 730
Lonibow (TI 1573)
Lonibow (TI 1613)
McNair 10 (TC 330)
McNair 135 (TC 337)
McNair 30 (TC 334)
McNair 373 (TC 338)
McNair 944 (TC 339)
MK94 (TI 1512)
MS K 326
MS NC 71
MS NC 72
NC 100
NC 102
NC 1071 (TC 364)
NC 1125-2
NC 12 (TC 346)
NC 1226
NC 196
NC 2326 (TC 365)
NC 27 NF (TC 349)
NC 291
NC 297
NC 299
NC 37 NF (TC 350)
NC 471
NC 55
NC 567 (TC 362)
NC 60 (TC 352)
NC 606
NC 6140
NC 71
NC 72
NC 729 (TC 557)
NC 810 (TC 659)
NC 82 (TC 356)
NC 8640
NC 89 (TC 359)
NC 92
NC 925
NC 95 (TC 360)
NC 98 (TC 361)
NC EX 24
NC PY 10 (TC 367)
NC TG 61
Oxford 1 (TC 369)
Oxford 1-181 (TC 370)
Oxford 2 (TC 371)
Oxford 207 (TC 632)
Oxford 26 (TC 373)
Oxford 3 (TC 372)
Oxford 414 NF
PD 611 (TC 387)
PVH 03
PVH 09
PVH 1118
PVH 1452
PVH 1600
PVH 2110
PVH 2275
R 83 (Line 256-1) (TI 1400)
Reams 134
Reams 158
Reams 713
Reams 744
Reams M1
RG 11 (TC 600)
RG 13 (TC 601)
RG 17 (TC 627)
RG 22 (TC 584)
RG 8 (TC 585)
RG 81 (TC 618)
RG H51
RG4H 217
RGH 12
RGH 4
RGH 51
RGH 61

TABLE 2-continued

Flue-cured Tobacco Varieties

SC 58 (TC 400)
SC 72 (TC 403)
Sp. G-168
SPEIGHT 168
Speight 168 (TC 633)
Speight 172 (TC 634)
Speight 178
Speight 179
Speight 190
Speight 196
SPEIGHT 220
SPEIGHT 225
SPEIGHT 227
SPEIGHT 236
Speight G-10 (TC 416)
Speight G-102
Speight G-108
Speight G-111
Speight G-117
Speight G-126
Speight G-15 (TC 418)
Speight G-23
Speight G-28 (TC 420)
Speight G-33
Speight G-41
Speight G-5
Speight G-52
Speight G-58
Speight G-70
Speight G-70 (TC 426)
Speight G-80 (TC 427)
Speight NF3 (TC 629)
STNCB
VA 182
VA 45 (TC 559)
Vesta 30 (TC 439)
Vesta 33 (TC 440)
Vesta 5 (TC 438)
Vesta 62 (TC 441)
Virginia (TI 220)
Virginia (TI 273)
Virginia (TI 877)
Virginia 115 (TC 444)
Virginia 21 (TC 443)
Virginia Bright (TI 964)
Virginia Bright Leaf (TC 446)
Virginia Gold (TC 447)
White Stem Orinoco (TC 451)

Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, tobacco plants, seeds, or plant parts provided herein are of a Burley tobacco variety selected from the group consisting of the tobacco varieties listed in Table 3, and any variety essentially derived from any one of the foregoing varieties. In a further aspect, tobacco plants, seeds, or plant parts provided herein are in a Burley variety selected from the group consisting of TN 90, KT 209, KT 206, KT212, and HB 4488.

TABLE 3

Burley Tobacco Varieties

4407 LC
AA-37-1
Burley 21 (TC 7)
Burley 49 (TC 10)
Burley 64 (TC 11)
Burley Mammoth KY 16 (TC 12)
Clay 402
Clay 403
Clay 502
Clays 403
GR 10 (TC 19)
GR 10 (TC 19)
GR 10A (TC 20)
GR 13 (TC 21)
GR 14 (TC 22)
GR 149 LC
GR 153
GR 17 (TC 23)
GR 17B (TC 24)
GR 18 (TC 25)
GR 19 (TC 26)
GR 2 (TC 15)
GR 24 (TC 27)
GR 36 (TC 28)
GR 38 (TC 29)
GR 38A (TC 30)
GR 40 (TC 31)
GR 42 (TC 32)
GR 42C (TC 33)
GR 43 (TC 34)
GR 44 (TC 35)
GR 45 (TC 36)
GR 46 (TC 37)
GR 48 (TC 38)
GR 5 (TC 16)
GR 53 (TC 39)
GR 6 (TC 17)
GR 9 (TC 18)
GR139 NS
GR139 S
HB 04P
HB 04P LC
HB 3307P LC
HB 4108P
HB 4151P
HB 4192P
HB 4194P
HB 4196
HB 4488
HB 4488P
HB04P
HB 4488 LC
HIB 21
HPB 21
HY 403
Hybrid 403 LC
Hybrid 404 LC
Hybrid 501 LC
KDH-959 (TC 576)
KDH-960 (TC 577)
KT 200 LC
KT 204 LC
KT 206 LC
KT 209 LC
KT 210 LC
KT 212 LC
KT 215 LC
KY 1 (TC 52)
KY 10 (TC 55)
KY 12 (TC 56)
KY 14 (TC 57)
KY 14 × L8 LC
KY 15 (TC 58)
KY 16 (TC 59)
KY 17 (TC 60)
KY 19 (TC 61)
KY 21 (TC 62)
KY 22 (TC 63)

TABLE 3-continued

Burley Tobacco Varieties

KY 24 (TC 64)
KY 26 (TC 65)
KY 33 (TC 66)
KY 34 (TC 67)
KY 35 (TC 68)
KY 41A (TC 69)
KY 5 (TC 53)
KY 52 (TC 70)
KY 54 (TC 71)
KY 56 (TC 72)
KY 56 (TC 72)
KY 57 (TC 73)
KY 58 (TC 74)
KY 8654 (TC 77)
KY 8959
KY 9 (TC 54)
KY 907 LC
KY 908 (TC 630)
NBH 98 (Screened)
NC 1206
NC 129
NC 2000 LC
NC 2002 LC
NC 3 LC
NC 5 LC
NC 6 LC
NC 7 LC
NC BH 129 LC
NC03-42-2
Newton 98
R 610 LC
R 630 LC
R 7-11
R 7-12 LC
RG 17
TKF 1801 LC
TKF 2002 LC
TKF 4024 LC
TKF 4028 LC
TKF 6400 LC
TKF 7002 LC
TKS 2002 LC
TN 86 (TC 82)
TN 90 LC
TN 97 Hybrid LC
TN 97 LC
VA 116
VA 119
Virgin A Mutante (TI 1406)
Virginia 509 (TC 84)

In another aspect, tobacco plants, seeds, or plant parts provided herein are of a Maryland tobacco variety selected from the group consisting of the tobacco varieties listed in Table 4, and any variety essentially derived from any one of the foregoing varieties.

TABLE 4

Maryland Tobacco Varieties

Maryland 10 (TC 498)
Maryland 14 D2 (TC 499)
Maryland 201 (TC 503)
Maryland 21 (TC 500)
Maryland 341 (TC 504)
Maryland 40
Maryland 402
Maryland 59 (TC 501)
Maryland 601
Maryland 609 (TC 505)
Maryland 64 (TC 502)
Maryland 872 (TC 506)
Maryland Mammoth (TC 507)

Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, tobacco plants, seeds, or plant parts provided herein are of a dark air-cured tobacco variety selected from the group consisting of Sumatra, Jatim, Dominican Cubano, Besuki, One sucker, Green River, Virginia sun-cured, and Paraguan Passado, and any variety essentially derived from any one of the foregoing varieties.

Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, tobacco plants, seeds, or plant parts provided herein are of a dark fire-cured tobacco variety selected from the group consisting of the tobacco varieties listed in Table 5, and any variety essentially derived from any one of the foregoing varieties.

TABLE 5

Dark Fire-Cured Tobacco Varieties

Black Mammoth (TC 461)
Black Mammoth Small Stalk (TC 641)
Certified Madole (TC 463)
D-534-A-1 (TC 464)
DAC ULT 302
DAC ULT 303
DAC ULT 306
DAC ULT 308
DAC ULT 312
DF 300 (TC 465)
DF 485 (TC 466)
DF 516 (TC 467)
DF 911 (TC 468)
DT 508
DT 518 (Screened)
DT 538 LC
DT 592
Improved Madole (TC 471)
Jernigan's Madole (TC 472)
KT 14LC
KT D17LC
KT D4 LC
KT D6 LC
KT D8 LC
KY 153 (TC 216)
KY 157 (TC 217)
KY 160
KY 160 (TC 218)
KY 163 (TC 219)
KY 165 (TC 220)
KY 170 (TC 474)
KY 171 (PhPh)
KY 171 (TC 475)
KY 171 LC
KY 171 NS
KY 180 (TC 573)
KY 190 (TC 574)
Little Crittenden
Little Crittenden (TC 476)
Little Crittenden LC (certified)
Little Crittenden PhPh
Lizard Tail Turtle Foot
Madole (TC 478)
Madole (TC 479)
MS KY 171
MS NL Madole LC
MS TN D950 LC
Nance (TC 616)
Narrow Leaf Madole LC (certified)

TABLE 5-continued

Dark Fire-Cured Tobacco Varieties

Neal Smith Madole (TC 646)
Newtons VH Madole
NL Madole
NL Madole (PhPh)
NL Madole (TC 484)
NL Madole LC
NL Madole LC (PhPh)
NL Madole NS
One Sucker (TC 224)
OS 400
PD 302H
PD 312H
PD 318H
PD 7302 LC
PD 7305
PD 7309 LC
PD 7312 LC
PD 7318 LC
PD 7319 LC
Petico M PG04
PY KY 160 (TC 612)
PY KY 171 (TC 613)
Shirey
TI 1372
TN D94
TN D94 (TC 621)
TN D950
TN D950 (PhPh)
TN D950
TN D950 (TC 622)
TR Madole (TC 486)
VA 309
VA 309 (TC 560)
VA 309 LC (certified)
VA 310 (TC 487)
VA 331 (TC 592)
VA 355 (TC 638)
VA 359
VA 359 (Screened)
VA 359 (TC 639)
VA 359 LC (certified)
VA 403 (TC 580)
VA 405 (TC 581)
VA 409 (TC 562)
VA 510 (TC 572)

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, tobacco plants, seeds, or plant parts provided herein are of an Oriental tobacco variety selected from the group consisting of the tobacco varieties listed in Table 6, and any variety essentially derived from any one of the foregoing varieties.

TABLE 6

Oriental Tobacco Varieties

Bafra (TI 1641)
Bahce (TI 1730)
Bahia (TI 1416)
Bahia (TI 1455)
Baiano (TI 128)
Basma
Basma (TI 1666)
Basma Drama
Basma Hybrid (PhPh)

TABLE 6-continued

Oriental Tobacco Varieties

Basma Zihna I
Bitlis (TI 1667)
Bitlis (TI 1725)
Bubalovac (TI 1282)
Bursa (TI 1650)
Bursa (TI 1668)
Canik (TI 1644)
Djebel 174 (TI 1492)
Djebel 359 (TI 1493)
Djebel 81
Dubec 566 (TI 1409)
Dubec 7 (TI 1410)
Dubek 566 (TI 1567)
Duzce (TI 1670)
Edirne (TI 1671)
Ege (TI 1642)
Ege-64 (TI 1672)
Izmir (Akhisar) (TI 1729)
Izmir (Gavurkoy) (TI 1727)
Izmir Ege 64
Izmir-Incekara (TI 1674)
Izmir-Ozbas (TI 1675)
Jaka Dzebel (TI 1326)
Kaba-Kulak
Kagoshima Maruba (TI 158)
Katerini
Katerini S53
Krumovgrad 58
MS Basma
MS Katerini S53
Nevrokop 1146
Ozbas (TI 1645)
Perustitza (TI 980)
Prilep (TI 1291)
Prilep (TI 1325)
Prilep 12-2/1
Prilep 23
Samsun (TC 536)
Samsun 959 (TI 1570)
Samsun Evkaf (TI 1723)
Samsun Holmes NN (TC 540)
Samsun Maden (TI 1647)
Samsun NO 15 (TC 541)
Samsun-BLK SHK Tol (TC 542)
Samsun-Canik (TI 1678)
Samsun-Maden (TI 1679)
Saribaptar 407 - Izmir Region
Smyrna (TC 543)
Smyrna No. 23 (TC 545)
Smyrna No. 9 (TC 544)
Smyrna-Blk Shk Tol (TC 546)
Trabzon (TI 1649)
Trabzon (TI 1682)
Trapezund 161 (TI 1407)
Turkish (TC 548)
Turkish Angshit (TI 90)
Turkish Samsum (TI 92)
Turkish Tropizoid (TI 93)
Turkish Varotic (TI 89)
Xanthi (TI 1662)

In an aspect, tobacco plants, seeds, or plant parts provided herein are of a cigar tobacco variety selected from the group consisting of the tobacco varieties listed in Table 7, and any variety essentially derived from any one of the foregoing varieties.

TABLE 7

Cigar Tobacco Varieties

Bahai (TI 62)
Beinhart 1000
Beinhart 1000 (TI 1562)
Beinhart 1000-1 (TI 1561)

TABLE 7-continued

Cigar Tobacco Varieties

Bergerac C
Bergerac C (TI 1529)
Big Cuban (TI 1565)
Castillo Negro, Blanco, Pina (TI 448)
Castillo Negro, Blanco, Pina (TI 448A)
Castillo Negro, Blanco, Pina (TI 449)
Caujaro (TI 893)
Chocoa (TI 289)
Chocoa (TI 313)
Connecticut 15 (TC 183)
Connecticut Broadleaf
Connecticut Broadleaf (TC 186)
Connecticut Shade (TC 188)
Criollo, Colorado (TI 1093)
Enshu (TI 1586)
Florida 301
Florida 301 (TC 195)
PA Broadleaf (TC 119)
Pennsylvania Broadleaf
Pennsylvania Broadleaf (TC 119)
Petite Havana SR1
Petite Havana SR1 (TC 105)

In an aspect, tobacco plants, seeds, or plant parts provided herein are of a tobacco variety selected from the group consisting of the tobacco varieties listed in Table 8, and any variety essentially derived from any one of the foregoing varieties.

TABLE 8

Other Tobacco Varieties

Chocoa (TI 319)
Hoja Parada (TI 1089)
Hoja Parado (Galpoa) (TI 1068)
Perique (St. James Parrish)
Perique (TC 556)
Perique (TI 1374)
Sylvestris (TI 984)
TI 179

In an aspect, a tobacco plant or plant part is from a variety selected from the group consisting of the tobacco varieties listed in Table 2, Table 3, Table 4, Table 5, Table 6, Table 7, and Table 8. In another aspect, a tobacco plant or plant part is from a variety listed in Table 2. In another aspect, a tobacco plant or plant part is from a variety listed in Table 3. In another aspect, a tobacco plant or plant part is from a variety listed in Table 4. In another aspect, a tobacco plant or plant part is from a variety listed in Table 5. In another aspect, a tobacco plant or plant part is from a variety listed in Table 6. In another aspect, a tobacco plant or plant part is from a variety listed in Table 7. In another aspect, a tobacco plant or plant part is from a variety listed in Table 8.

In an aspect, a tobacco seed is from a variety selected from the group consisting of the tobacco varieties listed in Table 2, Table 3, Table 4, Table 5, Table 6, Table 7, and Table 8. In another aspect, a tobacco seed is from a variety listed in Table 2. In another aspect, a tobacco seed is from a variety listed in Table 3. In another aspect, a tobacco seed is from a variety listed in Table 4. In another aspect, a tobacco seed is from a variety listed in Table 5. In another aspect, a tobacco seed is from a variety listed in Table 6. In another aspect, a tobacco seed is from a variety listed in Table 7. In another aspect, a tobacco seed is from a variety listed in Table 8.

In an aspect, a tobacco cell is from a variety selected from the group consisting of the tobacco varieties listed in Table 2, Table 3, Table 4, Table 5, Table 6, Table 7, and Table 8. In another aspect, a tobacco cell is from a variety listed in Table 2. In another aspect, a tobacco cell is from a variety listed in Table 3. In another aspect, a tobacco cell is from a variety listed in Table 4. In another aspect, a tobacco cell is from a variety listed in Table 5. In another aspect, a tobacco cell is from a variety listed in Table 6. In another aspect, a tobacco cell is from a variety listed in Table 7. In another aspect, a tobacco cell is from a variety listed in Table 8.

All foregoing mentioned specific varieties of flue-cured, dark air-cured, Burley, Maryland, dark fire-cured, cigar, or Oriental type are listed only for exemplary purposes. Any additional flue-cured, dark air-cured, Burley, Maryland, dark fire-cured, cigar, or Oriental varieties are also contemplated in the present application.

In an aspect, a plant or variety provided herein is an inbred plant or variety. As used herein, an "inbred" variety is a variety that has been bred for genetic homogeneity.

As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an Ex F hybrid. The first and second hybrids can be further crossed to create the higher order hybrid (C×D)×(E×F) comprising genetic information from all four parent varieties. In an aspect, a plant or seed provided herein is a hybrid plant or seed.

In an aspect, a tobacco plant provided herein is an inbred tobacco plant. In an aspect, a tobacco seed provided herein is an inbred tobacco seed. In an aspect, a tobacco plant provided herein is a hybrid tobacco plant. In another aspect, a tobacco seed provided herein is a hybrid tobacco seed.

In an aspect, a cannabis plant provided herein is an inbred cannabis plant. In an aspect, a cannabis seed provided herein is an inbred cannabis seed. In an aspect, a cannabis plant provided herein is a hybrid cannabis plant. In an aspect, a cannabis seed provided herein is a hybrid cannabis seed.

Unless specified otherwise, all comparisons to control plants require similar growth conditions or comparable growth conditions for the two plants being compared. As used herein, "grown under comparable conditions," "similar growth conditions" or "comparable growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103. As used herein, a "control plant" refers to a plant of identical, or nearly identical, genetic makeup as the modified plant being compared, except for the non-natural mutation or recombinant DNA construct provided herein that was introduced to the modified plant.

In an aspect, a plant or variety provided herein is male sterile. In another aspect, a plant or variety provided herein is cytoplasmic male sterile (CMS). Male sterile plants can be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Co., Inc., New York, N.Y. 761 pp.

In another aspect, a plant or variety provided herein is female sterile. As a non-limiting example, female sterile plants can be made by mutating the STIG1 gene. See, for example, Goldman et al. 1994, *EMBO Journal* 13:2976-2984.

In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 85% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 90% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 92.5% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 95% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 96% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 97% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 98% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 99% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence at least 99.9% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous polynucleotide, where the promoter comprises a nucleic acid sequence 100% identical to a sequence selected from the group consisting of SEQ ID NOs: 10-17, 45-47, and 80-82, or a functional fragment thereof; and (b) selecting at least one progeny seed produced in step (a), or a plant germinated therefrom, where the at least one progeny seed or plant germinated therefrom comprises the recombinant nucleic acid molecule.

In an aspect, a first plant variety and a second plant variety are the same variety. In an aspect, a first plant variety and a second plant variety are two different varieties. In an aspect, a second plant variety comprises a recombinant nucleic acid molecule.

In an aspect, a first plant variety is heterozygous for a recombinant nucleic acid molecule. In an aspect, a first plant variety is hemizygous for a recombinant nucleic acid molecule. In an aspect, a first plant variety is homozygous for a recombinant nucleic acid molecule. In an aspect, a second plant variety is heterozygous for a recombinant nucleic acid molecule. In an aspect, a second plant variety is hemizygous for a recombinant nucleic acid molecule. In an aspect, a second plant variety is homozygous for a recombinant nucleic acid molecule. In an aspect, a progeny seed, or a plant germinated therefrom, is heterozygous for a recombinant nucleic acid molecule. In an aspect, a progeny seed, or a plant germinated therefrom, is hemizygous for a recombinant nucleic acid molecule. In an aspect, a progeny seed, or a plant germinated therefrom, is homozygous for a recombinant nucleic acid molecule.

In an aspect, a first plant variety is a tobacco plant variety. In an aspect, a second plant variety is a tobacco plant variety. In an aspect, a first plant variety is a cannabis plant variety. In an aspect, a second plant variety is a cannabis plant variety.

As used herein, the term "crossing" refers to the deliberate mating of two plants. In an aspect, crossing comprises pollination and/or fertilization of a first plant by a second plant. The two plants being crossed can be distantly related, closely related, or identical. In an aspect, the two plants being crossed are both modified plants. In an aspect, the two plants being crossed are of the same variety. In an aspect, the two plants being crossed are of two different varieties. In an aspect, one of the two plants being crossed is male sterile. In an aspect, one of the two plants being crossed is female sterile. In an aspect, at least one of the two plants being crossed is a hybrid tobacco plant. In an aspect, at least one of the two plants being crossed is a modified plant.

In an aspect, a plant of a first variety is the male parent in a crossing step. In an aspect, a plant of a first variety is the female parent in a crossing step. In an aspect, a plant of a second variety is the male parent in a crossing step. In an aspect, a plant of a second variety is the female parent in a crossing step.

Nucleic Acids and Amino Acids

As used herein, "heterologous" refers to a sequence (nucleic acid or amino acid) that originates from a foreign species, or, if from the same species, is substantially modified from its native form in composition and/or genomic locus by deliberate human intervention. The term also is applicable to nucleic acid constructs, also referred to herein as "polynucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest. It will be appreciated that an endogenous promoter can be considered heterologous to an operably linked endogenous gene if the endogenous promoter and endogenous gene are not naturally operably linked (e.g., human intervention is required to put them in operable linkage). As used herein, an "endogenous" nucleic acid sequence refers to a nucleic acid sequence that occurs naturally in the genome of an organism.

In an aspect, a heterologous polynucleotide comprises a gene. In an aspect, a heterologous polynucleotide encodes a small RNA molecule or a precursor thereof. In an aspect, a heterologous polynucleotide encodes a polypeptide.

As used herein, a "gene" refers to a polynucleotide that can produce a functional unit (e.g., without being limiting, for example, a polypeptide, or a small RNA molecule). A gene can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a small RNA molecule or a precursor thereof. In another aspect, a gene encodes a polypeptide.

In an aspect, a gene encodes a polypeptide that has anti-herbivore properties. In an aspect, a gene encodes a polypeptide that has anti-insect properties. In an aspect, a gene encodes a polypeptide that has anti-fungal properties. In an aspect, a gene encodes a polypeptide that has anti-microbial properties.

In an aspect, a gene encodes a premnaspirodiene oxygenase-like gene. In an aspect, a gene encodes a polypeptide involved in cembratrieneol biosynthesis.

In an aspect, a gene comprises a nucleic acid sequence at least 80% identical to a nucleic acid sequence selected from the group consisting of SEQ ID NOs: 27-35 and 48-63. In an aspect, a gene comprises a nucleic acid sequence at least 85% identical to a nucleic acid sequence selected from the group consisting of SEQ ID NOs: 27-35 and 48-63. In an aspect, a gene comprises a nucleic acid sequence at least 90% identical to a nucleic acid sequence selected from the group consisting of SEQ ID NOs: 27-35 and 48-63. In an aspect, a gene comprises a nucleic acid sequence at least 92.5% identical to a nucleic acid sequence selected from the group consisting of SEQ ID NOs: 27-35 and 48-63. In an aspect, a gene comprises a nucleic acid sequence at least 95% identical to a nucleic acid sequence selected from the group consisting of SEQ ID NOs: 27-35 and 48-63. In an aspect, a gene comprises a nucleic acid sequence at least 96% identical to a nucleic acid sequence selected from the group consisting of SEQ ID NOs: 27-35 and 48-63. In an aspect, a gene comprises a nucleic acid sequence at least 97% identical to a nucleic acid sequence selected from the group consisting of SEQ ID NOs: 27-35 and 48-63. In an aspect, a gene comprises a nucleic acid sequence at least 98% identical to a nucleic acid sequence selected from the group consisting of SEQ ID NOs: 27-35 and 48-63. In an aspect, a gene comprises a nucleic acid sequence at least 99% identical to a nucleic acid sequence selected from the group consisting of SEQ ID NOs: 27-35 and 48-63. In an aspect, a gene comprises a nucleic acid sequence at least 99.5% identical to a nucleic acid sequence selected from the group consisting of SEQ ID NOs: 27-35 and 48-63. In an aspect, a gene comprises a nucleic acid sequence 100% identical to a nucleic acid sequence selected from the group consisting of SEQ ID NOs: 27-35 and 48-63.

In an aspect, a gene comprises a nucleic acid sequence at least 80% identical to a nucleic acid sequence selected from the group consisting of SEQ ID NOs: 29 and 30. In an aspect, a gene comprises a nucleic acid sequence at least 85% identical to a nucleic acid sequence selected from the group consisting of SEQ ID NOs: 29 and 30. In an aspect, a gene comprises a nucleic acid sequence at least 90% identical to a nucleic acid sequence selected from the group consisting of SEQ ID NOs: 29 and 30. In an aspect, a gene comprises a nucleic acid sequence at least 92.5% identical to a nucleic acid sequence selected from the group consisting of SEQ ID NOs: 29 and 30. In an aspect, a gene comprises a nucleic acid sequence at least 95% identical to a nucleic acid sequence selected from the group consisting of SEQ ID NOs: 29 and 30. In an aspect, a gene comprises a nucleic acid sequence at least 96% identical to a nucleic acid sequence selected from the group consisting of SEQ ID NOs: 29 and 30. In an aspect, a gene comprises a nucleic acid sequence at least 97% identical to a nucleic acid sequence selected from the group consisting of SEQ ID NOs: 29 and 30. In an aspect, a gene comprises a nucleic acid sequence at least 98% identical to a nucleic acid sequence selected from the group consisting of SEQ ID NOs: 29 and 30. In an aspect, a gene comprises a nucleic acid sequence at least 99% identical to a nucleic acid sequence selected from the group consisting of SEQ ID NOs: 29 and 30. In an aspect, a gene comprises a nucleic acid sequence at least 99.5% identical to a nucleic acid sequence selected from the group consisting of SEQ ID NOs: 29 and 30. In an aspect, a gene comprises a nucleic acid sequence 100% identical to a nucleic acid sequence selected from the group consisting of SEQ ID NOs: 29 and 30.

In an aspect, a gene comprises a nucleic acid sequence encoding an amino acid sequence at least 80% identical or similar to an amino acid sequence selected from the group consisting of SEQ ID NOs: 18-26 and 64-79. In an aspect, a gene comprises a nucleic acid sequence encoding an amino acid sequence at least 85% identical or similar to an amino acid sequence selected from the group consisting of SEQ ID NOs: 18-26 and 64-79. In an aspect, a gene comprises a nucleic acid sequence encoding an amino acid sequence at least 90% identical or similar to an amino acid sequence selected from the group consisting of SEQ ID NOs: 18-26 and 64-79. In an aspect, a gene comprises a nucleic acid sequence encoding an amino acid sequence at least 92.5% identical or similar to an amino acid sequence selected from the group consisting of SEQ ID NOs: 18-26 and 64-79. In an aspect, a gene comprises a nucleic acid sequence encoding an amino acid sequence at least 95% identical or similar to an amino acid sequence selected from the group consisting of SEQ ID NOs: 18-26 and 64-79. In an aspect, a gene comprises a nucleic acid sequence encoding an amino acid sequence at least 96% identical or similar to an amino acid sequence selected from the group consisting of SEQ ID NOs: 18-26 and 64-79. In an aspect, a gene comprises a nucleic acid sequence encoding an amino acid sequence at least 97% identical or similar to an amino acid sequence selected from the group consisting of SEQ ID NOs: 18-26 and 64-79. In an aspect, a gene comprises a nucleic acid sequence encoding an amino acid sequence at least 98% identical or similar to an amino acid sequence selected from the group consisting of SEQ ID NOs: 18-26 and 64-79. In an aspect, a gene comprises a nucleic acid sequence encoding an amino acid sequence at least 99% identical or similar to an amino acid sequence selected from the group consisting of SEQ ID NOs: 18-26 and 64-79. In an aspect, a gene comprises a nucleic acid sequence encoding an amino acid sequence at least 99.9% identical or similar to an amino acid sequence selected from the group consisting of SEQ ID NOs: 18-26 and 64-79. In an aspect, a gene comprises a nucleic acid sequence encoding an amino acid sequence 100% identical or similar to an amino acid sequence selected from the group consisting of SEQ ID NOs: 18-26 and 64-79.

In an aspect, a gene comprises a nucleic acid sequence encoding an amino acid sequence at least 80% identical or similar to an amino acid sequence selected from the group consisting of SEQ ID NOs: 20 and 21. In an aspect, a gene comprises a nucleic acid sequence encoding an amino acid sequence at least 85% identical or similar to an amino acid sequence selected from the group consisting of SEQ ID NOs: 20 and 21. In an aspect, a gene comprises a nucleic acid sequence encoding an amino acid sequence at least 90% identical or similar to an amino acid sequence selected from the group consisting of SEQ ID NOs: 20 and 21. In an aspect, a gene comprises a nucleic acid sequence encoding an amino acid sequence at least 92.5% identical or similar to an amino acid sequence selected from the group consisting of SEQ ID NOs: 20 and 21. In an aspect, a gene comprises a nucleic acid sequence encoding an amino acid sequence at least 95% identical or similar to an amino acid sequence selected from the group consisting of SEQ ID NOs: 20 and 21. In an aspect, a gene comprises a nucleic acid sequence encoding an amino acid sequence at least 96% identical or similar to an amino acid sequence selected from the group consisting of SEQ ID NOs: 20 and 21. In an aspect, a gene comprises a nucleic acid sequence encoding an amino acid sequence at least 97% identical or similar to an amino acid sequence selected from the group consisting of SEQ ID NOs: 20 and 21. In an aspect, a gene comprises a nucleic acid sequence encoding an amino acid sequence at least 98% identical or similar to an amino acid sequence selected from the group consisting of SEQ ID NOs: 20 and 21. In an aspect, a gene comprises a nucleic acid sequence encoding an amino acid sequence at least 99% identical or similar to an amino acid sequence selected from the group consisting of SEQ ID NOs: 20 and 21. In an aspect, a gene comprises a nucleic acid sequence encoding an amino acid sequence at least 99.9% identical or similar to an amino acid sequence selected from the group consisting of SEQ ID NOs: 20 and 21. In an aspect, a gene comprises a nucleic acid sequence encoding an amino acid sequence 100% identical or similar to an amino acid sequence selected from the group consisting of SEQ ID NOs: 20 and 21.

In an aspect, a polypeptide comprises an amino acid sequence at least 80% identical or similar to an amino acid sequence selected from the group consisting of SEQ ID NOs: 18-26 and 64-79. In an aspect, a polypeptide comprises an amino acid sequence at least 85% identical or similar to an amino acid sequence selected from the group consisting of SEQ ID NOs: 18-26 and 64-79. In an aspect, a polypeptide comprises an amino acid sequence at least 90% identical or similar to an amino acid sequence selected from the group consisting of SEQ ID NOs: 18-26 and 64-79. In an aspect, a polypeptide comprises an amino acid sequence at least 92.5% identical or similar to an amino acid sequence selected from the group consisting of SEQ ID NOs: 18-26 and 64-79. In an aspect, a polypeptide comprises an amino acid sequence at least 95% identical or similar to an amino acid sequence selected from the group consisting of SEQ ID NOs: 18-26 and 64-79. In an aspect, a polypeptide comprises an amino acid sequence at least 96% identical or similar to an amino acid sequence selected from the group consisting of SEQ ID NOs: 18-26 and 64-79. In an aspect, a polypeptide comprises an amino acid sequence at least 97% identical or similar to an amino acid sequence selected from the group consisting of SEQ ID NOs: 18-26 and 64-79. In an aspect, a polypeptide comprises an amino acid sequence at least 98% identical or similar to an amino acid sequence selected from the group consisting of SEQ ID NOs: 18-26 and 64-79. In an aspect, a polypeptide comprises an amino acid sequence at least 99% identical or similar to an amino acid sequence selected from the group consisting of SEQ ID NOs: 18-26 and 64-79. In an aspect, a polypeptide comprises an amino acid sequence at least 99.9% identical or similar to an amino acid sequence selected from the group consisting of SEQ ID NOs: 18-26 and 64-79. In an aspect, a polypeptide comprises an amino acid sequence 100% identical or similar to an amino acid sequence selected from the group consisting of SEQ ID NOs: 18-26 and 64-79.

In an aspect, a polypeptide comprises an amino acid sequence at least 80% identical or similar to an amino acid sequence selected from the group consisting of SEQ ID NOs: 20 and 21. In an aspect, a polypeptide comprises an amino acid sequence at least 85% identical or similar to an amino acid sequence selected from the group consisting of SEQ ID NOs: 20 and 21. In an aspect, a polypeptide comprises an amino acid sequence at least 90% identical or similar to an amino acid sequence selected from the group consisting of SEQ ID NOs: 20 and 21. In an aspect, a polypeptide comprises an amino acid sequence at least 92.5% identical or similar to an amino acid sequence selected from the group consisting of SEQ ID NOs: 20 and 21. In an aspect, a polypeptide comprises an amino acid sequence at least 95% identical or similar to an amino acid sequence selected from the group consisting of SEQ ID NOs: 20 and 21. In an aspect, a polypeptide comprises an amino acid sequence at least 96% identical or similar to an amino acid sequence selected from the group consisting of SEQ ID NOs: 20 and 21. In an aspect, a polypeptide comprises an amino acid sequence at least 97% identical or similar to an amino acid sequence selected from the group consisting of SEQ ID NOs: 20 and 21. In an aspect, a polypeptide comprises an amino acid sequence at least 98% identical or similar to an amino acid sequence selected from the group consisting of SEQ ID NOs: 20 and 21. In an aspect, a polypeptide comprises an amino acid sequence at least 99% identical or similar to an amino acid sequence selected from the group consisting of SEQ ID NOs: 20 and 21. In an aspect, a polypeptide comprises an amino acid sequence at least 99.9% identical or similar to an amino acid sequence selected from the group consisting of SEQ ID NOs: 20 and 21. In an aspect, a polypeptide comprises an amino acid sequence 100% identical or similar to an amino acid sequence selected from the group consisting of SEQ ID NOs: 20 and 21.

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," *Nucleic Acids Research* 31:3497-3500 (2003); Thompson et al., "Clustal W: Improving the sensitivity of progressive multiple sequence alignment through sequence weighting, position-specific gap penalties and weight matrix choice," *Nucleic Acids Research* 22:4673-4680 (1994); Larkin M A et al., "Clustal W and Clustal X version 2.0," *Bioinformatics* 23:2947-48 (2007); and Altschul et al. "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. A nucleic acid molecule can encode a polypeptide or a small RNA.

As used herein, a "recombinant nucleic acid molecule" refers to a nucleic acid molecule formed by laboratory methods of genetic recombination, such as, without being limiting, molecular cloning. Similarly, a "recombinant DNA construct" refers to a DNA molecule formed by laboratory methods of genetic recombination.

In an aspect, this disclosure provides a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 85% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 90% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 92.5% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 95% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 96% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 97% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 98% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 99% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence at least 99.9% identical to a sequence selected from the group consisting of SEQ ID NOs: 10-17, 45-47, and 80-82, or a functional fragment thereof. In an aspect, this disclosure provides a recombinant nucleic acid molecule comprising a promoter operably linked to a heterologous polynucleotide, where the promoter comprises a nucleic acid sequence 100% identical to a sequence selected from the group consisting of SEQ ID NOs: 10-17, 45-47, and 80-82, or a functional fragment thereof.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell.

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In an aspect, this disclosure provides a small RNA molecule, or a precursor thereof. As used herein, a "small RNA molecule" refers to a non-coding RNA molecule of between 16 nucleotides and 50 nucleotides in length. In an aspect, a small RNA molecule comprises between 16 nucleotides and 40 nucleotides. In another aspect, a small RNA molecule comprises between 16 nucleotides and 30 nucleotides. In another aspect, a small RNA molecule comprises between 18 nucleotides and 50 nucleotides. In another aspect, a small RNA molecule comprises between 18 nucleotides and 40 nucleotides. In another aspect, a small RNA molecule comprises between 18 nucleotides and 30 nucleotides. In another aspect, a small RNA molecule comprises between 18 nucleotides and 25 nucleotides. In another aspect, a small RNA molecule comprises between 20 nucleotides and 28 nucleotides. In another aspect, a small RNA molecule comprises between 20 nucleotides and 24 nucleotides. In another aspect, a small RNA molecule comprises between 21 nucleotides and 23 nucleotides. In another aspect, a small RNA molecule comprises 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In an aspect, a small RNA molecule is selected from the group consisting of a double-stranded RNA, a small interfering RNA (siRNA), a trans-acting siRNA, and a microRNA (miRNA).

miRNAs are generally of between about 19 to about 25 nucleotides (commonly about 20-24 nucleotides in plants), that guide cleavage in trans of target transcripts, negatively regulating the expression of genes involved in various regulation and development pathways. In some cases, miRNAs serve to guide in-phase processing of siRNA primary transcripts.

Many microRNA genes (MIR genes) have been identified and made publicly available in a database ("miRBase", available online at microrna[dot]sanger[dot]ac[dot]uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript. Recognition sites of miRNAs have been validated in all regions of an mRNA, including the 5' untranslated region, coding region, and 3' untranslated region, indicating that the position of the miRNA target site relative to the coding sequence may not necessarily affect suppression. Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "ΔΔG") (see Khvorova et al. (2003) Cell, 115:209-216). Preferably 19-mers are selected that have all or most of the following characteristics: (1) a Reynolds score>4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna[dot]chem[dot]t[dot]u-tokyo[dot]ac[dot]jp/siexplorer.htm (see Katoh and Suzuki (2007) Nucleic Acids Res., 10.1093/nar/gk11120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

Terpenes

Terpenes are a class of aromatic organic compound produced by plants and some insects. Terpenes are hydrocarbon molecules that are often used by plants to either directly deter herbivory or to attract predators or parasites of plant herbivores. Non-limiting examples of terpenes include citral, menthol, camphor, salvinorin A, cannabinoids, and curcuminoids.

As used herein, a "terpene" refers to a volatile unsaturated hydrocarbon found in the essential oils of plants based on a cyclic molecule having the formula $C_{10}H_{16}$, as well as related structures and simple derivatives. As a non-limiting example, a sesquiterpene having the formula $C_{15}H_{24}$ is a terpene.

In an aspect, a terpene is a terpenoid. Terpenoids (also referred to as isoprenoids) are modified terpenes that contain additional functional groups, which often include oxygen. Terpenoids, which can be cyclic or acyclic, vary in size from five-carbon hemiterpenes to long complex molecules containing thousands of isoprene units. Terpenoids are produced through the condensation of five-carbon isoprene units (e.g., dimethylallyl diphosphate (DMAPP) and isopentenyl diphosphate (IPP)), most often by the sequential head-to-tail addition of DMAPP to IPP. The initial cyclization processes are catalyzed by different terpene synthases and enzyme variation leads to variation in monoterpene structure.

Terpenoids are classified according to the number of isoprene units that comprise the parent terpene. A hemiterpenoid comprises one isoprene unit. A monoterpenoid comprises two isoprene units. A sesquiterpenoid comprises three isoprene units. A diterpenoid comprises four isoprene units. A sesterterpenoid comprises five isoprene units. A triterpenoid comprises six isoprene units. A tetraterpenoid comprises eight isoprene units. A polyterpenoid comprises more than eight isoprene units.

In an aspect, a terpene is a hemiterpene. In an aspect, a terpene is a monoterpene. In an aspect, a terpene is a sesquiterpene. In an aspect, a terpene is a diterpene. In an aspect, a terpene is a sesterterpene. In an aspect, a terpene is a triterpene. In an aspect, a terpene is a tetraterpene. In an aspect, a terpene is a polyterpene.

In an aspect, a polypeptide is involved in the biosynthesis of at least one terpene. In an aspect, a polypeptide is involved in the biosynthesis of at least one terpenoid. In an aspect, a polypeptide is involved in the biosynthesis of at least one terpenoid selected from the group consisting of a hemiterpenoid, a monoterpenoid, a sesquiterpenoid, a diterpenoid, a sesterterpenoid, a triterpenoid, a tetraterpenoid, and a polyterpenoid.

As used herein, the term "biosynthesis" refers to the production of a complex molecule (e.g., without being limiting, a terpene or terpenoid) within a plant or plant cell. To be "involved" with the biosynthesis of a compound, a polypeptide can directly interact with a substrate during the biosynthesis of the compound, or the polypeptide can affect the expression (positively or negatively) of a polypeptide that directly interacts with a substrate (e.g., a transcription factor that promotes the expression of an enzyme that converts a substrate to a new form or a repressor that inhibits expression of an enzyme that converts a substrate to a new form). Examples of biosynthetic pathways can be found in FIGS. 9-13.

In an aspect, a polypeptide is involved in the biosynthesis of a hemiterpene. In an aspect, a polypeptide is involved in the biosynthesis of a hemiterpenoid. In an aspect, a polypeptide is involved in the biosynthesis of a monoterpene. In an aspect, a polypeptide is involved in the biosynthesis of a monoterpenoid. In an aspect, a polypeptide is involved in the biosynthesis of a sesquiterpene. In an aspect, a polypeptide is involved in the biosynthesis of a sesquiterpenoid. In an aspect, a polypeptide is involved in the biosynthesis of a diterpene. In an aspect, a polypeptide is involved in the biosynthesis of a diterpenoid. In an aspect, a polypeptide is involved in the biosynthesis of a sesterterpene. In an aspect, a polypeptide is involved in the biosynthesis of a sesterterpenoid. In an aspect, a polypeptide is involved in the biosynthesis of a triterpene. In an aspect, a polypeptide is involved in the biosynthesis of a triterpenoid. In an aspect, a polypeptide is involved in the biosynthesis of a tetraterpene. In an aspect, a polypeptide is involved in the biosynthesis of a polyterpenoid. In an aspect, a polypeptide is involved in the biosynthesis of a monoterpene. In an aspect, a polypeptide is involved in the biosynthesis of a polyterpenoid.

Terpene synthase (TPS) genes can be grouped into seven clades: TPS-a, TPS-b, TPS-c, TPS-d, TPS-e/f, TPS-g, and TPS-h. TPS-a, TPS-b, and TPS-g are restricted to angiosperms, and TPS-d and TPS-h are specific to gymnosperms and the lycopod *Selaginalla moellendorffii*. The TPS-a clade comprises mostly sesquiterpene synthases and diterpene synthases, while the TPS-b and TPS-g clades comprise mostly monoterpene synthases.

In an aspect, a polypeptide involved in the biosynthesis of at least one terpenoid is a TPS-a clade member. In an aspect, a polypeptide involved in the biosynthesis of at least one terpenoid is a TPS-b clade member. In an aspect, a polypeptide involved in the biosynthesis of at least one terpenoid is a TPS-c clade member. In an aspect, a polypeptide involved in the biosynthesis of at least one terpenoid is a TPS-e/f clade member. In an aspect, a polypeptide involved in the biosynthesis of at least one terpenoid is a TPS-g clade member. In an aspect, a polypeptide involved in the biosynthesis of at least one terpenoid is a member of a clade selected from the group consisting of TPS-a, TPS-b, TPS-c, TPS-e/f, and TPS-g.

In an aspect, a terpene is menthol. In an aspect, a terpene is menthol or a related compound. In an aspect, a terpene is a labdanoid. In an aspect, a terpene is cembratrienediol. In an aspect, a terpene is levopimaric acid. In an aspect, a terpene is L-leucine. In an aspect, a terpene is neophytadiene. In an aspect, a labdanoid is cis-abienol. In an aspect, a terpene is selected from the group consisting of menthol or a related compound, a labdanoid, cembratrienediol, levopimaric acid, and L-leucine. In an aspect, a terpene is selected from the group consisting of menthol or a related compound, a labdanoid, cembratrienediol, levopimaric acid, L-leucine, and neophytadiene. In an aspect, a terpene is selected from the group consisting of menthol, a labdanoid, cembratrienediol, levopimaric acid, and L-leucine. In an aspect, a terpene is selected from the group consisting of menthol, a labdanoid, cembratrienediol, levopimaric acid, L-leucine, and neophytadiene.

As used herein, "menthol" refers to the organic compound having a chemical formula of $C_{10}H_{20}O$ and the International Union of Pure and Applied Chemistry (IUPAC) name 5-Methyl-2-(propan-2-yl)cyclohexan-1-ol. Menthol is also referred to as "(−)-Menthol." Related compounds of menthol include, but are not limited to, (+)-Menthol, (+)-Isomenthol, (+)-Neomenthol, (+)-Neoisomenthol, (−)-Isomenthol, (−)-Neomethol, and (−)-Neoisomenthol. In an aspect, a related compound of menthol is selected from the group consisting of (+)-Menthol, (+)-Isomenthol, (+)-Neomenthol, (+)-Neoisomenthol, (−)-Isomenthol, (−)-Neomethol, and (−)-Neoisomenthol.

As used herein, "neophytadiene" refers to the organic compound having a chemical formula of $C_{20}H_{38}$ and the IUPAC name of 7,11,15-trimethyl-3-methylidenehexadec-1-ene.

As used herein, "cembratrienediol" refers to the organic compound having a chemical formula of $C_{20}H_{34}O_2$ and the IUPAC name (1R,3R,4Z,8Z,12S,13Z)-1,5,9-trimethyl-12-propan-2-ylcyclotetradeca-4,8,13-triene-1,3-diol. Cembratrienediol is also referred to as "beta-Cembrenediol."

As used herein, "levopimaric acid" refers to the organic compound having a chemical formula of $C_{20}H_{30}O_2$ and the IUPAC name (1R,4aR,4bS,10aR)-1,4a-dimethyl-7-propan-2-yl-2,3,4,4b,5,9,10,10a-octahydrophenanthrene-1-carboxylic acid. Levopimaric acid is also referred to as "L-Pimaric acid."

As used herein, "L-leucine" refers to the amino acid having the chemical formula $C_6H_{12}NO_2$ and the IUPAC name (2S)-2-amino-4-methylpentanoic acid.

As used herein, a "labdanoid" refers to a terpenoid derivative of the fundamental parent labdane, a diterpene. A labdane has the chemical formula $C_{20}H_{38}$ and the IUPAC name (1S,2S,4aS,8aR)-2,5,5,8a-tetramethyl-1-[(3R)-3-methylpentyl]-1,2,3,4,4a,6,7,8-octahydronaphthalene.

A non-limiting example of a labdanoid is cis-abienol. As used herein, "cis-abienol" refers to the organic compound having a chemical formula of $C_{20}H_{34}O$ and the IUPAC name (1R,2R,4aS,8aS)-2,5,5,8a-tetramethyl-1-[(2Z)-3-methylpenta-2,4-dienyl]-3,4,4a,6,7,8-hexahydro-1H-naphthalen-2-ol.

In an aspect, a polypeptide is geranylgeranyl diphosphate synthase. In an aspect, a polypeptide is 8-hydroxy-copalyl diphosphate synthase. In an aspect, a polypeptide is cis-abienol synthase. In an aspect, a polypeptide is cembratrienol synthase 2a. In an aspect, a polypeptide is levopimardiene synthase. In an aspect, a polypeptide is 2-isopropylmalate synthetase. In an aspect, a polypeptide is 2-oxoisovalerate dehydrogenase. In an aspect, a polypeptide is neomenthol dehydrogenase. In an aspect, a polypeptide is selected from the group consisting of geranylgeranyl diphosphate synthase, 8-hydroxy-copalyl diphosphate synthase, cis-abienol synthase, cembratrienol synthase 2a, levopimaradiene synthetase, 2-isopropylmalate synthetase, 2-oxoisovalerate dehydrogenase, and neomenthol dehydrogenase.

As a non-limiting example, SEQ ID NOs: 18 and 27 are representative examples of amino acid and nucleic acid sequences, respectively, for geranylgeranyl diphosphate synthase. As a non-limiting example, SEQ ID NOs: 19 and 28 are representative examples of amino acid and nucleic acid sequences, respectively, for 8-hydroxy-copalyl diphosphate synthase. As a non-limiting example, SEQ ID NOs: 22 and 31 are representative examples of amino acid and nucleic acid sequences, respectively, for cembratrienol synthase 2a. As a non-limiting example, SEQ ID NOs: 23 and 32 are representative examples of amino acid and nucleic acid sequences, respectively, for levopimaradiene synthetase. As a non-limiting example, SEQ ID NOs: 24 and 33 are representative examples of amino acid and nucleic acid sequences, respectively, for 2-isopropylmalate synthetase. As a non-limiting example, SEQ ID NOs: 25 and 34 are representative examples of amino acid and nucleic acid sequences, respectively, for 2-oxoisovalerate dehydrogenase. As a non-limiting example, SEQ ID NOs: 26 and 35 are representative examples of amino acid and nucleic acid sequences, respectively, for neomenthol dehydrogenase.

In an aspect, a cis-abienol synthase is selected from the group consisting of cis-abienol synthase ISOFORM1 and cis-abienol synthase ISOFORM 2. In an aspect, a cis-abienol synthase is cis-abienol synthase ISOFORM 1. In an aspect, a cis-abienol synthase is cis-abienol synthase ISOFORM 2. As a non-limiting example, SEQ ID NOs: 20 and 29 are representative examples of amino acid and nucleic acid sequences, respectively, for cis-abienol synthase ISOFORM 1. As a non-limiting example, SEQ ID NOs: 21 and 30 are representative examples of amino acid and nucleic acid sequences, respectively, for cis-abienol synthase ISOFORM 2.

In an aspect, a modified plant, seed, or plant part comprising a recombinant nucleic acid provided herein comprises an increased amount of at least one terpene as compared to a control plant, seed, or plant part lacking the recombinant nucleic acid molecule when grown under comparable conditions. In an aspect, a modified tobacco plant, tobacco seed, or tobacco plant part comprising a recombinant nucleic acid provided herein comprises an increased amount of at least one terpene as compared to a control tobacco plant, tobacco seed, or tobacco plant part lacking the recombinant nucleic acid molecule when grown under comparable conditions. In an aspect, a modified cannabis plant, cannabis seed, or cannabis plant part comprising a recombinant nucleic acid provided herein comprises an increased amount of at least one terpene as compared to a control cannabis plant, cannabis seed, or cannabis plant part lacking the recombinant nucleic acid molecule when grown under comparable conditions.

In an aspect, an increased amount of at least one terpene comprises an increase of at least 0.5%. In an aspect, an increased amount of at least one terpene comprises an increase of at least 1%. In an aspect, an increased amount of at least one terpene comprises an increase of at least 2%. In an aspect, an increased amount of at least one terpene comprises an increase of at least 3%. In an aspect, an increased amount of at least one terpene comprises an increase of at least 4%. In an aspect, an increased amount of at least one terpene comprises an increase of at least 5%. In an aspect, an increased amount of at least one terpene comprises an increase of at least 10%. In an aspect, an increased amount of at least one terpene comprises an increase of at least 12.5%. In an aspect, an increased amount of at least one terpene comprises an increase of at least 15%. In an aspect, an increased amount of at least one terpene comprises an increase of at least 17.5%. In an aspect, an increased amount of at least one terpene comprises an increase of at least 20%. In an aspect, an increased amount of at least one terpene comprises an increase of at least 25%. In an aspect, an increased amount of at least one terpene comprises an increase of at least 30%. In an aspect, an increased amount of at least one terpene comprises an increase of at least 40%. In an aspect, an increased amount of at least one terpene comprises an increase of at least 50%. In an aspect, an increased amount of at least one terpene comprises an increase of at least 60%. In an aspect, an increased amount of at least one terpene comprises an increase of at least 70%. In an aspect, an increased amount of at least one terpene comprises an increase of at least 80%. In an aspect, an increased amount of at least one terpene comprises an increase of at least 90%. In an aspect, an increased amount of at least one terpene comprises an increase of at least 100%. In an aspect, an increased amount of at least one terpene comprises an increase of at least 150%. In an aspect, an increased amount of at least one terpene comprises an increase of at least 200%. In an aspect, an increased amount of at least one terpene comprises an increase of at least 250%. In an aspect, an increased amount of at least one terpene comprises an increase of at least 500%.

In an aspect, an increased amount of at least one terpene comprises an increase of between 0.5% and 500%. In an aspect, an increased amount of at least one terpene comprises an increase of between 0.5% and 250%. In an aspect, an increased amount of at least one terpene comprises an increase of between 0.5% and 100%. In an aspect, an increased amount of at least one terpene comprises an increase of between 0.5% and 75%. In an aspect, an increased amount of at least one terpene comprises an increase of between 0.5% and 50%. In an aspect, an increased amount of at least one terpene comprises an increase of between 0.5% and 25%. In an aspect, an increased amount of at least one terpene comprises an increase of between 0.5% and 10%. In an aspect, an increased amount of at least one terpene comprises an increase of between 0.5% and 5%. In an aspect, an increased amount of at least one terpene comprises an increase of between 0.5% and 500%. In an aspect, an increased amount of at least one terpene comprises an increase of between 5% and 250%. In an aspect, an increased amount of at least one terpene comprises an increase of between 5% and 100%. In an aspect, an increased amount of at least one terpene comprises an increase of between 5% and 50%. In an aspect, an increased amount of at least one terpene comprises an increase of between 25% and 500%. In an aspect, an increased amount of at least one terpene comprises an increase of between 25% and 250%. In an aspect, an increased amount of at least one terpene comprises an increase of between 50% and 100%. In an aspect, an increased amount of at least one terpene comprises an increase of between 100% and 500%.

The amount of terpenes in a plant can be measured using any method known in the art, including, without being limiting, gas chromatography mass spectrometry (GC-MS), Nuclear Magnetic Resonance Spectroscopy, and liquid chromatography-linked mass spectrometry. See The Handbook of Plant Metabolomics, edited by Weckwerth and Kahl, (Wiley-Blackwell) (May 28, 2013). In an aspect, an amount of at least one terpene refers to the concentration of the at least one terpene in the tissue sampled.

Cannabinoids are chemicals found in *Cannabis* plants. Many cannabinoids are concentrated in a resin produced in glandular trichomes, and at least 113 cannabinoids are known.

In an aspect, a heterologous polynucleotide is involved in the biosynthesis of a cannabinoid. In an aspect, a cannabinoid is selected from the group consisting of a cannabigerol-type (CBG) cannabinoid, a cannabichromene-type (CBC) cannabinoid, a cannabidiol-type (CBD) cannabinoid, a tetrahydrocannabinol-type (THC) cannabinoid, a cannabinol-type (CBN) cannabinoid, a cannabielsoin-type (CBE) cannabinoid, an iso-tetrahydrocannabinol-type (iso-THC) cannabinoid, a cannabicyclol-type (CBL) cannabinoid, and a cannabicitrain-type (CBT) cannaboinoid.

In an aspect, a cannabinoid is selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran.

Products

In an aspect, this disclosure provides cured plant material from any plant or plant part provided herein. In an aspect, this disclosure provides cured tobacco material from any tobacco plant or tobacco plant part provided herein.

In an aspect, cured plant material is made by a curing process selected from the group consisting of flue curing, air curing, fire curing, and sun curing. In an aspect, cured tobacco material is made by a curing process selected from the group consisting of flue curing, air curing, fire curing, and sun curing. In an aspect, cured tobacco material is selected from the group consisting of flue cured tobacco material, air cured tobacco material, fire cured tobacco material, and sun cured tobacco material.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation.

Information regarding the harvesting of burley and dark tobacco varieties can be found in the 2019-2020 *Burley and Dark Tobacco Production Guide* (December 2018) published by the University of Kentucky, The University of Tennessee, Virginia Tech, and North Carolina State University, which is incorporated herein by reference in its entirety.

In an aspect, cured tobacco material comprises tobacco material selected from the group selected from cured leaf material, cured stem material, cured bud material, cured flower material, and cured root material. In an aspect, cured tobacco material comprises cured leaf material, cured stem material, or both. In an aspect, cured tobacco material comprises cured leaf material. In an aspect, cured tobacco material comprises cured stem material.

In an aspect, cured tobacco material comprises flue-cured tobacco material. In an aspect, cured tobacco material comprises air-cured tobacco material. In an aspect, cured tobacco material comprises fire-cured tobacco material. In an aspect, cured tobacco material comprises sun-cured tobacco material. In an aspect, cured tobacco material provided herein is selected from the group consisting of air-cured tobacco material, fire-cured tobacco material, sun-cured tobacco material, and flue-cured tobacco material. In an aspect, cured tobacco material is from a tobacco variety selected from the group consisting of a flue-cured variety, a bright variety, a Burley variety, a Virginia variety, a Maryland variety, a dark variety, an Oriental variety, and a Turkish variety.

In an aspect, cured tobacco leaf provided herein is selected from the group consisting of air-cured tobacco leaf, fire-cured tobacco leaf, sun-cured tobacco leaf, and flue-cured tobacco leaf. In an aspect, cured tobacco leaf is from a tobacco variety selected from the group consisting of a flue-cured variety, a bright variety, a Burley variety, a Virginia variety, a Maryland variety, a dark variety, an Oriental variety, and a Turkish variety.

Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In an aspect, this disclosure provides fermented tobacco material from any tobacco plant, or part thereof, provided herein. In another aspect, this disclosure provides fermented tobacco material from any modified tobacco plant, or part thereof, provided herein.

Tobacco material obtained from the tobacco lines, varieties or hybrids of the present disclosure can be used to make tobacco products. As used herein, "tobacco product" is defined as any product made or derived from tobacco that is intended for human use or consumption. In an aspect, this disclosure provides a tobacco product comprising plant material from a tobacco plant provided herein. In another aspect, this disclosure provides a tobacco product comprising plant material from a modified tobacco plant provided herein. In another aspect, this disclosure provides a tobacco product comprising cured tobacco material. In another aspect, this disclosure provides a tobacco product comprising fermented tobacco material. In another aspect, this disclosure provides a tobacco product comprising a tobacco blend.

Tobacco products include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In an aspect, a tobacco product comprises reconstituted tobacco. In another aspect, this disclosure provides reconstituted tobacco comprising cured tobacco material. As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

In an aspect, a tobacco product comprises expanded tobacco. As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a kretek, a bidi cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco.

In an aspect, a tobacco product of the present disclosure is selected from the group consisting of a cigarette, a heated tobacco product, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

In an aspect, a tobacco product of the present disclosure is a smokeless tobacco product. In an aspect, a smokeless tobacco product is selected from the group consisting of loose leaf chewing tobacco, plug chewing tobacco, moist snuff, nasal snuff, dry snuff, and snus.

Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat-treated smokeless tobacco. Dry snuff is finely ground tobacco that is placed in the mouth or used nasally.

In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product.

In another aspect, this disclosure provides a tobacco blend comprising cured tobacco material. A tobacco blend can comprise any combination of cured tobacco, uncured tobacco, fermented tobacco, unfermented tobacco, expanded tobacco, and reconstituted tobacco.

In an aspect, a tobacco blend comprises at least 5% cured tobacco by weight. In an aspect, a tobacco blend comprises at least 10% cured tobacco by weight. In an aspect, a tobacco blend comprises at least 15% cured tobacco by weight. In an aspect, a tobacco blend comprises at least 20% cured tobacco by weight. In an aspect, a tobacco blend comprises at least 25% cured tobacco by weight. In an aspect, a tobacco blend comprises at least 30% cured tobacco by weight. In an aspect, a tobacco blend comprises at least 35% cured tobacco by weight. In an aspect, a tobacco blend comprises at least 40% cured tobacco by weight. In an aspect, a tobacco blend comprises at least 45% cured tobacco by weight. In an aspect, a tobacco blend comprises at least 50% cured tobacco by weight. In an aspect, a tobacco blend comprises at least 55% cured tobacco by weight. In an aspect, a tobacco blend comprises at least 60% cured tobacco by weight. In an aspect, a tobacco blend comprises at least 65% cured tobacco by weight. In an aspect, a tobacco blend comprises at least 70% cured tobacco by weight. In an aspect, a tobacco blend comprises at least 75% cured tobacco by weight. In an aspect, a tobacco blend comprises at least 80% cured tobacco by weight. In an aspect, a tobacco blend comprises at least 85% cured tobacco by weight. In an aspect, a tobacco blend comprises at least 90% cured tobacco by weight. In an aspect, a tobacco blend comprises at least 95% cured tobacco by weight.

In an aspect, a tobacco blend comprises at least 5% cured tobacco by volume. In an aspect, a tobacco blend comprises at least 10% cured tobacco by volume. In an aspect, a tobacco blend comprises at least 15% cured tobacco by volume. In an aspect, a tobacco blend comprises at least 20% cured tobacco by volume. In an aspect, a tobacco blend comprises at least 25% cured tobacco by volume. In an aspect, a tobacco blend comprises at least 30% cured tobacco by volume. In an aspect, a tobacco blend comprises at least 35% cured tobacco by volume. In an aspect, a tobacco blend comprises at least 40% cured tobacco by volume. In an aspect, a tobacco blend comprises at least 45% cured tobacco by volume. In an aspect, a tobacco blend comprises at least 50% cured tobacco by volume. In an aspect, a tobacco blend comprises at least 55% cured tobacco by volume. In an aspect, a tobacco blend comprises at least 60% cured tobacco by volume. In an aspect, a tobacco blend comprises at least 65% cured tobacco by volume. In an aspect, a tobacco blend comprises at least 70% cured tobacco by volume. In an aspect, a tobacco blend comprises at least 75% cured tobacco by volume. In an aspect, a tobacco blend comprises at least 80% cured tobacco by volume. In an aspect, a tobacco blend comprises at least 85% cured tobacco by volume. In an aspect, a tobacco blend comprises at least 90% cured tobacco by volume. In an aspect, a tobacco blend comprises at least 95% cured tobacco by volume.

In an aspect, this disclosure provides a cannabis product comprising material from a cannabis plant, cannabis seed, or cannabis plant part provided herein. In an aspect, a cannabis product is a smokeless product. In an aspect, a cannabis product is an edible product. In an aspect, a cannabis product is a smokable product. In a further aspect, a smokeless cannabis product is a fiber based product. In an aspect, a cannabis product is derived from cannabis biomass. In an aspect, a cannabis product is a distillate derived from cannabis biomass.

In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 85% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 90% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 92.5% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 95% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 96% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 97% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 98% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 99% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 99.9% identical to a sequence selected from the group consisting of SEQ ID NOs: 10-17, 45-47, and 80-82, or a functional fragment thereof. In an aspect, this disclosure provides a method comprising preparing a tobacco producing using cured tobacco material from a modified tobacco plant or part therefrom, where the modified tobacco plant or part therefrom comprises a recombinant nucleic acid molecule comprising a promoter operably linked to a heterologous polynucleotide, where the promoter comprises a nucleic acid sequence at least 100% identical to a sequence selected from the group consisting of SEQ ID NOs: 10-17, 45-47, and 80-82, or a functional fragment thereof.

In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 85% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 90% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 92.5% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 95% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 96% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 97% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 98% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 99% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence at least 99.9% identical to a sequence selected from the group consisting of SEQ ID NOs: 10-17, 45-47, and 80-82, or a functional fragment thereof. In an aspect, this disclosure provides a method comprising preparing a cannabis product using material from a modified cannabis plant or part therefrom, where the modified cannabis plant or part therefrom comprises a recombinant nucleic acid molecule comprising a promoter operably linked to a heterologous polynucleotide, where the promoter comprises a nucleic acid sequence 100% identical to a sequence selected from the group consisting of SEQ ID NOs: 10-17, 45-47, and 80-82, or a functional fragment thereof.

Transformation

In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 80% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 85% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 90% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 92.5% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 95% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 96% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 97% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 98% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 99% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence at least 99.9% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous polynucleotide to at least one plant cell, where the promoter comprises a nucleic acid sequence 100% identical to a sequence selected from the group consisting of SEQ ID NOs: 10-17, 45-47, and 80-82, or a functional fragment thereof; (b) selecting at least one plant cell from step (a), where the at least one plant cell comprises the recombinant nucleic acid molecule; and (c) regenerating a modified plant from the at least one plant cell selected in step (b).

In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 80% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 85% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 90% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 92.5% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 95% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 96% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 97% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 98% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 99% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence at least 99.9% identical to a sequence selected from the group consisting of SEQ ID NOs: 10-17, 45-47, and 80-82, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where the promoter comprises a nucleic acid sequence 100% identical to a sequence selected from the group consisting of SEQ ID NOs: 10-17, 45-47, and 80-82, or a functional fragment thereof.

Numerous methods for "introducing" a recombinant nucleic acid molecule to a plant cell are known in the art, which can be used according to methods of the present application to produce a modified plant cell, plant, seed, or plant part. As used herein, the terms "introducing" and "transforming" can be used interchangeably. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, polyethylene glycol (PEG)-mediated transformation, etc., are also known in the art. Modified plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell (e.g., tobacco cell, cannabis cell) with any of the nucleic acid molecules provided herein.

In an aspect, a method of introducing a recombinant nucleic acid molecule to a plant cell comprises *Agrobacterium*-mediated transformation. In another aspect, a method of introducing a recombinant nucleic acid molecule to a plant cell comprises PEG-mediated transformation. In another aspect, a method of introducing a recombinant nucleic acid molecule to a plant cell comprises biolistic transformation. In another aspect, a method of introducing a recombinant nucleic acid molecule to a plant cell comprises liposome-mediated transfection (lipofection). In another aspect, a method of introducing a recombinant nucleic acid molecule to a plant cell comprises lentiviral transfection.

Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of WO 91/17424 and WO 91/16024. Delivery can be to cells (e.g. in vitro or ex vivo administration) or target tissues (e.g. in vivo administration).

Any plant cell from which a fertile plant can be regenerated is contemplated as a useful recipient cell for practice of this disclosure.

In an aspect, a recombinant nucleic acid molecule is introduced to a tobacco cell. In an aspect, a recombinant nucleic acid molecule is introduced to a tobacco protoplast cell. In another aspect, a recombinant nucleic acid molecule is introduced to a tobacco callus cell. In an aspect, a recombinant nucleic acid molecule is introduced to a tobacco cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

In an aspect, a recombinant nucleic acid molecule is introduced to a cannabis cell. In an aspect, a recombinant nucleic acid molecule is introduced to a cannabis protoplast cell. In another aspect, a recombinant nucleic acid molecule is introduced to a cannabis callus cell. In an aspect, a recombinant nucleic acid molecule is introduced to a cannabis cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

Embodiments

The following examples of non-limiting embodiments are envisioned:

1. A modified plant, seed, or plant part, comprising a recombinant nucleic acid molecule comprising a promoter operably linked to a heterologous polynucleotide, wherein the promoter comprises a nucleic acid sequence at least 80% identical to a sequence selected from the group consisting of SEQ ID NOs: 10-17, 45-47, and 80-82, or a functional fragment thereof.

2. The modified plant, seed, or plant part, of embodiment 1, wherein the nucleic acid sequence is at least 90% identical to a sequence selected from the group consisting of SEQ ID NOs: 10-17, 45-47, and 80-82, or a functional fragment thereof.

3. The modified plant, seed, or plant part, of embodiment 1, wherein the nucleic acid sequence is 100% identical to a sequence selected from the group consisting of SEQ ID NOs: 10-17, 45-47, and 80-82, or a functional fragment thereof.

4. The modified plant, seed, or part thereof of any one of embodiments 1-3, wherein the modified plant, seed, or plant part is a tobacco plant, tobacco seed, or tobacco plant part.

5. The modified plant, seed, or part thereof of any one of embodiments 1-3, wherein the modified plant, seed, or plant part is a cannabis plant, cannabis seed, or cannabis plant part.

6. The modified plant, seed, or plant part, of one of embodiments 1-5, wherein the heterologous polynucleotide encodes a gene.

7. The modified plant, seed, or plant part of embodiment 6, wherein the gene comprises a nucleic acid sequence encoding an amino acid sequence at least 80% identical or similar to an amino acid sequence selected from the group consisting of SEQ ID NOs: 18-26 and 64-79.

8. The modified plant, seed, or plant part of embodiment 6, wherein the gene comprises a nucleic acid sequence at least 80% identical to a nucleic acid sequence selected from the group consisting of SEQ ID NOs: 27-35 and 48-63.

9. The modified plant, seed, or plant part, of embodiment 6, wherein the gene encodes a small RNA molecule, or a precursor thereof.

10. The modified plant, seed, or plant part, of embodiment 6, wherein the gene encodes a polypeptide.

11. The modified plant, seed, or plant part, of embodiment 10, wherein the polypeptide is involved in the biosynthesis of at least one terpene.

12. The modified plant, seed, or plant part, of embodiment 11, wherein the at least one terpene is selected from the group consisting of menthol or a related compound, a labdanoid, cembratrienediol, levopimaric acid, and L-leucine.

13. The modified plant, seed, or plant part of embodiment 12, wherein the labdanoid is cis-abienol.

14. The modified plant, seed, or plant part of embodiment 11, wherein the at least one terpene is neophytadiene.

15. The modified plant, seed, or plant part of embodiment 10, wherein the polypeptide is selected from the group consisting of geranylgeranyl diphosphate synthase, 8-hydroxy-copalyl diphosphate synthase, cis-abienol synthase, cembratrienol synthase 2a, levopimaradiene synthetase, 2-isopropylmalate synthetase, 2-oxoisovalerate dehydrogenase, and neomenthol dehydrogenase.

16. The modified plant, seed, or plant part of embodiment 15, wherein the polypeptide comprises an amino acid sequence at least 80% identical or similar to a sequence selected from the group consisting of SEQ ID NOs: 18-26 and 64-79.

17. The modified plant, seed, or plant part of embodiment 15, wherein the cis-abienol synthase is selected from the group consisting of cis-abienol synthase ISOFORM1 and cis-abienol synthase ISOFORM2.

18. The modified plant, seed, or plant part of embodiment 17, wherein the cis-abienol synthase comprises an amino acid sequence at least 80% identical or similar to a sequence selected from the group consisting of SEQ ID NOs: 20 and 21.

19. The modified plant, seed, or plant part of any one of embodiments 11-18, wherein the modified plant comprises an increased amount of the at least one terpene as compared to a control plant lacking the recombinant nucleic acid molecule when grown under comparable conditions.

20. The modified plant, seed, or plant part of embodiment 19, wherein the increased amount of the at least one terpene comprises an increase of at least 5% as compared to the control plant.

21. The modified plant, seed, or plant part of embodiment 4, wherein the tobacco plant, tobacco seed, or plant part is of a tobacco variety selected from the group consisting of a flue-cured variety, a bright variety, a Burley variety, a Virginia variety, a Maryland variety, a dark variety, a Galpão variety, an Oriental variety, and a Turkish variety.

22. The modified plant, seed, or plant part of any one of embodiments 1-21, wherein the plant is male sterile or cytoplasmically male sterile.

23. Cured tobacco material from the modified tobacco plant or tobacco plant part of any one of embodiments 4, 21, or 22.

24. The cured tobacco material of embodiment 23, wherein the cured tobacco material is made by a curing process selected from the group consisting of flue curing, air curing, fire curing, and sun curing.

25. A tobacco product comprising the cured tobacco material of embodiment 23 or 24, wherein the tobacco product is selected from the group consisting of a kretek, a bidi cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco.

26. The tobacco product of embodiment 25, wherein the tobacco product is a smokeless tobacco product.

27. The tobacco product of embodiment 26, wherein the smokeless tobacco product is selected from the group consisting of loose leaf chewing tobacco, plug chewing tobacco, moist snuff, nasal snuff, dry snuff, and snus.

28. A reconstituted tobacco comprising the cured tobacco material of embodiment 23 or 24.

29. A cannabis product comprising material from the modified cannabis plant, cannabis seed, or cannabis plant part of embodiment 5.

30. A recombinant nucleic acid molecule comprising a promoter operably linked to a heterologous polynucleotide, wherein the promoter comprises a nucleic acid sequence at least 80% identical to a sequence selected from the group consisting of SEQ ID NOs: 10-17, 45-47, and 80-82, or a functional fragment thereof.

31. A method of generating a modified plant, the method comprising:
   (a) introducing a recombinant nucleic acid molecule comprising a promoter operably linked to a heterologous polynucleotide to at least one plant cell, wherein the promoter comprises a nucleic acid sequence at least 80% identical to a sequence selected from the group consisting of SEQ ID NOs: 10-17, 45-47, and 80-82, or a functional fragment thereof;
   (b) selecting at least one plant cell from step (a), wherein the at least one plant cell comprises the recombinant nucleic acid molecule; and
   (c) regenerating a modified plant from the at least one plant cell selected in step (b).

32. A method comprising preparing a tobacco product using cured tobacco material from a modified tobacco plant or part therefrom, wherein the modified tobacco plant or part therefrom comprises a recombinant nucleic acid molecule comprising a promoter operably linked to a heterologous polynucleotide, wherein the promoter comprises a nucleic acid sequence at least 80% identical to a sequence selected from the group consisting of SEQ ID NOs: 10-17, 45-47, and 80-82, or a functional fragment thereof.

33. A method comprising preparing a cannabis product using material from a modified cannabis plant or part therefrom, wherein the modified cannabis plant or part therefrom comprises a recombinant nucleic acid molecule comprising a promoter operably linked to a heterologous polynucleotide, wherein the promoter comprises a nucleic acid sequence at least 80% identical to a sequence selected from the group consisting of SEQ ID NOs: 10-17, 45-47, and 80-82, or a functional fragment thereof.

34. A method comprising transforming a plant cell with a recombinant nucleic acid molecule, wherein the recombinant nucleic acid molecule comprises a promoter operably linked to a heterologous polynucleotide, wherein the promoter comprises a nucleic acid sequence at least 80% identical to a sequence selected from the group consisting of SEQ ID NOs: 10-17, 45-47, and 80-82, or a functional fragment thereof.

35. A method for producing a plant, the method comprising:
   (a) crossing at least one plant of a first variety with at least one plant of a second variety to produce at least one progeny seed, wherein the at least one plant of the first variety comprises a recombinant nucleic acid molecule comprising a promoter operably linked to a heterologous polynucleotide, wherein the promoter comprises a nucleic acid sequence at least 80% identical to a sequence selected from the group consisting of SEQ ID NOs: 10-17, 45-47, and 80-82, or a functional fragment thereof; and
   (b) selecting at least one progeny seed produced in step (a), or a plant germinated therefrom, wherein the at least one progeny seed or plant germinated therefrom comprises the recombinant nucleic acid molecule.

36. The method of embodiment 35, wherein the first variety and the second variety are the same variety.

37. The method of any one of embodiments 35-36, wherein the at least one plant of a second variety comprises the recombinant nucleic acid molecule.

38. The method of embodiment 35, wherein the at least one progeny seed, or the plant germinated therefrom, is heterozygous for the recombinant nucleic acid molecule.

39. The method of embodiment 35 or 37, wherein the at least one progeny seed, or the plant germinated therefrom, is homozygous for the recombinant nucleic acid molecule.

Having now generally described the disclosure, the same will be more readily understood through reference to the following examples that are provided by way of illustration, and are not intended to be limiting of the present disclosure, unless specified.

EXAMPLES

Example 1. Isolation of Trichome-Specific Promoter Sequences

Specific oligonucleotide primers (SEQ ID NOs: 1-9) are used to amplify and isolate the promoter regions from several tobacco genes, including ribulose-1,5-bisphosphate carboxylase/oxygenase (RUBISCO) small subunit (NtRbcST; SEQ ID NOs: 10 and 11), premnaspirodiene oxygenase (NtPSO; SEQ ID NOs: 12 and 13), phylloplanin (NtPHY; SEQ ID NOs: 14 and 15), and cyclase (NtCYC; SEQ ID NOs: 16 and 17), using PCR.

Example 2. NtRbcST is a Trichome-Specific RUBISCO Subunit

NtRbcST is a subunit of RUBISCO, which is the most abundant enzyme found in plants and is primarily involved on carbon dioxide fixation during photosynthesis. RUBISCO is assembled from eight large subunits (RbcL) encoded by a single chloroplast gene, and eight small subunits (RbcS) encoded by a nuclear gene family. In C3 plants, RUBISCO is mostly found in the chloroplasts of mesophyll cells, while RUBISCO is mostly found in the bundle-sheath and guard cells of C4 plants. However, RUBISCO can also be found in specialized cells like trichomes.

Figure 3:
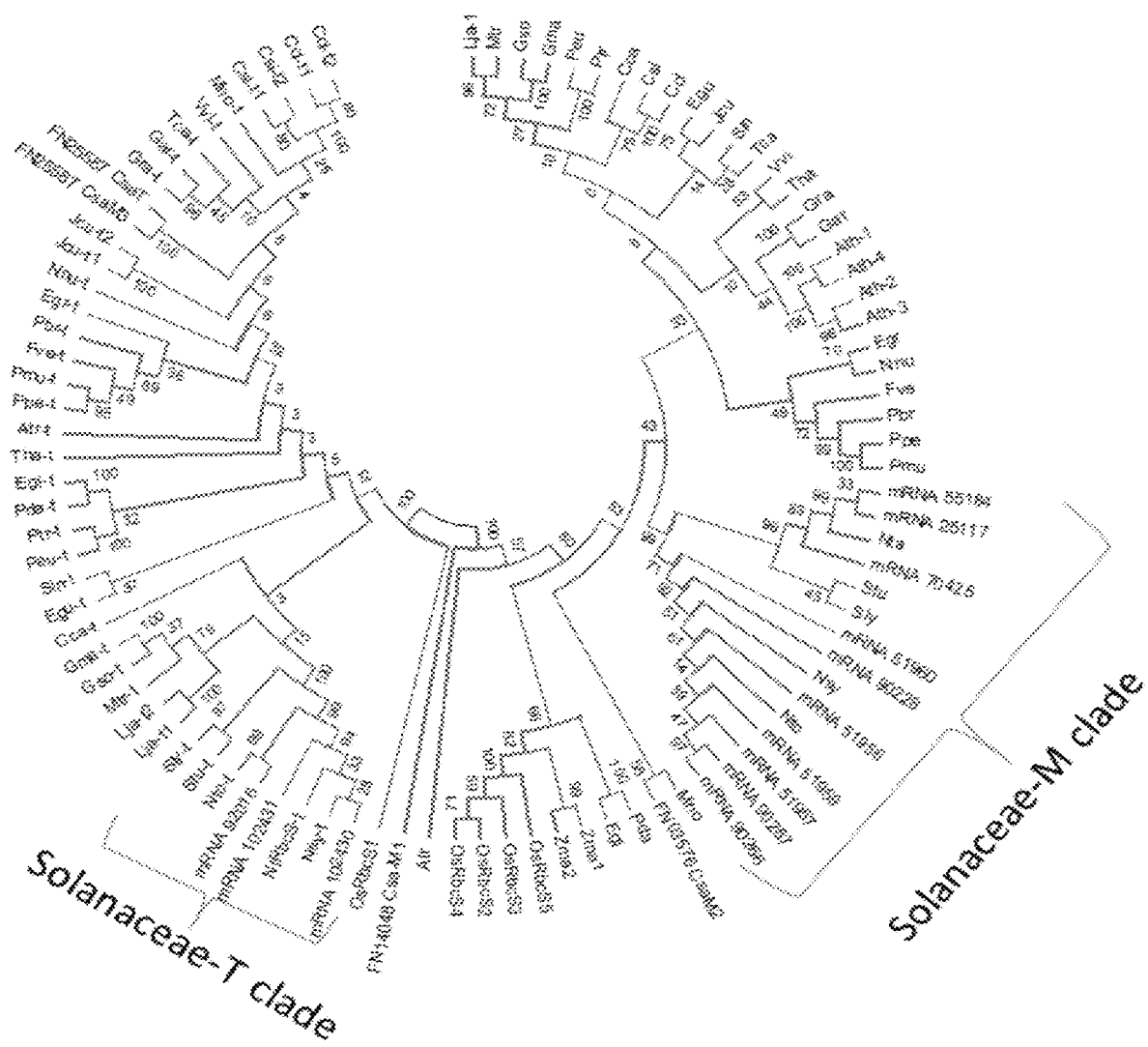
FIG. 3 depicts the phylogenetic analysis of the Rubisco gene family in plants. The figure depicts the split between trichome specific (T-clade) and mesophyll specific (M-clade) Rubsico groups.
Figure 4:
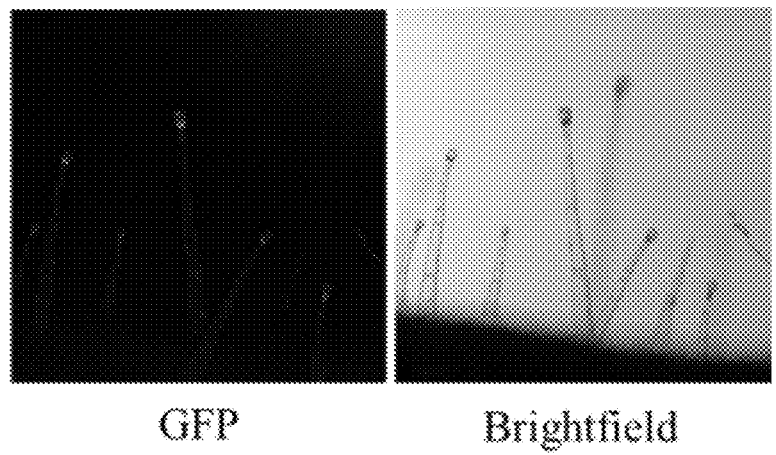
FIG. 4 depicts the expression of GREEN FLUORESCENT PROTEIN (G3GFP) driven by the Rubisco RbT 1.2 kb promoter (SEQ ID NO: 10) in a tobacco glandular trichome.
Figure 5:
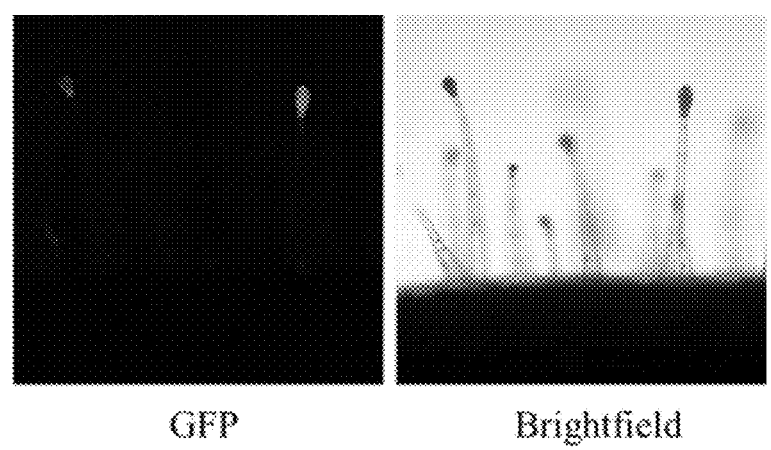
FIG. 5 depicts the expression of GREEN FLUORESCENT PROTEIN (G3GFP) driven by the Rubisco RbT 0.4 kb promoter (SEQ ID NO: 11) in a tobacco glandular trichome.
Figure 6:
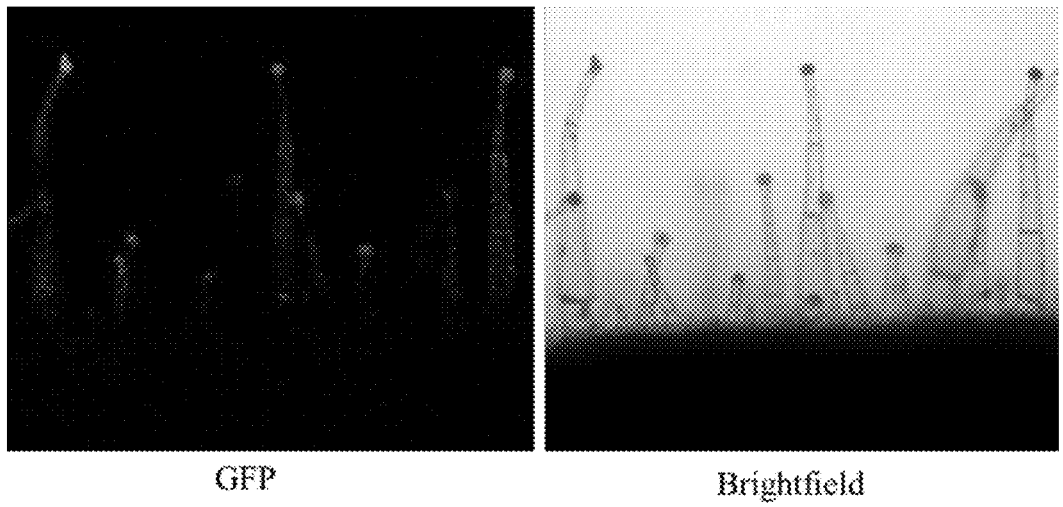
FIG. 6 depicts the expression of GREEN FLUORESCENT PROTEIN (G3GFP) driven by the NtPSO 1.0 kb promoter (SEQ ID NO: 13) in a tobacco glandular trichome.
Figure 7:
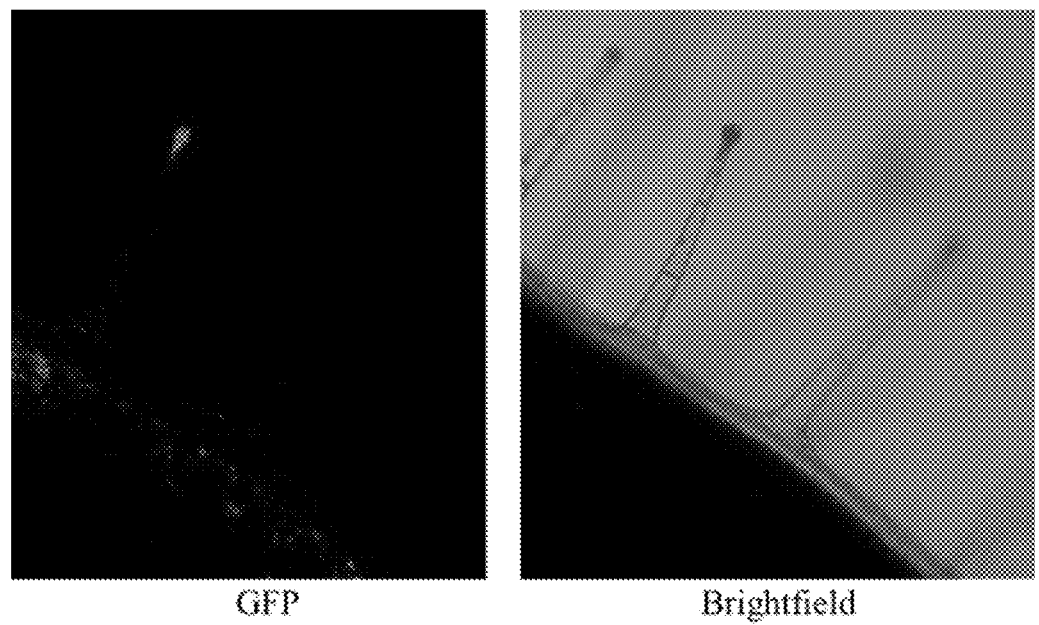
FIG. 7 depicts the expression of GREEN FLUORESCENT PROTEIN (G3GFP) driven by the NtPHY 0.5 kb promoter (SEQ ID NO: 15) in a tobacco glandular trichome.
Figure 8:
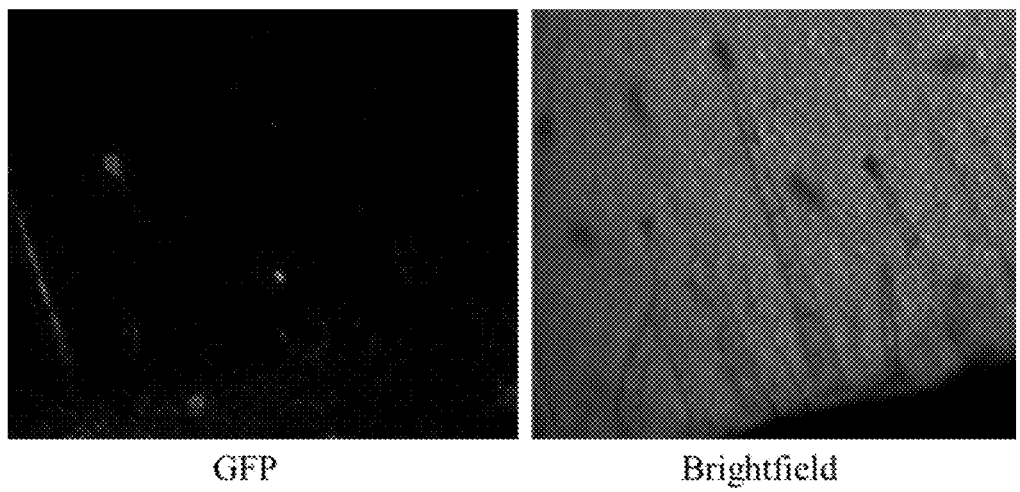
FIG. 8 depicts the expression of GREEN FLUORESCENT PROTEIN (G3GFP) driven by the NtCYC 0.5 kb promoter (SEQ ID NO: 17) in a tobacco glandular trichome.
Figure 9:
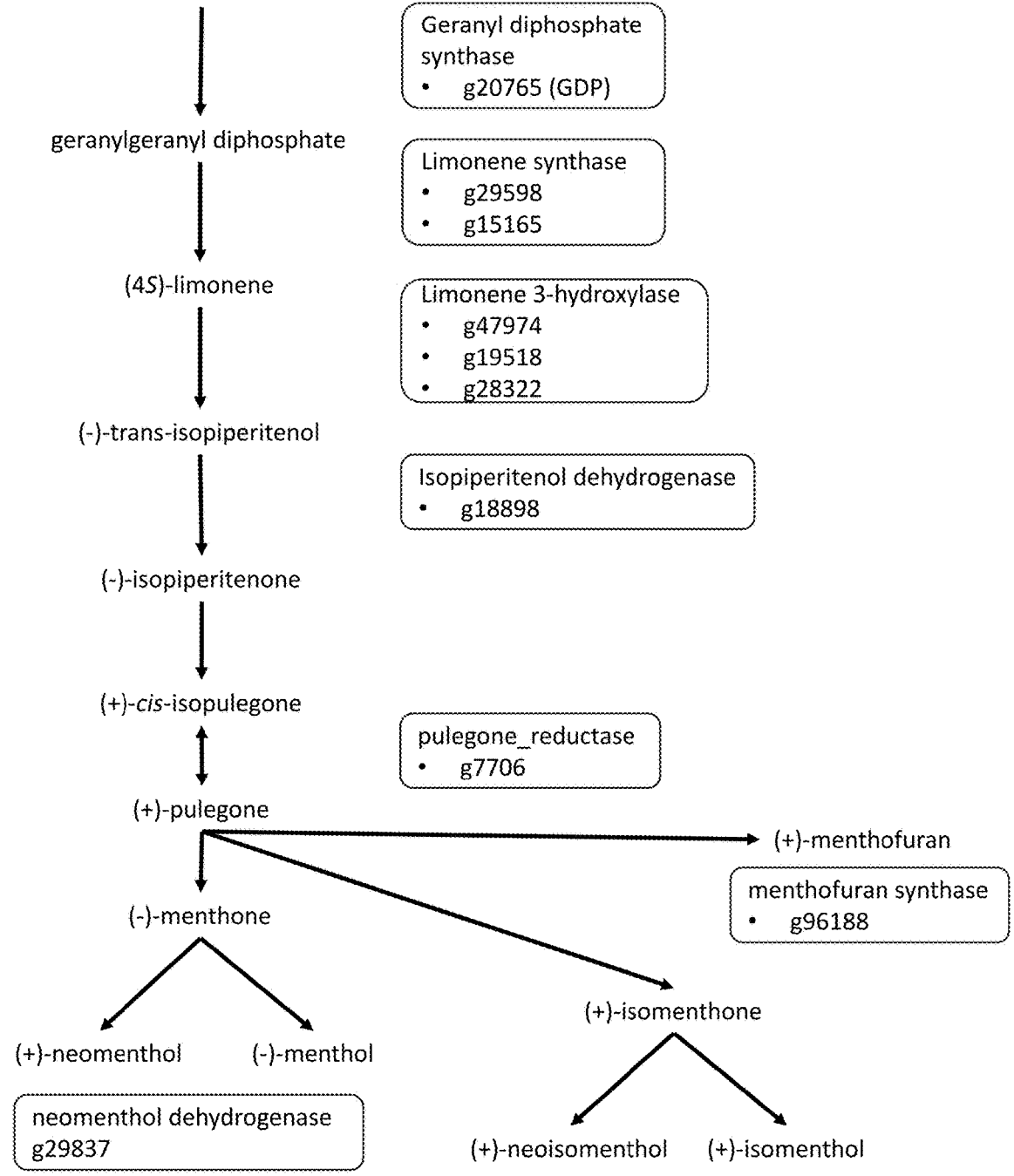
FIG. 9 depicts a menthol biosynthesis pathway.
Figure 10:
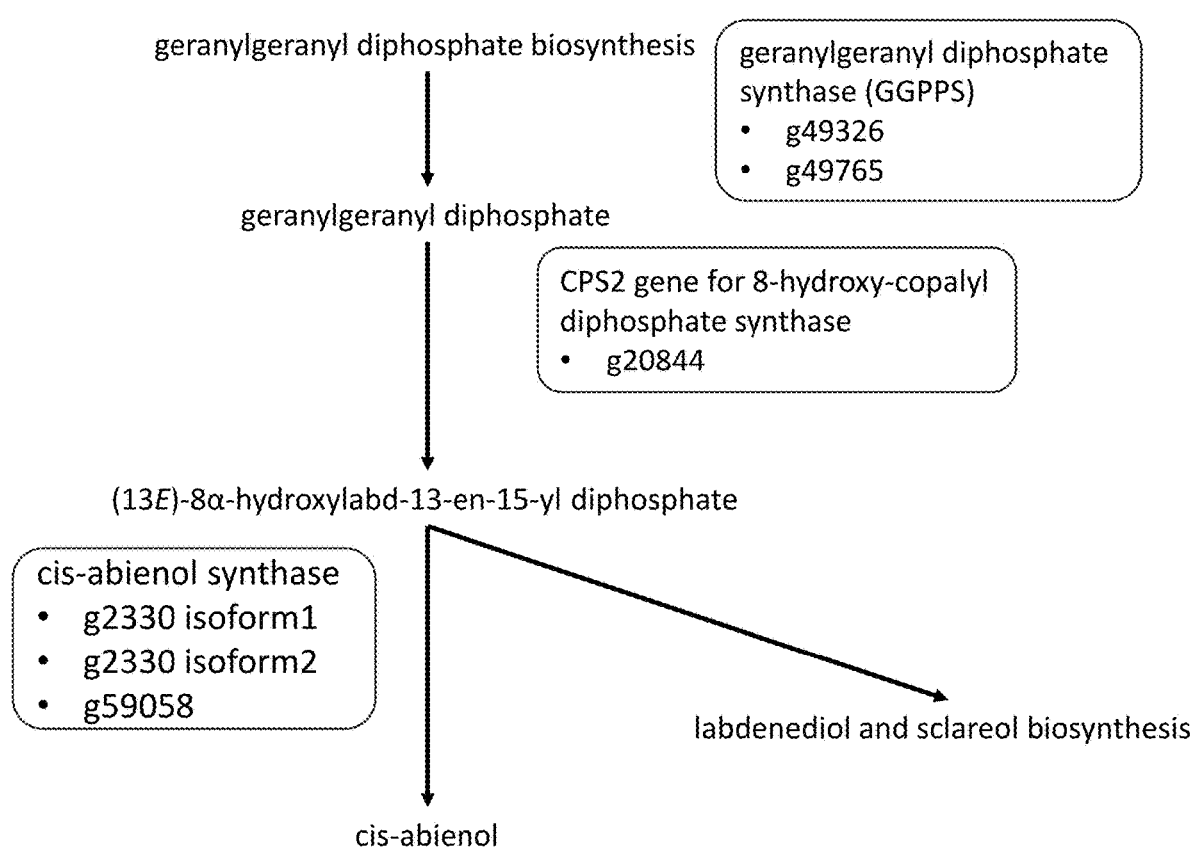
FIG. 10 depicts a cis-abienol biosynthesis pathway.
Figure 11:
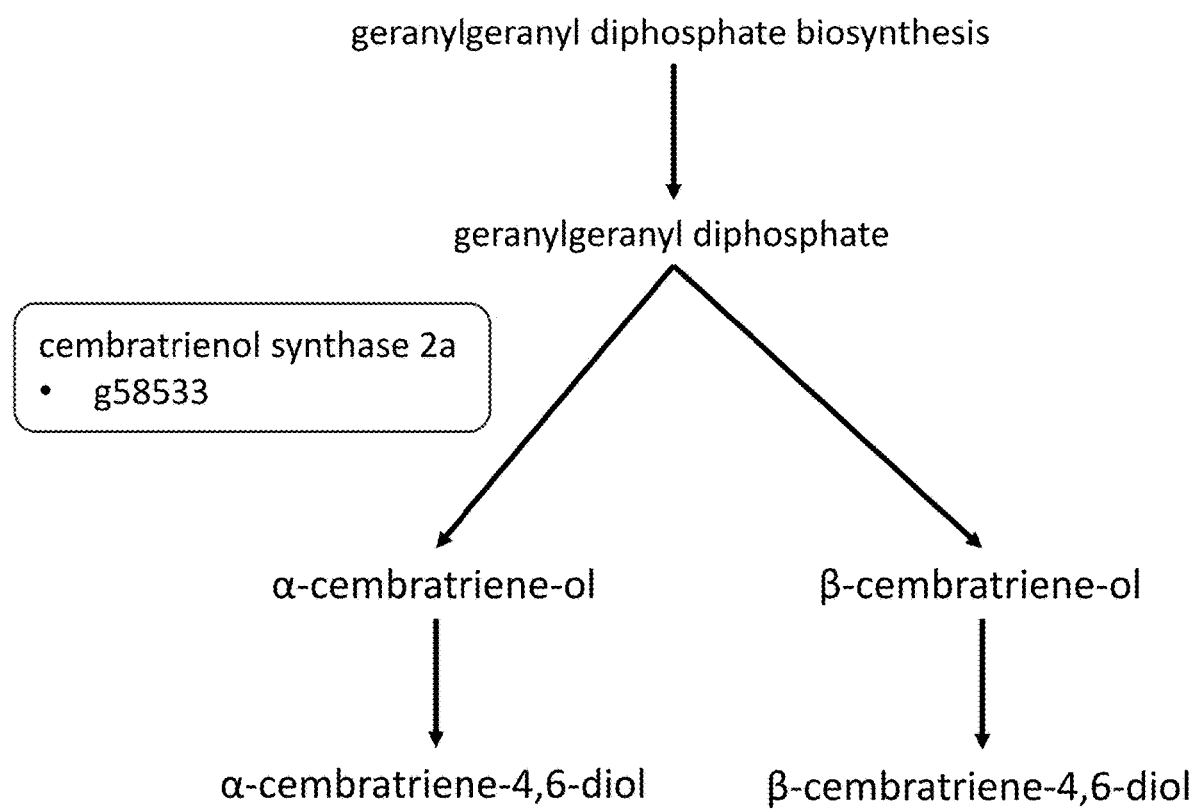
FIG. 11 depicts a cembratrienediol biosynthesis pathway.
Figure 12:
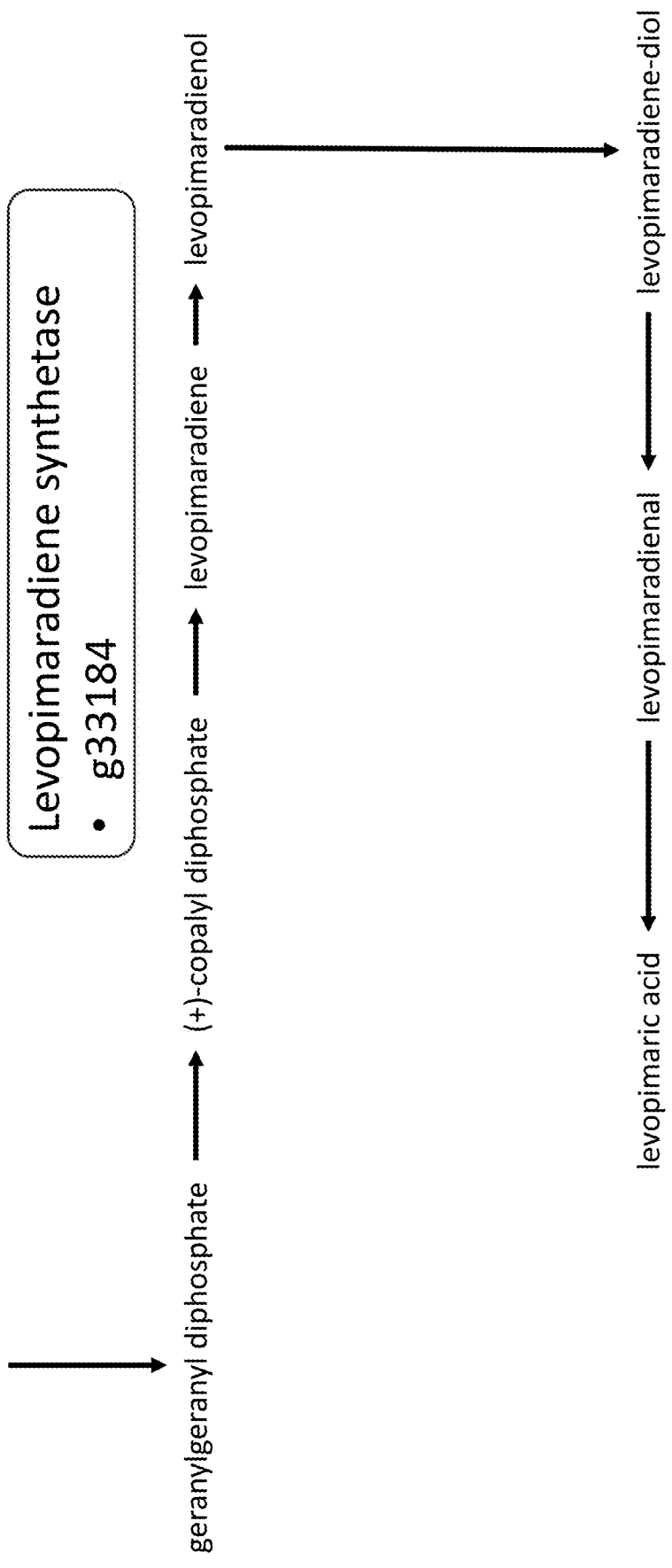
FIG. 12 depicts a levopimaric acid biosynthesis pathway.
Figure 13:
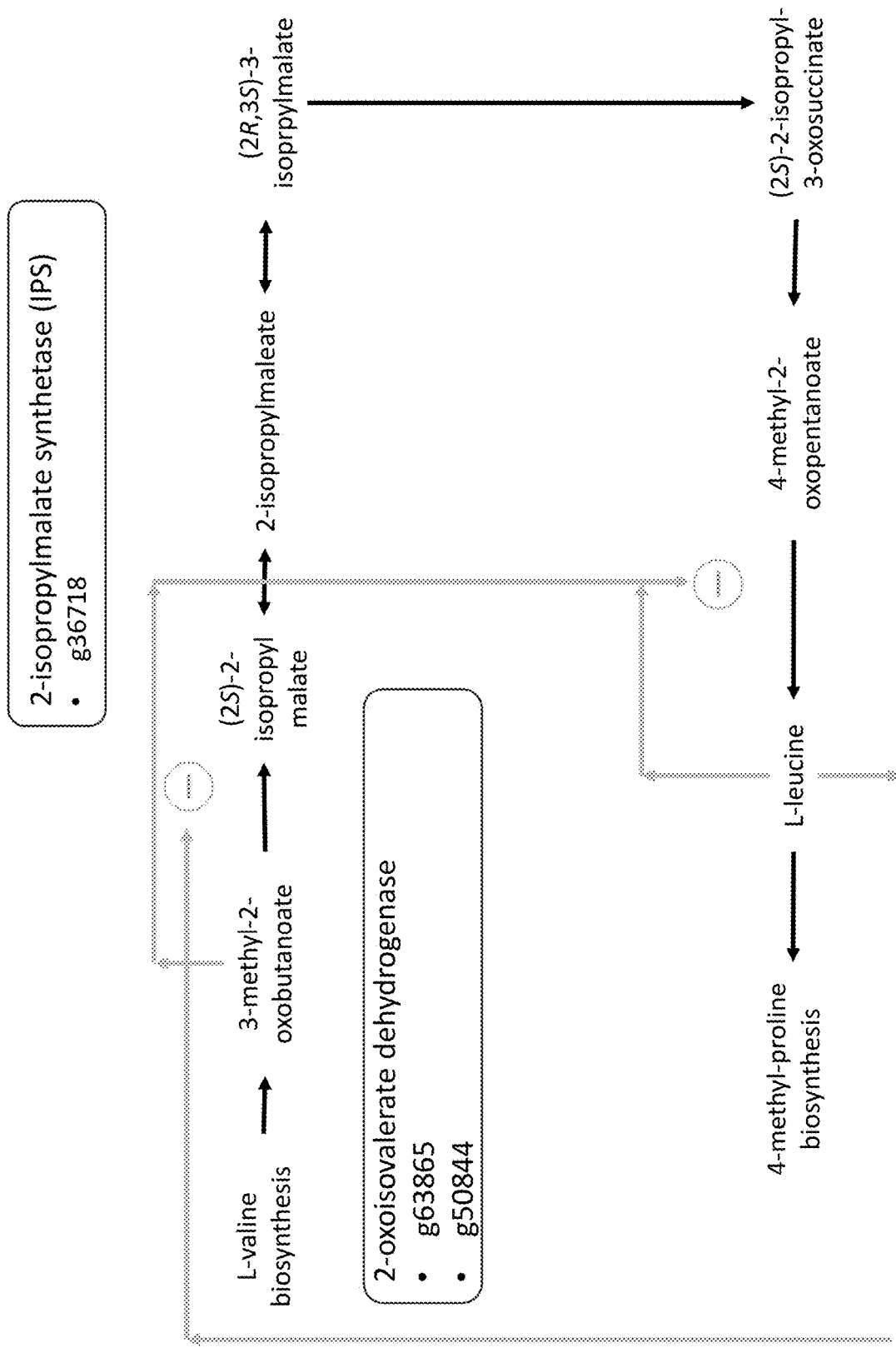
FIG. 13 depicts a L-leucine biosynthesis pathway.

Phylogenetic analysis of RUBISCO small subunits in plants found that there are two distinct clades of RUBISCO small subunits: a mesophyll-specific clade and a trichome-specific clade. See FIG. 3.

Example 3. Construction of Vectors

Figure 2:
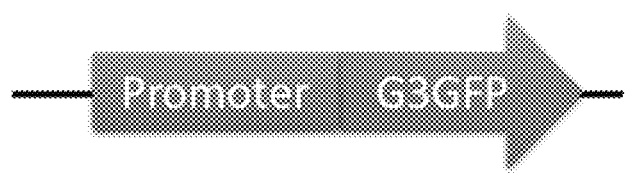
FIG. 2 depicts a vector construct used for promoter analysis in tobacco. Each promoter is operably linked to a sequence encoding GREEN FLUORESCENT PROTEIN (G3GFP).

The PCR products obtained in Example 1 are cloned using the GATEWAY cloning system (ThermoFisher Scientific). The cloned promoters are subsequently subcloned into a GATEWAY expression vector, where the subcloned promoter drives the expression of GREEN FUORESCENCE PROTEIN (G3GFP). See FIG. 2.

Various promoter lengths are used in different vector constructs. For example, an approximately 1.2 kilobase (kb) (SEQ ID NO: 10) and an approximately 0.4 kb (SEQ ID NO: 11) are tested for NtRbcST. Similarly, an approximately 1.0 kb promoter is tested for NtPSO (SEQ ID NO: 13); an approximately 0.5 kb promoter is tested for NtPHY (SEQ ID NO: 15); and an approximately 0.5 kb promoter is tested for NtCYC (SEQ ID NO: 17).

Additional constructs comprising SEQ ID NO: 80 operably linked to G3GFP, SEQ ID NO: 81 operably linked to G3GFP, and SEQ ID NO: 82 operably linked to G3GFP are also produced. See Example 9.

Example 4. Transformation and Regeneration of Modified Tobacco Plants

Each of the vector constructs generated in Example 3 is separately transformed into tobacco cells in separate experiments. Briefly, the vectors are introduced into tobacco leaf discs via *Agrobacterium* transformation. See, for example, Mayo et al., *Nat. Protoc.*, 1:1105-1111 (2006); and Horsch et al., *Science*, 227:1229-1231 (1985).

Tobacco plants (e.g., TN and K326 varieties; *Nicotiana benthamiana*) are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed, and the *Agrobacterium tumefaciens* cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog (MS) with B5 vitamin liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (1/2 MS medium) and discs are placed upside down in contact with filter paper overlaid on the co-cultivation TOM medium (MS medium with 30 g/L sucrose; 0.1 mg/L 1-napthaleneacetic acid (NAA); and 1 mg/L 6-benzyl aminopurine (BAP)). The Petri plate is sealed with parafilm and incubated in the dark for two days.

After incubation, leaf discs are transferred to regeneration/selection TOM-Hyg medium Petri plates (TOM medium plus 200 mg/L cefotaxime and 50 mg/L hygromycin). Calli formed from leaf discs are sub-cultured bi-weekly to fresh TOM-Hyg medium in dim light (between 60 and 80 mE/ms) with photoperiods of 18 hours light, 6 hours dark, at 24° C. until shoots (plantlets) become excisable. Plantlets formed from calli are removed with forceps and subculture into MS rooting medium (MS medium with 3 g/L sucrose; 7 g/L dextrose; 200 mg/L cefotaxime; 50 mg/L hygromycin). Shoots on MS basal medium with 50 mg/L hygromycin are incubated with the dim light with photoperiods of 18 hours light, 6 hours dark, at 24° C. to induce rooting.

When plantlets comprising both shoots and roots grow large enough (e.g., over half the height of a Magenta™ GA-7 box), they are transferred Jiffy peat pellets for acclimatization in the growth room. Once established, seedlings are transferred to a greenhouse for further growth, breeding, and analysis.

Example 5. Expression Pattern of Tested Promoters in Tobacco

The expression pattern of the trichome-specific promoters (see Example 3) is examined in the modified plants produced in Example 4. First generation (e.g., To) modified plants are sampled during the vegetative stage. Sections of young leaves are mounted onto glass slides with water, covered with a glass cover slip, and sealed with clear nail polish. Slides are viewed with a confocal laser scanning microscope under brightfield conditions and under conditions allowing the visualization of G3GFP (excitation/emission wavelengths are 488 nm/500-550 nm) expressed by the trichome-specific promoters.

FIGS. 4-8 depict glandular trichomes as visualized under brightfield conditions and under conditions that allow the visualization of G3GFP. The 1.2 kb and 0.4 kb fragments (SEQ ID NOs: 10 and 11) of the NtRbcST promoter both drive expression in tobacco trichomes. Similarly, the 1.0 kb NtPSO promoter (SEQ ID NO: 13), the 0.5 kb NtPHY promoter (SEQ ID NO: 15), and the 0.5 kb NtCYC promoter (SEQ ID NO: 17) also drive expression in tobacco trichomes.

Example 6. Expressing Terpenoid Biosynthesis Genes with Trichome-Specific Promoters Each of the trichome-specific promoters tested in Examples 3-5 is also used to drive the expression of genes involved in terpenoid biosynthesis. Fifteen constructs are produced as described in Example 3, with each trichome-specific promoter (e.g., SEQ ID NOs: 10-17, 45-47, and 80-82) driving the expression of NEOMENTHOL DEHYDROGENASE (NINMD); SEQ ID NO: 35) or one of two isoforms of CIS-ABIENOL SYNTHASE (NtaABS (Isoform 1; SEQ ID NO: 29) and NtABS (Isoform 2; SEQ ID NO: 30) in separate constructs.

Each of the fifteen constructs are separately transformed into tobacco cells and modified tobacco plants are regenerated as described in Example 4.

Example 7. Confirming Expression of Terpene Biosynthesis Genes in Modified Tobacco Plants During the vegetative stage of growth, RNA is extracted from young leaves from modified tobacco plants produced in Example 6, and from control tobacco plants lacking the recombinant nucleic acid constructs grown under comparable conditions. The extracted RNA is used to generate cDNA. Gene expression of NtNMD, NtaABS, and NtABS is quantified using quantitative real-time PCR (qRT-PCR). To confirm the constructs are functional, expression of NINMD, NtaABS, and NtABS in the modified plants is compared to control tobacco plants.

Example 8. Measuring Terpene Levels in Modified Tobacco Plants

During the vegetative stage of growth, young leaves are harvested from the modified tobacco plants from Example 6, and from control tobacco plants lacking the recombinant nucleic acid constructs grown under comparable conditions, for use in a qualitative metabolic profile analysis. Leaf samples are ground in liquid nitrogen, and then the samples are mixed with 60:40 hexane:ethyl acetate (v/v), supplemented with heptadecanol (an internal standard) and incubated overnight with shaking.

The solvent extracts are concentrated in a refrigerated SpeedVac™ (ThermoFisher Scientific) and placed into a silica column. The column is washed with hexane and allowed to flow through into collection tubes. Samples are aliquoted from the collection tubes and used for gas chromatography-mass spectrometry (GC-MS) analysis of metabolites.

Example 9. Identification of Trichome-Specific Promoter Motifs

Trichome-specific promoter sequences (e.g., SEQ ID NOs: 10-12, 14, and 16) are scanned for regulatory element motifs using the publicly available online database PLANTCARE (bioinformatics[dot]psb[dot]ugent[dot]be/webtools/plantcare/html) using default settings. Tables 9-13 detail the regulatory element motifs that were identified for each of the trichome-specific promoters.

TABLE 9

Regulatory elements in RbT (1243 nt) promoter (SEQ ID NO: 10).

| Motif | Sequence | Nucleotide Position | Strand | Function |
|---|---|---|---|---|
| ABRE | AACCCGG | 11 | − | cis-acting element involved in the abscisic acid responsiveness |
| ARE | AAACCA | 210 | + | cis-acting regulatory element essential for the anaerobic induction |
| as-1 | TGACG | 104 | − | |
| as-1 | TGACG | 964 | + | |
| AT~TATA-box | TATATAAA | 571 | − | |
| AT~TATA-box | TATATA | 573 | + | |
| ATC-motif | AGTAATCT | 1128 | − | part of a conserved DNA module involved in light responsiveness |
| Box 4 | ATTAAT | 1063 | − | part of a conserved DNA module involved in light responsiveness |
| CAAT-box | CAAT | 20 | + | |
| CAAT-box | CCAAT | 22 | − | common cis-acting element in promoter and enhancer regions |
| CAAT-box | CAAT | 33 | − | |

TABLE 9-continued

Regulatory elements in RbT (1243 nt) promoter (SEQ ID NO: 10).

| Motif | Sequence | Nucleotide Position | Strand | Function |
|---|---|---|---|---|
| CAAT-box | CAAAT | 69 | + | common cis-acting element in promoter and enhancer regions |
| CAAT-box | CAAT | 274 | + | |
| CAAT-box | CAAAT | 281 | − | common cis-acting element in promoter and enhancer regions |
| CAAT-box | CAAT | 325 | + | |
| CAAT-box | CAAAT | 338 | + | common cis-acting element in promoter and enhancer regions |
| CAAT-box | CAAAT | 346 | + | common cis-acting element in promoter and enhancer regions |
| CAAT-box | CAAT | 377 | − | |
| CAAT-box | CAAAT | 468 | + | common cis-acting element in promoter and enhancer regions |
| CAAT-box | CAAT | 488 | + | |
| CAAT-box | CAAT | 518 | − | |
| CAAT-box | TGCAAATCT | 666 | − | common cis-acting element in promoter and enhancer regions |
| CAAT-box | CAAAT | 668 | − | common cis-acting element in promoter and enhancer regions |
| CAAT-box | CAAT | 691 | − | |
| CAAT-box | CCAAT | 782 | + | common cis-acting element in promoter and enhancer regions |
| CAAT-box | CAAT | 783 | + | |
| CAAT-box | CAAT | 796 | − | |
| CAAT-box | CAAT | 818 | + | |
| CGTCA-motif | CGTCA | 104 | + | cis-acting regulatory element involved in the MeJA-responsiveness |
| CGTCA-motif | CGTCA | 964 | − | cis-acting regulatory element involved in the MeJA-responsiveness |
| chs-CMA2a | TCACTTGA | 113 | − | part of a light responsive element |
| GT1-motif | GGTTAA | 833 | − | light responsive element |
| LAMP-element | CTTTATCA | 1202 | + | part of a light responsive element |
| MYB | TAACCA | 393 | + | |
| MYB | CAACCA | 429 | − | |
| MYB-like sequence | TAACCA | 393 | + | |
| MYC | CAATTG | 20 | + | |
| MYC | CATTTG | 280 | + | |
| MYC | CATTTG | 468 | − | |
| MYC | CATGTG | 542 | + | |
| MYC | CATGTG | 718 | + | |
| STRE | AGGGG | 1028 | − | |
| STRE | AGGGG | 1043 | − | |

TABLE 9-continued

Regulatory elements in RbT (1243 nt) promoter (SEQ ID NO: 10).

| Motif | Sequence | Nucleotide Position | Strand | Function |
|---|---|---|---|---|
| TATA-box | TATTTAAA | 166 | - | core promoter element around -30 of transcription start |
| TATA-box | taTATAAAtc (SEQ ID NO: 102) | 526 | - | core promoter element around -30 of transcription start |
| TATA-box | TACAAAA | 549 | + | core promoter element around -30 of transcription start |
| TATA-box | taTATAAAg | 570 | - | core promoter element around -30 of transcription start |
| TATA-box | TATAAA | 571 | - | core promoter element around -30 of transcription start |
| TATA-box | TATATAA | 572 | - | core promoter element around -30 of transcription start |
| TATA-box | TATATA | 573 | + | core promoter element around -30 of transcription start |
| TATA-box | TATA | 575 | + | core promoter element around -30 of transcription start |
| TATA-box | TATA | 599 | + | core promoter element around -30 of transcription start |
| TATA-box | ATTATA | 842 | + | core promoter element around -30 of transcription start |
| TATA-box | TATAA | 843 | - | core promoter element around -30 of transcription start |
| TATA-box | TATA | 844 | - | core promoter element around -30 of transcription start |
| TATA-box | TATACA | 854 | - | core promoter element around -30 of transcription start |
| TATA-box | TATA | 856 | - | core promoter element around -30 of transcription start |
| TATA-box | TACAAAA | 1115 | + | core promoter element around -30 of transcription start |
| TATA-box | ATATAA | 1161 | + | core promoter element around -30 of transcription start |
| TATA-box | TATA | 1162 | - | core promoter element around -30 of transcription start |
| TATA-box | TATAAA | 1189 | - | core promoter element around -30 of transcription start |
| TATA-box | TATAA | 1190 | - | core promoter element around -30 of transcription start |
| TATA-box | TATA | 1191 | - | core promoter element around -30 of transcription start |
| TCCC-motif | TCTCCCT | 1151 | + | part of a light responsive element |
| TGACG-motif | TGACG | 104 | - | cis-acting regulatory element involved in the MeJA-responsiveness |
| TGACG-motif | TGACG | 964 | + | cis-acting regulatory element involved in the MeJA-responsiveness |
| Unnamed_1 | CGTGG | 234 | - | |
| Unnamed_2 | CCCCGG | 769 | - | |
| Unnamed_4 | CTCC | 46 | - | |

TABLE 9-continued

Regulatory elements in RbT (1243 nt) promoter (SEQ ID NO: 10).

| Motif | Sequence | Nucleotide Position | Strand | Function |
|---|---|---|---|---|
| Unnamed_4 | CTCC | 197 | - | |
| Unnamed_4 | CTCC | 581 | - | |
| Unnamed_4 | CTCC | 740 | + | |
| Unnamed_4 | CTCC | 824 | - | |
| Unnamed_4 | CTCC | 893 | - | |
| Unnamed_4 | CTCC | 1152 | + | |
| W box | TTGACC | 432 | + | |
| WUN-motif | CAATTACAT | 274 | + | |

TABLE 10

Regulatory elements in RbT (436 nt) promoter (SEQ ID NO: 11).

| Motif | Sequence | Nucleotide Position | Strand | Function |
|---|---|---|---|---|
| as-1 | TGACG | 157 | + | |
| ATC-motif | AGTAATCT | 321 | - | part of a conserved DNA module involved in light responsiveness |
| Box 4 | ATTAAT | 256 | - | part of a conserved DNA module involved in light responsiveness |
| CAAT-box | CAAT | 11 | + | |
| CGTCA-motif | CGTCA | 157 | - | cis-acting regulatory element involved in the MeJA-responsiveness |
| GT1-motif | GGTTAA | 26 | - | light responsive element |
| LAMP-element | CTTTATCA | 395 | + | part of a light responsive element |
| STRE | AGGGG | 221 | - | |
| STRE | AGGGG | 236 | - | |
| TATA-box | ATTATA | 35 | + | core promoter element around -30 of transcription start |
| TATA-box | TATAA | 36 | - | core promoter element around -30 of transcription start |
| TATA-box | TATA | 37 | + | core promoter element around -30 of transcription start |
| TATA-box | TATACA | 47 | - | core promoter element around -30 of transcription start |
| TATA-box | TATA | 49 | + | core promoter element around -30 of transcription start |
| TATA-box | TACAAAA | 308 | + | core promoter element around -30 of transcription start |
| TATA-box | ATATAA | 354 | + | core promoter element around -30 of transcription start |
| TATA-box | TATA | 355 | - | core promoter element around -30 of transcription start |
| TATA-box | TATAAA | 382 | - | core promoter element around -30 of transcription start |

TABLE 10-continued

Regulatory elements in RbT (436 nt) promoter (SEQ ID NO: 11).

| Motif | Sequence | Nucleotide Position | Strand | Function |
|---|---|---|---|---|
| TATA-box | TATAA | 383 | - | core promoter element around -30 of transcription start |
| TATA-box | TATA | 384 | - | core promoter element around -30 of transcription start |
| TCCC-motif | TCTCCCT | 344 | + | part of a light responsive element |
| TGACG-motif | TGACG | 157 | + | cis-acting regulatory element involved in the MeJA-responsiveness |
| Unnamed_4 | CTCC | 17 | | |
| Unnamed_4 | CTCC | 86 | - | |
| Unnamed_4 | CTCC | 345 | + | |

TABLE 11

Regulatory elements in PSO (1.5 kb) promoter (SEQ ID NO: 12).

| Motif | Sequence | Nucleotide Position | Strand | Function |
|---|---|---|---|---|
| AAGAA-motif | GAAAGAA | 9 | + | |
| ARE | AAACCA | 181 | + | cis-acting regulatory element essential for the anaerobic induction |
| ARE | AAACCA | 755 | + | cis-acting regulatory element essential for the anaerobic induction |
| as-1 | TGACG | 337 | - | |
| AT~TATA-box | TATATA | 701 | + | |
| AT~TATA-box | TATATA | 703 | + | |
| AT~TATA-box | TATATA | 858 | - | |
| AT~TATA-box | TATATA | 860 | - | |
| AT~TATA-box | TATATAAA | 938 | - | |
| AT~TATA-box | TATATA | 940 | - | |
| AT-rich sequence | TAAAATACT | 542 | - | element for maximal elicitor-mediated activation (2 copies) |
| Box 4 | ATTAAT | 718 | + | part of a conserved DNA module involved in light responsiveness |
| CAAT-box | CAAAT | 5 | - | common cis-acting element in promoter and enhancer regions |
| CAAT-box | CAAT | 19 | - | |
| CAAT-box | CAAT | 66 | + | |
| CAAT-box | CAAT | 160 | + | |
| CAAT-box | CAAAT | 194 | + | common cis-acting element in promoter and enhancer regions |
| CAAT-box | CAAT | 243 | + | |
| CAAT-box | CAAT | 281 | - | |
| CAAT-box | CAAT | 348 | + | |
| CAAT-box | CAAAT | 370 | - | common cis-acting element in promoter and enhancer regions |

TABLE 11-continued

Regulatory elements in PSO (1.5 kb) promoter (SEQ ID NO: 12).

| Motif | Sequence | Nucleotide Position | Strand | Function |
|---|---|---|---|---|
| CAAT-box | CAAAT | 392 | + | common cis-acting element in promoter and enhancer regions |
| CAAT-box | CAAAT | 453 | - | common cis-acting element in promoter and enhancer regions |
| CAAT-box | CAAT | 470 | + | |
| CAAT-box | CAAAT | 479 | + | common cis-acting element in promoter and enhancer regions |
| CAAT-box | CAAT | 535 | + | |
| CAAT-box | CAAT | 555 | + | |
| CAAT-box | CAAT | 600 | + | |
| CAAT-box | CAAT | 627 | + | |
| CAAT-box | CAAAT | 760 | - | common cis-acting element in promoter and enhancer regions |
| CAAT-box | CAAAT | 795 | - | common cis-acting element in promoter and enhancer regions |
| CAAT-box | CAAT | 829 | - | |
| CAAT-box | CAAAT | 865 | - | common cis-acting element in promoter and enhancer regions |
| CAAT-box | CAAAT | 894 | - | common cis-acting element in promoter and enhancer regions |
| CAAT-box | CAAT | 1002 | - | |
| CAAT-box | CAAT | 1050 | - | |
| CAAT-box | CCAAT | 1115 | - | common cis-acting element in promoter and enhancer regions |
| CAAT-box | CAAAT | 1289 | - | common cis-acting element in promoter and enhancer regions |
| CAAT-box | CAAT | 1311 | + | |
| CAAT-box | CAAT | 1336 | - | |
| CAAT-box | CAAAT | 1436 | - | common cis-acting element in promoter and enhancer regions |
| CAAT-box | CAAAT | 1469 | + | common cis-acting element in promoter and enhancer regions |
| CGTCA-motif | CGTCA | 337 | + | cis-acting regulatory element involved in the MeJA-responsiveness |
| chs-CMA2a | TCACTTGA | 1318 | - | part of a light responsive element |
| ERE | ATTTCATA | 575 | + | |
| ERE | ATTTTAAA | 878 | - | |
| ERE | ATTTCATA | 1068 | + | |
| ERE | ATTTTAAA | 1128 | - | |
| ERE | ATTTCATA | 1282 | + | |
| GATA-motif | AAGGATAAGG (SEQ ID NO: 101) | 1204 | + | part of a light responsive element |
| G-box | CACGAC | 1194 | + | cis-acting regulatory element involved in light responsiveness |

TABLE 11-continued

Regulatory elements in PSO (1.5 kb) promoter (SEQ ID NO: 12).

| Motif | Sequence | Nucleotide Position | Strand | Function |
|---|---|---|---|---|
| GCN4_motif | TGAGTCA | 1314 | + | cis-regulatory element involved in endosperm expression |
| GT1-motif | GGTTAA | 73 | + | light responsive element |
| GT1-motif | GGTTAA | 170 | - | light responsive element |
| GT1-motif | GGTTAA | 548 | - | light responsive element |
| I-box | ccttatcct | 1205 | - | part of a light responsive element |
| Myb | TAACTG | 654 | + | |
| Myb | TAACTG | 944 | + | |
| Myb | TAACTG | 1089 | + | |
| MYB | TAACCA | 171 | + | |
| MYB | TAACCA | 268 | + | |
| MYB | TAACCA | 549 | + | |
| MYB | TAACCA | 948 | - | |
| MYB | CAACAG | 1444 | + | |
| Myb-binding site | CAACAG | 1444 | + | |
| MYB-like sequence | TAACCA | 171 | + | |
| MYB-like sequence | TAACCA | 268 | + | |
| MYB-like sequence | TAACCA | 549 | + | |
| MYB-like sequence | TAACCA | 948 | - | |
| MYC | CATGTG | 85 | - | |
| MYC | CATTTG | 759 | + | |
| MYC | CATTTG | 893 | + | |
| STRE | AGGGG | 1479 | - | |
| TATA | TATAAAAT | 230 | + | |
| TATA-box | TATA | 69 | + | core promoter element around -30 of transcription start |
| TATA-box | TACAAAA | 109 | - | core promoter element around -30 of transcription start |
| TATA-box | ATATAA | 151 | + | core promoter element around -30 of transcription start |
| TATA-box | TATA | 152 | + | core promoter element around -30 of transcription start |
| TATA-box | TATA | 230 | + | core promoter element around -30 of transcription start |
| TATA-box | ATATAA | 265 | + | core promoter element around -30 of transcription start |
| TATA-box | TATA | 266 | + | core promoter element around -30 of transcription start |
| TATA-box | ATATAT | 277 | + | core promoter element around -30 of transcription start |

TABLE 11-continued

Regulatory elements in PSO (1.5 kb) promoter (SEQ ID NO: 12).

| Motif | Sequence | Nucleotide Position | Strand | Function |
|---|---|---|---|---|
| TATA-box | TATA | 278 | + | core promoter element around -30 of transcription start |
| TATA-box | TACAAAA | 383 | - | core promoter element around -30 of transcription start |
| TATA-box | TATA | 494 | + | core promoter element around -30 of transcription start |
| TATA-box | TATA | 513 | + | core promoter element around -30 of transcription start |
| TATA-box | TATAA | 562 | - | core promoter element around -30 of transcription start |
| TATA-box | TATA | 563 | + | core promoter element around -30 of transcription start |
| TATA-box | TACAAAA | 569 | + | core promoter element around -30 of transcription start |
| TATA-box | TACAAAA | 638 | + | core promoter element around -30 of transcription start |
| TATA-box | TATAA | 666 | - | core promoter element around -30 of transcription start |
| TATA-box | TATA | 667 | + | core promoter element around -30 of transcription start |
| TATA-box | TATA | 692 | + | core promoter element around -30 of transcription start |
| TATA-box | ATTATA | 699 | + | core promoter element around -30 of transcription start |
| TATA-box | TATATAA | 700 | - | core promoter element around -30 of transcription start |
| TATA-box | TATATA | 701 | + | core promoter element around -30 of transcription start |
| TATA-box | ATATAT | 702 | + | core promoter element around -30 of transcription start |
| TATA-box | TATATA | 703 | + | core promoter element around -30 of transcription start |
| TATA-box | TATA | 705 | + | core promoter element around -30 of transcription start |
| TATA-box | TATTTAAA | 728 | - | core promoter element around -30 of transcription start |
| TATA-box | ATTATA | 856 | + | core promoter element around -30 of transcription start |
| TATA-box | TATATAA | 857 | - | core promoter element around -30 of transcription start |
| TATA-box | TATATA | 858 | - | core promoter element around -30 of transcription start |
| TATA-box | ATATAT | 859 | - | core promoter element around -30 of transcription start |
| TATA-box | TATATA | 860 | - | core promoter element around -30 of transcription start |
| TATA-box | ATATAT | 861 | - | core promoter element around -30 of transcription start |
| TATA-box | TATA | 862 | - | core promoter element around -30 of transcription start |

TABLE 11-continued

Regulatory elements in PSO (1.5 kb) promoter (SEQ ID NO: 12).

| Motif | Sequence | Nucleotide Position | Strand | Function |
|---|---|---|---|---|
| TATA-box | ATATAT | 884 | - | core promoter element around -30 of transcription start |
| TATA-box | TATA | 885 | - | core promoter element around -30 of transcription start |
| TATA-box | TACATAAA | 906 | - | core promoter element around -30 of transcription start |
| TATA-box | TATAAAA | 937 | - | core promoter element around -30 of transcription start |
| TATA-box | TATAAA | 938 | - | core promoter element around -30 of transcription start |
| TATA-box | TATATAA | 939 | - | core promoter element around -30 of transcription start |
| TATA-box | TATATA | 940 | - | core promoter element around -30 of transcription start |
| TATA-box | ATATAA | 941 | + | core promoter element around -30 of transcription start |
| TATA-box | TATA | 942 | - | core promoter element around -30 of transcription start |
| TATA-box | TATAAGAA | 961 | - | core promoter element around -30 of transcription start |
| TATA-box | TATAA | 964 | - | core promoter element around -30 of transcription start |
| TATA-box | TATA | 965 | - | core promoter element around -30 of transcription start |
| TATA-box | TATTTAAA | 983 | - | core promoter element around -30 of transcription start |
| TATA-box | ATATAA | 1110 | + | core promoter element around -30 of transcription start |
| TATA-box | TATA | 1111 | - | core promoter element around -30 of transcription start |
| TATA-box | ccTATAAAaa (SEQ ID NO: 97) | 1419 | + | core promoter element around -30 of transcription start |
| TATA-box | TATA | 1421 | - | core promoter element around -30 of transcription start |
| TATA-box | ATATAT | 1432 | - | core promoter element around -30 of transcription start |
| TATA-box | TATA | 1433 | - | core promoter element around -30 of transcription start |
| TC-rich repeats | ATTCTCTAAC (SEQ ID NO: 100) | 294 | + | cis-acting element involved in defense and stress responsiveness |
| TC-rich repeats | ATTCTCTAAC (SEQ ID NO: 100) | 433 | - | cis-acting element involved in defense and stress responsiveness |
| TCT-motif | TCTTAC | 1119 | - | part of a light responsive element |
| TGACG-motif | TGACG | 337 | - | cis-acting regulatory element involved in the MeJA-responsiveness |
| Unnamed_1 | CGTGG | 134 | - | |
| Unnamed_1 | CGTGG | 271 | - | |

TABLE 11-continued

Regulatory elements in PSO (1.5 kb) promoter (SEQ ID NO: 12).

| Motif | Sequence | Nucleotide Position | Strand | Function |
|---|---|---|---|---|
| Unnamed_4 | CTCC | 900 | − | |
| Unnamed_4 | CTCC | 1139 | − | |
| Unnamed_4 | CTCC | 1199 | + | |
| Unnamed_4 | CTCC | 1269 | + | |
| Unnamed_4 | CTCC | 1295 | + | |
| Unnamed_4 | CTCC | 1492 | + | |
| WUN-motif | AAATTACT | 955 | − | |
| WUN-motif | AAATTACTA | 1242 | + | |

TABLE 12

Regulatory elements in PHY (1.5 kb) promoter (SEQ ID NO: 14).

| Motif | Sequence | Nucleotide Position | Strand | Function |
|---|---|---|---|---|
| ABRE | ACGTG | 390 | + | cis-acting element involved in the abscisic acid responsiveness |
| ABRE | ACGTG | 654 | + | cis-acting element involved in the abscisic acid responsiveness |
| ABRE | ACGTG | 827 | − | cis-acting element involved in the abscisic acid responsiveness |
| ABRE | ACGTG | 1346 | − | cis-acting element involved in the abscisic acid responsiveness |
| ABRE3a | TACGTG | 827 | − | |
| ABRE3a | TACGTG | 1346 | − | |
| ABRE4 | CACGTA | 827 | + | |
| ABRE4 | CACGTA | 1346 | + | |
| AE-box | AGAAACAA | 497 | + | part of a module for light response |
| ARE | AAACCA | 1389 | − | cis-acting regulatory element essential for the anaerobic induction |
| AT~TATA-box | TATATA | 447 | + | |
| AT~TATA-box | TATATA | 1413 | − | |
| AT-rich element | ATAGAAATCAA (SEQ ID NO: 99) | 44 | + | binding site of AT-rich DNA binding protein (ATBP-1) |
| AT-rich sequence | TAAAATACT | 1174 | + | element for maximal elicitor-mediated activation (2copies) |
| CAAT-box | CAAAT | 41 | + | common cis-acting element in promoter and enhancer regions |
| CAAT-box | CAAT | 52 | + | |
| CAAT-box | CCAAT | 77 | + | common cis-acting element in promoter and enhancer regions |
| CAAT-box | CAAT | 78 | + | |
| CAAT-box | CAAT | 115 | + | |

TABLE 12-continued

Regulatory elements in PHY (1.5 kb) promoter (SEQ ID NO: 14).

| Motif | Sequence | Nucleotide Position | Strand | Function |
|---|---|---|---|---|
| CAAT-box | CAAAT | 206 | + | common cis-acting element in promoter and enhancer regions |
| CAAT-box | CAAT | 225 | + | |
| CAAT-box | CAAAT | 294 | + | common cis-acting element in promoter and enhancer regions |
| CAAT-box | CAAT | 321 | + | |
| CAAT-box | CAAT | 356 | | |
| CAAT-box | CAAAT | 376 | + | common cis-acting element in promoter and enhancer regions |
| CAAT-box | CAAT | 502 | + | |
| CAAT-box | CAAT | 578 | + | |
| CAAT-box | CCAAT | 584 | + | common cis-acting element in promoter and enhancer regions |
| CAAT-box | CAAT | 585 | + | |
| CAAT-box | CAAT | 594 | + | |
| CAAT-box | CAAAT | 621 | + | common cis-acting element in promoter and enhancer regions |
| CAAT-box | CAAT | 626 | + | |
| CAAT-box | CAAT | 838 | − | |
| CAAT-box | CCAAT | 847 | − | common cis-acting element in promoter and enhancer regions |
| CAAT-box | CAAAT | 888 | − | common cis-acting element in promoter and enhancer regions |
| CAAT-box | CAAAT | 961 | + | common cis-acting element in promoter and enhancer regions |
| CAAT-box | CAAT | 982 | + | |
| CAAT-box | CAAT | 1090 | + | |
| CAAT-box | CAAAT | 1092 | − | common cis-acting element in promoter and enhancer regions |
| CAAT-box | CAAAT | 1102 | + | common cis-acting element in promoter and enhancer regions |
| CAAT-box | CAAAT | 1119 | − | common cis-acting element in promoter and enhancer regions |
| CAAT-box | CAAT | 1231 | − | |
| CAAT-box | CAAT | 1245 | + | |
| CAAT-box | CAAT | 1247 | − | |
| CAAT-box | CAAT | 1292 | + | |
| CAAT-box | CAAT | 1325 | + | |
| CAAT-box | CAAAT | 1338 | + | common cis-acting element in promoter and enhancer regions |
| CAAT-box | CCAAT | 1406 | + | common cis-acting element in promoter and enhancer regions |
| CAAT-box | CAAT | 1407 | + | |
| CAAT-box | CAAT | 1425 | − | |

TABLE 12-continued

Regulatory elements in PHY (1.5 kb) promoter (SEQ ID NO: 14).

| Motif | Sequence | Nucleotide Position | Strand | Function |
|---|---|---|---|---|
| CAAT-box | CAAT | 1446 | − | |
| CAAT-box | CAAT | 1457 | + | |
| CAAT-box | CAAT | 1470 | + | |
| CAAT-box | CAAT | 1489 | + | |
| CAT-box | GCCACT | 1364 | + | cis-acting regulatory element related to meristem expression |
| circadian | CAAAGATATC (SEQ ID NO: 98) | 1059 | + | cis-acting regulatory element involved in circadian control |
| ERE | ATTTCATA | 84 | − | |
| ERE | ATTTTAAA | 1314 | + | |
| GATA-motif | GATAGGA | 239 | − | part of a light responsive element |
| G-Box | CACGTT | 389 | − | cis-acting regulatory element involved in light responsiveness |
| G-Box | CACGTT | 653 | − | cis-acting regulatory element involved in light responsiveness |
| G-box | TACGTG | 827 | − | cis-acting regulatory element involved in light responsiveness |
| G-box | TACGTG | 1346 | − | cis-acting regulatory element involved in light responsiveness |
| MRE | AACCTAA | 803 | − | MYB binding site involved in light responsiveness |
| MYB | CAACAG | 1374 | + | |
| MYB | CAACCA | 1403 | + | |
| Myb | TAACTG | 1492 | + | |
| Myb-binding site | CAACAG | 1374 | + | |
| MYC | CATTTG | 961 | − | |
| MYC | CAATTG | 1245 | − | |
| STRE | AGGGG | 811 | − | |
| TATA-box | ATTATA | 427 | + | core promoter element around −30 of transcription start |
| TATA-box | TATAA | 428 | − | core promoter element around −30 of transcription start |
| TATA-box | TATA | 429 | + | core promoter element around −30 of transcription start |
| TATA-box | TATATA | 447 | + | core promoter element around −30 of transcription start |
| TATA-box | TATA | 449 | + | core promoter element around −30 of transcription start |
| TATA-box | ATATAA | 545 | + | core promoter element around −30 of transcription start |
| TATA-box | TATA | 546 | + | core promoter element around −30 of transcription start |
| TATA-box | ATTATA | 863 | + | core promoter element around −30 of transcription start |

TABLE 12-continued

Regulatory elements in PHY (1.5 kb) promoter (SEQ ID NO: 14).

| Motif | Sequence | Nucleotide Position | Strand | Function |
|---|---|---|---|---|
| TATA-box | TATAA | 864 | - | core promoter element around -30 of transcription start |
| TATA-box | TATA | 865 | - | core promoter element around -30 of transcription start |
| TATA-box | ATATAA | 998 | + | core promoter element around -30 of transcription start |
| TATA-box | TATA | 999 | - | core promoter element around -30 of transcription start |
| TATA-box | ccTATAAAaa (SEQ ID NO: 97) | 1007 | + | core promoter element around -30 of transcription start |
| TATA-box | ATTATA | 1025 | + | core promoter element around -30 of transcription start |
| TATA-box | TATAA | 1026 | - | core promoter element around -30 of transcription start |
| TATA-box | TATA | 1027 | - | core promoter element around -30 of transcription start |
| TATA-box | TATAA | 1258 | - | core promoter element around -30 of transcription start |
| TATA-box | TATA | 1259 | - | core promoter element around -30 of transcription start |
| TATA-box | TATA | 1287 | - | core promoter element around -30 of transcription start |
| TATA-box | TATA | 1342 | - | core promoter element around -30 of transcription start |
| TATA-box | ATTATA | 1357 | + | core promoter element around -30 of transcription start |
| TATA-box | TATAA | 1358 | - | core promoter element around -30 of transcription start |
| TATA-box | TATA | 1359 | - | core promoter element around -30 of transcription start |
| TATA-box | ATATAT | 1412 | - | core promoter element around -30 of transcription start |
| TATA-box | TATATA | 1413 | - | core promoter element around -30 of transcription start |
| TATA-box | TATA | 1415 | - | core promoter element around -30 of transcription start |
| TATA-box | TATA | 1420 | - | core promoter element around -30 of transcription start |
| TATA-box | ATATAA | 1483 | + | core promoter element around -30 of transcription start |
| TATA-box | TATA | 1484 | - | core promoter element around -30 of transcription start |
| TCT-motif | TCTTAC | 489 | - | part of a light responsive element |
| TCT-motif | TCTTAC | 1462 | + | part of a light responsive element |
| TGA-element | AACGAC | 419 | - | auxin-responsive element |
| Unnamed_1 | CGTGG | 529 | - | |
| Unnamed_4 | CTCC | 695 | + | |

TABLE 12-continued

Regulatory elements in PHY (1.5 kb) promoter (SEQ ID NO: 14).

| Motif | Sequence | Nucleotide Position | Strand | Function |
|---|---|---|---|---|
| Unnamed_4 | CTCC | 1056 | + | |
| Unnamed_4 | CTCC | 1143 | + | |
| Unnamed_6 | taTAAATATct (SEQ ID NO: 96) | 999 | + | |
| Unnamed_1 | GGATTTTACAGT (SEQ ID NO: 95) | 230 | - | cis-acting element involved in phytochrome down-regulation expression |
| W box | TTGACC | 222 | - | |
| WUN-motif | TAATTACTC | 869 | - | |
| WUN-motif | TTATTACAT | 1072 | + | |

TABLE 13

Regulatory elements in CYC (1.5 kb) promoter (SEQ ID NO: 16).

| Motif | Sequence | Nucleotide Position | Strand | Function |
|---|---|---|---|---|
| ABRE | ACGTG | 956 | + | cis-acting element involved in the abscisic acid responsiveness |
| AT~TATA-box | TATATA | 1375 | - | |
| AT~TATA-box | TATATA | 1377 | - | |
| Box 4 | ATTAAT | 931 | - | part of a conserved DNA module involved in light responsiveness |
| Box 4 | ATTAAT | 1018 | - | part of a conserved DNA module involved in light responsiveness |
| CAAT-box | CAAT | 19 | - | |
| CAAT-box | CAAT | 23 | + | |
| CAAT-box | CAAT | 27 | - | |
| CAAT-box | CAAT | 361 | - | |
| CAAT-box | CAAT | 371 | - | |
| CAAT-box | CAAAT | 379 | + | common cis-acting element in promoter and enhancer regions |
| CAAT-box | CAAT | 404 | - | |
| CAAT-box | CAAT | 480 | - | |
| CAAT-box | CAAT | 558 | - | |
| CAAT-box | CAAT | 613 | - | |
| CAAT-box | CAAAT | 646 | + | common cis-acting element in promoter and enhancer regions |
| CAAT-box | CAAAT | 692 | - | common cis-acting element in promoter and enhancer regions |
| CAAT-box | CAAAT | 732 | + | common cis-acting element in promoter and enhancer regions |
| CAAT-box | CAAT | 741 | - | |
| CAAT-box | CAAAT | 772 | - | common cis-acting element in promoter and enhancer regions |

TABLE 13-continued

Regulatory elements in CYC (1.5 kb) promoter (SEQ ID NO: 16).

| Motif | Sequence | Nucleotide Position | Strand | Function |
|---|---|---|---|---|
| CAAT-box | CAAT | 783 | + | |
| CAAT-box | CAAT | 811 | − | |
| CAAT-box | CAAAT | 855 | + | common cis-acting element in promoter and enhancer regions |
| CAAT-box | CAAT | 867 | − | |
| CAAT-box | CAAT | 937 | − | |
| CAAT-box | CAAT | 990 | − | |
| CAAT-box | CAAT | 1000 | + | |
| CAAT-box | CAAT | 1025 | + | |
| CAAT-box | CCAAT | 1112 | − | common cis-acting element in promoter and enhancer regions |
| CAAT-box | CAAT | 1118 | − | |
| CAAT-box | CAAAT | 1134 | + | common cis-acting element in promoter and enhancer regions |
| CAAT-box | CAAT | 1174 | − | |
| CAAT-box | CAAT | 1181 | + | |
| CAAT-box | CAAT | 1190 | − | |
| CAAT-box | CAAT | 1197 | + | |
| CAAT-box | CAAAT | 1203 | − | common cis-acting element in promoter and enhancer regions |
| CAAT-box | CAAAT | 1213 | − | common cis-acting element in promoter and enhancer regions |
| CAAT-box | CAAT | 1224 | − | |
| CAAT-box | CAAT | 1241 | + | |
| CAAT-box | CAAT | 1324 | − | |
| CAAT-box | CAAT | 1342 | + | |
| CAAT-box | CAAAT | 1366 | − | common cis-acting element in promoter and enhancer regions |
| CAAT-box | CAAAT | 1399 | + | common cis-acting element in promoter and enhancer regions |
| CAAT-box | CAAT | 1410 | − | |
| CAT-box | GCCACT | 1394 | − | cis-acting regulatory element related to meristem expression |
| circadian | CAAAGATATC (SEQ ID NO: 94) | 1057 | + | cis-acting regulatory element involved in circadian control |
| DRE1 | ACCGAGA | 677 | − | |
| ERE | ATTTCATA | 156 | − | |
| ERE | ATTTTAAA | 179 | − | |
| ERE | ATTTTAAA | 250 | + | |
| ERE | ATTTTAAA | 252 | − | |
| ERE | ATTTTAAA | 297 | − | |

TABLE 13-continued

Regulatory elements in CYC (1.5 kb) promoter (SEQ ID NO: 16).

| Motif | Sequence | Nucleotide Position | Strand | Function |
|---|---|---|---|---|
| ERE | ATTTTAAA | 430 | − | |
| ERE | ATTTTAAA | 698 | + | |
| ERE | ATTTTAAA | 700 | − | |
| ERE | ATTTCATA | 1300 | − | |
| G-box | CACGTC | 955 | − | cis-acting regulatory element involved in light responsiveness |
| GT1-motif | GGTTAAT | 54 | − | light responsive element |
| GT1-motif | GGTTAA | 55 | − | light responsive element |
| MYB | TAACCA | 56 | + | |
| Myb | TAACTG | 598 | + | |
| Myb | TAACTG | 1234 | − | |
| MYB-like sequence | TAACCA | 56 | + | |
| MYC | CATTTG | 379 | − | |
| MYC | CATGTG | 578 | − | |
| MYC | CATTTG | 1134 | − | |
| TATA | TATAAAAT | 1106 | + | |
| TATA-box | TACAAAA | 9 | − | core promoter element around −30 of transcription start |
| TATA-box | TATAA | 64 | − | core promoter element around −30 of transcription start |
| TATA-box | TATA | 65 | + | core promoter element around −30 of transcription start |
| TATA-box | TATAAA | 77 | − | core promoter element around −30 of transcription start |
| TATA-box | TATAA | 78 | − | core promoter element around −30 of transcription start |
| TATA-box | TATA | 79 | + | core promoter element around −30 of transcription start |
| TATA-box | ATATAT | 153 | + | core promoter element around −30 of transcription start |
| TATA-box | TATA | 154 | + | core promoter element around −30 of transcription start |
| TATA-box | TATTTAAA | 177 | + | core promoter element around −30 of transcription start |
| TATA-box | TATA | 237 | + | core promoter element around −30 of transcription start |
| TATA-box | ATATAA | 270 | + | core promoter element around −30 of transcription start |
| TATA-box | TATA | 27 | + | core promoter element around −30 of transcription start |
| TATA-box | TATTTAAA | 295 | + | core promoter element around −30 of transcription start |
| TATA-box | TATA | 401 | + | core promoter element around −30 of transcription start |

TABLE 13-continued

Regulatory elements in CYC (1.5 kb) promoter (SEQ ID NO: 16).

| Motif | Sequence | Nucleotide Position | Strand | Function |
|---|---|---|---|---|
| TATA-box | TATAAAA | 423 | − | core promoter element around −30 of transcription start |
| TATA-box | TATAAA | 424 | − | core promoter element around −30 of transcription start |
| TATA-box | TATAA | 425 | − | core promoter element around −30 of transcription start |
| TATA-box | TATA | 426 | + | core promoter element around −30 of transcription start |
| TATA-box | TATTTAAA | 428 | + | core promoter element around −30 of transcription start |
| TATA-box | TACAAAA | 442 | − | core promoter element around −30 of transcription start |
| TATA-box | TATAA | 476 | − | core promoter element around −30 of transcription start |
| TATA-box | TATA | 477 | + | core promoter element around −30 of transcription start |
| TATA-box | ATTATA | 590 | + | core promoter element around −30 of transcription start |
| TATA-box | TATAA | 591 | − | core promoter element around −30 of transcription start |
| TATA-box | TATA | 592 | + | core promoter element around −30 of transcription start |
| TATA-box | TATA | 636 | + | core promoter element around −30 of transcription start |
| TATA-box | ATATAA | 687 | + | core promoter element around −30 of transcription start |
| TATA-box | TATA | 688 | + | core promoter element around −30 of transcription start |
| TATA-box | TATAA | 756 | − | core promoter element around −30 of transcription start |
| TATA-box | TATA | 757 | − | core promoter element around −30 of transcription start |
| TATA-box | TATAA | 789 | − | core promoter element around −30 of transcription start |
| TATA-box | TATA | 790 | − | core promoter element around −30 of transcription start |
| TATA-box | TACAAAA | 800 | + | core promoter element around −30 of transcription start |
| TATA-box | TATAAAA | 860 | − | core promoter element around −30 of transcription start |
| TATA-box | TATAAA | 861 | − | core promoter element around −30 of transcription start |
| TATA-box | TATAA | 862 | − | core promoter element around −30 of transcription start |
| TATA-box | TATA | 863 | − | core promoter element around −30 of transcription start |
| TATA-box | TACAAAA | 899 | − | core promoter element around −30 of transcription start |
| TATA-box | TACAAAA | 982 | + | core promoter element around −30 of transcription start |

TABLE 13-continued

Regulatory elements in CYC (1.5 kb) promoter (SEQ ID NO: 16).

| Motif | Sequence | Nucleotide Position | Strand | Function |
|---|---|---|---|---|
| TATA-box | TATAAAA | 1008 | - | core promoter element around -30 of transcription start |
| TATA-box | TATAAA | 1009 | - | core promoter element around -30 of transcription start |
| TATA-box | TATAA | 1010 | - | core promoter element around -30 of transcription start |
| TATA-box | TATA | 1011 | - | core promoter element around -30 of transcription start |
| TATA-box | TATAAAA | 1042 | - | core promoter element around -30 of transcription start |
| TATA-box | TATAAA | 1043 | - | core promoter element around -30 of transcription start |
| TATA-box | TATAA | 1044 | - | core promoter element around -30 of transcription start |
| TATA-box | TATA | 1045 | - | core promoter element around -30 of transcription start |
| TATA-box | TATA | 1074 | - | core promoter element around -30 of transcription start |
| TATA-box | TATA | 1106 | - | core promoter element around -30 of transcription start |
| TATA-box | ATTATA | 1243 | + | core promoter element around -30 of transcription start |
| TATA-box | TATAA | 1244 | - | core promoter element around -30 of transcription start |
| TATA-box | TATA | 1245 | - | core promoter element around -30 of transcription start |
| TATA-box | TACAAAA | 1281 | - | core promoter element around -30 of transcription start |
| TATA-box | ATATAT | 1350 | - | core promoter element around -30 of transcription start |
| TATA-box | TATA | 1351 | - | core promoter element around -30 of transcription start |
| TATA-box | TATATA | 1375 | - | core promoter element around -30 of transcription start |
| TATA-box | ATATAT | 1376 | - | core promoter element around -30 of transcription start |
| TATA-box | TATATA | 1377 | - | core promoter element around -30 of transcription start |
| TATA-box | TATA | 1379 | - | core promoter element around -30 of transcription start |
| TATA-box | TACAAAA | 1442 | + | core promoter element around -30 of transcription start |
| TCT-motif | TCTTAC | 13 | - | part of a light responsive element |
| Unnamed_1 | CGTGG | 1140 | + | |
| Unnamed_4 | CTCC | 776 | - | |
| WUN-motif | AAATTACT | 160 | + | |
| WUN-motif | AAATTTCTT | 287 | + | |
| WUN-motif | AAATTACT | 945 | - | |

TABLE 13-continued

Regulatory elements in CYC (1.5 kb) promoter (SEQ ID NO: 16).

| Motif | Sequence | Nucleotide Position | Strand | Function |
|---|---|---|---|---|
| WUN-motif | AAATTACT | 1091 | − | |
| WUN-motif | AAATTACT | 1126 | − | |

Figure 14:
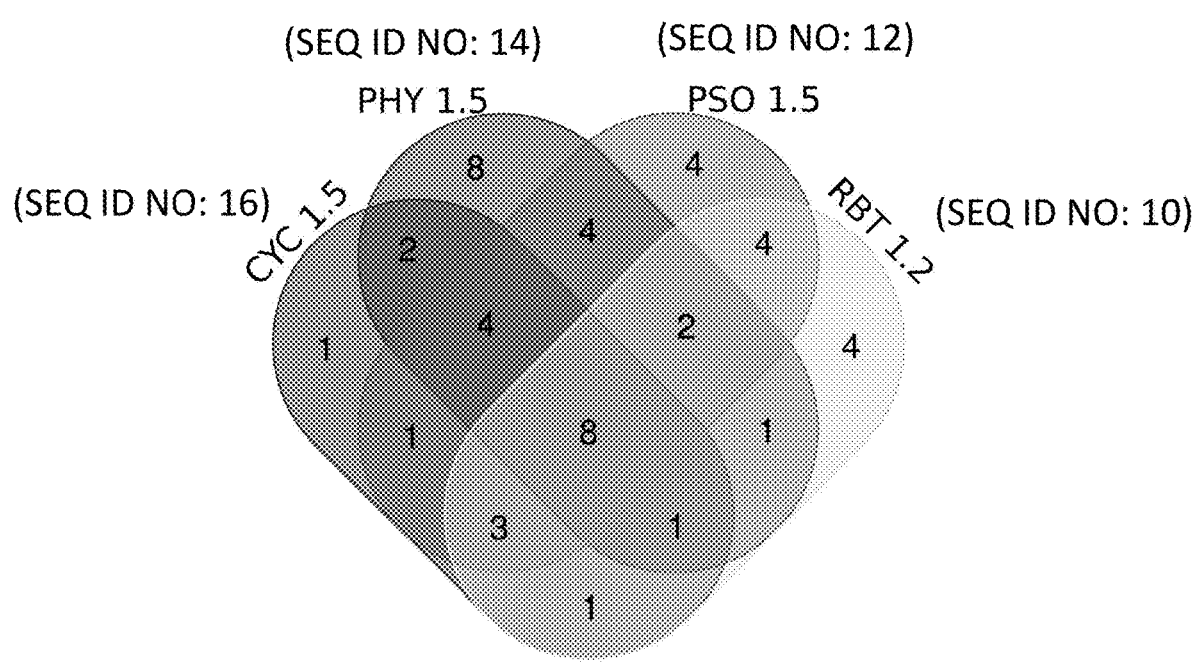
FIG. 14 depicts a Venn diagram showing which trichome promoters share different promoter motifs.

Several regulatory element motifs (e.g., TATA, CGTGG, TATATAAA, CATTTG, CAAAT, CAAT, CTCC, TAACCA, CAACAG, and SEQ ID NOs: 41 and 42) were identified as common elements. FIG. 14 depicts which promoters contain each of the common regulatory element motifs. Table 14 provides the regulatory element motifs used to generate FIG. 14.

TABLE 14

List of regulatory elements used to create FIG. 14.

| CYC 1.5 (SEQ ID NO: 16) | PHY 1.5 (SEQ ID NO: 14) | PSO 1.5 (SEQ ID NO: 12) | RBT 1.2 (SEQ ID NO: 10) |
|---|---|---|---|
| Unnamed | Unnamed | Unnamed | Unnamed |
| ABRE | ABRE | AAGAA-MOTIF | ABRE |
| AT-TATA-BOX | ABRE3a | ARE | ARE |
| BOX4 | ABRE4 | AT-RICH SEQ | ATC-MOTIF |
| CAAT-BOX | AE-BOX | AT-TATA-BOX | AT-TATA-BOX |
| CAT-BOX | ARE | BOX4 | BOX4 |
| DRE1 | AT-RICH ELEMENT | CAAT-BOX | CAAT-BOX |
| ERE | AT-RICH SEQ | CGTCA-MOTIF | CGTCA-MOTIF |
| G-BOX | AT-TATA-BOX | ERE | GT1-MOTIF |
| GT1-MOTIF | CAAT-BOX | G-BOX | LAMP-ELEMENT |
| MYB | CAT-BOX | GATA-MOTIF | MYB |
| MYB-LIKE SEQ | ERE | GCN4 MOTIF | MYB-LIKE SEQ |
| MYC | G-BOX | GT1-MOTIF | MYC |
| Myb | G-BOX | I-BOX | STRE |
| TATA | GATA-MOTIF | MYB | TATA-BOX |
| TATA-BOX | MRE | MYB-LIKE SEQ | TCCC-MOTIF |
| TCT-MOTIF | MYB | MYC | TGACG-MOTIF |
| Unnamed_1 | MYC | Myb | Unnamed_1 |
| Unnamed_4 | Myb | Myb-BINDING SITE | Unnamed_2 |
| WUN-MOTIF | Myb-BINDING SITE | STRE | Unnamed_4 |
| CIRCADIAN | STRE | TATA | W-BOX |
| | TATA-BOX | TATA-BOX | WUN-MOTIF |
| | TCT-MOTIF | TC-RICH REPEATS | AS-1 |
| | TGA-ELEMENT | TCT-MOTIF | CHS-CMA2a |
| | Unnamed_1 | TGACG-MOTIF | |
| | Unnamed_1 | Unnamed_1 | |
| | Unnamed_4 | Unnamed_4 | |
| | Unnamed-6 | WUN MOTIF | |
| | W-BOX | AS-1 | |
| | WUN MOTIF | CHS-CMA2a | |
| | CIRCADIAN | | |

FIG. 15 depicts the accumulation of G3GFP in tobacco trichomes. Each of SEQ ID NOs: 80-82 drive the expression/accumulation of G3GFP in trichomes in tobacco. See FIG. 15B, FIG. 15C, and FIG. 15D.

Figure 16:
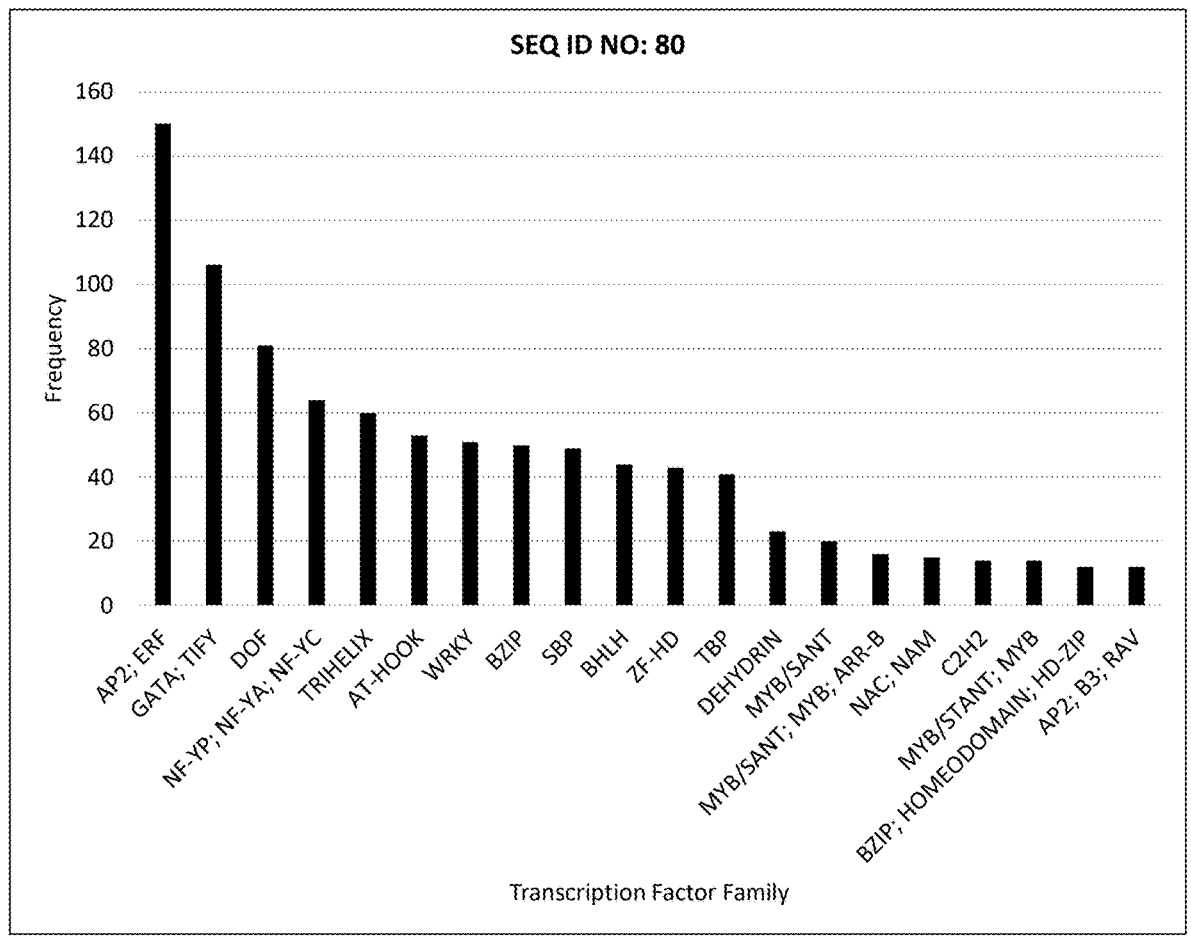
FIG. 16 depicts the frequency of cis-elements identified in SEQ ID NO: 80.
Figure 17:
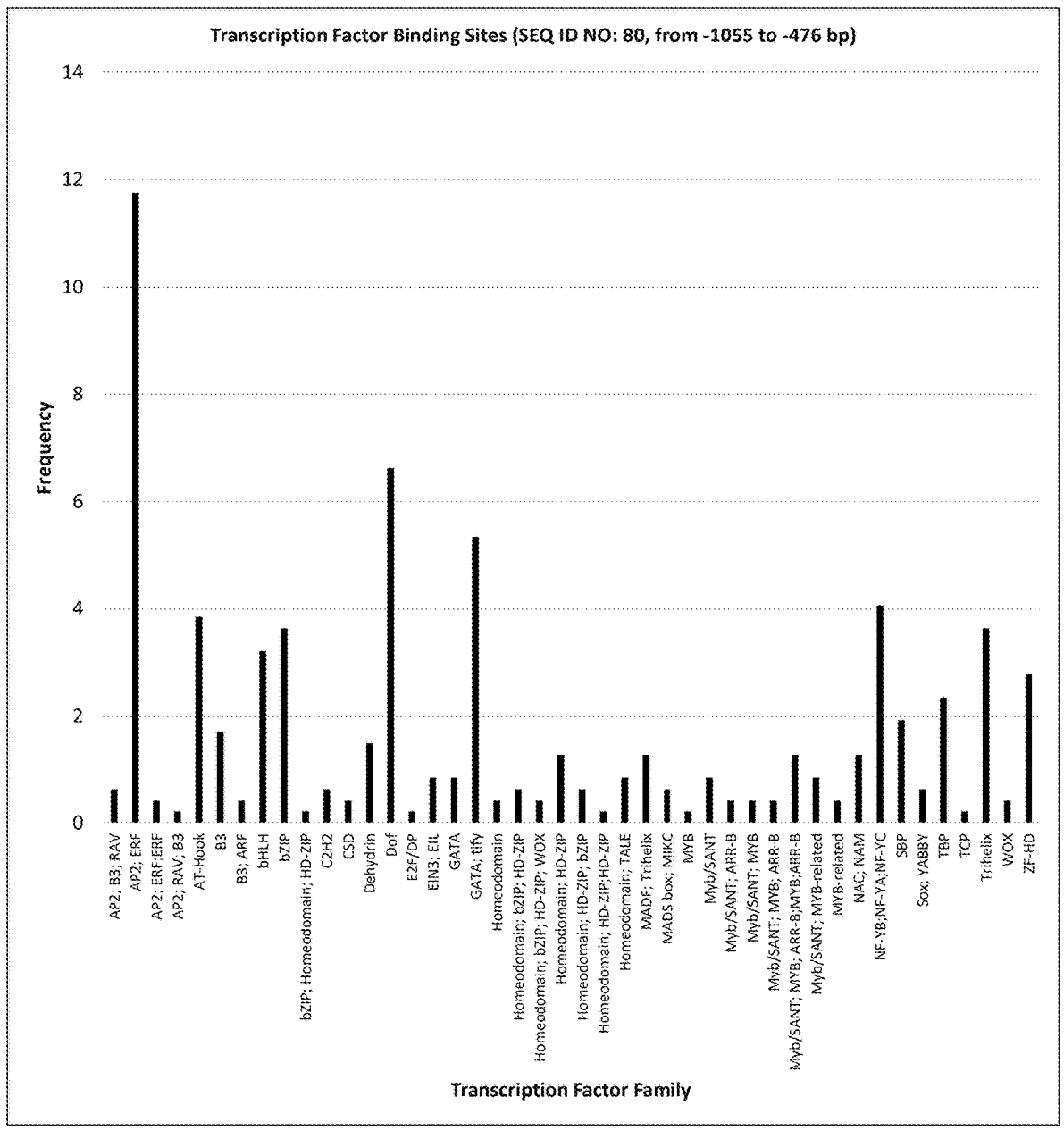
FIG. 17 depicts the frequency of cis-elements identified between positions −1055 and −476 of SEQ ID NO: 80, where the final nucleotide position (e.g., the most 3') of SEQ ID NO: 80 has the position-1. These cis-elements can be found in SEQ ID NO: 81, but not in SEQ ID NO: 82.
Figure 18:
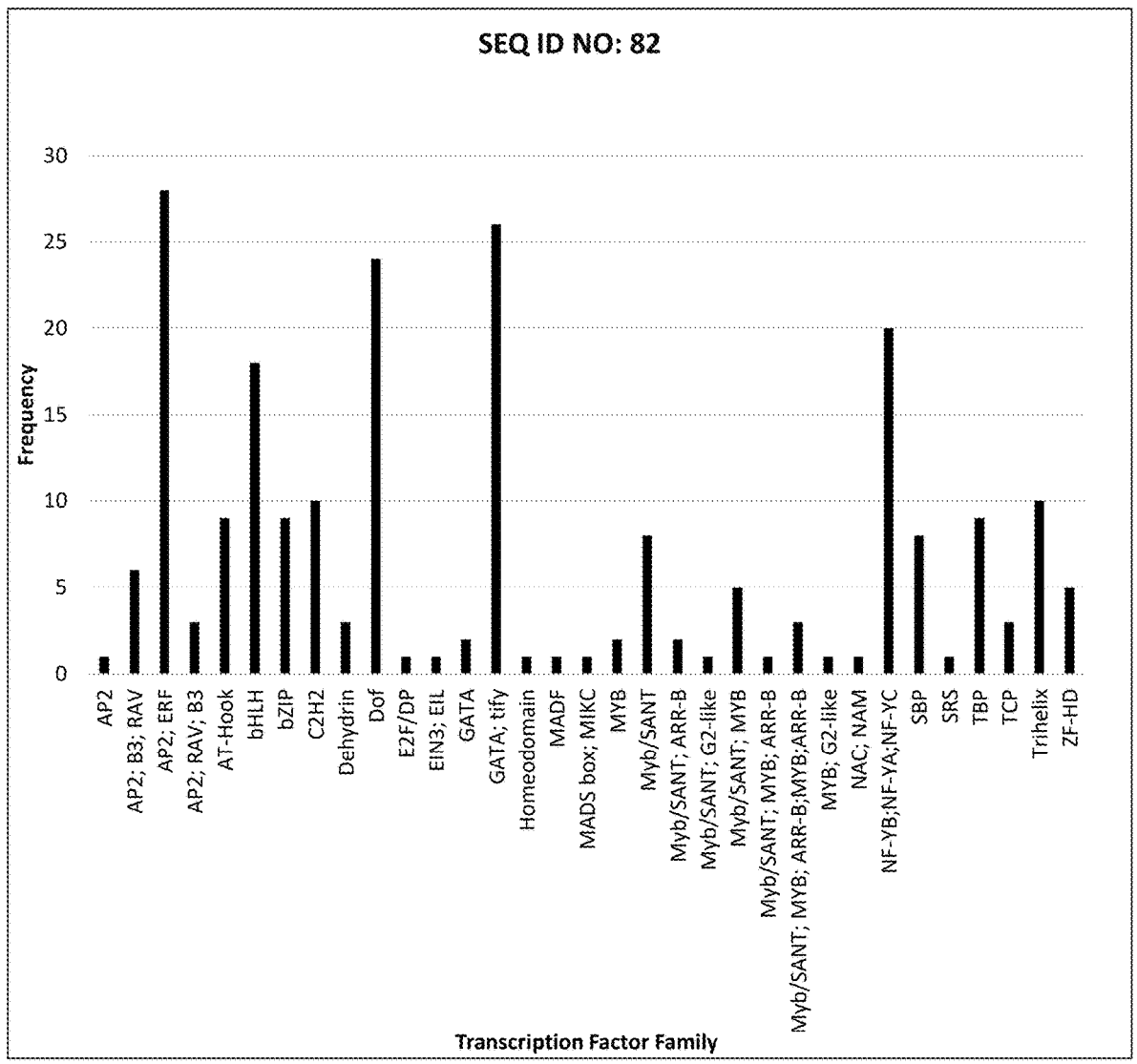
FIG. 18 depicts the frequency of cis-elements identified in SEQ ID NO: 82.

Trichome-specific promoter sequences (e.g., SEQ ID NOs: 80-82) are scanned for cis-regulatory element motifs using the publicly available online database PlantPAN3.0 (plantpan[dot]itps[dot]ncku[dot]edu[dot]tw/index[dot]html) using default settings. Graphs depicting the frequency of the cis-elements are shown in FIGS. 16-18. Further, Tables 15 and 16 detail the cis-regulatory element motifs that were identified that are unique to SEQ ID NO: 81 when compared to SEQ ID NO: 82, and the cis-elements that are unique to SEQ ID NO: 82 when compared to SEQ ID NO: 81, respectively.

Example 10. MALDI Promoter is a Trichome-Specific Promoter

The expression pattern of trichome-specific promoters (SEQ ID NOs: 80-82; see Example 3) is examined in the modified plants as produced in Example 4. First generation (e.g., T0) modified plants are sampled during the vegetative stage. Young leaves, inflorescences, or both are examined for G3GFP accumulation under conditions allowing the visualization of G3GFP (excitation/emission wavelengths are 488 nm/500-550 nm) expressed by the trichome-specific promoters.

TABLE 15

Cis-acting regulatory elements that are unique to SEQ ID NO: 81 when compared to SEQ ID NO: 82. Uppercase nucleotides are considered invariable essential core sequences for the motifs.

| Transcription Factor Family (e.g., cis-acting regulatory element motif) | Binding Sequence | Frequency |
|---|---|---|
| AP2; ERF; ERF | tGTCGGca | 2 |
| B3 | atGCATGc | 8 |
| B3; ARF | atGTCGGcat (SEQ ID NO: 83) | 2 |
| bZIP; Homeodomain; HD-ZIP | gaATTATtat (SEQ ID NO: 84) | 1 |
| CSD | aATAAAaa | 2 |
| Homeodomain; bZIP; HD-ZIP | gttgaATTATtatt (SEQ ID NO: 85) | 3 |
| Homeodomain; bZIP; HD-ZIP; WOX | ttTAATTatc (SEQ ID NO: 86) | 2 |
| Homeodomain; HD-ZIP | catTTAATgc (SEQ ID NO: 87) | 6 |
| Homeodomain; HD-ZIP; bZIP | gaATTATt | 3 |
| Homeodomain; HD-ZIP; HD-ZIP | TAAATgtt | 1 |
| Homeodomain; TALE | gaTGACAggt (SEQ ID NO: 88) | 4 |
| MADF; Trihelix | tGGTTAag | 6 |
| Myb/SANT; MYB-related | aaATATCta | 4 |
| MYB-related | taaATATCta (SEQ ID NO: 89) | 2 |
| Sox; YABBY | cttTAATTat (SEQ ID NO: 90) | 3 |
| WOX | TTAATgc | 2 |

TABLE 16

Cis-acting regulatory elements that are unique to SEQ ID NO: 82 when compared to SEQ ID NO: 81. Uppercase nucleotides are considered invariable essential core sequences for the motifs.

| Transcription Factor Family (e.g., cis-acting regulatory element motif) | Binding Sequence | Frequency |
|---|---|---|
| AP2 | CACATgtacccatg (SEQ ID NO: 91) | 1 |
| MADF | ctTACCGc | 1 |
| Myb/SANT; G2-like | taGATTCtag (SEQ ID NO: 92) | 1 |
| MYB; G2-like | atAGATTcta (SEQ ID NO: 93) | 1 |
| SRS | ggAGAGT | 1 |

Table 17 provides the frequency of cis elements identified in SEQ ID NO: 80.

TABLE 17

Frequency of cis-acting regulator elements identified in SEQ ID NO: 80.

| Transcription Factor Family (e.g., cis-acting regulatory element motif) | Frequency |
| --- | --- |
| AP2; ERF | 150 |
| GATA; tify | 106 |
| Dof | 81 |
| NF-YB; NF-YA; NF-YC | 64 |
| Trihelix | 60 |
| AT-Hook | 53 |
| WRKY | 51 |
| bZIP | 50 |
| SBP | 49 |
| bHLH | 44 |
| ZF-HD | 43 |
| TBP | 41 |
| Dehydrin | 23 |
| Myb/SANT | 20 |
| Myb/SANT; MYB; ARR-B; MYB; ARR-B | 16 |
| NAC; NAM | 15 |
| C2H2 | 14 |
| Myb/SANT; MYB | 14 |
| bZIP; Homeodomain; HD-ZIP | 12 |
| AP2; B3; RAV | 12 |
| Homeodomain; HD-ZIP | 12 |
| Homeodomain; HD-ZIP; bZIP | 12 |
| GATA | 11 |
| Homeodomain; TALE | 11 |
| AP2; RAV; B3 | 11 |
| (Others) | 9 |
| Homeodomain; bZIP; HD-ZIP | 8 |
| B3 | 8 |
| Myb/SANT; MYB-related | 8 |

TABLE 17-continued

Frequency of cis-acting regulator elements identified in SEQ ID NO: 80.

| Transcription Factor Family (e.g., cis-acting regulatory element motif) | Frequency |
| --- | --- |
| Myb/SANT; ARR-B | 7 |
| MADS box; MIKC | 7 |
| MYB-related | 6 |
| EIN3; EIL | 6 |
| MADF; Trihelix | 6 |
| TCP | 6 |
| Homeodomain | 5 |
| Sox; YABBY | 5 |
| B3; ARF | 4 |
| HSF | 4 |
| MYB | 4 |
| Homeodomain; bZIP; HD-ZIP; WOX | 4 |
| Myb/SANT; MYB; ARR-B | 3 |
| TCR; CPP | 3 |
| WOX | 3 |
| AP2; RAV | 2 |
| AP2; ERF; ERF | 2 |
| CSD | 2 |
| HD-ZIP | 2 |
| Homeodomain; HD-ZIP; HD-ZIP | 2 |
| E2F/DP | 2 |
| MYB; ARR-B | 1 |
| MYB; G2-like | 1 |
| AP2; B3 | 1 |
| GRAS | 1 |
| MADF | 1 |
| Myb/SANT; G2-like | 1 |
| AP2 | 1 |
| VOZ | 1 |
| SRS | 1 |
| Unknown | 373 |

The invention claimed is:

1. A modified plant having glandular trichomes, a modified seed giving rise to a plant having glandular trichomes, or a modified plant part comprising glandular trichomes, wherein the modified plant, modified seed, or modified plant part comprises a recombinant nucleic acid molecule comprising a promoter operably linked to a heterologous polynucleotide encoding a polypeptide, wherein the promoter comprises a nucleic acid sequence at least 95% identical to a nucleic acid sequence selected from the group consisting of SEQ ID NOs: 46 and 47.

2. The modified plant, modified seed, or modified plant part, of claim 1, wherein the nucleic acid sequence is 100% identical to a nucleic acid sequence selected from the group consisting of SEQ ID NOs: 46 and 47.

3. The modified plant, modified seed, or modified part thereof of claim 1, wherein the modified plant, modified seed, or modified plant part is a modified tobacco plant, a modified tobacco seed, or a modified tobacco plant part.

4. The modified plant, modified seed, or modified plant part of claim 1, wherein the modified plant, modified seed, or modified plant part is a *Cannabis* plant, a *Cannabis* seed, or a *Cannabis* plant part.

5. The modified plant, modified seed, or modified plant part of claim 1, wherein the heterologous polynucleotide encoding a polypeptide comprises a nucleic acid sequence encoding an amino acid sequence at least 95% identical to an amino acid sequence selected from the group consisting of SEQ ID NOs: 18 to 26 and 64 to 79.

6. The modified plant, modified seed, or modified plant part of claim 1, wherein the heterologous polynucleotide encoding a polypeptide comprises a nucleic acid sequence at least 95% identical to a nucleic acid sequence selected from the group consisting of SEQ ID NOs: 27 to 35 and 48 to 63.

7. The modified plant, modified seed, or modified plant part, of claim 1, wherein the polypeptide is involved in the biosynthesis of at least one terpene.

8. The modified plant, modified seed, or modified plant part, of claim 7, wherein the at least one terpene is cis-abienol.

9. The modified plant, modified seed, or modified plant part of claim 7, wherein the polypeptide is selected from the group consisting of geranylgeranyl diphosphate synthase, 8-hydroxy-copalyl diphosphate synthase, cis-abienol synthase, cembratrienol synthase 2a, levopimaradiene synthetase, 2-isopropylmalate synthetase, 2-oxoisovalerate dehydrogenase, and neomenthol dehydrogenase.

10. The modified plant, seed, or plant part of claim 9, wherein the cis-abienol synthase is selected from the group consisting of cis-abienol synthase ISOFORM1 and cis-abienol synthase ISOFORM2.

11. The modified plant, modified seed, or modified plant part of claim 3, wherein the modified tobacco plant, modified tobacco seed, or modified tobacco plant part is of a tobacco variety selected from the group consisting of a flue-cured variety, a bright variety, a Burley variety, a Virginia variety, a Maryland variety, a dark variety, a Galpão variety, an Oriental variety, and a Turkish variety.

12. The modified plant, modified seed, or modified plant part of claim 1, wherein the modified plant part is selected from the group consisting of a leaf and a stem.

13. The modified plant, modified seed, or modified plant part of claim 4, wherein the modified *Cannabis* plant, modified *Cannabis* seed, or modified *Cannabis* plant part is of a species selected from the group consisting of *Cannabis sativa* and *Cannabis indica*.

14. The modified plant, modified seed, or modified plant part of claim 3, wherein the modified tobacco plant, modified tobacco seed, or modified tobacco plant part is of the species *Nicotiana tabacum*.

15. The modified plant, modified seed, or modified plant part of claim 1, wherein the heterologous polynucleotide encoding a polypeptide comprises a nucleic acid sequence encoding an amino acid sequence 100% identical to an amino acid sequence selected from the group consisting of SEQ ID NOs: 18 to 26 and 64 to 79.

16. The modified plant, modified seed, or modified plant part of claim 1, wherein the heterologous nucleic acid encoding a polypeptide comprises a nucleic acid sequence 100% identical to a nucleic acid sequence selected from the group consisting of SEQ ID NOs: 27 to 35 and 48 to 63.

17. The modified plant, modified seed, or modified plant part, of claim 1, wherein the nucleic acid sequence is at least 98% identical to a nucleic acid sequence selected from the group consisting of SEQ ID NOs: 46 and 47.

18. The modified plant, modified seed, or modified plant part of claim 1, wherein the glandular trichomes are capitate glandular trichomes.

19. The modified plant, modified seed, or modified plant part of claim 1, wherein the glandular trichomes are peltate glandular trichomes.

* * * * *